(12) United States Patent
Kamikawaji et al.

(10) Patent No.: US 11,667,713 B2
(45) Date of Patent: *Jun. 6, 2023

(54) CYTOTOXICITY-INDUCING THERAPEUTIC AGENT

(71) Applicant: Chugai Seiyaku Kabushiki Kaisha, Tokyo (JP)

(72) Inventors: Shogo Kamikawaji, Kanagawa (JP); Yasuko Kinoshita, Kanagawa (JP); Shinya Ishii, Singapore (SG)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/957,837

(22) PCT Filed: Dec. 28, 2018

(86) PCT No.: PCT/JP2018/048409
§ 371 (c)(1),
(2) Date: Jun. 25, 2020

(87) PCT Pub. No.: WO2019/131988
PCT Pub. Date: Jul. 4, 2019

(65) Prior Publication Data
US 2021/0363250 A1    Nov. 25, 2021

(30) Foreign Application Priority Data
Dec. 28, 2017   (JP) .............................. JP2017-254279

(51) Int. Cl.
*C07K 16/28* (2006.01)
*A61P 35/00* (2006.01)

(52) U.S. Cl.
CPC .......... *C07K 16/2809* (2013.01); *A61P 35/00* (2018.01); *C07K 16/28* (2013.01); *C07K 2317/52* (2013.01); *C07K 2317/56* (2013.01)

(58) Field of Classification Search
CPC ................ C07K 16/2809; C07K 16/28; C07K 2317/52; C07K 2317/56; A61P 35/00
See application file for complete search history.

(56) References Cited

U.S. PATENT DOCUMENTS

| | | | |
|---|---|---|---|
| 9,127,071 B2 | 9/2015 | Yoshida et al. | |
| 9,834,606 B2* | 12/2017 | Li | A61P 35/00 |
| 11,274,151 B2* | 3/2022 | Naoi | C07K 16/2878 |
| 2003/0180784 A1 | 9/2003 | Mccarthy et al. | |
| 2005/0137130 A1 | 6/2005 | Bodmer et al. | |
| 2007/0141066 A1 | 6/2007 | Phillips et al. | |
| 2008/0220495 A1 | 9/2008 | Mccarthy et al. | |
| 2012/0328624 A1 | 12/2012 | Yoshida et al. | |
| 2014/0112914 A1 | 4/2014 | Nezu et al. | |
| 2016/0244530 A2 | 8/2016 | Yoshida et al. | |
| 2017/0037130 A1* | 2/2017 | Raum | C07K 16/28 |
| 2017/0306036 A1 | 10/2017 | Vu et al. | |
| 2017/0349668 A1 | 12/2017 | Rattel et al. | |
| 2018/0326058 A1 | 11/2018 | Tsunenari et al. | |
| 2021/0301016 A1 | 9/2021 | Naoi et al. | |
| 2021/0380715 A1 | 12/2021 | Yoshida et al. | |
| 2022/0251201 A1 | 8/2022 | Naoi et al. | |

FOREIGN PATENT DOCUMENTS

| | | |
|---|---|---|
| EP | 2 078 731 A1 | 7/2009 |
| EP | 2317338 B1 | 7/2017 |
| JP | H11299493 A | 11/1999 |
| JP | 2008273973 A | 11/2008 |
| JP | 2009523709 A | 6/2009 |
| JP | 2016513094 A | 5/2016 |
| JP | 2017526350 A | 9/2017 |
| JP | 2018527908 A | 9/2018 |
| JP | 2018188437 A | 11/2018 |
| TW | 201708261 A | 3/2017 |
| WO | WO9845434 A1 | 10/1998 |
| WO | 00/47602 | 8/2000 |
| WO | 01/12664 A2 | 2/2001 |
| WO | 01/075067 A3 | 10/2001 |
| WO | 02/14358 A2 | 2/2002 |
| WO | 03/025138 A2 | 3/2003 |
| WO | 04/030615 A3 | 4/2004 |
| WO | 2004/053102 A2 | 6/2004 |
| WO | 2008/077090 A2 | 8/2005 |
| WO | 2007/080597 A2 | 7/2007 |
| WO | 2007/111733 A2 | 10/2007 |
| WO | 2008/047925 A1 | 4/2008 |
| WO | 2009/124931 A2 | 10/2009 |
| WO | 2011/093097 A1 | 8/2011 |
| WO | WO2012073985 A1 | 6/2012 |
| WO | 2013/126748 A2 | 8/2013 |
| WO | WO2014125273 A1 | 8/2014 |
| WO | 2015/127407 A1 | 8/2015 |
| WO | WO2016016415 A1 | 2/2016 |
| WO | WO2016016859 A1 | 2/2016 |

(Continued)

OTHER PUBLICATIONS

Campoli et al., "Immunotherapy of Malignant Disease with Tumor Antigen-Specific Monoclonal Antibodies", Clinical Cancer Research, vo. 16, No. 1, Jan. 1, 2010, pp. 11-20 (10 pages total).

(Continued)

*Primary Examiner* — Mark Halvorson
*Assistant Examiner* — Dennis J Sullivan
(74) *Attorney, Agent, or Firm* — Nixon & Vanderhye P.C.

(57) ABSTRACT

The present inventors discovered novel multispecific antigen-binding molecules with excellent cellular cytotoxicity, which comprise a first domain comprising a first antigen variable region which binds to DLL3 and a second domain comprising a second antigen variable region which binds to T cell receptor complex. The present inventors prepared further bispecific antibodies, and assessed their T cell-dependent cell cytotoxicity (TDCC), and found that they also show strong TDCC activity. Since the molecules/antibodies of the present invention show a strong cytotoxicity against cells expressing DLL3, novel pharmaceutical compositions comprising the molecules/antibodies for treating or preventing various cancers associated with DLL3 can be provided.

14 Claims, 10 Drawing Sheets

Specification includes a Sequence Listing.

(56) References Cited

FOREIGN PATENT DOCUMENTS

| WO | WO2017010874 A1 | 1/2017 | | |
|---|---|---|---|---|
| WO | 2017/021349 A1 | 2/2017 | | |
| WO | WO-2017086367 A1 * | 5/2017 | ......... | A61K 31/7068 |
| WO | WO2017201442 A1 | 11/2017 | | |
| WO | WO2018204907 A1 | 11/2018 | | |
| WO | WO2019111871 A1 | 6/2019 | | |
| WO | WO2019131988 A1 | 7/2019 | | |
| WO | WO2019234220 A1 | 12/2019 | | |
| WO | WO2020067419 A1 | 4/2020 | | |
| WO | WO2021200898 A1 | 10/2021 | | |

OTHER PUBLICATIONS

Staerz et al., "Hybrid antibodies can target sites for attack by T cells", NATURE. vol. 314, No. 6012, Apr. 18, 1985, pp. 628-631 (2 pages total).
Mezzanzanica et al., "Human Ovarian Carcinoma Lysis by Cytotoxic T Cells Targeted by Bispecific Monoclonal Antibodies: Analysis of the Antibody Components", Int. J. Cancer, vol. 41, No. 4, pp. 609-615, 1988 (4 pages total).
Staerz et al., "Hybrid hybridoma producing a bispecific monoclonal antibody that can focus effector T-cell activity", Proc. Natl. Acad. Sci. USA, vol. 83, vol. 5, pp. 1453-1457, Mar. 1986, Immunology (3 pages total).
Mack et al., "A small bispecific antibody construct expressed as a functional single-chain molecule with high tumor cell cytotoxicity", Proc. Natl. Acad. Sci. USA, vol. 92, pp. 7021-7025, Jul. 1995 (3 pages total).
Wolf et al., "BiTEs: bispecific antibody constructs with unique anti-tumor activity", Drug Discov Today, vol. 10, No. 18, pp. 1237-1244, Sep. 2005 (8 pages total).
Dreier et al., "Extremely Potent Rapid and Costimulation-Independent Cytotoxic T-Cell Response Against Lymphoma Cells Catalyzed by a Single-Chain Bispecific Antibody", Int. J Cancer, Aug. 20, 2002, vol. 100, No. 6, pp. 690-697 (8 pages total).
Sebastian et al., "Treatment of non-small cell lung cancer patients with the trifunctional monoclonal antibody catumaxomab (anti-EpCAM x anti-CD3): a phase I study", Cncer Immunol Immunother, 2007, vol. 56, No. 10, pp. 1637-1644 (8 pages total).
Schlereth et al., "T-cell activation and B-cell depletion in chimpanzees treated with a bispecific anti-CD 19/anti-CD3 single-chain antibody construct", Cancer Immunol Immunother, 2006, vol. 55, No. 5, pp. 503-514 (12 pages total).
Amann el al., "Therapeutic window of art EpCAM/CD3-specific BiTE antibody in mice is determined by a subpopulation of EpCAM-expressing lymphocytes that is absent in humans", Cancer Immunol Immunother, 2009, vol. 58, No. 1, pp. 98-108 (15 pages total).
Bulman et al., "Mutations in the human *Delta* homologue, *DLL3*, cause axial skeletal defects in spondylocostal dysostosis", Nature Genetics, Apr. 2000, vol. 24, No. 4, pp. 438-441(4 pages total).
Turnpenny et al., "Novel mutations in *DLL3*, a somitogenesis gene encoding a ligand for the Notch signalling pathway, cause a consistent pattern of abnomal vertebral segmentation in spondylocustal dysostosis", J Med Genet., May 2003, vol. 40, No. 5, pp. 333-339 (7 pages total).
Phillips et al., "Moleculer subclasses of high-grade glioma predict prognosis, delineate a pattern of disease progression and resemble stages in neurogenesis", Cancer Cell, vol. 9, vol. 1, pp. 157-173, Mar. 2006 (17 pages total).
Mullendore et al., "Ligand-dependent Notch Signaling is Involved in Tumor Initiation and Tumor Maintenance in Pancreatic Cancer", Clin. Cancer Res., Apr. 2009, vol. 15, No. 7, pp. 2291-2301 (11 pages total).
Saunders et al., "A DLL3-tasgeled antibody-drug conjugate eradicates high-grade pulmonary neuroendorine tumor-initiating cells in vivo," Science Translational Medicine, Aug. 26, 2015, vol. 7, issue 302, pp. 1-13.

Declaration from Dr. William Decker, dated Dec. 2020, filed in the defence of Oppositions Against European Patent No. 2,530,091.
Spirin, Alexander S., "Storage of Messenger RNA in Eukaryotes: Envelopment With Protein, Translational Barrier at 5' Side, or Conformational Masking by3' Side?," Molecular Reproduction and Development, May 1994, vol. 38, issue 1, pp. 107-117.
Renjan et al., "Masking mRNA from translation in somatic cells," Genes and Development (1993) vol. 7, pp. 17254-1736.
Declaration from Professor Mark Gerstein, "Expert Opinion," dated Feb. 2020, submitted in opposition proceedings against European Patent No. 2,530,091.
Gad et al., "Nonclinical Vehicle Use in Studies by Multiple Routes in Multiple Species," International Journal of Toxicology, Nov.-Dec. 2006, vol. 25, issue 6, pp. 499-521.
Katch et al., "Precision medicine for human cancers with Notch signaling dysregulation (Review)," International Journal of Molecular Medicine, Feb. 2020, vol. 45, issue 2, pp. 279-297.
Espinoza et al. "Notch Inhibitors for Cancer Treatment," Pharmacology & Therapeutics, Aug. 2013, vol. 139, Issue 2, pp. 95-110.
Von Meerten et al. "Complement-Induced Cell Death by rituximab Depends on CD20 Expression Level and Acts Complementary to Antibody-Dependent Cellular Cytotoxicity," Clinical Cancer Research, Jul. 1, 2006, vol. 12, Issue 13, pp. 4027-4035.
Gershoni et al., "Epitope Mapping-the First Step in Developing Epitope-Based Vaccines," Biodrugs, 2007, vol. 21, Issue 3, pp. 145-156.
Knowles et al., "Advances in Immuno-Positron Emission Tomography: Antibodies for Molecular Imaging in Oncology," Journal of Clinical Oncology, Nov. 1, 2012, vol. 30, No. 31, pp. 3884-3892.
Communication, dated Mar. 22, 2019, issued by European Patent Office in European Patent No. 2,990,420.
De La Lastra et al., "Epitope mapping of 10 monoclonal antibodies against the pig analogue of human membrane cofactor protein (MCP)," Immunology, Apr. 1999, vol. 96, No. 4, pp. 663-670.
Coullu et al., "Cooperation between Wnt and Notch signalling in human breast cancer," (2007) Breast Cancer Research, May 11, 2007, vol. 9: No. 3, (3 pages).
Guo et al., "Role of Notch and its oncogenic signaling crosstalk in breast cancer," Biochimica et Biophysica Acta (BBA)—Reviews on Cancer, Apr. 2011, vol. 1815, Issue 2, pp. 197-213.
Ercan et al., "Marrimary Development and Breast Cancer; The Role of Stem Cells," Current Molecular Medicine, Jun. 2011, vol. 11, No. 4, pp. 270-285.
Wang et al., "Epithelial-mesenchymal transition in breast cancer progression and metastasis," Chinese Journal of Cancer; Sep. 2011, vol. 30, No. 9, pp. 603-611.
Information about the result of oral proceedings in European Patent Application NO. 11736812.6, dated Mar. 4, 2021.
Communication, dated Jun. 10, 2020, issued by European Patent Office in European Application No. 18 156 974.0.
Commonication, dated Oct. 10.2019, issued by European Patent Office in European Application No. 11736812.6.
Weinzierl, et al., Notice of opposition filed against EP 2 530 091 B1 dated Jan. 2, 2019 (50 pages).
Unsin, Dr. Claudia E, Notice of opposition filed against EP 2 530 091 B1 dated Jan. 2, 2019 (16 pages).
Livingston et al., "Selection of GM2, fucosyl GM1, globo H and polysialic acid as targets on small cell lung cancers for antibody mediated Immunotherapy," Cancer Immunol. Immunother., 2005, 54: 1018-1025.
Chugai Selyaku Kabushiki Kaisha, "Sequence Alignments," dated Mar. 6, 2020, submitted in counterpart European Patent Application No. 11736812.6, 2 pages.
Maler et al., "Corelation of mRNA and protein in complex biological samples," FEBS Letters, 2009, 583: 3966-3973.
Communication, dated Jun. 10, 2020, issued by the European Patent Office a counterpart European Patent Application No. 18 156 974.0-1111.
Chugai Selyaku Kabushiki Kaisha, Final Written Submission, dated Mar. 6, 2020, submitted in counterpart European Patent Application No. 11736812.6.
Communication, dated Oct. 10, 2019, from the European Patent Office in counterpart European Application No. 11736812.6.

(56) References Cited

OTHER PUBLICATIONS

Brendan D'Souza, et al. "Canonical and Non-Canonical Notch Ligands", Current Topics in Developmental Biology, 2010, vol. 92, pp. 73-129 (57 pages total).
Dov Greenbaum, et al., "Comparing protein abundance and mRNA expression levels of a genomic seals", Genome Biology, Aug. 28, 2003, vol. 4, issue 9, article 117, pp. 117.1-117.8 (8 pages total).
Communication, dated Jan. 30, 2019, issued by the European Patent Office in counterpart Application No. 11738812.6.
Communication, dated Jan. 8, 2019, issued by the European Patent Office in counterpart Application No. 11736812.6.
Communication, dated Jandary 8.2019. issued by the Ruropsan Patent Office in countetpart Apiplicaon No. 11738812,6.
Communication, dated Jan. 15, 2019, issued: by the European Patent Office in counterpart Application No. 11736812.6.
"Monoclonal Anti-human DLL3 Antibody", Product sheet for Human DLL3 Antibody, MAB4315, R&D Systems, Inc., 2007.
"Immunoglobulin G" Immunoglobulin G, Review InvivoGen, 2011.
Nimmerjahn, Falk et al., "Fcγ Receptors old Friends and New Family Members" Immunity, 2006, pp. 19-28, vol. 24, pp.
Stockwin, LH et al., "Antibodies as therapeutic agents: vive la renaissance!", Expert Opinion on Biological Therapy, 2008, vol. 3; no. 7, pp. 1133-1152.
Shields, Robert L. et al., "High Resolution Mapping of the Binding Site on Human IgG1 for FcγRI, FcγRII FcγRIII, and FcRη and Design of IgG1 Variants with Improved Binding to the FcγR", The Journal of Biological Chemistry, 2001, vol. 276, No. 9 pp. 6591-6604.
Zanetti, M et al., "The Antibodies," Harwood Academic Publishers, 2000, vol. 6 pp. 36-37.
Goding, James W. et al., "Monoclonal Antibodies: Principles and Practice", Academic Press, 1996, Third Edition, pp. 134-135.
Carter, Paul et al., "Identification and validation of cell surface antigens for antibody targeting in oncology", Endocrine-Related Cancer, 2004, vol. 11, pp. 659-687.
Carter, Paul J. et al., "Antibody-Drug Corjugates for Cancer Therapy", The Cancer Journal, 2008, vol. 14, No. 3, pp. 154-169.
Adams, Gregory P et al., "Monoclonal antibody therapy of cancer", Nature Biotechnology, 2005, vol. 23, No. 9, pp. 1147-1157.
Sun, Yu et al., "Antibody-drug conjugates as targeted cancer therapeutics", Acta Pharmaceutica Sinica, 2009, vol. 44, No. 9, pp. 943-952.
Chen, Jin et al., "Antibody-cylotaxic agent conjugates for cancer therapy", Expert Opinion on Drug Delivery, 2005, vol. 2, No. 5, pp. 873-890.
Grant, Stefan C. et al., "Targeting of small-cell lung cancer using the anti-GD2 gangfloside monoclonal antibody 3F8: a pilot trial", European Journal of Nuclear Medicine, 1996; vol. 23, No. 2, pp. 145-149.
Dunwoodie, Sally L. "The role at Notch in patterning the human vertebral column", Current Opinion in Genetics & Development, 2009, vol. 19, pp. 329-337.
D'Souza, B. et al., "The many facets of Notch ligands", Oncogene, 2008, vol. 27, pp. 5148-5167.
Henke, R. Michael et al., "Ascl1 and Neurog2 Form Novel Complexes and Regulate *Delta-like3* (Dll3) Expression in the Neural Tube", Dev Biol., 2009, vol. 328, No. 2, pp. 529-540.
Ball, Douglas W., "Achaete—scute homolog-1 and Notch in lung neurcendocrine development and cancer", Cancer Letters, 2004, vol. 204, pp. 159-169.
Choi, Kulcheon, et al., "Distinct Biological Roles for the Notch Ligands Jagged-1 and Jagged-2", The Journal of Biological Chemistry, 2009, vol. 284, No. 26, pp. 17766-17774.
"Compugen Announces Discovery of Blood Based Biomarker for Diagnosis of Lung Cancer", Apr. 29, 2008 (2 pages), retrieved from https://www.cgen.com/mediacenter/compugen-announces-discovery-of-blood-based-biomarker-for-diagnosis-of-lung-cancer.
Taneja, Tarvinder K., et al.. "Markers of small cell lung cancer", World Journal of Surgical Oncolgy, 2004, vol. 2, No. 10, pp. 1-5.

Chung, Shan et al., "Characterization of in vitro antibody-dependent cell-mediated cytotoxicity activity of therapeutic antibodies—Impact of effector cells", Journal of Immunological Methods, 2014, vol. 407, pp. 63-75.
Weng, Wen-Kal et al., "Two Immunoglobulin G Fragment C Receptor Polymorphisms Independently Predict Response to Rituximab in Patients With Follicular Lymphoma", Journal of Clinical Oncology, 2003, vol. 21, No. 21, pp. 3940-3947.
Ayyakannu Ayyanan et al., "Increased Wnt signaling triggers oncogenic conversion of human breast epithelial cells by a Notch-dependent mechanism", Proceedings of the National Academy of Sciences of USA, 2006, pp. 3799-3804, vol. 103, No. 10.
Communication dated Mar. 24, 2015, issued by the Japanese Patent Office in counterpart Application No. 2011551775.
Communication for EP 11736812.6 dated Jun. 6, 2013, along with Supplementary European Search Repon dated May 29, 2013.
Ena Ladi at al., "The divergent DSL ligand Dll3 does not activate Notch signaling but cell autonomously attenuates signaling induced by other DSL ligands", The Journal of Cell Biology, 2005, pp. 983-992, vol. 170, No. 6.
Heidi S. Phillips et al., "Molecular subclasses of high-grade glioma predict prognosis, delineate a pattern of disease progression, and resemble stages in neurogenesis", Cancer Cell, 2006, pp. 157-173, vol. 9.
Insa Geffers et al., "Divergent functions and distinct localization of the Notch ligands DLL1 and DLL3 in vivo", The Journal of Cell Biology, 2007, pp. 465-476, vol. 178, No. 3.
International Preliminary Report on Patentability for Intemational Application No. PCT/JP2011/000485, dated Sep. 27, 2012.
International Search Report for PCT/JP2011/000485 dated Mar. 1, 2011.
Jiang et al., "Achaete-Scute Complex Homologue 1 Regulates Tumor-Initiating Capacity in Human Small Cell Lung Cancer", Cancer Research, 69(3):845-854. (2009), Abstract No. XP002697824.
Kenya Shitara, "Potelligent Antibodies as Next Generation Therapeutic Antibodies", Yakugaku Zaschi, 2009, pp. 3-9, vol. 129, No. 1.
Michael E. Mullendore et al., "Ligand-dependent Notch Signaling Is Involved in Tumor Initiation and Tumor Maintenance in Pancreatic Cancer", Clin Cancer Res, 2009, pp. 2291-2301, vol. 15.
Michael P. Bulman et al., "Mutations in the human Della homologue, DLL3, cause axial skeletal defects in spondylocostal dysostosis", Nature Genetics, 2000, pp. 438-441, vol. 24.
Millipore: "Anti-Delta3, clone 1E7.2", Internet citation, Abstract No. XP002697359, pp. 1-3 (Jul. 15, 2008).
P D Turnpenny et al., "Novel mutations in DLL3, a somitogenesis gene encoding a ligand for the Notch signaling pathway, cause a consistent pattern of abnormal vertebral segmentation in spondylcostal dysostosis", J Med Genet, 2003, pp. 333-339, vol. 40.
R&D Systems; "Human DLL3 Antibody", Monoclonal Mouse IgG2B Clone #378703, Catalog No. MAB4315, Internet Citation, Abstract No. XP002697358 (May 20, 2010).
De Pascalis et al. The Journal of Immunology (2002) 169, 3076-3084.
Lamminmak et al. (JBC 2001, 276:36687-36694).
Padlan et al. (PNAS 1989, 86:5938-5942).
Song st al. (Biochem Biophys Res Comm 268:390-394 (2000)).
Kumar et al. (J. Biol. Chem. 275:35129-35136 (2000)).
Smith-Gill et al. (J. Immunol. 139:4135-4144 (1987)).
Ward et al. (Nature 341:544-546 (1989)).
Holm et al. ((2007) Mol. Immunol. 44: 1075-1084).
Vajdos et al. ((2002) J. Mol. Biol. 320, 415-428).
Cassel et al. ((2003) BBRC 307, 198-205).
MacCallum et al. (J. Mol. Biol. (1996) 262:732-745).
Rudikoff et al. (Proc Natl Acad Sci USA 1982 vol. 79 p. 1979-1983).
Baeuerle, P. A., et al., "BiTE: Teaching antibodies to engage T-cells for cancer therapy," Curr Opin Mol Ther., 11(1 ):22-30 (2009).
Bluemel, C., et al., "Epitope distance to the target cell membrane and antigen size determine the potency of T cell-mediated lysis by BiTE antibodies specific for a large melanoma surface antigen," Cancer Immunol Immunother., 59:1197-1209 (2010).
Communication of Notices of Oppositions in European Application No. 18156974.0/Patent No. 3342786 dated Apr. 13, 2022.

(56) References Cited

OTHER PUBLICATIONS

Curriculum Vitae of Professor Dr. William K. Decker, cited in the Grounds of Appeal in European Patent Application No. 11736812.6 on Sep. 17, 2021.
Decision Revoking European Patent No. 2530091 dated May 7, 2021.
Second Declaration of Professor Dr. William K. Decker dated Sep. 13, 2021, cited in the Grounds of Appeal in European Patent Application No. 11736812.6 on Sep. 17, 2021.
Dickopf, S., et al., "Format and geometries matter: Structure-based design defines the functionality of bispecific antibodies," Computational and Structural Biotechnology Journal, 18:1221-1227 (2020).
Final Office Action dated Oct. 3, 2014 in U.S. Appl. No. 13/575,861, filed Sep. 12, 2012, Yoshida et al.
Final Office Action dated Feb. 16, 2017 in U.S. Appl. No. 14/846,135, filed Sep. 4, 2015, Yoshida et al.
Edwards, B. M., et al., "The Remarkable Flexibility of the Human Antibody Repertoire; Isolation of Over One Thousand Different Antibodies to a Single Protein, BLyS," J Mol Biol., 334:103-118(2003).
Goldenberg, D. M., et al., "Veltuzumab (humanized anti-CD20 monoclonal antibody): characterization, current clinical results, and future prospects," Leukemia & Lymphoma, 51(5):747-755 (2010), cited in the Grounds of Appeal in European Patent Application No. 11736812.6 on Sep. 17, 2021.
Ingle, G. S., et al., "High CD21 expression inhibits internalization of anti-CD19 antibodies and cytotoxicity of an anti-CD19-drug conjugate," British Journal of Haematology, 140:46-58 (2008), cited in the Grounds of Appeal in European Patent Application No. 11736812.6 on Sep. 17, 2021.
Kontermann, R, E., "Recombinant bispecific antibodies for cancer therapy," Acta Pharm Sininca, 26(1):1 -9 (2005).
Lloyd, C., et al., "Modelling the human immune response: performance of a $10^{11}$ human antibody repertoire against a broad panel of therapeutically relevant antigens," Prot Eng Des Sel., 22(3):159-168 (2009).
Magro, G., et al., "Differential expression of mucins I-6 in papillary thyroid carcinoma: evidence for transformation-dependent post-translational modifications of MUCI in situ," J Pathol., 200:357-369 (2003), cited in the Grounds of Appeal in European Patent Application No. 11736812.6 on Sep. 17, 2021.
Minutes of the oral proceedings before the Examining Division in European Application No. 18156974.0 dated Apr. 16, 2021.
National Library of Medicine, COVID-19 Information, Cited in for PMID: 16501043, Mar. 1, 2022.
Notice of Opposition 1 in European Application No. 18156974.0/ Patent No. 3342786 dated Mar. 16, 2022.
Notice of Opposition 2 in European Application No. 18156974.0/ Patent No. 3342786 dated Mar. 21, 2022.
Office Action dated Jun. 5, 2014 in U.S. Appl. No. 13/575,861, filed Sep. 12, 2012, Yoshida et al.
Office Action dated Jun. 5, 2020 in U.S. Appl. No. 14/846,135, filed Sep. 4, 2015, Yoshida et al.
Office Action dated Aug. 19, 2019 in U.S. Appl. No. 14/846,135, filed Sep. 4, 2015, Yoshida et al.
Office Action dated Jan. 7, 2019 in U.S. Appl. No. 14/846.135, filed Sep. 4, 2015, Yoshida et al.
Office Action dated Jun. 11, 2018 in U.S. Appl. No. 14/846,135, filed Sep. 4. 2015, Yoshida et al.
Office Action dated Oct. 20, 2017 in U.S. Appl. No. 14/846,135, filed Sep. 4, 2015, Yoshida et al.
Owonikoko, T., et al., "Two Novel Immunotherapy Agents Targeting DLL3 in SCLC: Trials in Progress of AMG 757 and AMG 119," J Thorac Oncol., 13(10S):S351-S353 (2018).
Roda-Navarro and Alvarez-Vallina, L., "Understanding the Spatial Topology of Artificial Immunological Synapses Assembled in T Cell-Redirecting Strategies: a Major Issue in Cancer Immunotherapy," Front Cell Dev Biol., 7:370 (2020).
Schwarz, S., et al., "Twelve of fourteen surface epitopes of receptor-bound human chorionic gonadotropin (hCG) being antibody-inaccessible suggest an extensive involvement of the long extracellular domain of the hCG receptor," Mol Cell Endocrinology, 82:71-79 (1991).
Zhang, Y. and Pastan, I., "High Shed Antigen Levels within Tumors: an Additional Barrier to Immunoconjugate Therapy," Clin Cancer Res., 14(24):7981-7986 (2008), cited in the Grounds of Appeal in European Patent Application No. 11736812.6 on Sep. 17, 2021.
U.S. Appl. No. 17/216,981, filed Mar. 30, 2021, Naoi et al., related application.
U.S. Appl. No. 17/670,917, filed Feb. 14, 2022, Naoi et al., related application.
U.S. Appl. No. 17/406,504, filed Aug. 19, 2021, Yoshida et al., related application.
Japanese Office Action dated Dec. 6, 2022 in Japanese Patent Application No. 2020-536283.
U.S. Appl. No. 17/216,981, filed Mar. 30, 2021, Naoi et al.
U.S. Appl. No. 17/670,917, filed Feb. 14, 2022, Naoi et al.
U.S. Appl. No. 17/406,504, filed Aug. 19, 2021, Yoshida et al.

* cited by examiner

Fig. 3 FCM

Fig. 7 Evaluation of the in vivo drug efficacy in SCLC xenograft models

Fig. 9
In vitro TDCC activity of humanized and optimized anti-DLL3/CD3 antibodies
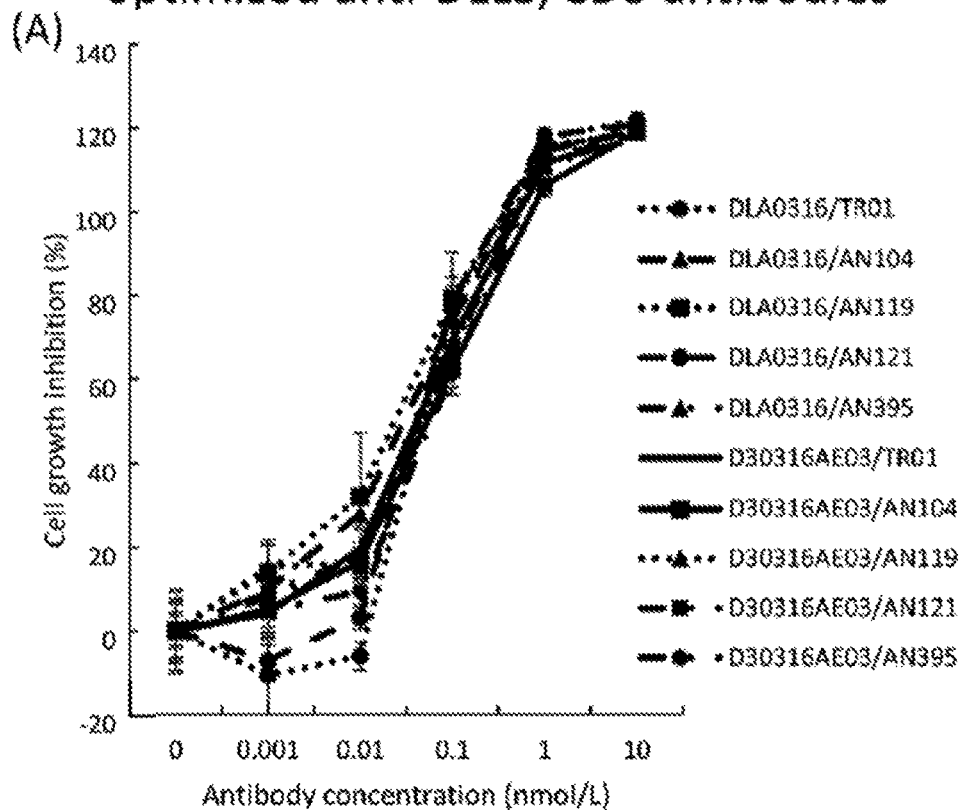
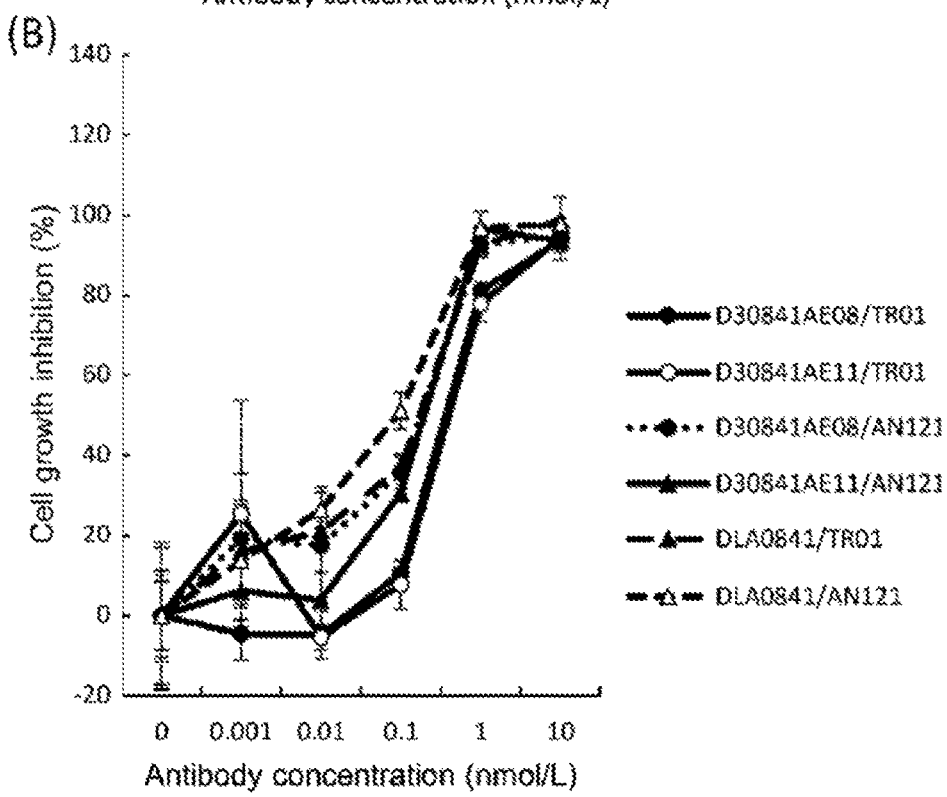

```
                         SEQUENCE LISTING

<160> NUMBER OF SEQ ID NOS: 391

<210> SEQ ID NO 1
<211> LENGTH: 490
<212> TYPE: PRT
<213> ORGANISM: Artificial Sequence
<220> FEATURE:
<223> OTHER INFORMATION: an artificial synthesized sequence

<400> SEQUENCE: 1

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320
```

```
Cys Phe Asn Gly Gly Leu Cys Val Gly Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
        355                 360                 365

Leu Asp Leu Gly His Ala Leu Arg Cys Arg Cys Arg Ala Gly Phe Ala
    370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Ala His Arg Cys Ser
                405                 410                 415

Cys Ala Leu Gly Phe Gly Gly Arg Asp Cys Arg Glu Arg Ala Asp Pro
                420                 425                 430

Cys Ala Ala Arg Pro Cys Ala His Gly Gly Arg Cys Tyr Ala His Phe
            435                 440                 445

Ser Gly Leu Val Cys Ala Cys Ala Pro Gly Tyr Met Gly Ala Arg Cys
        450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg
                485                 490

<210> SEQ ID NO 2
<211> LENGTH: 301
<212> TYPE: PRT
<213> ORGANISM: Artificial Sequence
<220> FEATURE:
<223> OTHER INFORMATION: an artificial synthesized sequence

<400> SEQUENCE: 2

Met Val Leu Ala Ser Ser Thr Thr Ser Ile His Thr Met Leu Leu Leu
1               5                   10                  15

Leu Leu Met Leu Ala Gln Pro Ala Met Ala Ala Pro Leu Val Cys Arg
            20                  25                  30

Ala Gly Cys Ser Pro Glu His Gly Phe Cys Glu Gln Pro Gly Glu Cys
        35                  40                  45

Arg Cys Leu Glu Gly Trp Thr Gly Pro Leu Cys Thr Val Pro Val Ser
    50                  55                  60

Thr Ser Ser Cys Leu Ser Pro Arg Gly Pro Ser Ser Ala Thr Thr Gly
65                  70                  75                  80

Cys Leu Val Pro Gly Pro Gly Pro Cys Asp Gly Asn Pro Cys Ala Asn
                85                  90                  95

Gly Gly Ser Cys Ser Glu Thr Pro Arg Ser Phe Glu Cys Thr Cys Pro
            100                 105                 110

Arg Gly Phe Tyr Gly Leu Arg Cys Glu Val Ser Gly Val Thr Cys Ala
        115                 120                 125

Asp Gly Pro Cys Phe Asn Gly Gly Leu Cys Val Gly Gly Ala Asp Pro
    130                 135                 140

Asp Ser Ala Tyr Ile Cys His Cys Pro Pro Gly Phe Gln Gly Ser Asn
145                 150                 155                 160

Cys Glu Lys Arg Val Asp Arg Cys Ser Leu Gln Pro Cys Arg Asn Gly
                165                 170                 175

Gly Leu Cys Leu Asp Leu Gly His Ala Leu Arg Cys Arg Cys Arg Ala
            180                 185                 190
```

```
Gly Phe Ala Gly Pro Arg Cys Glu His Asp Leu Asp Cys Ala Gly
            195                 200                 205

Arg Ala Cys Ala Asn Gly Gly Thr Cys Val Glu Gly Gly Ala His
210                 215                 220

Arg Cys Ser Cys Ala Leu Gly Phe Gly Gly Arg Asp Cys Arg Glu Arg
225                 230                 235                 240

Ala Asp Pro Cys Ala Ala Arg Pro Cys Ala His Gly Gly Arg Cys Tyr
            245                 250                 255

Ala His Phe Ser Gly Leu Val Cys Ala Cys Ala Pro Gly Tyr Met Gly
                260                 265                 270

Ala Arg Cys Glu Phe Pro Val His Pro Asp Gly Ala Ser Ala Leu Pro
            275                 280                 285

Ala Ala Pro Pro Gly Leu Arg Pro Gly Asp Pro Gln Arg
    290                 295                 300

<210> SEQ ID NO 3
<211> LENGTH: 243
<212> TYPE: PRT
<213> ORGANISM: Artificial Sequence
<220> FEATURE:
<223> OTHER INFORMATION: an artificial synthesized sequence

<400> SEQUENCE: 3

Met Val Leu Ala Ser Ser Thr Thr Ser Ile His Thr Met Leu Leu Leu
1               5                   10                  15

Leu Leu Met Leu Ala Gln Pro Ala Met Ala Gly Pro Gly Pro Cys Asp
                20                  25                  30

Gly Asn Pro Cys Ala Asn Gly Gly Ser Cys Ser Glu Thr Pro Arg Ser
            35                  40                  45

Phe Glu Cys Thr Cys Pro Arg Gly Phe Tyr Gly Leu Arg Cys Glu Val
        50                  55                  60

Ser Gly Val Thr Cys Ala Asp Gly Pro Cys Phe Asn Gly Gly Leu Cys
65                  70                  75                  80

Val Gly Gly Ala Asp Pro Asp Ser Ala Tyr Ile Cys His Cys Pro Pro
                85                  90                  95

Gly Phe Gln Gly Ser Asn Cys Glu Lys Arg Val Asp Arg Cys Ser Leu
            100                 105                 110

Gln Pro Cys Arg Asn Gly Gly Leu Cys Leu Asp Leu Gly His Ala Leu
        115                 120                 125

Arg Cys Arg Cys Arg Ala Gly Phe Ala Gly Pro Arg Cys Glu His Asp
130                 135                 140

Leu Asp Asp Cys Ala Gly Arg Ala Cys Ala Asn Gly Gly Thr Cys Val
145                 150                 155                 160

Glu Gly Gly Gly Ala His Arg Cys Ser Cys Ala Leu Gly Phe Gly Gly
                165                 170                 175

Arg Asp Cys Arg Glu Arg Ala Asp Pro Cys Ala Ala Arg Pro Cys Ala
            180                 185                 190

His Gly Gly Arg Cys Tyr Ala His Phe Ser Gly Leu Val Cys Ala Cys
        195                 200                 205

Ala Pro Gly Tyr Met Gly Ala Arg Cys Glu Phe Pro Val His Pro Asp
210                 215                 220

Gly Ala Ser Ala Leu Pro Ala Ala Pro Pro Gly Leu Arg Pro Gly Asp
225                 230                 235                 240

Pro Gln Arg
```

```
<210> SEQ ID NO 4
<211> LENGTH: 205
<212> TYPE: PRT
<213> ORGANISM: Artificial Sequence
<220> FEATURE:
<223> OTHER INFORMATION: an artificial synthesized sequence

<400> SEQUENCE: 4
```

Met Val Leu Ala Ser Ser Thr Thr Ser Ile His Thr Met Leu Leu
1               5                   10                  15

Leu Leu Met Leu Ala Gln Pro Ala Met Ala Ser Gly Val Thr Cys Ala
            20                  25                  30

Asp Gly Pro Cys Phe Asn Gly Gly Leu Cys Val Gly Gly Ala Asp Pro
                35                  40                  45

Asp Ser Ala Tyr Ile Cys His Cys Pro Pro Gly Phe Gln Gly Ser Asn
    50                  55                  60

Cys Glu Lys Arg Val Asp Arg Cys Ser Leu Gln Pro Cys Arg Asn Gly
65                  70                  75                  80

Gly Leu Cys Leu Asp Leu Gly His Ala Leu Arg Cys Arg Cys Arg Ala
                85                  90                  95

Gly Phe Ala Gly Pro Arg Cys Glu His Asp Leu Asp Asp Cys Ala Gly
                100                 105                 110

Arg Ala Cys Ala Asn Gly Gly Thr Cys Val Glu Gly Gly Gly Ala His
            115                 120                 125

Arg Cys Ser Cys Ala Leu Gly Phe Gly Gly Arg Asp Cys Arg Glu Arg
    130                 135                 140

Ala Asp Pro Cys Ala Ala Arg Pro Cys Ala His Gly Gly Arg Cys Tyr
145                 150                 155                 160

Ala His Phe Ser Gly Leu Val Cys Ala Cys Ala Pro Gly Tyr Met Gly
                165                 170                 175

Ala Arg Cys Glu Phe Pro Val His Pro Asp Gly Ala Ser Ala Leu Pro
            180                 185                 190

Ala Ala Pro Pro Gly Leu Arg Pro Gly Asp Pro Gln Arg
        195                 200                 205

```
<210> SEQ ID NO 5
<211> LENGTH: 164
<212> TYPE: PRT
<213> ORGANISM: Artificial Sequence
<220> FEATURE:
<223> OTHER INFORMATION: an artificial synthesized sequence

<400> SEQUENCE: 5
```

Met Val Leu Ala Ser Ser Thr Thr Ser Ile His Thr Met Leu Leu Leu
1               5                   10                  15

Leu Leu Met Leu Ala Gln Pro Ala Met Ala Arg Val Asp Arg Cys Ser
            20                  25                  30

Leu Gln Pro Cys Arg Asn Gly Gly Leu Cys Leu Asp Leu Gly His Ala
        35                  40                  45

Leu Arg Cys Arg Cys Arg Ala Gly Phe Ala Gly Pro Arg Cys Glu His
    50                  55                  60

Asp Leu Asp Asp Cys Ala Gly Arg Ala Cys Ala Asn Gly Gly Thr Cys
65                  70                  75                  80

Val Glu Gly Gly Gly Ala His Arg Cys Ser Cys Ala Leu Gly Phe Gly
                85                  90                  95

Gly Arg Asp Cys Arg Glu Arg Ala Asp Pro Cys Ala Ala Arg Pro Cys
            100                 105                 110

```
Ala His Gly Gly Arg Cys Tyr Ala His Phe Ser Gly Leu Val Cys Ala
        115                 120                 125

Cys Ala Pro Gly Tyr Met Gly Ala Arg Cys Glu Phe Pro Val His Pro
    130                 135                 140

Asp Gly Ala Ser Ala Leu Pro Ala Ala Pro Gly Leu Arg Pro Gly
145                 150                 155                 160

Asp Pro Gln Arg

<210> SEQ ID NO 6
<211> LENGTH: 126
<212> TYPE: PRT
<213> ORGANISM: Artificial Sequence
<220> FEATURE:
<223> OTHER INFORMATION: an artificial synthesized sequence

<400> SEQUENCE: 6

Met Val Leu Ala Ser Ser Thr Thr Ser Ile His Thr Met Leu Leu Leu
1               5                   10                  15

Leu Leu Met Leu Ala Gln Pro Ala Met Ala Asp Leu Asp Asp Cys Ala
            20                  25                  30

Gly Arg Ala Cys Ala Asn Gly Gly Thr Cys Val Glu Gly Gly Gly Ala
        35                  40                  45

His Arg Cys Ser Cys Ala Leu Gly Phe Gly Gly Arg Asp Cys Arg Glu
    50                  55                  60

Arg Ala Asp Pro Cys Ala Ala Arg Pro Cys Ala His Gly Gly Arg Cys
65                  70                  75                  80

Tyr Ala His Phe Ser Gly Leu Val Cys Ala Cys Ala Pro Gly Tyr Met
                85                  90                  95

Gly Ala Arg Cys Glu Phe Pro Val His Pro Asp Gly Ala Ser Ala Leu
            100                 105                 110

Pro Ala Ala Pro Pro Gly Leu Arg Pro Gly Asp Pro Gln Arg
        115                 120                 125

<210> SEQ ID NO 7
<211> LENGTH: 88
<212> TYPE: PRT
<213> ORGANISM: Artificial Sequence
<220> FEATURE:
<223> OTHER INFORMATION: an artificial synthesized sequence

<400> SEQUENCE: 7

Met Val Leu Ala Ser Ser Thr Thr Ser Ile His Thr Met Leu Leu Leu
1               5                   10                  15

Leu Leu Met Leu Ala Gln Pro Ala Met Ala Arg Ala Asp Pro Cys Ala
            20                  25                  30

Ala Arg Pro Cys Ala His Gly Gly Arg Cys Tyr Ala His Phe Ser Gly
        35                  40                  45

Leu Val Cys Ala Cys Ala Pro Gly Tyr Met Gly Ala Arg Cys Glu Phe
    50                  55                  60

Pro Val His Pro Asp Gly Ala Ser Ala Leu Pro Ala Ala Pro Pro Gly
65                  70                  75                  80

Leu Arg Pro Gly Asp Pro Gln Arg
                85

<210> SEQ ID NO 8
<211> LENGTH: 501
<212> TYPE: PRT
<213> ORGANISM: Macaca fascicularis
```

```
<400> SEQUENCE: 8

Met Gly Trp Ser Cys Ile Ile Leu Phe Leu Val Ala Thr Ala Thr Gly
1               5                   10                  15

Val His Ser Glu Gln Lys Leu Ile Ser Glu Glu Asp Leu Ala Gly Val
            20                  25                  30

Phe Glu Leu Gln Ile His Ser Phe Gly Pro Gly Pro Gly Pro Gly Ala
        35                  40                  45

Pro Arg Ser Pro Cys Ser Ala Arg Gly Pro Cys Arg Leu Phe Phe Arg
    50                  55                  60

Val Cys Leu Lys Pro Gly Leu Ser Glu Glu Ala Ala Glu Ser Pro Cys
65                  70                  75                  80

Ala Leu Gly Ala Ala Leu Ser Ala Arg Gly Pro Val Tyr Thr Glu Gln
                85                  90                  95

Pro Glu Ala Pro Ala Pro Asp Leu Pro Leu Pro Asn Gly Leu Leu Gln
            100                 105                 110

Val Pro Phe Arg Asp Ala Trp Pro Gly Thr Phe Ser Leu Ile Ile Glu
        115                 120                 125

Thr Trp Arg Glu Glu Leu Gly Asp Gln Ile Gly Gly Pro Ala Trp Ser
    130                 135                 140

Leu Leu Ala Arg Val Thr Arg Arg Arg Leu Ala Ala Gly Gly Pro
145                 150                 155                 160

Trp Ala Arg Asp Ile Gln Arg Ala Gly Ala Trp Glu Leu Arg Phe Ser
                165                 170                 175

Tyr Arg Ala Arg Cys Glu Leu Pro Ala Val Gly Thr Ala Cys Thr Arg
            180                 185                 190

Leu Cys Arg Pro Arg Ser Ala Pro Ser Arg Cys Gly Pro Gly Leu Arg
        195                 200                 205

Pro Cys Ala Pro Leu Glu Asp Glu Cys Glu Ala Pro Pro Val Cys Arg
    210                 215                 220

Ala Gly Cys Ser Leu Glu His Gly Phe Cys Glu Gln Pro Gly Glu Cys
225                 230                 235                 240

Arg Cys Leu Glu Gly Trp Thr Gly Pro Leu Cys Thr Val Pro Ala Ser
                245                 250                 255

Thr Ser Ser Cys Leu Gly Leu Arg Gly Pro Ser Ser Ala Thr Thr Gly
            260                 265                 270

Cys Leu Val Pro Gly Pro Gly Pro Cys Asp Gly Asn Pro Cys Ala Asn
        275                 280                 285

Gly Gly Ser Cys Ser Glu Thr Pro Gly Ser Phe Glu Cys Thr Cys Pro
    290                 295                 300

Arg Gly Phe Tyr Gly Leu Arg Cys Glu Val Ser Gly Val Thr Cys Ala
305                 310                 315                 320

Asp Gly Pro Cys Phe Asn Gly Gly Leu Cys Val Gly Gly Ala Asp Pro
                325                 330                 335

Asp Ser Ala Tyr Ile Cys His Cys Pro Pro Gly Phe Gln Gly Ser Asn
            340                 345                 350

Cys Glu Lys Arg Val Asp Arg Cys Ser Leu Gln Pro Cys Arg Asn Gly
        355                 360                 365

Gly Leu Cys Leu Asp Leu Gly His Ala Leu Arg Cys Arg Cys Arg Ala
    370                 375                 380

Gly Phe Ala Gly Pro Arg Cys Glu His Asn Leu Asp Asp Cys Ala Gly
385                 390                 395                 400

Arg Ala Cys Ala Asn Gly Gly Thr Cys Val Glu Gly Gly Gly Ala His
                405                 410                 415
```

```
Arg Cys Ser Cys Ala Leu Gly Phe Gly Gly Arg Asp Cys Arg Glu Arg
            420                 425                 430

Ala Asp Pro Cys Ala Ala Arg Pro Cys Ala His Gly Gly Arg Cys Tyr
            435                 440                 445

Ala His Phe Ser Gly Leu Val Cys Ala Cys Ala Pro Gly Tyr Met Gly
            450                 455                 460

Ser Arg Cys Glu Phe Pro Val His Pro Asp Gly Val Ser Ala Leu Pro
465                 470                 475                 480

Ala Ala Pro Pro Gly Leu Arg Pro Gly Asp Pro Gln Arg His His His
                    485                 490                 495

His His His His His
            500

<210> SEQ ID NO 9
<211> LENGTH: 618
<212> TYPE: PRT
<213> ORGANISM: Homo sapiens

<400> SEQUENCE: 9

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Pro Gly Ala Pro Arg Ser
            35                  40                  45

Pro Cys Ser Ala Arg Leu Pro Cys Arg Leu Phe Phe Arg Val Cys Leu
50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
            85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
            115                 120                 125

Glu Glu Leu Gly Asp Gln Ile Gly Gly Pro Ala Trp Ser Leu Leu Ala
            130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
            165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
            195                 200                 205

Pro Leu Glu Asp Glu Cys Glu Ala Pro Leu Val Cys Arg Ala Gly Cys
            210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                    245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
```

-continued

```
                    275                 280                 285
Cys Ser Glu Thr Pro Arg Ser Phe Glu Cys Thr Cys Pro Arg Gly Phe
    290                 295                 300
Tyr Gly Leu Arg Cys Glu Val Ser Gly Val Thr Cys Ala Asp Gly Pro
305                 310                 315                 320
Cys Phe Asn Gly Gly Leu Cys Val Gly Gly Ala Asp Pro Asp Ser Ala
                325                 330                 335
Tyr Ile Cys His Cys Pro Pro Gly Phe Gln Gly Ser Asn Cys Glu Lys
            340                 345                 350
Arg Val Asp Arg Cys Ser Leu Gln Pro Cys Arg Asn Gly Gly Leu Cys
        355                 360                 365
Leu Asp Leu Gly His Ala Leu Arg Cys Arg Cys Arg Ala Gly Phe Ala
370                 375                 380
Gly Pro Arg Cys Glu His Asp Leu Asp Asp Cys Ala Gly Arg Ala Cys
385                 390                 395                 400
Ala Asn Gly Gly Thr Cys Val Glu Gly Gly Gly Ala His Arg Cys Ser
                405                 410                 415
Cys Ala Leu Gly Phe Gly Gly Arg Asp Cys Arg Glu Arg Ala Asp Pro
            420                 425                 430
Cys Ala Ala Arg Pro Cys Ala His Gly Gly Arg Cys Tyr Ala His Phe
        435                 440                 445
Ser Gly Leu Val Cys Ala Cys Ala Pro Gly Tyr Met Gly Ala Arg Cys
    450                 455                 460
Glu Phe Pro Val His Pro Asp Gly Ala Ser Ala Leu Pro Ala Ala Pro
465                 470                 475                 480
Pro Gly Leu Arg Pro Gly Asp Pro Gln Arg Tyr Leu Pro Pro Ala
                485                 490                 495
Leu Gly Leu Leu Val Ala Ala Gly Val Ala Gly Ala Ala Leu Leu Leu
                500                 505                 510
Val His Val Arg Arg Arg Gly His Ser Gln Asp Ala Gly Ser Arg Leu
            515                 520                 525
Leu Ala Gly Thr Pro Glu Pro Ser Val His Ala Leu Pro Asp Ala Leu
        530                 535                 540
Asn Asn Leu Arg Thr Gln Glu Gly Ser Gly Asp Gly Pro Ser Ser Ser
545                 550                 555                 560
Val Asp Trp Asn Arg Pro Glu Asp Val Asp Pro Gln Gly Ile Tyr Val
                565                 570                 575
Ile Ser Ala Pro Ser Ile Tyr Ala Arg Glu Val Ala Thr Pro Leu Phe
            580                 585                 590
Pro Pro Leu His Thr Gly Arg Ala Gly Gln Arg Gln His Leu Leu Phe
        595                 600                 605
Pro Tyr Pro Ser Ser Ile Leu Ser Val Lys
    610                 615
```

<210> SEQ ID NO 10
<211> LENGTH: 107
<212> TYPE: PRT
<213> ORGANISM: Artificial Sequence
<220> FEATURE:
<223> OTHER INFORMATION: an artificial synthesized sequence

<400> SEQUENCE: 10

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Cys
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 11
<211> LENGTH: 122
<212> TYPE: PRT
<213> ORGANISM: Artificial Sequence
<220> FEATURE:
<223> OTHER INFORMATION: an artificial synthesized sequence

<400> SEQUENCE: 11

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Ser Trp Val Arg Gln Ala Pro Gly Lys Gly Leu Glu Trp Ile Gly
        35                  40                  45

Ile Ile Ser Asn Ser Gly Ser Gly Phe Tyr Ala Asn Trp Ala Lys Gly
    50                  55                  60

Arg Phe Thr Ile Ser Lys Thr Ser Ser Thr Val Asp Val Lys Ile
65                  70                  75                  80

Ser Ser Pro Thr Thr Glu Asp Thr Ala Thr Tyr Phe Cys Ala Arg Val
                85                  90                  95

Phe Asp Ala Asp Ser Ser Gly Tyr Tyr Tyr Tyr Gly Met Asp Pro Trp
            100                 105                 110

Gly Pro Gly Thr Leu Val Thr Val Ser Ser
        115                 120

<210> SEQ ID NO 12
<211> LENGTH: 111
<212> TYPE: PRT
<213> ORGANISM: Artificial Sequence
<220> FEATURE:
<223> OTHER INFORMATION: an artificial synthesized sequence

<400> SEQUENCE: 12

Asp Val Val Met Thr Gln Thr Pro Ser Ser Val Ser Glu Pro Val Gly
1               5                   10                  15

Gly Thr Val Thr Ile Lys Cys Gln Ala Ser Glu Asp Ile Glu Ser Tyr
            20                  25                  30

Leu Ala Trp Tyr Gln Gln Lys Pro Gly Gln Pro Lys Leu Leu Ile
        35                  40                  45

Tyr Ala Ala Ser Thr Leu Ala Ser Gly Val Ser Ser Arg Phe Arg Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Thr Tyr Tyr Asp Ser Ser
                85                  90                  95
```

Gly Val Asp Trp Ala Phe Gly Gly Gly Thr Glu Val Val Lys
            100                 105                 110

<210> SEQ ID NO 13
<211> LENGTH: 123
<212> TYPE: PRT
<213> ORGANISM: Artificial Sequence
<220> FEATURE:
<223> OTHER INFORMATION: an artificial synthesized sequence

<400> SEQUENCE: 13

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Arg Tyr Ala
            20                  25                  30

Met Ser Trp Val Arg Gln Ala Pro Gly Lys Gly Leu Glu Trp Ile Gly
        35                  40                  45

Ile Ile Thr Gly Gly Gly Asp Pro Tyr Tyr Ala Ser Trp Ala Lys Gly
    50                  55                  60

Arg Phe Thr Ile Ser Lys Thr Ser Thr Thr Met Asp Leu Lys Ile Thr
65                  70                  75                  80

Ser Pro Thr Thr Glu Asp Thr Ala Thr Tyr Phe Cys Ala Arg Met Ile
                85                  90                  95

Gly Ser Glu Tyr Ala Ser Ser Ser Glu Tyr Tyr Asp Ala Phe Asp Pro
            100                 105                 110

Trp Gly Pro Gly Thr Leu Val Thr Val Ser Ser
        115                 120

<210> SEQ ID NO 14
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 14

Ala Leu Val Met Thr Gln Thr Pro Ser Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Glu Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Asp Asp Ala Ala Ile Tyr Tyr Cys Gln Ser Ala Tyr Tyr Thr Thr Ser
                85                  90                  95

Val Asp Val Leu Tyr Pro Phe Gly Gly Gly Thr Glu Val Val Val Lys
            100                 105                 110

<210> SEQ ID NO 15
<211> LENGTH: 124
<212> TYPE: PRT
<213> ORGANISM: Artificial Sequence
<220> FEATURE:
<223> OTHER INFORMATION: an artificial synthesized sequence

<400> SEQUENCE: 15

Gln Glu Gln Leu Val Glu Ser Gly Gly Gly Leu Val Gln Pro Gly Gly

```
1               5                   10                  15
Ser Leu Lys Leu Ser Cys Lys Val Ser Gly Phe Asp Phe Ser Asn Tyr
            20                  25                  30

Gly Val Ser Trp Val Arg Gln Ala Pro Gly Lys Gly Leu Glu Trp Ile
            35                  40                  45

Gly Tyr Ile Asp Pro Ala Phe Gly Arg Thr Tyr Tyr Ala Ser Trp Val
        50                  55                  60

Asn Gly Arg Phe Thr Ile Ser Ser His Asn Ala Gln Asn Thr Leu Tyr
65                  70                  75                  80

Leu Gln Leu Asn Ser Leu Thr Ala Ala Asp Thr Ala Thr Tyr Phe Cys
            85                  90                  95

Val Arg Val Ala Leu Val Val Ala Gly Val Ala Tyr Tyr Gly Met Asp
            100                 105                 110

Val Trp Gly Pro Gly Thr Leu Val Thr Val Ser Ser
            115                 120
```

<210> SEQ ID NO 16
<211> LENGTH: 114
<212> TYPE: PRT
<213> ORGANISM: Artificial Sequence
<220> FEATURE:
<223> OTHER INFORMATION: an artificial synthesized sequence

<400> SEQUENCE: 16

```
Ala Asp Val Val Met Thr Gln Thr Pro Ala Ser Val Glu Ala Ala Val
1               5                   10                  15

Gly Gly Thr Val Thr Ile Asn Cys Gln Ala Ser Gln Asn Ile Tyr Ser
            20                  25                  30

Tyr Leu Ser Trp Tyr Gln Gln Lys Pro Gly Gln Pro Pro Lys Leu Leu
            35                  40                  45

Ile Tyr Arg Thr Ser Thr Leu Ala Ser Gly Val Pro Ser Arg Phe Lys
        50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Gln Ser Tyr Tyr Tyr Ser Ser
            85                  90                  95

Gly Ser Ser Tyr Gly Ala Phe Ala Phe Gly Gly Gly Thr Glu Val Val
            100                 105                 110

Val Lys
```

<210> SEQ ID NO 17
<211> LENGTH: 114
<212> TYPE: PRT
<213> ORGANISM: Artificial Sequence
<220> FEATURE:
<223> OTHER INFORMATION: an artificial synthesized sequence

<400> SEQUENCE: 17

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Asn Thr Tyr His
            20                  25                  30

Met Ile Trp Val Arg Gln Ala Pro Gly Lys Gly Leu Glu Trp Ile Gly
            35                  40                  45

Ile Val Asp Ser Gly Gly Ser Thr Tyr Tyr Ala Ser Trp Ala Lys Gly
        50                  55                  60

Arg Phe Thr Ile Ser Arg Thr Ser Thr Thr Val Asp Leu Lys Ala Thr
```

```
                65                  70                  75                  80
Ser Leu Thr Thr Glu Asp Thr Ala Thr Tyr Phe Cys Ala Arg Gly Gly
                    85                  90                  95

Ser Trp Asp Gly Phe Asn Ile Trp Gly Pro Gly Thr Leu Val Thr Val
                100                 105                 110

Ser Ser

<210> SEQ ID NO 18
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 18

Asp Val Val Met Thr Gln Thr Pro Ser Ser Val Ser Ala Ala Val Gly
1               5                   10                  15

Gly Thr Val Thr Ile Asn Cys Gln Ser Ser Gln Ser Val Tyr Asn Ser
                20                  25                  30

Asp Phe Leu Ala Trp Tyr Gln Gln Lys Pro Gly Gln Pro Pro Lys Leu
            35                  40                  45

Leu Ile Tyr Ala Ala Ser Thr Leu Ala Ser Gly Val Pro Ser Arg Phe
        50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Gln Gly Thr Tyr Glu Asp
                85                  90                  95

Val Gly Trp Phe Asn Asp Phe Gly Gly Gly Thr Glu Val Val Val Lys
                100                 105                 110

<210> SEQ ID NO 19
<211> LENGTH: 128
<212> TYPE: PRT
<213> ORGANISM: Artificial Sequence
<220> FEATURE:
<223> OTHER INFORMATION: an artificial synthesized sequence

<400> SEQUENCE: 19

Gln Glu Gln Leu Val Glu Ser Gly Gly Gly Leu Val Gln Pro Gly Ala
1               5                   10                  15

Ser Leu Thr Leu Thr Cys Lys Ala Ser Gly Phe Asp Phe Thr Ser Asn
                20                  25                  30

Ala Met Cys Trp Val Arg Gln Ala Pro Gly Lys Gly Pro Glu Trp Ile
            35                  40                  45

Ala Cys Ile Tyr Asn Asp Asp Gly Ser Ala Tyr Ser Ala Ser Trp Ala
        50                  55                  60

Lys Gly Arg Phe Thr Val Ser Lys Thr Ser Ser Thr Ala Val Thr Leu
65                  70                  75                  80

Gln Val Thr Gly Leu Thr Ala Ala Asp Thr Ala Thr Tyr Phe Cys Ala
                85                  90                  95

Arg Ser Pro Tyr Tyr Thr Tyr Gly Gly Ala Pro Ser Ala Tyr Ala Ser
                100                 105                 110

Gly Tyr Phe Asn Leu Trp Gly Pro Gly Thr Leu Val Thr Val Ser Ser
            115                 120                 125

<210> SEQ ID NO 20
<211> LENGTH: 113
<212> TYPE: PRT
```

```
<213> ORGANISM: Artificial Sequence
<220> FEATURE:
<223> OTHER INFORMATION: an artificial synthesized sequence

<400> SEQUENCE: 20

Ala Asp Ile Val Met Thr Gln Thr Pro Ala Ser Val Glu Ala Ala Val
1               5                   10                  15

Gly Gly Thr Val Thr Ile Lys Cys Gln Ala Ser Glu Asn Ile Tyr Asn
            20                  25                  30

Ser Leu Ala Trp Tyr Gln Gln Lys Pro Gly Gln Pro Pro Lys Leu Leu
        35                  40                  45

Met His Asp Ala Ser Val Leu Thr Ser Gly Val Pro Ser Arg Phe Ser
50                  55                  60

Gly Ser Gly Tyr Gly Thr Glu Phe Thr Leu Thr Ile Ser Asp Leu Glu
65                  70                  75                  80

Cys Ala Asp Ala Ala Thr Tyr Tyr Cys Gln Ser Asp Tyr Tyr Ser Thr
                85                  90                  95

Gly Gly Ser Tyr Gly Phe Ala Phe Gly Gly Gly Thr Glu Val Val Val
            100                 105                 110

Lys

<210> SEQ ID NO 21
<211> LENGTH: 121
<212> TYPE: PRT
<213> ORGANISM: Artificial Sequence
<220> FEATURE:
<223> OTHER INFORMATION: an artificial synthesized sequence

<400> SEQUENCE: 21

Gln Glu Gln Leu Val Glu Ser Gly Gly Leu Val Gln Pro Gly Ala
1               5                   10                  15

Ser Leu Thr Leu Thr Cys Lys Ala Ser Gly Phe Ser Phe Asn Thr Ser
            20                  25                  30

Tyr Cys Pro Cys Trp Val Arg Gln Val Pro Gly Lys Gly Pro Glu Trp
        35                  40                  45

Ile Ala Cys Ile Asp Ala Gly Tyr Ser Gly Ala Thr Trp Tyr Ala Asn
50                  55                  60

Trp Ala Lys Gly Arg Phe Thr Ile Ser Lys Thr Ser Thr Thr Val
65                  70                  75                  80

Thr Leu Gln Met Thr Ser Leu Thr Gly Ala Asp Thr Ala Thr Tyr Phe
                85                  90                  95

Cys Val Arg Cys Asp Ala Ala Gly Ser Gly Ala Phe Asn Leu Trp Gly
            100                 105                 110

Pro Gly Thr Leu Val Thr Val Ser Ser
        115                 120

<210> SEQ ID NO 22
<211> LENGTH: 110
<212> TYPE: PRT
<213> ORGANISM: Artificial Sequence
<220> FEATURE:
<223> OTHER INFORMATION: an artificial synthesized sequence

<400> SEQUENCE: 22

Ala Tyr Asp Met Thr Gln Thr Pro Ala Ser Val Glu Val Pro Val Gly
1               5                   10                  15

Gly Thr Val Thr Ile Lys Cys Gln Ala Ser Gln Ser Ile Tyr Ser Tyr
            20                  25                  30
```

```
Leu Ser Trp Tyr Gln Gln Lys Pro Gly Gln Pro Lys Leu Leu Ile
         35                  40                  45

Tyr Glu Ala Ser Lys Leu Thr Ser Gly Val Pro Ser Arg Phe Ser Gly
 50                  55                  60

Ser Gly Ser Gly Thr Glu Phe Thr Leu Thr Ile Ser Gly Val Gln Cys
 65                  70                  75                  80

Asp Asp Ala Ala Thr Tyr Tyr Cys Gln Gln Gly Ser Gly Tyr Met Asp
                 85                  90                  95

Val Asp Asn Val Phe Gly Gly Thr Glu Val Val Lys
                100                 105                 110

<210> SEQ ID NO 23
<211> LENGTH: 123
<212> TYPE: PRT
<213> ORGANISM: Artificial Sequence
<220> FEATURE:
<223> OTHER INFORMATION: an artificial synthesized sequence

<400> SEQUENCE: 23

Gln Glu Gln Leu Val Glu Ser Gly Gly Gly Leu Val Gln Pro Glu Gly
 1               5                  10                  15

Ser Leu Thr Leu Thr Cys Thr Ala Ser Gly Phe Ser Phe Ser Ser Ser
                 20                  25                  30

Gly Tyr Met Cys Trp Val Arg Gln Ala Pro Gly Lys Gly Leu Glu Trp
         35                  40                  45

Ile Ala Cys Ile Ser Gly Gly Ser Gly Asp Thr Asp Tyr Ala Asn
 50                  55                  60

Trp Ala Lys Gly Arg Phe Ser Ile Ser Lys Thr Ser Thr Thr Val
 65                  70                  75                  80

Thr Leu Gln Met Thr Ser Leu Thr Val Ala Asp Thr Ala Thr Tyr Phe
                 85                  90                  95

Cys Ala Arg Asp Val Tyr Ile Asp Ser Thr Ile Phe Asn Phe Asn Leu
                100                 105                 110

Trp Gly Pro Gly Thr Leu Val Thr Val Ser Ser
        115                 120

<210> SEQ ID NO 24
<211> LENGTH: 111
<212> TYPE: PRT
<213> ORGANISM: Artificial Sequence
<220> FEATURE:
<223> OTHER INFORMATION: an artificial synthesized sequence

<400> SEQUENCE: 24

Gln Val Leu Thr Gln Thr Pro Ser Pro Val Ser Ala Ala Val Gly Gly
 1               5                  10                  15

Thr Val Thr Ile Ser Cys Gln Ala Ser Gln Ser Val Tyr Asn Asn Asn
                 20                  25                  30

Asn Leu Ala Trp Tyr Gln Gln Lys Pro Gly Gln Pro Pro Lys Leu Leu
         35                  40                  45

Ile Tyr Ala Ala Ser Ser Leu Ala Ser Gly Val Pro Ser Arg Phe Lys
 50                  55                  60

Gly Ser Gly Ala Gly Thr Gln Phe Thr Leu Thr Ile Ser Asp Leu Glu
 65                  70                  75                  80

Cys Asp Asp Ala Ala Thr Tyr Tyr Cys Gln Gly Thr Tyr Tyr Ser Ser
                 85                  90                  95

Gly Trp Tyr Ser Thr Phe Gly Gly Thr Glu Val Val Val Lys
                100                 105                 110
```

<210> SEQ ID NO 25
<211> LENGTH: 118
<212> TYPE: PRT
<213> ORGANISM: Artificial Sequence
<220> FEATURE:
<223> OTHER INFORMATION: an artificial synthesized sequence

<400> SEQUENCE: 25

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
            20                  25                  30

Tyr Asp Met Cys Trp Val Arg Gln Ala Pro Gly Lys Gly Pro Glu Trp
        35                  40                  45

Ile Ala Cys Ile Tyr Thr Gly Asp Gly Ser Thr Asp Tyr Ala Ser Trp
    50                  55                  60

Ala Lys Gly Arg Phe Thr Val Ser Lys Ala Ser Ser Thr Thr Val Thr
65                  70                  75                  80

Leu Gln Met Thr Ser Leu Ala Val Ala Asp Thr Ala Thr Tyr Phe Cys
                85                  90                  95

Ala Arg Asn Ser Gly Tyr Gly Tyr Phe Gly Leu Trp Gly Pro Gly Thr
            100                 105                 110

Leu Val Thr Val Ser Ser
        115

<210> SEQ ID NO 26
<211> LENGTH: 109
<212> TYPE: PRT
<213> ORGANISM: Artificial Sequence
<220> FEATURE:
<223> OTHER INFORMATION: an artificial synthesized sequence

<400> SEQUENCE: 26

Gln Val Leu Thr Gln Thr Pro Ser Pro Val Ser Ala Ala Val Gly Gly
1               5                   10                  15

Thr Val Thr Ile Ser Cys Gln Ser Thr Glu Ser Val Tyr Gly Ser Asp
            20                  25                  30

Trp Leu Ser Trp Tyr Gln Gln Lys Pro Gly Gln Pro Pro Lys Val Leu
        35                  40                  45

Ile Tyr Gln Ala Ser Asn Leu Glu Ile Gly Val Pro Ser Arg Phe Lys
    50                  55                  60

Gly Ser Gly Ser Gly Thr Gln Phe Thr Leu Thr Ile Ser Gly Ala Gln
65                  70                  75                  80

Cys Asp Asp Ala Ala Thr Tyr Tyr Cys Gln Gly Tyr Tyr Ser Gly Tyr
                85                  90                  95

Ile Tyr Ala Phe Gly Gly Gly Thr Glu Val Val Val Lys
            100                 105

<210> SEQ ID NO 27
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 27

Asn Tyr Gly Val Ser
1               5

```
<210> SEQ ID NO 28
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 28

Tyr Ile Asp Pro Ala Phe Gly Arg Thr Tyr Tyr Ala Ser Trp Val Asn
1               5                   10                  15

Gly

<210> SEQ ID NO 29
<211> LENGTH: 15
<212> TYPE: PRT
<213> ORGANISM: Artificial Sequence
<220> FEATURE:
<223> OTHER INFORMATION: an artificial synthesized sequence

<400> SEQUENCE: 29

Val Ala Leu Val Val Ala Gly Val Ala Tyr Tyr Gly Met Asp Val
1               5                   10                  15

<210> SEQ ID NO 30
<211> LENGTH: 11
<212> TYPE: PRT
<213> ORGANISM: Artificial Sequence
<220> FEATURE:
<223> OTHER INFORMATION: an artificial synthesized sequence

<400> SEQUENCE: 30

Gln Ala Ser Gln Asn Ile Tyr Ser Tyr Leu Ser
1               5                   10

<210> SEQ ID NO 31
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 31

Arg Thr Ser Thr Leu Ala Ser
1               5

<210> SEQ ID NO 32
<211> LENGTH: 15
<212> TYPE: PRT
<213> ORGANISM: Artificial Sequence
<220> FEATURE:
<223> OTHER INFORMATION: an artificial synthesized sequence

<400> SEQUENCE: 32

Gln Ser Tyr Tyr Tyr Ser Ser Gly Ser Ser Tyr Gly Ala Phe Ala
1               5                   10                  15

<210> SEQ ID NO 33
<211> LENGTH: 6
<212> TYPE: PRT
<213> ORGANISM: Artificial Sequence
<220> FEATURE:
<223> OTHER INFORMATION: an artificial synthesized sequence

<400> SEQUENCE: 33

Ser Ser Tyr Asp Met Cys
1               5
```

```
<210> SEQ ID NO 34
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 34

Cys Ile Tyr Thr Gly Asp Gly Ser Thr Asp Tyr Ala Ser Trp Ala Lys
1               5                   10                  15
Gly

<210> SEQ ID NO 35
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 35

Asn Ser Gly Tyr Gly Tyr Phe Gly Leu
1               5

<210> SEQ ID NO 36
<211> LENGTH: 13
<212> TYPE: PRT
<213> ORGANISM: Artificial Sequence
<220> FEATURE:
<223> OTHER INFORMATION: an artificial synthesized sequence

<400> SEQUENCE: 36

Gln Ser Thr Glu Ser Val Tyr Gly Ser Asp Trp Leu Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 37

Gln Ala Ser Asn Leu Glu Ile
1               5

<210> SEQ ID NO 38
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 38

Gln Gly Tyr Tyr Ser Gly Tyr Ile Tyr Ala
1               5                   10

<210> SEQ ID NO 39
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 39

Ser Asn Ala Met Cys
```

```
<210> SEQ ID NO 40
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 40

Cys Ile Tyr Asn Asp Asp Gly Ser Ala Tyr Ser Ala Ser Trp Ala Lys
1               5                   10                  15

Gly

<210> SEQ ID NO 41
<211> LENGTH: 20
<212> TYPE: PRT
<213> ORGANISM: Artificial Sequence
<220> FEATURE:
<223> OTHER INFORMATION: an artificial synthesized sequence

<400> SEQUENCE: 41

Ser Pro Tyr Tyr Thr Tyr Gly Gly Ala Pro Ser Ala Tyr Ala Ser Gly
1               5                   10                  15

Tyr Phe Asn Leu
            20

<210> SEQ ID NO 42
<211> LENGTH: 11
<212> TYPE: PRT
<213> ORGANISM: Artificial Sequence
<220> FEATURE:
<223> OTHER INFORMATION: an artificial synthesized sequence

<400> SEQUENCE: 42

Gln Ala Ser Glu Asn Ile Tyr Asn Ser Leu Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 43

Asp Ala Ser Val Leu Thr Ser
1               5

<210> SEQ ID NO 44
<211> LENGTH: 14
<212> TYPE: PRT
<213> ORGANISM: Artificial Sequence
<220> FEATURE:
<223> OTHER INFORMATION: an artificial synthesized sequence

<400> SEQUENCE: 44

Gln Ser Asp Tyr Tyr Ser Thr Gly Gly Ser Tyr Gly Phe Ala
1               5                   10

<210> SEQ ID NO 45
<211> LENGTH: 6
<212> TYPE: PRT
<213> ORGANISM: Artificial Sequence
<220> FEATURE:
<223> OTHER INFORMATION: an artificial synthesized sequence
```

```
<400> SEQUENCE: 45

Ser Ser Gly Tyr Met Cys
1               5

<210> SEQ ID NO 46
<211> LENGTH: 18
<212> TYPE: PRT
<213> ORGANISM: Artificial Sequence
<220> FEATURE:
<223> OTHER INFORMATION: an artificial synthesized sequence

<400> SEQUENCE: 46

Cys Ile Ser Gly Gly Ser Ser Gly Asp Thr Asp Tyr Ala Asn Trp Ala
1               5                   10                  15

Lys Gly

<210> SEQ ID NO 47
<211> LENGTH: 13
<212> TYPE: PRT
<213> ORGANISM: Artificial Sequence
<220> FEATURE:
<223> OTHER INFORMATION: an artificial synthesized sequence

<400> SEQUENCE: 47

Asp Val Tyr Ile Asp Ser Thr Ile Phe Asn Phe Asn Leu
1               5                   10

<210> SEQ ID NO 48
<211> LENGTH: 13
<212> TYPE: PRT
<213> ORGANISM: Artificial Sequence
<220> FEATURE:
<223> OTHER INFORMATION: an artificial synthesized sequence

<400> SEQUENCE: 48

Gln Ala Ser Gln Ser Val Tyr Asn Asn Asn Asn Leu Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 49

Ala Ala Ser Ser Leu Ala Ser
1               5

<210> SEQ ID NO 50
<211> LENGTH: 12
<212> TYPE: PRT
<213> ORGANISM: Artificial Sequence
<220> FEATURE:
<223> OTHER INFORMATION: an artificial synthesized sequence

<400> SEQUENCE: 50

Gln Gly Thr Tyr Tyr Ser Ser Gly Trp Tyr Ser Thr
1               5                   10

<210> SEQ ID NO 51
<211> LENGTH: 5
<212> TYPE: PRT
<213> ORGANISM: Artificial Sequence
<220> FEATURE:
```

<223> OTHER INFORMATION: an artificial synthesized sequence

<400> SEQUENCE: 51

Asp Tyr Tyr Met Asn
1               5

<210> SEQ ID NO 52
<211> LENGTH: 19
<212> TYPE: PRT
<213> ORGANISM: Artificial Sequence
<220> FEATURE:
<223> OTHER INFORMATION: an artificial synthesized sequence

<400> SEQUENCE: 52

Leu Ile Arg Asn Lys Ala Asn Gly Tyr Thr Thr Glu Tyr Asn Ala Ser
1               5                   10                  15

Val Lys Gly

<210> SEQ ID NO 53
<211> LENGTH: 12
<212> TYPE: PRT
<213> ORGANISM: Artificial Sequence
<220> FEATURE:
<223> OTHER INFORMATION: an artificial synthesized sequence

<400> SEQUENCE: 53

Asp Ser Asp Gly Tyr Tyr Glu Tyr Tyr Phe Asp Tyr
1               5                   10

<210> SEQ ID NO 54
<211> LENGTH: 11
<212> TYPE: PRT
<213> ORGANISM: Artificial Sequence
<220> FEATURE:
<223> OTHER INFORMATION: an artificial synthesized sequence

<400> SEQUENCE: 54

Arg Ala Ser Gln Glu Ile Ser Asp Tyr Leu Ser
1               5                   10

<210> SEQ ID NO 55
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 55

Ala Ala Ser Thr Leu Asp Ser
1               5

<210> SEQ ID NO 56
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 56

Leu Gln Tyr Ala Ser Tyr Pro Tyr Thr
1               5

<210> SEQ ID NO 57
<211> LENGTH: 125
<212> TYPE: PRT
<213> ORGANISM: Artificial Sequence
<220> FEATURE:
<223> OTHER INFORMATION: an artificial synthesized sequence

<400> SEQUENCE: 57

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 58
<211> LENGTH: 109
<212> TYPE: PRT
<213> ORGANISM: Artificial Sequence
<220> FEATURE:
<223> OTHER INFORMATION: an artificial synthesized sequence

<400> SEQUENCE: 58

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 59
<211> LENGTH: 987
<212> TYPE: PRT
<213> ORGANISM: Artificial Sequence
<220> FEATURE:
<223> OTHER INFORMATION: an artificial synthesized sequence

<400> SEQUENCE: 59

Gly Cys Thr Thr Cys Cys Ala Cys Cys Ala Gly Gly Cys Cys
1               5                   10                  15

Cys Ala Thr Cys Gly Gly Thr Cys Thr Thr Cys Cys Cys Thr
            20                  25                  30

Gly Gly Cys Ala Cys Cys Cys Thr Cys Cys Thr Cys Ala Ala Gly
        35                  40                  45

-continued

```
Thr Cys Gly Ala Cys Cys Thr Cys Gly Gly Gly Gly Cys Ala
    50              55              60
Cys Ala Gly Cys Gly Gly Cys Cys Cys Thr Gly Gly Gly Cys Thr Gly
65              70              75              80
Cys Cys Thr Gly Gly Thr Cys Ala Ala Gly Gly Ala Cys Thr Ala Cys
            85              90              95
Thr Thr Cys Cys Cys Cys Gly Ala Ala Cys Cys Gly Gly Thr Gly Ala
            100             105             110
Cys Gly Gly Thr Gly Thr Cys Gly Thr Gly Gly Ala Ala Cys Thr Cys
            115             120             125
Ala Gly Gly Cys Gly Cys Cys Thr Gly Ala Cys Cys Ala Gly Thr
130             135             140
Gly Gly Cys Gly Thr Gly Cys Ala Cys Ala Cys Cys Thr Thr Cys Cys
145             150             155             160
Cys Gly Gly Cys Thr Gly Thr Cys Cys Thr Ala Cys Ala Gly Thr Cys
            165             170             175
Cys Thr Cys Ala Gly Gly Ala Cys Thr Cys Thr Ala Cys Thr Cys Cys
            180             185             190
Cys Thr Cys Ala Gly Thr Ala Gly Thr Gly Thr Gly Gly Thr Gly Ala
            195             200             205
Cys Cys Gly Thr Gly Cys Cys Cys Thr Cys Cys Ala Gly Thr Ala Gly
            210             215             220
Thr Thr Thr Gly Gly Gly Cys Ala Cys Cys Cys Ala Gly Ala Cys Cys
225             230             235             240
Thr Ala Cys Ala Thr Cys Thr Gly Cys Ala Ala Cys Gly Thr Gly Ala
            245             250             255
Ala Thr Cys Ala Cys Ala Ala Gly Cys Cys Cys Ala Gly Thr Ala Ala
            260             265             270
Cys Ala Cys Cys Ala Ala Gly Gly Thr Gly Gly Ala Cys Ala Ala Gly
            275             280             285
Ala Ala Ala Gly Thr Thr Gly Ala Gly Cys Cys Cys Ala Ala Ala Thr
290             295             300
Cys Thr Thr Gly Thr Gly Ala Cys Ala Ala Ala Ala Cys Thr Cys Ala
305             310             315             320
Cys Ala Cys Ala Thr Gly Cys Cys Cys Ala Cys Cys Gly Thr Gly Cys
            325             330             335
Cys Cys Ala Gly Cys Ala Cys Cys Thr Gly Ala Ala Cys Thr Cys Cys
            340             345             350
Thr Gly Gly Gly Gly Gly Gly Ala Cys Cys Gly Thr Cys Ala Gly Thr
            355             360             365
Cys Thr Thr Cys Cys Thr Cys Thr Thr Cys Cys Cys Cys Cys Cys Ala
370             375             380
Ala Ala Ala Cys Cys Cys Ala Ala Gly Gly Ala Cys Ala Cys Cys Cys
385             390             395             400
Thr Cys Ala Thr Gly Ala Thr Cys Thr Cys Cys Cys Gly Gly Ala Cys
            405             410             415
Cys Cys Cys Thr Gly Ala Gly Gly Thr Cys Ala Cys Ala Thr Gly Cys
            420             425             430
Gly Thr Gly Gly Thr Gly Gly Thr Gly Gly Ala Cys Gly Thr Gly Ala
            435             440             445
Gly Thr Cys Ala Cys Gly Ala Ala Gly Ala Cys Cys Cys Thr Gly Ala
            450             455             460
Gly Gly Thr Cys Ala Ala Gly Thr Thr Cys Ala Ala Cys Thr Gly Gly
```

-continued

```
            465                 470                 475                 480
Thr Ala Cys Gly Thr Gly Gly Ala Cys Gly Gly Cys Gly Thr Gly Gly
                    485                 490                 495
Ala Gly Gly Thr Gly Cys Ala Thr Ala Ala Thr Gly Cys Cys Ala Ala
                    500                 505                 510
Gly Ala Cys Ala Ala Ala Gly Cys Gly Cys Gly Gly Gly Ala Gly
                    515                 520                 525
Gly Ala Gly Cys Ala Gly Thr Ala Cys Ala Ala Cys Ala Gly Thr Ala
                    530                 535                 540
Cys Gly Thr Ala Cys Cys Gly Thr Gly Thr Gly Thr Cys Ala Gly
545                 550                 555                 560
Thr Gly Thr Cys Cys Thr Cys Ala Cys Gly Thr Cys Cys Thr Gly
                    565                 570                 575
Cys Ala Cys Cys Ala Gly Gly Ala Cys Thr Gly Gly Cys Thr Gly Ala
                    580                 585                 590
Ala Thr Gly Gly Cys Ala Ala Gly Gly Ala Gly Thr Ala Cys Ala Ala
                    595                 600                 605
Gly Thr Gly Cys Ala Ala Gly Gly Thr Cys Thr Cys Cys Ala Ala Cys
610                 615                 620
Ala Ala Ala Gly Cys Cys Cys Thr Cys Cys Cys Ala Gly Cys Cys Cys
625                 630                 635                 640
Cys Cys Ala Thr Cys Gly Ala Gly Ala Ala Ala Cys Cys Ala Thr
                    645                 650                 655
Cys Thr Cys Cys Ala Ala Ala Gly Cys Cys Ala Ala Gly Gly Gly
                    660                 665                 670
Cys Ala Gly Cys Cys Cys Gly Ala Gly Ala Ala Cys Cys Ala Cys
                    675                 680                 685
Ala Gly Gly Thr Gly Thr Ala Cys Ala Cys Cys Thr Gly Cys Cys
                    690                 695                 700
Cys Cys Cys Ala Thr Cys Cys Gly Gly Gly Ala Gly Gly Ala Gly
705                 710                 715                 720
Ala Thr Gly Ala Cys Cys Ala Ala Gly Ala Ala Cys Cys Ala Gly Gly
                    725                 730                 735
Thr Cys Ala Gly Thr Cys Thr Gly Ala Cys Cys Thr Gly Cys Cys Thr
                    740                 745                 750
Gly Gly Thr Cys Ala Ala Ala Gly Gly Cys Thr Thr Cys Thr Ala Thr
                    755                 760                 765
Cys Cys Cys Ala Gly Thr Gly Ala Cys Ala Thr Cys Gly Cys Cys Gly
                    770                 775                 780
Thr Gly Gly Ala Gly Thr Gly Gly Gly Ala Gly Ala Gly Thr Ala Ala
785                 790                 795                 800
Thr Gly Gly Gly Cys Ala Gly Cys Cys Gly Gly Ala Gly Ala Ala Cys
                    805                 810                 815
Ala Ala Cys Thr Ala Cys Ala Ala Gly Ala Cys Ala Cys Gly Cys
                    820                 825                 830
Cys Thr Cys Cys Cys Gly Thr Gly Cys Thr Gly Gly Ala Cys Thr Cys
                    835                 840                 845
Cys Gly Ala Cys Gly Gly Cys Thr Cys Cys Thr Thr Cys Thr Thr Cys
                    850                 855                 860
Cys Thr Cys Thr Ala Cys Ala Gly Thr Ala Ala Gly Cys Thr Cys Ala
865                 870                 875                 880
Cys Cys Gly Thr Gly Gly Ala Cys Ala Ala Gly Ala Gly Thr Ala Gly
                    885                 890                 895
```

```
Gly Thr Gly Gly Cys Ala Gly Cys Ala Gly Gly Gly Ala Ala Cys
            900             905             910

Gly Thr Cys Thr Thr Cys Thr Cys Ala Thr Gly Cys Thr Cys Gly
            915             920             925

Thr Gly Ala Thr Gly Cys Ala Thr Gly Ala Gly Cys Thr Cys Thr
            930             935             940

Gly Cys Ala Cys Ala Ala Cys Cys Ala Cys Thr Ala Cys Ala Cys Gly
945             950             955             960

Cys Ala Gly Ala Ala Gly Ala Gly Thr Cys Thr Cys Thr Cys Cys Cys
                965             970             975

Thr Gly Thr Cys Thr Cys Cys Gly Thr Gly Ala
            980             985
```

<210> SEQ ID NO 60
<211> LENGTH: 328
<212> TYPE: PRT
<213> ORGANISM: Artificial Sequence
<220> FEATURE:
<223> OTHER INFORMATION: an artificial synthesized sequence

<400> SEQUENCE: 60

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 61
<211> LENGTH: 324
<212> TYPE: PRT
<213> ORGANISM: Artificial Sequence
<220> FEATURE:
<223> OTHER INFORMATION: an artificial synthesized sequence

<400> SEQUENCE: 61

Cys Gly Thr Ala Cys Gly Gly Thr Gly Cys Thr Gly Cys Ala Cys
1               5                   10                  15

Cys Ala Thr Cys Thr Gly Thr Cys Thr Thr Cys Ala Thr Cys Thr Thr
            20                  25                  30

Cys Cys Cys Gly Cys Cys Ala Thr Cys Thr Gly Ala Thr Gly Ala Gly
            35                  40                  45

Cys Ala Gly Thr Thr Gly Ala Ala Ala Thr Cys Thr Gly Gly Thr Ala
            50                  55                  60

Cys Cys Gly Cys Thr Cys Thr Gly Thr Thr Gly Thr Gly Thr Gly
65                  70                  75                  80

Cys Cys Thr Gly Cys Thr Gly Ala Ala Thr Ala Ala Cys Thr Thr Cys
            85                  90                  95

Thr Ala Thr Cys Cys Cys Ala Gly Ala Gly Ala Gly Gly Cys Cys Ala
            100                 105                 110

Ala Ala Gly Thr Ala Cys Ala Gly Thr Gly Gly Ala Ala Gly Gly Thr
            115                 120                 125

Gly Gly Ala Thr Ala Ala Cys Gly Cys Cys Thr Cys Cys Ala Ala
            130                 135                 140

Thr Cys Gly Gly Gly Thr Ala Ala Cys Thr Cys Cys Cys Ala Gly Gly
145                 150                 155                 160

Ala Gly Ala Gly Thr Gly Thr Cys Ala Cys Ala Gly Ala Gly Cys Ala
                165                 170                 175

Gly Gly Ala Cys Ala Gly Thr Ala Ala Gly Gly Ala Cys Ala Gly Thr
            180                 185                 190

Ala Cys Cys Thr Ala Cys Ala Gly Thr Cys Thr Cys Ala Gly Thr Ala
            195                 200                 205

Gly Thr Ala Cys Cys Cys Thr Gly Ala Cys Gly Cys Thr Gly Thr Cys
            210                 215                 220

Cys Ala Ala Ala Gly Cys Ala Gly Ala Cys Thr Ala Cys Gly Ala Gly
225                 230                 235                 240

Ala Ala Ala Cys Ala Cys Ala Ala Ala Gly Thr Cys Thr Ala Cys Gly
                245                 250                 255

Cys Cys Thr Gly Cys Gly Ala Ala Gly Thr Cys Ala Cys Cys Cys Ala
            260                 265                 270

Thr Cys Ala Gly Gly Gly Cys Cys Thr Gly Cys Cys Thr Cys Gly
            275                 280                 285

Cys Cys Cys Gly Thr Cys Ala Cys Ala Ala Ala Gly Thr Cys Cys Thr
            290                 295                 300

```
Thr Cys Ala Ala Cys Ala Gly Gly Gly Ala Gly Ala Gly Thr Gly
305                 310                 315                 320

Thr Thr Gly Ala
```

<210> SEQ ID NO 62
<211> LENGTH: 107
<212> TYPE: PRT
<213> ORGANISM: Artificial Sequence
<220> FEATURE:
<223> OTHER INFORMATION: an artificial synthesized sequence

<400> SEQUENCE: 62

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 63
<211> LENGTH: 124
<212> TYPE: PRT
<213> ORGANISM: Artificial Sequence
<220> FEATURE:
<223> OTHER INFORMATION: an artificial synthesized sequence

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Val Ser Trp Val Arg Gln Ala Pro Gly Gln Gly Leu Glu Trp Met
        35                  40                  45

Gly Tyr Ile Asp Pro Ala Phe Gly Arg Thr Tyr Tyr Ala Ser Trp Val
    50                  55                  60

Asn Gly Arg Ile Thr Ile Asn Pro Asp Thr Ser Lys Asn Gln Phe Ser
65                  70                  75                  80

Leu Gln Leu Asn Ser Val Thr Pro Glu Asp Thr Ala Val Tyr Tyr Cys
                85                  90                  95

Ala Arg Val Ala Leu Val Val Ala Gly Val Ala Tyr Tyr Gly Met Asp
            100                 105                 110

Val Trp Gly Gln Gly Thr Leu Val Thr Val Ser Ser
        115                 120
```

<210> SEQ ID NO 64
<211> LENGTH: 124
<212> TYPE: PRT
<213> ORGANISM: Artificial Sequence
<220> FEATURE:
<223> OTHER INFORMATION: an artificial synthesized sequence

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Val Ser Trp Val Arg Gln Ala Pro Gly Gln Gly Leu Glu Trp Met
        35                  40                  45

Gly Tyr Ile Asp Ile Ala Phe Gly Arg Thr Tyr Tyr Ala Ser Trp Val
    50                  55                  60

Gln Gly Arg Ile Thr Ile Asn Pro Asp Thr Ser Lys Asn Gln Phe Ser
65                  70                  75                  80

Leu Gln Leu Asn Ser Val Thr Pro Glu Asp Thr Ala Val Tyr Tyr Cys
                85                  90                  95

Ala Arg Val Ala Leu Val Val Ala Gly Val Ala Tyr Tyr Gly Met Asp
            100                 105                 110

Val Trp Gly Gln Gly Thr Leu Val Thr Val Ser Ser
        115                 120

<210> SEQ ID NO 65
<211> LENGTH: 124
<212> TYPE: PRT
<213> ORGANISM: Artificial Sequence
<220> FEATURE:
<223> OTHER INFORMATION: an artificial synthesized sequence

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Val Ser Trp Val Arg Gln Ala Pro Gly Gln Gly Leu Glu Trp Met
        35                  40                  45

Gly Tyr Ile Asp Ile Ala Phe Gly Arg Thr Tyr Tyr Ala Ser Trp Val
    50                  55                  60

Thr Gly Arg Ile Thr Ile Asn Pro Asp Thr Ser Lys Asn Gln Phe Ser
65                  70                  75                  80

Leu Gln Leu Asn Ser Val Thr Pro Glu Asp Thr Ala Val Tyr Tyr Cys
                85                  90                  95

Ala Arg Val Ala Leu Val Val Ala Gly Val Ala Tyr Tyr Gly Met Asp
            100                 105                 110

Val Trp Gly Gln Gly Thr Leu Val Thr Val Ser Ser
        115                 120

<210> SEQ ID NO 66
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 66

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
            20                  25                  30

Tyr Asp Met Gly Trp Val Arg Gln Ala Pro Gly Gln Gly Leu Glu Trp
        35                  40                  45

```
Met Gly Thr Ile Tyr Thr Gly Asp Tyr Ser Thr Asp Tyr Ala Ser Trp
    50                  55                  60

Ala Lys Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Asn Thr Gly Tyr Gly Tyr Phe Gly Leu Trp Gly Gln Gly
            100                 105                 110

Thr Leu Val Thr Val Ser Ser
            115

<210> SEQ ID NO 67
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 67

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
                20                  25                  30

Tyr Asp Met Gly Trp Val Arg Gln Ala Pro Gly Gln Gly Leu Glu Trp
            35                  40                  45

Met Gly Thr Ile Tyr Thr Gly Asp Tyr Ser Asp Tyr Ala Ser Trp
    50                  55                  60

Ala Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110

Thr Leu Val Thr Val Ser Ser
            115

<210> SEQ ID NO 68
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 68

Gln Val Thr Leu Arg Glu Ser Gly Pro Ala Leu Val Lys Pro Thr Gln
1               5                   10                  15

Thr Leu Thr Leu Thr Cys Ala Phe Ser Gly Phe Ser Leu Ser Ser Ser
                20                  25                  30

Tyr Asp Met Gly Trp Val Arg Gln Ala Pro Gly Gln Gly Leu Glu Trp
            35                  40                  45

Met Gly Thr Ile Tyr Thr Gly Asp Tyr Ser Asp Tyr Ala Ser Trp
    50                  55                  60

Ala Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110
```

Thr Leu Val Thr Val Ser Ser
        115

<210> SEQ ID NO 69
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 69

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
            20                  25                  30

Tyr Asp Met Gly Trp Val Arg Gln Ala Pro Gly Gln Gly Leu Glu Trp
        35                  40                  45

Met Gly Thr Ile Tyr Thr Gly Asp Tyr Ser Thr Asp Tyr Ala Ser Trp
    50                  55                  60

Ala Lys Gly Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110

Thr Leu Val Thr Val Ser Ser
        115

<210> SEQ ID NO 70
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 70

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
            20                  25                  30

Tyr Asp Met Gly Trp Val Arg Gln Ala Pro Gly Gln Gly Leu Glu Trp
        35                  40                  45

Met Gly Thr Ile Tyr Thr Gly Asp Tyr Ser Thr Asp Tyr Ala Ser Trp
    50                  55                  60

Ala Lys Gly Arg Val Thr Ile Ser Val Asp Ser Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110

Thr Leu Val Thr Val Ser Ser
        115

<210> SEQ ID NO 71
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 71

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
            20                  25                  30

Tyr Asp Met Gly Trp Val Arg Gln Ala Pro Gly Gln Gly Leu Glu Trp
        35                  40                  45

Met Gly Thr Ile Tyr Thr Gly Asp Tyr Ser Thr Asp Tyr Ala Ser Trp
50                  55                  60

Ala Lys Gly Arg Val Thr Ile Ser Val Asp Lys Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110

Thr Leu Val Thr Val Ser Ser
        115

<210> SEQ ID NO 72
<211> LENGTH: 113
<212> TYPE: PRT
<213> ORGANISM: Artificial Sequence
<220> FEATURE:
<223> OTHER INFORMATION: an artificial synthesized sequence

<400> SEQUENCE: 72

Asp Ile Val Met Thr Gln Ser Pro Asp Ser Leu Ala Val Ser Leu Gly
1               5                   10                  15

Glu Arg Ala Thr Ile Asn Cys Gln Ala Ser Gln Asn Ile Tyr Ser Tyr
            20                  25                  30

Leu Ser Trp Tyr Gln Gln Lys Pro Gly Lys Ala Pro Lys Leu Leu Ile
        35                  40                  45

Tyr Arg Thr Ser Thr Leu Ala Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Ser Tyr Tyr Ser Ser Ser Gly
                85                  90                  95

Ser Ser Tyr Gly Ala Phe Ala Phe Gly Gln Gly Thr Lys Val Glu Ile
            100                 105                 110

Lys

<210> SEQ ID NO 73
<211> LENGTH: 110
<212> TYPE: PRT
<213> ORGANISM: Artificial Sequence
<220> FEATURE:
<223> OTHER INFORMATION: an artificial synthesized sequence

<400> SEQUENCE: 73

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

```
Leu Ile Tyr Gln Ala Ser Asn Leu Glu Ile Gly Val Pro Ser Arg Phe
        50                  55                  60

Ser Gly Ser Gly Ser Gly Thr Asp Phe Thr Leu Thr Ile Asn Ser Leu
 65                  70                  75                  80

Glu Ala Glu Asp Ala Ala Thr Tyr Tyr Cys Gln Gly Tyr Tyr Ser Gly
                 85                  90                  95

Tyr Ile Tyr Ala Phe Gly Gly Gly Thr Lys Val Glu Ile Lys
            100                 105                 110

<210> SEQ ID NO 74
<211> LENGTH: 110
<212> TYPE: PRT
<213> ORGANISM: Artificial Sequence
<220> FEATURE:
<223> OTHER INFORMATION: an artificial synthesized sequence

<400> SEQUENCE: 74

Asp Ile Gln Leu Thr Gln Ser Pro Ser Phe Leu Ser Ala Ser Val Gly
 1               5                  10                  15

Asp Arg Val Thr Ile Thr Cys Gln Ser Thr Glu Ser Val Tyr Gly Ser
                 20                  25                  30

Asp Trp Leu Ser Trp Tyr Gln Gln Lys Pro Gly Gln Pro Pro Lys Leu
             35                  40                  45

Leu Ile Tyr Gln Ala Ser Asn Leu Glu Ile Gly Val Pro Ser Arg Phe
        50                  55                  60

Ser Gly Ser Gly Ser Gly Thr Asp Phe Thr Leu Thr Ile Asn Ser Leu
 65                  70                  75                  80

Glu Ala Glu Asp Ala Ala Thr Tyr Tyr Cys Gln Gly Tyr Tyr Ser Gly
                 85                  90                  95

Tyr Ser Tyr Ala Phe Gly Gly Gly Thr Lys Val Glu Ile Lys
            100                 105                 110

<210> SEQ ID NO 75
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 75

Tyr Ile Asp Ile Ala Phe Gly Arg Thr Tyr Tyr Ala Ser Trp Val Gln
 1               5                  10                  15

Gly

<210> SEQ ID NO 76
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 76

Tyr Ile Asp Ile Ala Phe Gly Arg Thr Tyr Tyr Ala Ser Trp Val Thr
 1               5                  10                  15

Gly

<210> SEQ ID NO 77
<211> LENGTH: 6
<212> TYPE: PRT
<213> ORGANISM: Artificial Sequence
<220> FEATURE:
```

```
<223> OTHER INFORMATION: an artificial synthesized sequence

<400> SEQUENCE: 77

Ser Ser Tyr Asp Met Gly
1               5

<210> SEQ ID NO 78
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 78

Thr Ile Tyr Thr Gly Asp Tyr Ser Thr Asp Tyr Ala Ser Trp Ala Lys
1               5                   10                  15

Gly

<210> SEQ ID NO 79
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 79

Asn Thr Gly Tyr Gly Tyr Phe Gly Leu
1               5

<210> SEQ ID NO 80
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 80

His Thr Gly Tyr Gly Tyr Phe Gly Leu
1               5

<210> SEQ ID NO 81
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 81

Gln Gly Tyr Tyr Ser Gly Tyr Ser Tyr Ala
1               5                   10

<210> SEQ ID NO 82
<211> LENGTH: 121
<212> TYPE: PRT
<213> ORGANISM: Artificial Sequence
<220> FEATURE:
<223> OTHER INFORMATION: an artificial synthesized sequence

<400> SEQUENCE: 82

Gln Val Gln Leu Gln Gln Ser Gly Ala Asp Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Ile Lys Gln Arg Pro Gly Gln Gly Leu Glu Trp Ile
        35                  40                  45
```

```
Gly Val Met Asn Pro Ser Gly Gly Thr His Tyr Ser Glu Lys Phe
            50                  55                  60
Arg Gly Lys Ala Thr Leu Thr Ala Asp Lys Ser Ser Thr Ala Tyr
 65                  70                  75                  80
Met Gln Leu Ile Ser Leu Thr Ser Asp Asp Ser Ala Val Tyr Phe Cys
                 85                  90                  95
Ala Arg Ser Asp Tyr Asp Tyr Val Thr Tyr Ala Met Asp Tyr Trp Gly
                100                 105                 110
Gln Gly Thr Ser Val Thr Val Ser Ser
                115                 120
```

<210> SEQ ID NO 83
<211> LENGTH: 118
<212> TYPE: PRT
<213> ORGANISM: Artificial Sequence
<220> FEATURE:
<223> OTHER INFORMATION: an artificial synthesized sequence

<400> SEQUENCE: 83

```
Glu Val Gln Leu Gln Gln Ser Gly Pro Glu Leu Val Lys Pro Gly Ala
 1               5                  10                  15
Ser Val Lys Met Ser Cys Arg Ala Ser Gly Tyr Thr Phe Thr Asp Tyr
                 20                  25                  30
Tyr Met Lys Trp Val Lys Gln Ser His Gly Lys Ser Leu Glu Trp Ile
             35                  40                  45
Gly Asp Ile Asn Pro Asn Asn Gly Asp Thr Phe Tyr Asn Gln Lys Phe
         50                  55                  60
Lys Gly Lys Ala Thr Leu Thr Ile Asp Lys Ser Ser Ser Thr Ala Tyr
 65                  70                  75                  80
Met Gln Leu Asn Ser Leu Thr Ser Asp Asp Ser Ala Val Tyr Tyr Cys
                 85                  90                  95
Ala Arg Asp Gly Asn Tyr Ala Tyr Phe Asp Tyr Trp Gly Gln Gly Thr
                100                 105                 110
Thr Leu Thr Val Ser Ser
                115
```

<210> SEQ ID NO 84
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 84

```
Gln Val Gln Leu Gln Gln Ser Gly Gly Asp Leu Met Lys Pro Gly Ala
 1               5                  10                  15
Ser Val Lys Ile Ser Cys Lys Ala Ala Gly Tyr Thr Phe Ser Asn Tyr
                 20                  25                  30
Tyr Ile Glu Trp Val Lys Gln Arg Pro Gly His Gly Leu Glu Trp Ile
             35                  40                  45
Gly Glu Ile Leu Pro Gly Ser Gly Ser Thr Tyr Tyr Asn Glu Lys Phe
         50                  55                  60
Lys Gly Lys Ala Ser Phe Thr Ala Asp Thr Ser Ser Asn Thr Ala Tyr
 65                  70                  75                  80
Met Gln Leu Ser Ser Leu Thr Ser Glu Asp Ser Ala Val Tyr Tyr Cys
                 85                  90                  95
Ala Arg Trp Gly Ala Arg Glu Pro Gly Phe Pro Tyr Trp Gly Gln Gly
```

Thr Leu Val Thr Val Ser Ala
        115

<210> SEQ ID NO 85
<211> LENGTH: 123
<212> TYPE: PRT
<213> ORGANISM: Artificial Sequence
<220> FEATURE:
<223> OTHER INFORMATION: an artificial synthesized sequence

<400> SEQUENCE: 85

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Ala Leu Ile Arg Asn Lys Ala Asn Gly Tyr Thr Thr Glu Tyr Asn Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Ala Leu Arg Ala Glu Asp Ser Ala Thr Tyr
                85                  90                  95

Tyr Cys Ala Arg Asp Ser Asp Gly Tyr Tyr Glu Tyr Tyr Phe Asp Tyr
            100                 105                 110

Trp Gly Gln Gly Thr Thr Leu Thr Val Ser Ser
        115                 120

<210> SEQ ID NO 86
<211> LENGTH: 123
<212> TYPE: PRT
<213> ORGANISM: Artificial Sequence
<220> FEATURE:
<223> OTHER INFORMATION: an artificial synthesized sequence

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Leu Gly Leu Glu Trp Met
        35                  40                  45

Gly Ile Ile Asn Pro Ser Asp Gly Ser Thr Ser Tyr Ala Gln Lys Phe
    50                  55                  60

Gln Gly Arg Val Thr Met Thr Arg Asp Thr Ser Thr Asn Thr Val Tyr
65                  70                  75                  80

Met Asp Leu Ser Ser Leu Arg Ser Glu Asp Thr Ala Val Tyr Tyr Cys
                85                  90                  95

Ala Arg Gly Gly Asn Ser Ala Phe Tyr Ser Tyr Tyr Asp Met Asp Val
            100                 105                 110

Trp Gly Gln Gly Thr Thr Val Thr Val Ser Ser
        115                 120

<210> SEQ ID NO 87
<211> LENGTH: 118
<212> TYPE: PRT
<213> ORGANISM: Artificial Sequence
<220> FEATURE:

-continued

<223> OTHER INFORMATION: an artificial synthesized sequence

<400> SEQUENCE: 87

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Val Asp Thr Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Arg Gly Phe Phe Asp Tyr Trp Gly Gln Gly Thr
            100                 105                 110

Leu Val Thr Val Ser Ser
        115

<210> SEQ ID NO 88
<211> LENGTH: 118
<212> TYPE: PRT
<213> ORGANISM: Artificial Sequence
<220> FEATURE:
<223> OTHER INFORMATION: an artificial synthesized sequence

<400> SEQUENCE: 88

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser
        115

<210> SEQ ID NO 89
<211> LENGTH: 118
<212> TYPE: PRT
<213> ORGANISM: Artificial Sequence
<220> FEATURE:
<223> OTHER INFORMATION: an artificial synthesized sequence

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Phe
            20                  25                  30

Tyr Trp Ser Trp Ile Arg Gln Pro Pro Gly Lys Gly Leu Glu Trp Ile

```
                35                  40                  45
Gly Tyr Ile Tyr Tyr Ser Gly Thr Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ile Ala Val Ala Gly Phe Phe Asp Tyr Trp Gly Gln Gly Thr
                100                 105                 110

Leu Val Thr Val Ser Ser
        115
```

<210> SEQ ID NO 90
<211> LENGTH: 107
<212> TYPE: PRT
<213> ORGANISM: Artificial Sequence
<220> FEATURE:
<223> OTHER INFORMATION: an artificial synthesized sequence

<400> SEQUENCE: 90

```
Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                 20                  25                  30

Leu Ile Trp Phe Gln Gln Lys Pro Gly Lys Ser Pro Lys Thr Leu Ile
         35                  40                  45

Tyr Arg Thr Asn Arg Leu Val Asp Gly Val Pro Ser Arg Phe Ser Gly
     50                  55                  60

Ser Gly Ser Gly Gln Asp Tyr Ser Leu Thr Ile Ser Ser Leu Glu Tyr
 65                  70                  75                  80

Gly Asp Met Gly Ile Tyr Tyr Cys Leu Gln Tyr Asp Glu Phe Pro Phe
                 85                  90                  95

Thr Phe Gly Ser Gly Thr Lys Leu Glu Ile Lys
            100                 105
```

<210> SEQ ID NO 91
<211> LENGTH: 111
<212> TYPE: PRT
<213> ORGANISM: Artificial Sequence
<220> FEATURE:
<223> OTHER INFORMATION: an artificial synthesized sequence

<400> SEQUENCE: 91

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
                 20                  25                  30

Gly Tyr Ser Tyr Met His Trp Tyr Gln Gln Lys Pro Gly Gln Pro Pro
         35                  40                  45

Lys Leu Leu Ile Phe Leu Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

His Leu Pro Trp Thr Phe Gly Gly Gly Thr Lys Leu Glu Ile Lys
            100                 105                 110
```

<210> SEQ ID NO 92
<211> LENGTH: 107
<212> TYPE: PRT
<213> ORGANISM: Artificial Sequence
<220> FEATURE:
<223> OTHER INFORMATION: an artificial synthesized sequence

<400> SEQUENCE: 92

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys
            100                 105
```

<210> SEQ ID NO 93
<211> LENGTH: 107
<212> TYPE: PRT
<213> ORGANISM: Artificial Sequence
<220> FEATURE:
<223> OTHER INFORMATION: an artificial synthesized sequence

<400> SEQUENCE: 93

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Asp Tyr
            20                  25                  30

Leu Ser Trp Leu Gln Gln Lys Pro Asp Gly Thr Ile Lys Arg Leu Ile
        35                  40                  45

Phe Ala Ala Ser Thr Leu Asp Ser Gly Val Pro Lys Arg Phe Ser Gly
    50                  55                  60

Ser Arg Ser Gly Ser Asp Phe Ser Leu Ser Ile Ser Ser Leu Glu Ser
65                  70                  75                  80

Glu Asp Phe Ala Asp Tyr Tyr Cys Leu Gln Tyr Ala Ser Tyr Pro Tyr
                85                  90                  95

Thr Phe Gly Ser Gly Thr Lys Leu Glu Ile Lys
            100                 105
```

<210> SEQ ID NO 94
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 94

```
Asp Val Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val Tyr Arg
            20                  25                  30

Asp Gly Asn Thr Tyr Leu Ser Trp Phe Gln Gln Arg Pro Gly Gln Ser
```

```
                35                  40                  45
Pro Arg Arg Leu Ile Tyr Lys Val Ser Asn Trp Gln Ser Gly Val Pro
             50                  55                  60
Asp Arg Phe Ser Gly Gly Gly Ser Gly Thr Asp Phe Thr Leu Lys Ile
 65                  70                  75                  80
Ser Arg Val Glu Ala Glu Asp Val Gly Val Tyr Tyr Cys Met Gln Gly
                 85                  90                  95
Thr His Trp Pro Pro Thr Phe Gly Gln Gly Thr Lys Val Glu Ile Lys
                100                 105                 110
```

<210> SEQ ID NO 95
<211> LENGTH: 108
<212> TYPE: PRT
<213> ORGANISM: Artificial Sequence
<220> FEATURE:
<223> OTHER INFORMATION: an artificial synthesized sequence

<400> SEQUENCE: 95

```
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
             20                  25                  30
Tyr Leu Ala Trp Tyr Gln Gln Lys Pro Gly Gln Ala Pro Arg Leu Leu
         35                  40                  45
Ile Tyr Gly Ala Ser Thr Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Thr Ser Pro
                 85                  90                  95
Leu Thr Phe Gly Gly Gly Thr Lys Val Glu Ile Lys
                100                 105
```

<210> SEQ ID NO 96
<211> LENGTH: 108
<212> TYPE: PRT
<213> ORGANISM: Artificial Sequence
<220> FEATURE:
<223> OTHER INFORMATION: an artificial synthesized sequence

<400> SEQUENCE: 96

```
Glu Ile Val Leu Thr Gln Ser Pro Gly Thr Leu Ser Leu Ser Pro Gly
 1               5                  10                  15
Glu Arg Val Thr Leu Ser Cys Arg Ala Ser Gln Arg Val Asn Asn Asn
             20                  25                  30
Tyr Leu Ala Trp Tyr Gln Gln Arg Pro Gly Gln Ala Pro Arg Leu Leu
         35                  40                  45
Ile Tyr Gly Ala Ser Ser Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Asp Arg Ser Pro
                 85                  90                  95
Leu Thr Phe Gly Gly Gly Thr Lys Leu Glu Ile Lys
                100                 105
```

<210> SEQ ID NO 97
<211> LENGTH: 108

```
<212> TYPE: PRT
<213> ORGANISM: Artificial Sequence
<220> FEATURE:
<223> OTHER INFORMATION: an artificial synthesized sequence

<400> SEQUENCE: 97

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Lys Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Gly Gly Thr Lys Val Glu Ile Lys
            100                 105

<210> SEQ ID NO 98
<211> LENGTH: 122
<212> TYPE: PRT
<213> ORGANISM: Artificial Sequence
<220> FEATURE:
<223> OTHER INFORMATION: an artificial synthesized sequence

<400> SEQUENCE: 98

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Gln Asn Tyr Ala Thr Tyr Val Ala Glu
    50                  55                  60

Ser Val Lys Gly Arg Phe Thr Ile Ser Arg Ala Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Ala Gly Tyr Gly Val Asp Ile Trp
            100                 105                 110

Gly Gln Gly Thr Thr Val Thr Val Ser Ser
        115                 120

<210> SEQ ID NO 99
<211> LENGTH: 128
<212> TYPE: PRT
<213> ORGANISM: Artificial Sequence
<220> FEATURE:
<223> OTHER INFORMATION: an artificial synthesized sequence

<400> SEQUENCE: 99

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
```

```
                35                  40                  45
Ala Gln Ile Lys Asp Arg Gln Asn Gly Tyr Asn Thr Tyr Tyr Ala Glu
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Thr Tyr Gly Ser Tyr Tyr Gln
            100                 105                 110

Phe Gly Val Asp Ala Trp Gly Gln Gly Thr Thr Val Thr Val Ser Ser
            115                 120                 125

<210> SEQ ID NO 100
<211> LENGTH: 128
<212> TYPE: PRT
<213> ORGANISM: Artificial Sequence
<220> FEATURE:
<223> OTHER INFORMATION: an artificial synthesized sequence

<400> SEQUENCE: 100

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
            35                  40                  45

Ala Gln Ile Lys Asp Lys Gln Asn Ser Tyr Ala Ala Tyr Tyr Ala Glu
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Ser Gly Phe Phe Ser
            100                 105                 110

Tyr Gly Val Asp Ala Trp Gly Gln Gly Thr Thr Val Thr Val Ser Ser
            115                 120                 125

<210> SEQ ID NO 101
<211> LENGTH: 128
<212> TYPE: PRT
<213> ORGANISM: Artificial Sequence
<220> FEATURE:
<223> OTHER INFORMATION: an artificial synthesized sequence

<400> SEQUENCE: 101

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
            35                  40                  45

Ala Gln Ile Lys Asp Arg Ala Asn Ser Tyr Asn Thr Tyr Tyr Ala Glu
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95
```

Tyr Cys Arg Tyr Val His Tyr Thr Thr Tyr Ala Gly Ser Ser Phe Ser
                100                 105                 110

Tyr Gly Val Asp Ala Trp Gly Gln Gly Thr Thr Val Thr Val Ser Ser
            115                 120                 125

<210> SEQ ID NO 102
<211> LENGTH: 128
<212> TYPE: PRT
<213> ORGANISM: Artificial Sequence
<220> FEATURE:
<223> OTHER INFORMATION: an artificial synthesized sequence

<400> SEQUENCE: 102

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ala Asn Gly Tyr Asn Ala Tyr Tyr Ala Pro
    50                  55                  60

Ser Val Lys Gly Arg Phe Thr Ile Ser Arg Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Phe Gly Phe Gly Leu Ser Tyr
                100                 105                 110

Gly Gly Val Asp Ala Trp Gly Gln Gly Thr Thr Val Thr Val Ser Ser
            115                 120                 125

<210> SEQ ID NO 103
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 103

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
                100                 105                 110

<210> SEQ ID NO 104
<211> LENGTH: 141
<212> TYPE: PRT
<213> ORGANISM: Homo sapiens

<400> SEQUENCE: 104

```
Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Ser Gln Thr
            20                  25                  30

Asn Val Ser Gln Ser Lys Asp Ser Asp Val Tyr Ile Thr Asp Lys Thr
                35                  40                  45

Val Leu Asp Met Arg Ser Met Asp Phe Lys Ser Asn Ser Ala Val Ala
50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
130                 135                 140
```

<210> SEQ ID NO 105
<211> LENGTH: 179
<212> TYPE: PRT
<213> ORGANISM: Homo sapiens

<400> SEQUENCE: 105

```
Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
                35                  40                  45

Gly Lys Glu Val His Ser Gly Val Ser Thr Asp Pro Gln Pro Leu Lys
50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

<210> SEQ ID NO 106
<211> LENGTH: 173
<212> TYPE: PRT
<213> ORGANISM: Homo sapiens

<400> SEQUENCE: 106

```
Asp Lys Gln Leu Asp Ala Asp Val Ser Pro Lys Pro Thr Ile Phe Leu
```

```
1               5                   10                  15
Pro Ser Ile Ala Glu Thr Lys Leu Gln Lys Ala Gly Thr Tyr Leu Cys
                20                  25                  30

Leu Leu Glu Lys Phe Phe Pro Asp Val Ile Lys Ile His Trp Gln Glu
                35                  40                  45

Lys Lys Ser Asn Thr Ile Leu Gly Ser Gln Glu Gly Asn Thr Met Lys
                50                  55                  60

Thr Asn Asp Thr Tyr Met Lys Phe Ser Trp Leu Thr Val Pro Glu Lys
 65                 70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
                100                 105                 110

Ile Thr Met Asp Pro Lys Asp Asn Cys Ser Lys Asp Ala Asn Asp Thr
                115                 120                 125

Leu Leu Leu Gln Leu Thr Asn Thr Ser Ala Tyr Tyr Met Tyr Leu Leu
                130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170

<210> SEQ ID NO 107
<211> LENGTH: 204
<212> TYPE: PRT
<213> ORGANISM: Homo sapiens

<400> SEQUENCE: 107

Lys Gln Leu Asp Ala Asp Val Ser Pro Lys Pro Thr Ile Phe Leu Pro
1               5                   10                  15

Ser Ile Ala Glu Thr Lys Leu Gln Lys Ala Gly Thr Tyr Leu Cys Leu
                20                  25                  30

Leu Glu Lys Phe Phe Pro Asp Ile Ile Lys Ile His Trp Gln Glu Lys
                35                  40                  45

Lys Ser Asn Thr Ile Leu Gly Ser Gln Glu Gly Asn Thr Met Lys Thr
                50                  55                  60

Asn Asp Thr Tyr Met Lys Phe Ser Trp Leu Thr Val Pro Glu Glu Ser
65                  70                  75                  80

Leu Asp Lys Glu His Arg Cys Ile Val Arg His Glu Asn Asn Lys Asn
                85                  90                  95

Gly Ile Asp Gln Glu Ile Ile Phe Pro Pro Ile Lys Thr Asp Val Thr
                100                 105                 110

Thr Val Asp Pro Lys Asp Ser Tyr Ser Lys Asp Ala Asn Asp Val Thr
                115                 120                 125

Thr Val Asp Pro Lys Tyr Asn Tyr Ser Lys Asp Ala Asn Asp Val Ile
                130                 135                 140

Thr Met Asp Pro Lys Asp Asn Trp Ser Lys Asp Ala Asn Asp Thr Leu
145                 150                 155                 160

Leu Leu Gln Leu Thr Asn Thr Ser Ala Tyr Tyr Met Tyr Leu Leu Leu
                165                 170                 175

Leu Leu Lys Ser Val Val Tyr Phe Ala Ile Ile Thr Cys Cys Leu Leu
                180                 185                 190

Gly Arg Thr Ala Phe Cys Cys Asn Gly Glu Lys Ser
                195                 200
```

<210> SEQ ID NO 108
<211> LENGTH: 177
<212> TYPE: PRT
<213> ORGANISM: Homo sapiens

<400> SEQUENCE: 108

Pro Ser Tyr Thr Gly Gly Tyr Ala Asp Lys Leu Ile Phe Gly Lys Gly
1               5                   10                  15

Thr Arg Val Thr Val Glu Pro Arg Ser Gln Pro His Thr Lys Pro Ser
                20                  25                  30

Val Phe Val Met Lys Asn Gly Thr Asn Val Ala Cys Leu Val Lys Glu
            35                  40                  45

Phe Tyr Pro Lys Asp Ile Arg Ile Asn Leu Val Ser Ser Lys Lys Ile
    50                  55                  60

Thr Glu Phe Asp Pro Ala Ile Val Ile Ser Pro Ser Gly Lys Tyr Asn
65                  70                  75                  80

Ala Val Lys Leu Gly Lys Tyr Glu Asp Ser Asn Ser Val Thr Cys Ser
                85                  90                  95

Val Gln His Asp Asn Lys Thr Val His Ser Thr Asp Phe Glu Val Lys
            100                 105                 110

Thr Asp Ser Thr Asp His Val Lys Pro Lys Glu Thr Glu Asn Thr Lys
        115                 120                 125

Gln Pro Ser Lys Ser Cys His Lys Pro Lys Ala Ile Val His Thr Glu
    130                 135                 140

Lys Val Asn Met Met Ser Leu Thr Val Leu Gly Leu Arg Met Leu Phe
145                 150                 155                 160

Ala Lys Thr Val Ala Val Asn Phe Leu Leu Thr Ala Lys Leu Phe Phe
                165                 170                 175

Leu

<210> SEQ ID NO 109
<211> LENGTH: 182
<212> TYPE: PRT
<213> ORGANISM: Homo sapiens

<400> SEQUENCE: 109

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
                20                  25                  30

Val Tyr Asp Tyr Gln Glu Asp Gly Ser Val Leu Leu Thr Cys Asp Ala
            35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr

```
                145                 150                 155                 160
Gln Pro Leu Lys Asp Arg Glu Asp Gln Tyr Ser His Leu Gln Gly
                    165                 170                 175

Asn Gln Leu Arg Arg Asn
                180

<210> SEQ ID NO 110
<211> LENGTH: 171
<212> TYPE: PRT
<213> ORGANISM: Homo sapiens

<400> SEQUENCE: 110

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
                35                  40                  45

Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
                100                 105                 110

Ile Ala Thr Leu Leu Leu Ala Leu Gly Val Phe Cys Phe Ala Gly His
            115                 120                 125

Glu Thr Gly Arg Leu Ser Gly Ala Ala Asp Thr Gln Ala Leu Leu Arg
        130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 111
<211> LENGTH: 207
<212> TYPE: PRT
<213> ORGANISM: Homo sapiens

<400> SEQUENCE: 111

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
            35                  40                  45

Cys Pro Gln Tyr Pro Gly Ser Glu Ile Leu Trp Gln His Asn Asp Lys
        50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
```

```
            115                 120                 125
Ser Val Ala Thr Ile Val Ile Val Asp Ile Cys Ile Thr Gly Gly Leu
        130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Arg Gln Arg Gly Gln Asn
                165                 170                 175

Lys Glu Arg Pro Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
            195                 200                 205

<210> SEQ ID NO 112
<211> LENGTH: 330
<212> TYPE: PRT
<213> ORGANISM: Homo sapiens

<400> SEQUENCE: 112

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 113
<211> LENGTH: 326
<212> TYPE: PRT
<213> ORGANISM: Homo sapiens

<400> SEQUENCE: 113

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 114
<211> LENGTH: 377
<212> TYPE: PRT
<213> ORGANISM: Homo sapiens

<400> SEQUENCE: 114

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
```

<210> SEQ ID NO 115
<211> LENGTH: 327
<212> TYPE: PRT
<213> ORGANISM: Homo sapiens

<400> SEQUENCE: 115

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 116
<211> LENGTH: 4
<212> TYPE: PRT
<213> ORGANISM: Artificial Sequence
<220> FEATURE:

<223> OTHER INFORMATION: an artificial synthesized sequence

<400> SEQUENCE: 116

Gly Gly Gly Ser
1

<210> SEQ ID NO 117
<211> LENGTH: 4
<212> TYPE: PRT
<213> ORGANISM: Artificial Sequence
<220> FEATURE:
<223> OTHER INFORMATION: an artificial synthesized sequence

<400> SEQUENCE: 117

Ser Gly Gly Gly
1

<210> SEQ ID NO 118
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 118

Gly Gly Gly Gly Ser
1               5

<210> SEQ ID NO 119
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 119

Ser Gly Gly Gly Gly
1               5

<210> SEQ ID NO 120
<211> LENGTH: 6
<212> TYPE: PRT
<213> ORGANISM: Artificial Sequence
<220> FEATURE:
<223> OTHER INFORMATION: an artificial synthesized sequence

<400> SEQUENCE: 120

Gly Gly Gly Gly Gly Ser
1               5

<210> SEQ ID NO 121
<211> LENGTH: 6
<212> TYPE: PRT
<213> ORGANISM: Artificial Sequence
<220> FEATURE:
<223> OTHER INFORMATION: an artificial synthesized sequence

<400> SEQUENCE: 121

Ser Gly Gly Gly Gly Gly
1               5

<210> SEQ ID NO 122
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 122

Gly Gly Gly Gly Gly Gly Ser
1               5

<210> SEQ ID NO 123
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 123

Ser Gly Gly Gly Gly Gly Gly
1               5

<210> SEQ ID NO 124
<211> LENGTH: 1125
<212> TYPE: DNA
<213> ORGANISM: Homo sapiens

<400> SEQUENCE: 124

```
atgtggttct tgacaactct gctcctttgg gttccagttg atgggcaagt ggacaccaca      60
aaggcagtga tcactttgca gcctccatgg gtcagcgtgt tccaagagga aaccgtaacc     120
ttgcactgtg aggtgctcca tctgcctggg agcagctcta cacagtggtt tctcaatggc     180
acagccactc agacctcgac ccccagctac agaatcacct ctgccagtgt caatgacagt     240
ggtgaataca ggtgccagag aggtctctca gggcgaagtg acccatacac agtctgaaatc     300
cacagaggct ggctactact gcaggtctcc agcagagtct tcacggaagg agaacctctg     360
gccttgaggt gtcatgcgtg aaggataag ctggtgtaca atgtgcttta ctatcgaaat      420
ggcaaagcct ttaagttttt ccactggaat tctaacctca ccattctgaa aaccaacata     480
agtcacaatg gcacctacca ttgctcaggc atgggaaagc atcgctacac atcagcagga     540
atatctgtca ctgtgaaaga gctatttcca gctccagtgc tgaatgcatc tgtgacatcc     600
ccactcctgg agggaatct ggtcaccctg agctgtgaaa caaagttgct cttgcagagg     660
cctggtttgc agctttactt ctccttctac atgggcagca gaccctgcg aggcaggaac     720
acatcctctg aataccaaat actaactgct agaagagaag actctgggtt atactggtgc     780
gaggctgcca cagaggatgg aaatgtcctt aagcgcagcc tgagttgga gcttcaagtg     840
cttggcctcc agttaccaac tcctgtctgg tttcatgtcc ttttctatct ggcagtggga     900
ataatgtttt tagtgaacac tgttctctgg gtgacaatac gtaaagaact gaaaagaaag     960
aaaaagtggg atttagaaat ctctttggat tctggtcatg agaagaaggt aatttccagc    1020
cttcaagaag acagacattt agaagaagag ctgaaatgtc aggaacaaaa agaagaacag    1080
ctgcaggaag gggtgcaccg gaaggagccc caggggggcca cgtag                   1125
```

<210> SEQ ID NO 125
<211> LENGTH: 374
<212> TYPE: PRT
<213> ORGANISM: Homo sapiens

<400> SEQUENCE: 125

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

```
Val Phe Gln Glu Glu Thr Val Thr Leu His Cys Glu Val Leu His Leu
             35                  40                  45

Pro Gly Ser Ser Thr Gln Trp Phe Leu Asn Gly Thr Ala Thr Gln
 50                  55                  60

Thr Ser Thr Pro Ser Tyr Arg Ile Thr Ser Ala Ser Val Asn Asp Ser
 65                  70                  75                  80

Gly Glu Tyr Arg Cys Gln Arg Gly Leu Ser Gly Arg Ser Asp Pro Ile
                 85                  90                  95

Gln Leu Glu Ile His Arg Gly Trp Leu Leu Leu Gln Val Ser Ser Arg
                100                 105                 110

Val Phe Thr Glu Gly Glu Pro Leu Ala Leu Arg Cys His Ala Trp Lys
            115                 120                 125

Asp Lys Leu Val Tyr Asn Val Leu Tyr Tyr Arg Asn Gly Lys Ala Phe
130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
370

<210> SEQ ID NO 126
<211> LENGTH: 951
<212> TYPE: DNA
<213> ORGANISM: Homo sapiens

<400> SEQUENCE: 126
atgactatgg agacccaaat gtctcagaat gtatgtccca gaaacctgtg ctgcttcaa      60 ccattgacag ttttgctgct gctggcttct gcagacagtc aagctgctcc cccaaaggct    120
gtgctgaaac ttgagccccc gtggatcaac gtgctccagg aggactctgt gactctgaca    180
```

-continued

```
tgccagggggg ctcgcagccc tgagagcgac tccattcagt ggttccacaa tgggaatctc      240
attcccaccc acacgcagcc cagctacagg ttcaaggcca acaacaatga cagcggggag      300
tacacgtgcc agactggcca gaccagcctc agcgaccctg tgcatctgac tgtgctttcc      360
gaatggctgg tgctccagac ccctcacctg gagttccagg agggagaaac catcatgctg      420
aggtgccaca gctggaagga caagcctctg tcaaggtca cattcttcca gaatggaaaa      480
tcccagaaat ctcccatttt ggatcccacc ttctccatcc cacaagcaaa ccacagtcac      540
agtggtgatt accactgcac aggaaacata ggctacacgc tgttctcatc caagcctgtg      600
accatcactg tccaagtgcc cagcatgggc agctcttcac caatgggggt cattgtggct      660
gtggtcattg cgactgctgt agcagccatt gttgctgctg tagtggcctt gatctactgc      720
aggaaaaagc ggatttcagc caattccact gatcctgtga aggctgccca atttgagcca      780
cctggacgtc aaatgattgc catcagaaag agacaacttg aagaaccaa caatgactat      840 gaaacagctg acggcggcta catgactctg aaccccaggg cacctactga cgatgataaa      900
aacatctacc tgactcttcc tcccaacgac catgtcaaca gtaataacta a                951
```

<210> SEQ ID NO 127
<211> LENGTH: 316
<212> TYPE: PRT
<213> ORGANISM: Homo sapiens

<400> SEQUENCE: 127

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
                20                  25                  30

Ser Gln Ala Ala Pro Pro Lys Ala Val Leu Lys Leu Glu Pro Pro Trp
            35                  40                  45

Ile Asn Val Leu Gln Glu Asp Ser Val Thr Leu Thr Cys Gln Gly Ala
        50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Val Ile Val Ala Val Val Ile Ala
    210                 215                 220

Thr Ala Val Ala Ala Ile Val Ala Ala Val Val Ala Leu Ile Tyr Cys
225                 230                 235                 240
```

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Lys Asn Ile Tyr Leu
    290                 295                 300

Thr Leu Pro Pro Asn Asp His Val Asn Ser Asn Asn
305                 310                 315

<210> SEQ ID NO 128
<211> LENGTH: 876
<212> TYPE: DNA
<213> ORGANISM: Homo sapiens

<400> SEQUENCE: 128

```
atgggaatcc tgtcattctt acctgtcctt gccactgaga gtgactgggc tgactgcaag      60
tcccccagc cttggggtca tatgcttctg tggacagctg tgctattcct ggctcctgtt     120
gctgggacac ctgcagctcc cccaaaggct gtgctgaaac tcgagcccca gtggatcaac     180
gtgctccagg aggactctgt gactctgaca tgccggggga ctcacagccc tgagagcgac     240
tccattcagt ggttccacaa tgggaatctc attcccaccc acacgcagcc cagctacagg     300
ttcaaggcca caacaatga cagcggggag tacacgtgcc agactggcca gaccagcctc     360
agcgaccctg tgcatctgac tgtgctttct gagtggctgg tgctccagac ccctcacctg     420
gagttccagg agggagaaac catcgtgctg aggtgccaca gctggaagga caagcctctg     480
gtcaaggtca cattcttcca gaatggaaaa tccaagaaat ttcccgttc ggatcccaac     540
ttctccatcc acaagcaaa ccacagtcac agtggtgatt accactgcac aggaaacata     600
ggctacacgc tgtactcatc caagcctgtg accatcactg tccaagctcc cagctcttca     660
ccgatgggga tcattgtggc tgtggtcact gggattgctg tagcggccat tgttgctgct     720
gtagtggcct tgatctactg caggaaaaag cggatttcag ccaatcccac taatcctgat     780
gaggctgaca agttggggc tgagaacaca atcacctatt cacttctcat gcacccggat     840
gctctggaag agcctgatga ccagaaccgt atttag                              876
```

<210> SEQ ID NO 129
<211> LENGTH: 291
<212> TYPE: PRT
<213> ORGANISM: Homo sapiens

<400> SEQUENCE: 129

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

-continued

Pro Ser Tyr Arg Phe Lys Ala Asn Asn Asn Asp Ser Gly Glu Tyr Thr
                100                 105                 110
Cys Gln Thr Gly Gln Thr Ser Leu Ser Asp Pro Val His Leu Thr Val
            115                 120                 125
Leu Ser Glu Trp Leu Val Leu Gln Thr Pro His Leu Glu Phe Gln Glu
130                 135                 140
Gly Glu Thr Ile Val Leu Arg Cys His Ser Trp Lys Asp Lys Pro Leu
145                 150                 155                 160
Val Lys Val Thr Phe Phe Gln Asn Gly Lys Ser Lys Lys Phe Ser Arg
                165                 170                 175
Ser Asp Pro Asn Phe Ser Ile Pro Gln Ala Asn His Ser His Ser Gly
            180                 185                 190
Asp Tyr His Cys Thr Gly Asn Ile Gly Tyr Thr Leu Tyr Ser Ser Lys
        195                 200                 205
Pro Val Thr Ile Thr Val Gln Ala Pro Ser Ser Ser Pro Met Gly Ile
    210                 215                 220
Ile Val Ala Val Val Thr Gly Ile Ala Val Ala Ala Ile Val Ala Ala
225                 230                 235                 240
Val Val Ala Leu Ile Tyr Cys Arg Lys Lys Arg Ile Ser Ala Asn Pro
                245                 250                 255
Thr Asn Pro Asp Glu Ala Asp Lys Val Gly Ala Glu Asn Thr Ile Thr
            260                 265                 270
Tyr Ser Leu Leu Met His Pro Asp Ala Leu Glu Glu Pro Asp Asp Gln
        275                 280                 285
Asn Arg Ile
    290

<210> SEQ ID NO 130
<211> LENGTH: 765
<212> TYPE: DNA
<213> ORGANISM: Homo sapiens

<400> SEQUENCE: 130

```
atgtggcagc tgctcctccc aactgctctg ctacttctag tttcagctgg catgcggact      60
gaagatctcc caaaggctgt ggtgttcctg agcctcaat ggtacagggt gctcgagaag      120
gacagtgtga ctctgaagtg ccaggggagcc tactcccctg aggacaattc cacacagtgg    180
tttcacaatg agagcctcat ctcaagccag gcctcgagct acttcattga cgctgccaca    240
gttgacgaca gtggagagta caggtgccag acaaacctct ccaccctcag tgacccggtg    300
cagctagaag tccatatcgg ctggctgttg ctccaggccc ctcggtgggt gttcaaggag    360
gaagacccta ttcacctgag gtgtcacagc tggaagaaca ctgctctgca taaggtcaca    420
tatttacaga tggcaaagg caggaagtat tttcatcata attctgactt ctacattcca    480
aaagccacac tcaaagacag cggctcctac ttctgcaggg ggcttgttgg gagtaaaaat    540
gtgtcttcag agactgtgaa catcaccatc actcaaggtt tgtcagtgtc aaccatctca    600
tcattctttc cacctgggta ccaagtctct ttctgcttgg tgatggtact cctttttgca    660
gtggacacag gactatattt ctctgtgaag acaaacattc gaagctcaac aagagactgg    720
aaggaccata aatttaaatg gagaaaggac cctcaagaca aatga                    765
```

<210> SEQ ID NO 131
<211> LENGTH: 254
<212> TYPE: PRT
<213> ORGANISM: Homo sapiens

<400> SEQUENCE: 131

| | | | | | | | | | | | | | | |
|---|---|---|---|---|---|---|---|---|---|---|---|---|---|---|
| Met | Trp | Gln | Leu | Leu | Pro | Thr | Ala | Leu | Leu | Leu | Val | Ser | Ala |
| 1 | | | | 5 | | | | | 10 | | | | | 15 |
| Gly | Met | Arg | Thr | Glu | Asp | Leu | Pro | Lys | Ala | Val | Val | Phe | Leu | Glu | Pro |
| | | | 20 | | | | | 25 | | | | | 30 | | |
| Gln | Trp | Tyr | Arg | Val | Leu | Glu | Lys | Asp | Ser | Val | Thr | Leu | Lys | Cys | Gln |
| | | | 35 | | | | | 40 | | | | | 45 | | |
| Gly | Ala | Tyr | Ser | Pro | Glu | Asp | Asn | Ser | Thr | Gln | Trp | Phe | His | Asn | Glu |
| | 50 | | | | | 55 | | | | | 60 | | | | |
| Ser | Leu | Ile | Ser | Ser | Gln | Ala | Ser | Ser | Tyr | Phe | Ile | Asp | Ala | Ala | Thr |
| 65 | | | | | 70 | | | | | 75 | | | | | 80 |
| Val | Asp | Asp | Ser | Gly | Glu | Tyr | Arg | Cys | Gln | Thr | Asn | Leu | Ser | Thr | Leu |
| | | | | 85 | | | | | 90 | | | | | 95 | |
| Ser | Asp | Pro | Val | Gln | Leu | Glu | Val | His | Ile | Gly | Trp | Leu | Leu | Leu | Gln |
| | | | 100 | | | | | 105 | | | | | 110 | | |
| Ala | Pro | Arg | Trp | Val | Phe | Lys | Glu | Glu | Asp | Pro | Ile | His | Leu | Arg | Cys |
| | | | 115 | | | | | 120 | | | | | 125 | | |
| His | Ser | Trp | Lys | Asn | Thr | Ala | Leu | His | Lys | Val | Thr | Tyr | Leu | Gln | Asn |
| | 130 | | | | | 135 | | | | | 140 | | | | |
| Gly | Lys | Gly | Arg | Lys | Tyr | Phe | His | His | Asn | Ser | Asp | Phe | Tyr | Ile | Pro |
| 145 | | | | | 150 | | | | | 155 | | | | | 160 |
| Lys | Ala | Thr | Leu | Lys | Asp | Ser | Gly | Ser | Tyr | Phe | Cys | Arg | Gly | Leu | Val |
| | | | | 165 | | | | | 170 | | | | | 175 | |
| Gly | Ser | Lys | Asn | Val | Ser | Ser | Glu | Thr | Val | Asn | Ile | Thr | Ile | Thr | Gln |
| | | | 180 | | | | | 185 | | | | | 190 | | |
| Gly | Leu | Ser | Val | Ser | Thr | Ile | Ser | Ser | Phe | Phe | Pro | Pro | Gly | Tyr | Gln |
| | | | 195 | | | | | 200 | | | | | 205 | | |
| Val | Ser | Phe | Cys | Leu | Val | Met | Val | Leu | Leu | Phe | Ala | Val | Asp | Thr | Gly |
| | 210 | | | | | 215 | | | | | 220 | | | | |
| Leu | Tyr | Phe | Ser | Val | Lys | Thr | Asn | Ile | Arg | Ser | Ser | Thr | Arg | Asp | Trp |
| 225 | | | | | 230 | | | | | 235 | | | | | 240 |
| Lys | Asp | His | Lys | Phe | Lys | Trp | Arg | Lys | Asp | Pro | Gln | Asp | Lys |
| | | | | 245 | | | | | 250 | | | | | |

<210> SEQ ID NO 132
<211> LENGTH: 702
<212> TYPE: DNA
<213> ORGANISM: Homo sapiens

<400> SEQUENCE: 132

| | | |
|---|---|---|
| atgtggcagc tgctcctccc aactgctctg ctacttctag tttcagctgg catgcggact | 60 |
| gaagatctcc caaaggctgt ggtgttcctg gagcctcaat ggtacagcgt gcttgagaag | 120 |
| gacagtgtga ctctgaagtg ccagggagcc tactcccctg aggacaattc cacacagtgg | 180 |
| tttcacaatg agagcctcat ctcaagccag gcctcgagct acttcattga cgctgccaca | 240 |
| gtcaacgaca gtggagagta caggtgccag acaaacctct ccaccctcag tgacccggtg | 300 |
| cagctagaag tccatatcgg ctggctgttg ctccaggccc ctcggtgggt gttcaaggag | 360 |
| gaagacccta ttcacctgag gtgtcacagc tggaagaaca ctgctctgca taaggtcaca | 420 |
| tatttacaga atggcaaaga caggaagtat tttcatcata attctgactt ccacattcca | 480 |
| aaagccacac tcaaagatag cggctcctac ttctgcaggg ggcttgttgg agtaaaaat | 540 |
| gtgtcttcag agactgtgaa catcaccatc actcaaggtt tggcagtgtc aaccatctca | 600 |

```
tcattctctc cacctgggta ccaagtctct ttctgcttgg tgatggtact cctttttgca    660
gtggacacag gactatattt ctctgtgaag acaaacattt ga                      702
```

<210> SEQ ID NO 133
<211> LENGTH: 233
<212> TYPE: PRT
<213> ORGANISM: Homo sapiens

<400> SEQUENCE: 133

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230
```

<210> SEQ ID NO 134
<211> LENGTH: 19
<212> TYPE: PRT
<213> ORGANISM: Artificial Sequence
<220> FEATURE:
<223> OTHER INFORMATION: an artificial synthesized sequence

<400> SEQUENCE: 134

```
Met Gly Trp Ser Cys Ile Ile Leu Phe Leu Val Ala Thr Ala Thr Gly
1               5                   10                  15

Val His Ser
```

<210> SEQ ID NO 135
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 135

Asp Tyr Lys Asp Asp Asp Lys
1               5

<210> SEQ ID NO 136
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 136

Asn Tyr Tyr Ile His
1               5

<210> SEQ ID NO 137
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 137

Trp Ile Tyr Pro Gly Asp Gly Asn Thr Lys Tyr Asn Glu Lys Phe Lys
1               5                   10                  15

Gly

<210> SEQ ID NO 138
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 138

Asp Ser Tyr Ser Asn Tyr Tyr Phe Asp Tyr
1               5                   10

<210> SEQ ID NO 139
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 139

Lys Ser Ser Gln Ser Leu Leu Asn Ser Arg Thr Arg Lys Asn Tyr Leu
1               5                   10                  15

Ala

<210> SEQ ID NO 140
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 140

Trp Ala Ser Thr Arg Glu Ser
1               5

<210> SEQ ID NO 141
<211> LENGTH: 8
<212> TYPE: PRT

```
<213> ORGANISM: Artificial Sequence
<220> FEATURE:
<223> OTHER INFORMATION: an artificial synthesized sequence

<400> SEQUENCE: 141

Thr Gln Ser Phe Ile Leu Arg Thr
1               5

<210> SEQ ID NO 142
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 142

Ser Tyr Tyr Ile His
1               5

<210> SEQ ID NO 143
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 143

Trp Ile Tyr Pro Glu Asn Asp Asn Thr Lys Tyr Asn Glu Lys Phe Lys
1               5                   10                  15

Asp

<210> SEQ ID NO 144
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 144

Asp Gly Tyr Ser Arg Tyr Tyr Phe Asp Tyr
1               5                   10

<210> SEQ ID NO 145
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 145

Lys Ser Ser Gln Ser Leu Leu Asn Ser Arg Thr Arg Lys Asn Tyr Leu
1               5                   10                  15

Ala

<210> SEQ ID NO 146
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 146

Trp Thr Ser Thr Arg Lys Ser
1               5
```

```
<210> SEQ ID NO 147
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 147

Lys Gln Ser Phe Ile Leu Arg Thr
1               5

<210> SEQ ID NO 148
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 148

Asp Ala Tyr Ser Arg Tyr Tyr Phe Asp Tyr
1               5                   10

<210> SEQ ID NO 149
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 149

Lys Gln Ser Phe Ala Leu Arg Thr
1               5

<210> SEQ ID NO 150
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 150

Lys Ala Ser Phe Ile Leu Arg Thr
1               5

<210> SEQ ID NO 151
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 151

Lys Gln Ser Ala Ile Leu Arg Thr
1               5

<210> SEQ ID NO 152
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 152

Thr Gly Tyr Ser Arg Tyr Tyr Phe Asp Tyr
1               5                   10

<210> SEQ ID NO 153
```

```
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 153

Asp Gly Tyr Ser Arg Tyr Ala Phe Asp Tyr
1               5                   10

<210> SEQ ID NO 154
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 154

Ser Gly Tyr Ser Arg Tyr Tyr Phe Asp Tyr
1               5                   10

<210> SEQ ID NO 155
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 155

Asp Gly Tyr Ser Arg Ala Tyr Phe Asp Tyr
1               5                   10

<210> SEQ ID NO 156
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 156

Asp Ser Tyr Ser Asn Tyr Tyr Phe Asp Tyr
1               5                   10

<210> SEQ ID NO 157
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 157

Thr Gln Ser Phe Ile Leu Arg Thr
1               5

<210> SEQ ID NO 158
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 158

Gly Tyr Thr Met Asn
1               5

<210> SEQ ID NO 159
<211> LENGTH: 17
```

```
<212> TYPE: PRT
<213> ORGANISM: Artificial Sequence
<220> FEATURE:
<223> OTHER INFORMATION: an artificial synthesized sequence

<400> SEQUENCE: 159

Leu Ile Asn Pro Tyr Lys Gly Val Ser Thr Tyr Asn Gln Lys Phe Lys
1               5                   10                  15

Asp

<210> SEQ ID NO 160
<211> LENGTH: 13
<212> TYPE: PRT
<213> ORGANISM: Artificial Sequence
<220> FEATURE:
<223> OTHER INFORMATION: an artificial synthesized sequence

<400> SEQUENCE: 160

Ser Gly Tyr Tyr Gly Asp Ser Asp Trp Tyr Phe Asp Val
1               5                   10

<210> SEQ ID NO 161
<211> LENGTH: 11
<212> TYPE: PRT
<213> ORGANISM: Artificial Sequence
<220> FEATURE:
<223> OTHER INFORMATION: an artificial synthesized sequence

<400> SEQUENCE: 161

Arg Ala Ser Gln Asp Ile Arg Asn Tyr Leu Asn
1               5                   10

<210> SEQ ID NO 162
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 162

Tyr Thr Ser Arg Leu Glu Ser
1               5

<210> SEQ ID NO 163
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 163

Gln Gln Gly Asn Thr Leu Pro Trp Thr
1               5

<210> SEQ ID NO 164
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 164

Leu Ile Asn Pro Tyr Lys Gly Val Thr Thr Tyr Ala Asp Ser Val Lys
1               5                   10                  15

Gly
```

<210> SEQ ID NO 165
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 165

Leu Ile Asn Pro Tyr Lys Gly Val Ser Thr Tyr Ala Asp Ser Val Lys
1               5                   10                  15

Gly

<210> SEQ ID NO 166
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 166

Thr Tyr Ala Met Asn
1               5

<210> SEQ ID NO 167
<211> LENGTH: 19
<212> TYPE: PRT
<213> ORGANISM: Artificial Sequence
<220> FEATURE:
<223> OTHER INFORMATION: an artificial synthesized sequence

<400> SEQUENCE: 167

Arg Ile Arg Ser Lys Tyr Asn Asn Tyr Ala Thr Tyr Tyr Ala Asp Ser
1               5                   10                  15

Val Lys Asp

<210> SEQ ID NO 168
<211> LENGTH: 14
<212> TYPE: PRT
<213> ORGANISM: Artificial Sequence
<220> FEATURE:
<223> OTHER INFORMATION: an artificial synthesized sequence

<400> SEQUENCE: 168

His Gly Asn Phe Gly Asn Ser Tyr Val Ser Trp Phe Ala Tyr
1               5                   10

<210> SEQ ID NO 169
<211> LENGTH: 14
<212> TYPE: PRT
<213> ORGANISM: Artificial Sequence
<220> FEATURE:
<223> OTHER INFORMATION: an artificial synthesized sequence

<400> SEQUENCE: 169

Arg Ser Ser Thr Gly Ala Val Thr Thr Ser Asn Tyr Ala Asn
1               5                   10

<210> SEQ ID NO 170
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 170

```
Gly Thr Asn Lys Arg Ala Pro
1               5
```

<210> SEQ ID NO 171
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 171

```
Ala Leu Trp Tyr Ser Asn Leu Trp Val
1               5
```

<210> SEQ ID NO 172
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 172

```
Asn Tyr Gly Met Asn
1               5
```

<210> SEQ ID NO 173
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 173

```
Trp Ile Asn Thr Asn Thr Gly Lys Pro Thr Tyr Ala Glu Glu Phe Lys
1               5                   10                  15

Gly
```

<210> SEQ ID NO 174
<211> LENGTH: 11
<212> TYPE: PRT
<213> ORGANISM: Artificial Sequence
<220> FEATURE:
<223> OTHER INFORMATION: an artificial synthesized sequence

<400> SEQUENCE: 174

```
Arg Gly Asp Tyr Arg Tyr Ala Trp Phe Leu Tyr
1               5                   10
```

<210> SEQ ID NO 175
<211> LENGTH: 14
<212> TYPE: PRT
<213> ORGANISM: Artificial Sequence
<220> FEATURE:
<223> OTHER INFORMATION: an artificial synthesized sequence

<400> SEQUENCE: 175

```
Arg Ser Ser Thr Gly Ala Val Thr Thr Ser Asn Tyr Ala Asn
1               5                   10
```

<210> SEQ ID NO 176
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 176

```
Gly Thr Ser Asn Arg Ala Pro
1               5

<210> SEQ ID NO 177
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 177

Ala Leu Trp Tyr Ser Thr His Phe Val
1               5

<210> SEQ ID NO 178
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 178

Ser Tyr Tyr Ile His
1               5

<210> SEQ ID NO 179
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 179

Trp Ile Tyr Pro Gly Asn Val Asn Thr Lys Tyr Asn Glu Lys Phe Lys
1               5                   10                  15

Gly

<210> SEQ ID NO 180
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 180

Asn His Asp Tyr Tyr Phe Asp Tyr
1               5

<210> SEQ ID NO 181
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 181

Lys Ser Ser Gln Ser Leu Leu Asn Ser Arg Thr Arg Lys Asn Tyr Leu
1               5                   10                  15

Ala

<210> SEQ ID NO 182
<211> LENGTH: 7
<212> TYPE: PRT
<213> ORGANISM: Artificial Sequence
<220> FEATURE:
```

<223> OTHER INFORMATION: an artificial synthesized sequence

<400> SEQUENCE: 182

Trp Ala Ser Thr Arg Glu Ser
1               5

<210> SEQ ID NO 183
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 183

Lys Gln Ser Tyr Ile Leu Arg Thr
1               5

<210> SEQ ID NO 184
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 184

Asn Tyr Ala Ile His
1               5

<210> SEQ ID NO 185
<211> LENGTH: 16
<212> TYPE: PRT
<213> ORGANISM: Artificial Sequence
<220> FEATURE:
<223> OTHER INFORMATION: an artificial synthesized sequence

<400> SEQUENCE: 185

Val Ile Trp Ala Gly Gly Asn Thr Lys Tyr Asn Ser Ala Leu Met Ser
1               5                   10                  15

<210> SEQ ID NO 186
<211> LENGTH: 11
<212> TYPE: PRT
<213> ORGANISM: Artificial Sequence
<220> FEATURE:
<223> OTHER INFORMATION: an artificial synthesized sequence

<400> SEQUENCE: 186

Glu Asp Ser Ser Gly Tyr Val Ala Leu Asp Tyr
1               5                   10

<210> SEQ ID NO 187
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 187

Lys Ser Ser Gln Ser Leu Leu Ser Gly Arg Thr Arg Lys Asn Tyr Leu
1               5                   10                  15

Ala

<210> SEQ ID NO 188
<211> LENGTH: 7
<212> TYPE: PRT
<213> ORGANISM: Artificial Sequence -continued

```
<220> FEATURE:
<223> OTHER INFORMATION: an artificial synthesized sequence

<400> SEQUENCE: 188

Trp Ala Ser Thr Arg Glu Ser
1               5

<210> SEQ ID NO 189
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 189

Lys Gln Ser Tyr Tyr Leu Leu Thr
1               5

<210> SEQ ID NO 190
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 190

Gly Phe Ser Leu Thr Asn Tyr Ala Ile His
1               5                   10

<210> SEQ ID NO 191
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 191

Gly Val Ile Trp Ala Gly Gly Asn Thr Lys Tyr Asn Ser Ala Leu Met
1               5                   10                  15

Ser

<210> SEQ ID NO 192
<211> LENGTH: 28
<212> TYPE: PRT
<213> ORGANISM: Artificial Sequence
<220> FEATURE:
<223> OTHER INFORMATION: an artificial synthesized sequence

<400> SEQUENCE: 192

Gln Met Asn Ser Leu Arg Ala Glu Asp Thr Ala Val Tyr Tyr Cys Ala
1               5                   10                  15

Arg Glu Asp Ser Ser Gly Tyr Val Ala Leu Asp Tyr
            20                  25

<210> SEQ ID NO 193
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 193

Lys Ser Ser Gln Ser Leu Leu Ser Gly Arg Thr Arg Lys Asn Tyr Leu
1               5                   10                  15

Ala
```

<210> SEQ ID NO 194
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 194

Trp Ala Ser Thr Arg Glu Ser
1               5

<210> SEQ ID NO 195
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 195

Lys Gln Ser Tyr Tyr Leu Leu Thr
1               5

<210> SEQ ID NO 196
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 196

Gly Ser Ala Met His
1               5

<210> SEQ ID NO 197
<211> LENGTH: 19
<212> TYPE: PRT
<213> ORGANISM: Artificial Sequence
<220> FEATURE:
<223> OTHER INFORMATION: an artificial synthesized sequence

<400> SEQUENCE: 197

Arg Ile Arg Ser Arg Ala Asn Ser Tyr Ala Thr Ala Tyr Ala Ala Ser
1               5                   10                  15

Val Lys Asp

<210> SEQ ID NO 198
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 198

Asp Thr Met Val Arg Gly Ile Asp Tyr
1               5

<210> SEQ ID NO 199
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 199

Lys Ser Ser Gln Ser Val Leu Tyr Ser Ser Asn Asn Lys Asn Tyr Leu

```
1               5                   10                  15
Val

<210> SEQ ID NO 200
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 200

Arg Ala Ser Thr Arg Glu Ser
1               5

<210> SEQ ID NO 201
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 201

Gln Gln Tyr Tyr Ser Val Pro Trp Thr
1               5

<210> SEQ ID NO 202
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 202

Ser Asp Tyr Ile His
1               5

<210> SEQ ID NO 203
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 203

Trp Ile Tyr Phe Gly Asn Val Asn Thr Lys Tyr Asn Glu Lys Phe Lys
1               5                   10                  15
Gly

<210> SEQ ID NO 204
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 204

Asp Gly Gly Tyr Tyr Phe Asp Tyr
1               5

<210> SEQ ID NO 205
<211> LENGTH: 17
<212> TYPE: PRT
<213> ORGANISM: Artificial Sequence
<220> FEATURE:
<223> OTHER INFORMATION: an artificial synthesized sequence
```

```
<400> SEQUENCE: 205

Lys Ser Ser Gln Ser Leu Leu Asn Ser Arg Thr Arg Lys Asn Tyr Leu
1               5                   10                  15
Ala

<210> SEQ ID NO 206
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 206

Trp Ala Ser Thr Arg Glu Ser
1               5

<210> SEQ ID NO 207
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 207

Lys Gln Ser Phe Thr Leu Arg Thr
1               5

<210> SEQ ID NO 208
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 208

Ser His Tyr Leu His
1               5

<210> SEQ ID NO 209
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 209

Trp Ile Asn Pro Gly Asp Gly Asn Val Lys Tyr Asn Glu Lys Phe Lys
1               5                   10                  15
Asp

<210> SEQ ID NO 210
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 210

Asp Gly Ala Tyr Tyr Phe Asp Tyr
1               5

<210> SEQ ID NO 211
<211> LENGTH: 17
<212> TYPE: PRT
<213> ORGANISM: Artificial Sequence
```

<220> FEATURE:
<223> OTHER INFORMATION: an artificial synthesized sequence

<400> SEQUENCE: 211

Lys Ser Ser Gln Ser Leu Leu Asn Ser Arg Thr Arg Lys Asn Tyr Leu
1               5                   10                  15
Ala

<210> SEQ ID NO 212
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 212

Trp Ala Ser Thr Arg Glu Ser
1               5

<210> SEQ ID NO 213
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 213

Lys Gln Ser Tyr Thr Leu Arg Thr
1               5

<210> SEQ ID NO 214
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 214

Ser Tyr Tyr Ile His
1               5

<210> SEQ ID NO 215
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 215

Trp Ile Phe Pro Gly Ser Asp Asn Thr Lys Tyr Asn Glu Lys Phe Lys
1               5                   10                  15
Gly

<210> SEQ ID NO 216
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 216

Asn Gly Asn Tyr Ala Met Asp Tyr
1               5

<210> SEQ ID NO 217

```
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 217

Lys Ser Ser Gln Ser Leu Leu Asn Ser Arg Thr Arg Lys Asn Tyr Leu
1               5                   10                  15
Ala

<210> SEQ ID NO 218
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 218

Trp Ala Ser Thr Arg Glu Ser
1               5

<210> SEQ ID NO 219
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 219

Lys Gln Ser Tyr Thr Leu Arg Thr
1               5

<210> SEQ ID NO 220
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 220

Ser Tyr Tyr Ile His
1               5

<210> SEQ ID NO 221
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 221

Trp Ile Tyr Pro Gly Asn Val Asn Thr Lys Tyr Asn Glu Lys Phe Lys
1               5                   10                  15
Gly

<210> SEQ ID NO 222
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 222

Asn His Asp Tyr Tyr Phe Asp Tyr
1               5
```

<210> SEQ ID NO 223
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 223

Lys Ser Ser Gln Ser Leu Leu Asn Ser Arg Thr Arg Lys Asn Tyr Leu
1               5                   10                  15

Ala

<210> SEQ ID NO 224
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 224

Trp Ala Ser Thr Arg Glu Ser
1               5

<210> SEQ ID NO 225
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 225

Lys Gln Ser Tyr Ile Leu Arg Thr
1               5

<210> SEQ ID NO 226
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 226

Asn Tyr Gly Met Asn
1               5

<210> SEQ ID NO 227
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 227

Trp Ile Asn Thr Asn Thr Gly Lys Pro Thr Tyr Ala Glu Asp Phe Lys
1               5                   10                  15

Gly

<210> SEQ ID NO 228
<211> LENGTH: 11
<212> TYPE: PRT
<213> ORGANISM: Artificial Sequence
<220> FEATURE:
<223> OTHER INFORMATION: an artificial synthesized sequence

<400> SEQUENCE: 228

```
Arg Gly Asp Tyr Arg Tyr Ala Trp Phe Thr Tyr
1               5                   10

<210> SEQ ID NO 229
<211> LENGTH: 14
<212> TYPE: PRT
<213> ORGANISM: Artificial Sequence
<220> FEATURE:
<223> OTHER INFORMATION: an artificial synthesized sequence

<400> SEQUENCE: 229

Arg Ser Ser Thr Gly Ala Val Thr Thr Ser Asn Tyr Ala Asn
1               5                   10

<210> SEQ ID NO 230
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 230

Gly Thr Ser Asn Arg Ala Pro
1               5

<210> SEQ ID NO 231
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 231

Ala Leu Trp Tyr Ser Thr His Phe Val
1               5

<210> SEQ ID NO 232
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 232

Asn Tyr Tyr Ile His
1               5

<210> SEQ ID NO 233
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 233

Trp Ile Tyr Pro Gly Ser Asp Asn Thr Lys Phe Asn Asp Lys Phe Lys
1               5                   10                  15

Gly

<210> SEQ ID NO 234
<211> LENGTH: 10
<212> TYPE: PRT
<213> ORGANISM: Artificial Sequence
<220> FEATURE:
<223> OTHER INFORMATION: an artificial synthesized sequence
```

```
<400> SEQUENCE: 234

Asp Ser Ile Thr Asn Tyr Tyr Phe Asp Tyr
1               5                   10

<210> SEQ ID NO 235
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 235

Lys Ser Ser Gln Ser Leu Leu Asn Ile Arg Thr Arg Lys Asn Cys Leu
1               5                   10                  15

Ala

<210> SEQ ID NO 236
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 236

Trp Ala Ser Thr Arg Tyr Ser
1               5

<210> SEQ ID NO 237
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 237

Thr Gln Ser Tyr Thr Leu Arg Thr
1               5

<210> SEQ ID NO 238
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 238

Ser Tyr Trp Met His
1               5

<210> SEQ ID NO 239
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 239

Asn Phe Tyr Pro Gly Asp Leu Thr Val Asn Tyr Asp Glu Lys Phe Lys
1               5                   10                  15

Asn

<210> SEQ ID NO 240
<211> LENGTH: 10
<212> TYPE: PRT
<213> ORGANISM: Artificial Sequence
```

```
<220> FEATURE:
<223> OTHER INFORMATION: an artificial synthesized sequence

<400> SEQUENCE: 240

Asp Ala Tyr Ser Arg Tyr Phe Phe Asp Tyr
1               5                   10

<210> SEQ ID NO 241
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 241

Lys Ser Ser Gln Ser Leu Leu Asn Ser Arg Thr Arg Lys Asn Tyr Leu
1               5                   10                  15
Ala

<210> SEQ ID NO 242
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 242

Trp Ala Ser Thr Arg Glu Ser
1               5

<210> SEQ ID NO 243
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 243

Cys Gln Ser Phe Ile Leu Arg Thr
1               5

<210> SEQ ID NO 244
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 244

Asn Tyr Tyr Met His
1               5

<210> SEQ ID NO 245
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 245

Trp Ile Ser Pro Gly Ser Gly Ser Ile Lys Tyr Asn Glu Lys Phe Lys
1               5                   10                  15
Gly

<210> SEQ ID NO 246
```

```
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 246

Asp Gly Tyr Ser Leu Tyr Phe Phe Asp Phe
1               5                   10

<210> SEQ ID NO 247
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 247

Lys Ser Ser Gln Ser Leu Leu Asn Ser Arg Thr Arg Lys Asn Tyr Leu
1               5                   10                  15

Ala

<210> SEQ ID NO 248
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 248

Trp Ala Ser Thr Arg Glu Ser
1               5

<210> SEQ ID NO 249
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 249

Lys Gln Ser Phe Ile Leu Arg Thr
1               5

<210> SEQ ID NO 250
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 250

Asn Tyr Tyr Thr His
1               5

<210> SEQ ID NO 251
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 251

Trp Ile Tyr Pro Gly Asn Gly Asn Ile Lys Tyr Asn Glu Lys Phe Met
1               5                   10                  15

Gly
```

<210> SEQ ID NO 252
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 252

Asp Ser Tyr Gly Ser Tyr Tyr Phe Asp Tyr
1               5                   10

<210> SEQ ID NO 253
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 253

Lys Ser Ser Gln Ser Leu Leu Asn Ser Arg Thr Arg Lys Asn Tyr Leu
1               5                   10                  15

Ala

<210> SEQ ID NO 254
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 254

Trp Ala Ser Thr Arg Glu Ser
1               5

<210> SEQ ID NO 255
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 255

Thr Gln Ser Phe Ile Leu Arg Thr
1               5

<210> SEQ ID NO 256
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 256

Asn Tyr Tyr Thr His
1               5

<210> SEQ ID NO 257
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 257

Trp Ile Tyr Pro Gly Asn Gly Asn Ile Lys Tyr Asn Glu Lys Phe Met

```
1               5                   10                  15

Gly

<210> SEQ ID NO 258
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 258

Asp Ser Tyr Gly Ser Tyr Tyr Phe Asp Tyr
1               5                   10

<210> SEQ ID NO 259
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 259

Lys Ser Ser Gln Ser Leu Leu Asn Ser Arg Thr Arg Lys Asn Tyr Leu
1               5                   10                  15

Ala

<210> SEQ ID NO 260
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 260

Trp Ala Ser Thr Arg Glu Ser
1               5

<210> SEQ ID NO 261
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 261

Lys Gln Ser Phe Ile Leu Arg Thr
1               5

<210> SEQ ID NO 262
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 262

Asn Tyr Tyr Thr His
1               5

<210> SEQ ID NO 263
<211> LENGTH: 17
<212> TYPE: PRT
<213> ORGANISM: Artificial Sequence
<220> FEATURE:
<223> OTHER INFORMATION: an artificial synthesized sequence
```

<400> SEQUENCE: 263

Trp Leu Tyr Pro Gly Asn Gly Asp Thr Arg Tyr Asn Glu Lys Phe Lys
1               5                   10                  15
Asp

<210> SEQ ID NO 264
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 264

Asp Ser Tyr Gly Asn Tyr Phe Phe Asp Tyr
1               5                   10

<210> SEQ ID NO 265
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 265

Lys Ser Ser Gln Ser Leu Leu Asn Ser Arg Thr Arg Lys Asn Tyr Leu
1               5                   10                  15
Ala

<210> SEQ ID NO 266
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 266

Trp Ala Ser Thr Arg Glu Ser
1               5

<210> SEQ ID NO 267
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 267

Lys Gln Ser Phe Ile Leu Arg Thr
1               5

<210> SEQ ID NO 268
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 268

Ser Tyr Trp Met His
1               5

<210> SEQ ID NO 269
<211> LENGTH: 17
<212> TYPE: PRT
<213> ORGANISM: Artificial Sequence

```
<220> FEATURE:
<223> OTHER INFORMATION: an artificial synthesized sequence

<400> SEQUENCE: 269

Asn Ser Tyr Pro Gly Asp Leu Asn Val Asn Tyr Asp Glu Lys Phe Lys
1               5                   10                  15

Asn

<210> SEQ ID NO 270
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 270

Asp Ala Tyr Ser Arg Tyr Phe Phe Asp Tyr
1               5                   10

<210> SEQ ID NO 271
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 271

Lys Ser Ser Gln Ser Leu Leu Asn Ser Arg Thr Arg Lys Asn Tyr Leu
1               5                   10                  15

Ala

<210> SEQ ID NO 272
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 272

Trp Ala Ser Thr Arg Glu Ser
1               5

<210> SEQ ID NO 273
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 273

Cys Gln Ser Phe Ile Leu Arg Thr
1               5

<210> SEQ ID NO 274
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 274

Ser Tyr Tyr Ile His
1               5

<210> SEQ ID NO 275
```

<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 275

Trp Leu Tyr Pro Gly Asp Val Ser Thr Arg Tyr Asn Glu Lys Phe Arg
1               5                   10                  15
Asp

<210> SEQ ID NO 276
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 276

Asp Ser Ser Ala Ser Tyr Tyr Phe Asp Phe
1               5                   10

<210> SEQ ID NO 277
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 277

Lys Ser Ser Gln Ser Leu Leu Asn Ile Arg Thr Arg Lys Asn Tyr Leu
1               5                   10                  15
Ala

<210> SEQ ID NO 278
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 278

Trp Ala Ser Thr Arg Ala Ser
1               5

<210> SEQ ID NO 279
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 279

Thr Gln Ser Phe Ile Leu Arg Thr
1               5

<210> SEQ ID NO 280
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 280

Ser Tyr Trp Met His
1               5

<210> SEQ ID NO 281
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 281

Asn Ile Tyr Pro Gly Gly Glu Ile Ile Asn Tyr Ala Glu Lys Phe Lys
1               5                   10                  15

Thr

<210> SEQ ID NO 282
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 282

Asp Thr Thr Gly Asn Tyr Phe Phe Asp Tyr
1               5                   10

<210> SEQ ID NO 283
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 283

Lys Ser Ser Gln Ser Leu Leu Asn Ser Arg Thr Arg Lys Asn Tyr Leu
1               5                   10                  15

Ala

<210> SEQ ID NO 284
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 284

Trp Ala Ser Thr Arg Glu Ser
1               5

<210> SEQ ID NO 285
<211> LENGTH: 8
<212> TYPE: PRT
<213> ORGANISM: Artificial Sequence
<220> FEATURE:
<223> OTHER INFORMATION: an artificial synthesized sequence

<400> SEQUENCE: 285

Thr Gln Ser Phe Ile Leu Arg Thr
1               5

<210> SEQ ID NO 286
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 286

```
Ser Cys Ala Ile Ser
1               5

<210> SEQ ID NO 287
<211> LENGTH: 16
<212> TYPE: PRT
<213> ORGANISM: Artificial Sequence
<220> FEATURE:
<223> OTHER INFORMATION: an artificial synthesized sequence

<400> SEQUENCE: 287

Phe Met Ser Val Thr Gly Ser Ala Tyr Tyr Ala Asn Trp Ala Lys Ser
1               5                   10                  15

<210> SEQ ID NO 288
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 288

Val Gly Ile Gly Ser Gly Leu Asn Ile
1               5

<210> SEQ ID NO 289
<211> LENGTH: 13
<212> TYPE: PRT
<213> ORGANISM: Artificial Sequence
<220> FEATURE:
<223> OTHER INFORMATION: an artificial synthesized sequence

<400> SEQUENCE: 289

Gln Ala Ser Glu Thr Val Tyr Ser Asn Asn Tyr Leu Ala
1               5                   10

<210> SEQ ID NO 290
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 290

Gly Val Ser Thr Leu Asp Ser
1               5

<210> SEQ ID NO 291
<211> LENGTH: 12
<212> TYPE: PRT
<213> ORGANISM: Artificial Sequence
<220> FEATURE:
<223> OTHER INFORMATION: an artificial synthesized sequence

<400> SEQUENCE: 291

Ala Gly Tyr Lys Thr Ser Ser Ser Tyr Ala Ile Ala
1               5                   10

<210> SEQ ID NO 292
<211> LENGTH: 5
<212> TYPE: PRT
<213> ORGANISM: Artificial Sequence
<220> FEATURE:
<223> OTHER INFORMATION: an artificial synthesized sequence

<400> SEQUENCE: 292
```

Asp Tyr Tyr Ile His
1               5

<210> SEQ ID NO 293
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 293

Trp Ile Tyr Pro Gly Asp Val Ser Thr Arg Phe Asn Glu Lys Phe Lys
1               5                   10                  15
Gly

<210> SEQ ID NO 294
<211> LENGTH: 10
<212> TYPE: PRT
<213> ORGANISM: Artificial Sequence
<220> FEATURE:
<223> OTHER INFORMATION: an artificial synthesized sequence

<400> SEQUENCE: 294

Asp Ser Tyr Gly Asn Tyr Phe Phe Asp Tyr
1               5                   10

<210> SEQ ID NO 295
<211> LENGTH: 17
<212> TYPE: PRT
<213> ORGANISM: Artificial Sequence
<220> FEATURE:
<223> OTHER INFORMATION: an artificial synthesized sequence

<400> SEQUENCE: 295

Lys Ser Ser Gln Ser Leu Leu Asn Ser Arg Thr Arg Lys Asn Tyr Leu
1               5                   10                  15
Ala

<210> SEQ ID NO 296
<211> LENGTH: 7
<212> TYPE: PRT
<213> ORGANISM: Artificial Sequence
<220> FEATURE:
<223> OTHER INFORMATION: an artificial synthesized sequence

<400> SEQUENCE: 296

Trp Ala Ser Thr Arg Glu Ser
1               5

<210> SEQ ID NO 297
<211> LENGTH: 9
<212> TYPE: PRT
<213> ORGANISM: Artificial Sequence
<220> FEATURE:
<223> OTHER INFORMATION: an artificial synthesized sequence

<400> SEQUENCE: 297

Cys Thr Gln Ser Phe Ile Leu Arg Thr
1               5

<210> SEQ ID NO 298
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 298

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 299
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 299

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 300
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 300

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asp Gly Asn Thr Lys Tyr Asn Glu Lys Phe
50                  55                  60

```
Lys Gly Lys Ala Thr Leu Thr Ala Asp Thr Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Ser Tyr Ser Asn Tyr Tyr Phe Asp Tyr Trp Gly Gln Gly
            100                 105                 110

Thr Thr Leu Thr Val Ser Ser
            115

<210> SEQ ID NO 301
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 301

Asp Ile Val Met Thr Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Thr Gln
                 85                  90                  95

Ser Phe Ile Leu Arg Thr Phe Gly Gly Gly Thr Lys Leu Glu Ile Lys
            100                 105                 110

<210> SEQ ID NO 302
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 302

Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Ser Tyr
             20                  25                  30

Tyr Ile His Trp Val Arg Gln Ala Pro Gly Gln Gly Leu Glu Trp Ile
         35                  40                  45

Gly Trp Ile Tyr Pro Glu Asn Asp Asn Thr Lys Tyr Asn Glu Lys Phe
     50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
            115
```

```
<210> SEQ ID NO 303
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 303

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 304
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 304

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ala Tyr Ser Arg Tyr Tyr Phe Asp Tyr Trp Gly Gln Gly
            100                 105                 110

Thr Leu Val Thr Val Ser Ser
        115

<210> SEQ ID NO 305
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 305

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30
```

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
                100                 105                 110

<210> SEQ ID NO 306
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 306

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
                20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
        50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
                100                 105                 110

Thr Leu Val Thr Val Ser Ser
        115

<210> SEQ ID NO 307
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 307

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ala Leu Arg Thr Phe Gly Gln Gly Thr Lys Val Glu Ile Lys

<210> SEQ ID NO 308
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 308

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 309
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 309

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Ala
                85                  90                  95

Ser Phe Ile Leu Arg Thr Phe Gly Gln Gly Thr Lys Val Glu Ile Lys
            100                 105                 110

<210> SEQ ID NO 310
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 310

Glu Val Gln Leu Val Gln Ser Gly Ala Glu Val Lys Lys Pro Gly Ala
1               5                   10                  15

```
Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Phe Asp Tyr Trp Gly Gln Gly
                100                 105                 110

Thr Leu Val Thr Val Ser Ser
            115

<210> SEQ ID NO 311
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 311

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Ala Ile Leu Arg Thr Phe Gly Gln Gly Thr Lys Val Glu Ile Lys
                100                 105                 110

<210> SEQ ID NO 312
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 312

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
```

85                  90                  95

Ala Arg Thr Gly Tyr Ser Arg Tyr Tyr Phe Asp Tyr Trp Gly Gln Gly
            100                 105                 110

Thr Leu Val Thr Val Ser Ser
        115

<210> SEQ ID NO 313
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 313

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 314
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 314

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Ala Phe Asp Tyr Trp Gly Gln Gly
            100                 105                 110

Thr Leu Val Thr Val Ser Ser
        115

<210> SEQ ID NO 315
<211> LENGTH: 112
<212> TYPE: PRT
<213> ORGANISM: Artificial Sequence
<220> FEATURE:

<223> OTHER INFORMATION: an artificial synthesized sequence

<400> SEQUENCE: 315

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gly Gly Thr Lys Val Glu Ile Lys
            100                 105                 110

<210> SEQ ID NO 316
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 316

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Tyr Ser Arg Tyr Tyr Phe Asp Tyr Trp Gly Gln Gly
            100                 105                 110

Thr Leu Val Thr Val Ser Ser
        115

<210> SEQ ID NO 317
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 317

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val

```
                    50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                     85                  90                  95

Ser Phe Ile Leu Arg Thr Phe Gly Gln Gly Thr Lys Val Glu Ile Lys
                100                 105                 110
```

<210> SEQ ID NO 318
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 318

```
Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Ser Tyr
                20                  25                  30

Tyr Ile His Trp Val Arg Gln Ala Pro Gly Gln Gly Leu Glu Trp Ile
             35                  40                  45

Gly Trp Ile Tyr Pro Glu Asn Asp Asn Thr Lys Tyr Asn Glu Lys Phe
 50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Gly Tyr Ser Arg Ala Tyr Phe Asp Tyr Trp Gly Gln Gly
                100                 105                 110

Thr Leu Val Thr Val Ser Ser
            115
```

<210> SEQ ID NO 319
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 319

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Thr Ser Arg Lys Ser Gly Val
             50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Phe Ile Leu Arg Thr Phe Gly Gln Gly Thr Lys Val Glu Ile Lys
                100                 105                 110
```

<210> SEQ ID NO 320
<211> LENGTH: 119

```
<212> TYPE: PRT
<213> ORGANISM: Artificial Sequence
<220> FEATURE:
<223> OTHER INFORMATION: an artificial synthesized sequence

<400> SEQUENCE: 320

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 321
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 321

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 322
<211> LENGTH: 122
<212> TYPE: PRT
<213> ORGANISM: Artificial Sequence
<220> FEATURE:
<223> OTHER INFORMATION: an artificial synthesized sequence

<400> SEQUENCE: 322

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Asp Leu Glu Trp Val
```

```
                35                  40                  45
Ala Leu Ile Asn Pro Tyr Lys Gly Val Ser Thr Tyr Asn Gln Lys Phe
         50                  55                  60

Lys Asp Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Tyr Gly Asp Ser Asp Trp Tyr Phe Asp Val Trp
             100                 105                 110

Gly Gln Gly Thr Leu Val Thr Val Ser Ser
         115                 120

<210> SEQ ID NO 323
<211> LENGTH: 107
<212> TYPE: PRT
<213> ORGANISM: Artificial Sequence
<220> FEATURE:
<223> OTHER INFORMATION: an artificial synthesized sequence

<400> SEQUENCE: 323

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Glu Ser Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Leu Glu Leu Lys
             100                 105

<210> SEQ ID NO 324
<211> LENGTH: 122
<212> TYPE: PRT
<213> ORGANISM: Artificial Sequence
<220> FEATURE:
<223> OTHER INFORMATION: an artificial synthesized sequence

<400> SEQUENCE: 324

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Phe Thr Gly Tyr
             20                  25                  30

Thr Met Asn Trp Val Arg Gln Ala Pro Gly Lys Gly Leu Glu Trp Val
         35                  40                  45

Ala Leu Ile Asn Pro Tyr Lys Gly Val Thr Thr Tyr Ala Asp Ser Val
     50                  55                  60

Lys Gly Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Tyr Gly Asp Ser Asp Trp Tyr Phe Asp Val Trp
             100                 105                 110
```

Gly Gln Gly Thr Leu Val Thr Val Ser Ser
            115                 120

```
<210> SEQ ID NO 325
<211> LENGTH: 107
<212> TYPE: PRT
<213> ORGANISM: Artificial Sequence
<220> FEATURE:
<223> OTHER INFORMATION: an artificial synthesized sequence

<400> SEQUENCE: 325
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

```
<210> SEQ ID NO 326
<211> LENGTH: 122
<212> TYPE: PRT
<213> ORGANISM: Artificial Sequence
<220> FEATURE:
<223> OTHER INFORMATION: an artificial synthesized sequence

<400> SEQUENCE: 326
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Ala Asp Ser Val
    50                  55                  60

Lys Gly Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
            115                 120

```
<210> SEQ ID NO 327
<211> LENGTH: 107
<212> TYPE: PRT
<213> ORGANISM: Artificial Sequence
<220> FEATURE:
<223> OTHER INFORMATION: an artificial synthesized sequence

<400> SEQUENCE: 327
```

Asp Ile Gln Met Thr Gln Ser Pro Ser Ser Leu Ser Ala Ser Val Gly

```
                1               5                  10                  15
Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 328
<211> LENGTH: 125
<212> TYPE: PRT
<213> ORGANISM: Artificial Sequence
<220> FEATURE:
<223> OTHER INFORMATION: an artificial synthesized sequence

<400> SEQUENCE: 328

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 329
<211> LENGTH: 109
<212> TYPE: PRT
<213> ORGANISM: Artificial Sequence
<220> FEATURE:
<223> OTHER INFORMATION: an artificial synthesized sequence

<400> SEQUENCE: 329

Glu Ala Val Val Thr Gln Glu Pro Ser Leu Thr Val Ser Pro Gly Gly
1               5                  10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
            50                  55                  60

Ser Gly Ser Leu Leu Gly Gly Lys Ala Ala Leu Thr Leu Ser Gly Ala
65                  70                  75                  80
```

```
Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 330
<211> LENGTH: 125
<212> TYPE: PRT
<213> ORGANISM: Mus musculus

<400> SEQUENCE: 330

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 331
<211> LENGTH: 109
<212> TYPE: PRT
<213> ORGANISM: Mus musculus

<400> SEQUENCE: 331

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 332
<211> LENGTH: 120
<212> TYPE: PRT
<213> ORGANISM: Artificial Sequence
<220> FEATURE:
<223> OTHER INFORMATION: an artificial synthesized sequence

<400> SEQUENCE: 332

Gln Val Gln Leu Val Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Asn Tyr
        20                  25                  30

Gly Met Asn Trp Val Arg Gln Ala Pro Gly Gln Gly Leu Glu Trp Met
            35                  40                  45

Gly Trp Ile Asn Thr Asn Thr Gly Lys Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Asp Tyr Arg Tyr Ala Trp Phe Leu Tyr Trp Gly Gln
            100                 105                 110

Gly Thr Leu Val Thr Val Ser Ser
        115                 120

<210> SEQ ID NO 333
<211> LENGTH: 109
<212> TYPE: PRT
<213> ORGANISM: Artificial Sequence
<220> FEATURE:
<223> OTHER INFORMATION: an artificial synthesized sequence

<400> SEQUENCE: 333

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Tyr Gly Thr Ser Asn Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Thr
                85                  90                  95

His Phe Val Phe Gly Thr Gly Thr Lys Val Thr Val Leu
            100                 105

<210> SEQ ID NO 334
<211> LENGTH: 120
<212> TYPE: PRT
<213> ORGANISM: Artificial Sequence
<220> FEATURE:
<223> OTHER INFORMATION: an artificial synthesized sequence

<400> SEQUENCE: 334

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Lys Pro Thr Tyr Ala Glu Glu Phe
    50                  55                  60

Lys Gly Arg Phe Val Phe Ser Leu Glu Thr Ser Ala Ser Thr Thr Tyr
65                  70                  75                  80

Leu Gln Ile Asn Asn Leu Lys Asn Glu Asp Thr Ala Thr Tyr Phe Cys
```

85                  90                  95
Ala Arg Arg Gly Asp Tyr Arg Tyr Ala Trp Phe Leu Tyr Trp Gly Gln
                100                 105                 110

Gly Thr Leu Val Thr Val Ser Ala
        115                 120

<210> SEQ ID NO 335
<211> LENGTH: 108
<212> TYPE: PRT
<213> ORGANISM: Artificial Sequence
<220> FEATURE:
<223> OTHER INFORMATION: an artificial synthesized sequence

<400> SEQUENCE: 335

Gln Ala Val Val Thr Gln Glu Ser Ala Leu Thr Thr Ser Pro Gly Gly
1               5                   10                  15

Thr Val Ile Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Ser Asn Arg Ala Pro Gly Val Pro Val Arg Phe
        50                  55                  60

Ser Gly Ser Leu Ile Gly Asp Lys Ala Ala Leu Thr Ile Thr Gly Ala
65                  70                  75                  80

Gln Thr Glu Asp Asp Ala Met Tyr Phe Cys Ala Leu Trp Tyr Ser Thr
                85                  90                  95

His Phe Val Phe Gly Gly Gly Thr Lys Val Thr Val
                100                 105

<210> SEQ ID NO 336
<211> LENGTH: 117
<212> TYPE: PRT
<213> ORGANISM: Artificial Sequence
<220> FEATURE:
<223> OTHER INFORMATION: an artificial synthesized sequence

<400> SEQUENCE: 336

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
            35                  40                  45

Gly Trp Ile Tyr Pro Gly Asn Val Asn Thr Lys Tyr Asn Glu Lys Phe
        50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asn His Asp Tyr Tyr Phe Asp Tyr Trp Gly Gln Gly Thr Leu
                100                 105                 110

Val Thr Val Ser Ser
        115

<210> SEQ ID NO 337
<211> LENGTH: 112
<212> TYPE: PRT
<213> ORGANISM: Artificial Sequence
<220> FEATURE:

<223> OTHER INFORMATION: an artificial synthesized sequence

<400> SEQUENCE: 337

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ile Leu Arg Thr Phe Gly Gly Gly Thr Lys Val Glu Ile Lys
            100                 105                 110
```

<210> SEQ ID NO 338
<211> LENGTH: 117
<212> TYPE: PRT
<213> ORGANISM: Artificial Sequence
<220> FEATURE:
<223> OTHER INFORMATION: an artificial synthesized sequence

<400> SEQUENCE: 338

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Arg Leu Glu Trp Met
        35                  40                  45

Gly Trp Ile Tyr Pro Gly Asn Val Asn Thr Lys Tyr Asn Glu Lys Phe
    50                  55                  60

Lys Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn His Asp Tyr Tyr Phe Asp Tyr Trp Gly Gln Gly Thr Leu
            100                 105                 110

Val Thr Val Ser Ser
        115
```

<210> SEQ ID NO 339
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 339

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
```

```
                    50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Tyr Ile Leu Arg Thr Phe Gly Gln Gly Thr Lys Val Glu Ile Lys
                100                 105                 110
```

<210> SEQ ID NO 340
<211> LENGTH: 117
<212> TYPE: PRT
<213> ORGANISM: Mus musculus

<400> SEQUENCE: 340

```
Glu Val Gln Leu Gln Gln Ser Gly Pro Glu Leu Val Lys Pro Gly Ala
 1               5                  10                  15

Ser Val Arg Ile Ser Cys Lys Ala Ser Gly Tyr Thr Phe Thr Ser Tyr
                20                  25                  30

Tyr Ile His Trp Met Lys Gln Arg Pro Gly Gln Gly Leu Glu Trp Ile
                35                  40                  45

Gly Trp Ile Tyr Pro Gly Asn Val Asn Thr Lys Tyr Asn Glu Lys Phe
 50                  55                  60

Lys Gly Lys Ala Thr Leu Thr Ala Asp Asn Ser Ser Thr Ala Asn
 65                  70                  75                  80

Met Gln Leu Ser Ser Leu Thr Ser Glu Asp Ser Ala Val Tyr Phe Cys
                85                  90                  95

Ala Arg Asn His Asp Tyr Tyr Phe Asp Tyr Trp Gly Gln Gly Thr Thr
                100                 105                 110

Leu Thr Val Ser Ser
        115
```

<210> SEQ ID NO 341
<211> LENGTH: 112
<212> TYPE: PRT
<213> ORGANISM: Mus musculus

<400> SEQUENCE: 341

```
Asp Ile Val Leu Thr Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                85                  90                  95

Ser Tyr Ile Leu Arg Thr Phe Gly Gly Gly Thr Lys Leu Glu Ile Lys
                100                 105                 110
```

<210> SEQ ID NO 342
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 342

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Ala Ile His Trp Ile Arg Gln Pro Pro Gly Lys Gly Leu Glu Trp Ile
        35                  40                  45

Gly Val Ile Trp Ala Gly Gly Asn Thr Lys Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asp Ser Ser Gly Tyr Val Ala Leu Asp Tyr Trp Gly Gln Gly
            100                 105                 110

Thr Leu Val Thr Val Ser Ser
        115

<210> SEQ ID NO 343
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 343

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Tyr Leu Leu Thr Phe Gly Gln Gly Thr Lys Val Glu Ile Lys
            100                 105                 110

<210> SEQ ID NO 344
<211> LENGTH: 119
<212> TYPE: PRT
<213> ORGANISM: Mus musculus

<400> SEQUENCE: 344

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Ile His Trp Val Arg Gln Pro Pro Gly Lys Gly Leu Asp Trp Leu
        35                  40                  45

Gly Val Ile Trp Ala Gly Gly Asn Thr Lys Tyr Asn Ser Ala Leu Met
    50                  55                  60

Ser Arg Leu Ser Phe Ser Lys Asp Asn Ser Lys Ser Gln Val Phe Leu

```
              65                  70                  75                  80
Glu Ile Asn Ser Leu Gln Thr Asp Thr Ala Met Tyr Tyr Cys Ala
                85                  90                  95

Arg Glu Asp Ser Ser Gly Tyr Val Ala Leu Asp Tyr Trp Gly Gln Gly
            100                 105                 110

Thr Ser Val Thr Val Ser Ser
        115

<210> SEQ ID NO 345
<211> LENGTH: 112
<212> TYPE: PRT
<213> ORGANISM: Mus musculus

<400> SEQUENCE: 345

Asn Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Ser Gly
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Leu Thr Phe Gly Ala Gly Thr Lys Leu Glu Leu Lys
            100                 105                 110

<210> SEQ ID NO 346
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 346

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Asn Tyr
            20                  25                  30

Ala Ile His Trp Val Arg Gln Ala Pro Gly Lys Gly Leu Glu Trp Val
        35                  40                  45

Gly Val Ile Trp Ala Gly Gly Asn Thr Lys Tyr Asn Ser Ala Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Asp Ser Ser Gly Tyr Val Ala Leu Asp Tyr Trp Gly Gln Gly
            100                 105                 110

Thr Leu Val Thr Val Ser Ser
        115

<210> SEQ ID NO 347
<211> LENGTH: 112
<212> TYPE: PRT
<213> ORGANISM: Artificial Sequence
```

```
<220> FEATURE:
<223> OTHER INFORMATION: an artificial synthesized sequence

<400> SEQUENCE: 347

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Tyr Leu Leu Thr Phe Gly Gln Gly Thr Lys Val Glu Ile Lys
            100                 105                 110

<210> SEQ ID NO 348
<211> LENGTH: 120
<212> TYPE: PRT
<213> ORGANISM: Artificial Sequence
<220> FEATURE:
<223> OTHER INFORMATION: an artificial synthesized sequence

<400> SEQUENCE: 348

Glu Val Gln Leu Val Glu Ser Gly Gly Gly Val Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Glu Lys Gly Leu Glu Trp Val
        35                  40                  45

Gly Arg Ile Arg Ser Arg Ala Asn Ser Tyr Ala Thr Ala Tyr Ala Ala
50                  55                  60

Ser Val Lys Asp Arg Phe Thr Ile Ser Arg Asp Asn Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Ile Arg Asp Thr Met Val Arg Gly Ile Asp Tyr Trp Gly Gln
            100                 105                 110

Gly Thr Leu Val Thr Val Ser Ser
        115                 120

<210> SEQ ID NO 349
<211> LENGTH: 113
<212> TYPE: PRT
<213> ORGANISM: Artificial Sequence
<220> FEATURE:
<223> OTHER INFORMATION: an artificial synthesized sequence

<400> SEQUENCE: 349

Asp Ile Gln Met Thr Gln Ser Pro Ser Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Leu Gly Gln
        35                  40                  45
```

Pro Pro Lys Leu Leu Ile Tyr Arg Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Val Pro Trp Thr Phe Gly Gln Gly Thr Lys Val Glu Ile
                100                 105                 110

Lys

<210> SEQ ID NO 350
<211> LENGTH: 117
<212> TYPE: PRT
<213> ORGANISM: Artificial Sequence
<220> FEATURE:
<223> OTHER INFORMATION: an artificial synthesized sequence

<400> SEQUENCE: 350

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Asp
                20                  25                  30

Tyr Ile His Trp Met Arg Gln Arg Pro Gly Gln Gly Leu Glu Trp Ile
            35                  40                  45

Gly Trp Ile Tyr Phe Gly Asn Val Asn Thr Lys Tyr Asn Glu Lys Phe
    50                  55                  60

Lys Gly Lys Ala Ile Leu Thr Ala Asp Lys Phe Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Gly Gly Tyr Tyr Phe Asp Tyr Trp Gly Gln Gly Thr Thr
                100                 105                 110

Leu Thr Val Ser Ser
        115

<210> SEQ ID NO 351
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 351

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Thr Leu Arg Thr Phe Gly Gln Gly Thr Lys Val Glu Ile Lys
                100                 105                 110

```
<210> SEQ ID NO 352
<211> LENGTH: 117
<212> TYPE: PRT
<213> ORGANISM: Artificial Sequence
<220> FEATURE:
<223> OTHER INFORMATION: an artificial synthesized sequence

<400> SEQUENCE: 352

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser His
            20                  25                  30

Tyr Leu His Trp Val Lys Gln Ser Pro Gly Gln Gly Leu Glu Trp Ile
        35                  40                  45

Val Trp Ile Asn Pro Gly Asp Gly Asn Val Lys Tyr Asn Glu Lys Phe
    50                  55                  60

Lys Asp Lys Thr Thr Val Thr Ala Asp Arg Ser Ser Thr Thr Val His
65                  70                  75                  80

Met Phe Leu Ser Ser Leu Thr Ser Glu Asp Ser Ala Ile Tyr Phe Cys
                85                  90                  95

Ala Arg Asp Gly Ala Tyr Tyr Phe Asp Tyr Trp Gly Gln Gly Thr Thr
            100                 105                 110

Leu Thr Val Ser Ser
        115

<210> SEQ ID NO 353
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 353

Asp Ile Val Met Thr Gln Ser Pro Ser Ser Leu Ala Val Ser Ala Gly
1               5                   10                  15

Glu Thr Val Thr Met Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Thr Val Gln Ala Glu Asp Leu Ala Val Tyr Tyr Cys Lys Gln
                85                  90                  95

Ser Tyr Thr Leu Arg Thr Phe Gly Gln Gly Thr Lys Val Glu Ile Lys
            100                 105                 110

<210> SEQ ID NO 354
<211> LENGTH: 117
<212> TYPE: PRT
<213> ORGANISM: Artificial Sequence
<220> FEATURE:
<223> OTHER INFORMATION: an artificial synthesized sequence

<400> SEQUENCE: 354

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
```

```
            20                  25                  30
Tyr Ile His Trp Val Lys Gln Arg Pro Gly Gln Gly Leu Glu Trp Ile
        35                  40                  45

Gly Trp Ile Phe Pro Gly Ser Asp Asn Thr Lys Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asn Gly Asn Tyr Ala Met Asp Tyr Trp Gly Gln Gly Thr Ser
            100                 105                 110

Val Thr Val Ser Ser
            115

<210> SEQ ID NO 355
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 355

Glu Ile Val Leu Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Thr Leu Arg Thr Phe Gly Gly Gly Thr Lys Leu Glu Ile Lys
            100                 105                 110

<210> SEQ ID NO 356
<211> LENGTH: 117
<212> TYPE: PRT
<213> ORGANISM: Artificial Sequence
<220> FEATURE:
<223> OTHER INFORMATION: an artificial synthesized sequence

<400> SEQUENCE: 356

Glu Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Tyr
            20                  25                  30

Tyr Ile His Trp Met Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Gly Lys Ala Thr Leu Thr Ala Asp Asn Ser Ser Ser Thr Ala Asn
65                  70                  75                  80

Met Gln Leu Ser Ser Leu Thr Ser Glu Asp Ser Ala Val Tyr Phe Cys
                85                  90                  95
```

Ala Arg Asn His Asp Tyr Tyr Phe Asp Tyr Trp Gly Gln Gly Thr Thr
            100                 105                 110

Leu Thr Val Ser Ser
        115

<210> SEQ ID NO 357
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 357

Gly Ile Val Met Thr Gln Ser Pro Ser Ser Leu Ala Val Ser Ala Gly
1               5                   10                  15

Glu Lys Val Thr Met Ser Cys Lys Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Ile Leu Arg Thr Phe Gly Gly Gly Thr Lys Leu Glu Ile Lys
            100                 105                 110

<210> SEQ ID NO 358
<211> LENGTH: 120
<212> TYPE: PRT
<213> ORGANISM: Artificial Sequence
<220> FEATURE:
<223> OTHER INFORMATION: an artificial synthesized sequence

<400> SEQUENCE: 358

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Lys Pro Thr Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Gly Asp Tyr Arg Tyr Ala Trp Phe Thr Tyr Trp Gly Gln
            100                 105                 110

Gly Thr Leu Val Thr Val Ser Ala
            115                 120

<210> SEQ ID NO 359
<211> LENGTH: 108
<212> TYPE: PRT
<213> ORGANISM: Artificial Sequence
<220> FEATURE:
<223> OTHER INFORMATION: an artificial synthesized sequence

```
<400> SEQUENCE: 359

Gln Ala Val Val Thr Gln Glu Ser Ala Leu Thr Thr Ser Pro Gly Gly
1               5                   10                  15

Thr Val Ile Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Ser Asn Arg Ala Pro Gly Val Pro Val Arg Phe
    50                  55                  60

Ser Gly Ser Leu Ile Gly Asp Lys Ala Ala Leu Thr Ile Thr Gly Ala
65              70                  75                  80

Gln Thr Glu Asp Asp Ala Met Tyr Phe Cys Ala Leu Trp Tyr Ser Thr
            85                  90                  95

His Phe Val Phe Gly Gly Gly Thr Lys Val Thr Val
            100                 105

<210> SEQ ID NO 360
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 360

Glu Val Gln Leu Gln Gln Ser Gly Pro Glu Leu Val Lys Pro Gly Thr
1               5                   10                  15

Ser Val Lys Ile Ser Cys Lys Ala Ser Gly Phe Ser Phe Thr Asn Tyr
            20                  25                  30

Tyr Ile His Trp Met Lys Gln Arg Pro Gly Gln Gly Leu Glu Trp Ile
        35                  40                  45

Gly Trp Ile Tyr Pro Gly Ser Asp Asn Thr Lys Phe Asn Asp Lys Phe
    50                  55                  60

Lys Gly Lys Ala Thr Leu Thr Ala Asp Thr Ser Ser Thr Thr Ala Tyr
65              70                  75                  80

Met Gln Leu Ser Ser Leu Thr Ser Glu Asp Ser Ala Val Tyr Tyr Cys
            85                  90                  95

Ala Arg Asp Ser Ile Thr Asn Tyr Tyr Phe Asp Tyr Trp Gly Gln Gly
            100                 105                 110

Thr Thr Leu Thr Val Ser Ser
        115

<210> SEQ ID NO 361
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 361

Asp Val Val Met Thr Gln Thr Pro Ser Ser Leu Ala Val Ser Thr Gly
1               5                   10                  15

Glu Lys Val Thr Met Thr Cys Lys Ser Ser Gln Ser Leu Leu Asn Ile
            20                  25                  30

Arg Thr Arg Lys Asn Cys Leu Ala Trp Tyr Gln Gln Lys Pro Gly Gln
        35                  40                  45

Ser Pro Lys Leu Leu Ile Phe Trp Ala Ser Thr Arg Tyr Ser Gly Val
    50                  55                  60
```

-continued

Pro Asp Arg Phe Thr Gly Ser Gly Ser Gly Thr Asp Phe Thr Leu Thr
 65                  70                  75                  80

Ile Arg Ser Val Gln Pro Glu Asp Leu Ala Val Tyr Tyr Cys Thr Gln
                 85                  90                  95

Ser Tyr Thr Leu Arg Thr Phe Gly Gly Gly Thr Lys Leu Glu Ile Lys
            100                 105                 110

<210> SEQ ID NO 362
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 362

Gln Val Gln Leu Gln Gln Ser Gly Ser Glu Leu Val Arg Pro Gly Ala
 1               5                  10                  15

Ser Leu Lys Leu Ser Cys Lys Ala Ser Gly Tyr Thr Phe Thr Ser Tyr
                20                  25                  30

Trp Met His Trp Val Arg Gln Arg Pro Gly Gln Gly Leu Glu Trp Ile
             35                  40                  45

Gly Asn Phe Tyr Pro Gly Asp Leu Thr Val Asn Tyr Asp Glu Lys Phe
 50                  55                  60

Lys Asn Lys Val Thr Leu Ala Val Asp Thr Ser Ser Thr Ala Phe
 65                  70                  75                  80

Leu Gln Leu Ser Ser Leu Thr Ser Glu Asp Ser Ala Val Tyr Tyr Cys
                85                  90                  95

Thr Arg Asp Ala Tyr Ser Arg Tyr Phe Phe Asp Tyr Trp Gly Gln Gly
            100                 105                 110

Thr Thr Leu Thr Val Ser Ser
        115

<210> SEQ ID NO 363
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 363

Asp Ile Val Met Thr Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Thr Glu Asp Leu Ala Val Tyr Tyr Cys Cys Gln
                 85                  90                  95

Ser Phe Ile Leu Arg Thr Phe Gly Gly Gly Thr Lys Leu Glu Ile Lys
            100                 105                 110

<210> SEQ ID NO 364
<211> LENGTH: 119
<212> TYPE: PRT
<213> ORGANISM: Artificial Sequence

```
<220> FEATURE:
<223> OTHER INFORMATION: an artificial synthesized sequence

<400> SEQUENCE: 364

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asn Tyr
            20                  25                  30

Tyr Met His Trp Val Lys Gln Arg Pro Gly Gln Gly Leu Glu Trp Ile
        35                  40                  45

Gly Trp Ile Ser Pro Gly Ser Gly Ser Ile Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Tyr Ser Leu Tyr Phe Phe Asp Phe Trp Gly Gln Gly
            100                 105                 110

Thr Thr Leu Thr Val Ser Ser
            115

<210> SEQ ID NO 365
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 365

Asp Ile Val Met Thr Gln Ser Pro Ser Ser Leu Ala Val Ser Ala Gly
1               5                   10                  15

Glu Lys Val Thr Met Thr Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Ile Leu Arg Thr Phe Gly Gly Gly Thr Lys Leu Glu Leu Lys
            100                 105                 110

<210> SEQ ID NO 366
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 366

Gln Val Gln Leu Gln Gln Ser Gly Pro Glu Leu Val Lys Pro Gly Thr
1               5                   10                  15

Ser Val Lys Ile Ser Cys Lys Thr Ser Gly Tyr Ser Phe Ile Asn Tyr
            20                  25                  30

Tyr Thr His Trp Val Lys Gln Arg Pro Gly Gln Gly Leu Glu Trp Ile
        35                  40                  45
```

Gly Trp Ile Tyr Pro Gly Asn Gly Asn Ile Lys Tyr Asn Glu Lys Phe
        50                  55                  60

Met Gly Lys Ala Thr Leu Thr Ala Asp Thr Ser Ser Thr Thr Ala His
65                  70                  75                  80

Met His Leu Ser Ser Leu Val Ser Glu Asp Ser Ala Val Tyr Tyr Cys
                85                  90                  95

Ala Arg Asp Ser Tyr Gly Ser Tyr Tyr Phe Asp Tyr Trp Gly Gln Gly
                100                 105                 110

Thr Thr Leu Thr Val Ser Ser
            115

<210> SEQ ID NO 367
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 367

Asp Ile Val Met Thr Gln Ser Pro Ser Ser Leu Ala Val Ser Val Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Val Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Phe Ile Leu Arg Thr Phe Gly Gly Gly Thr Lys Leu Glu Ile Lys
                100                 105                 110

<210> SEQ ID NO 368
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 368

Gln Val Gln Leu Gln Gln Ser Gly Pro Glu Leu Val Lys Pro Gly Thr
1               5                   10                  15

Ser Val Lys Ile Ser Cys Lys Thr Ser Gly Tyr Asn Phe Ile Asn Tyr
                20                  25                  30

Tyr Thr His Trp Val Lys Gln Arg Pro Gly Gln Gly Leu Glu Trp Ile
            35                  40                  45

Gly Trp Ile Tyr Pro Gly Asn Gly Asn Ile Lys Tyr Asn Glu Lys Phe
        50                  55                  60

Met Gly Lys Ala Thr Leu Thr Ala Asp Thr Ser Ser Thr Thr Ala His
65                  70                  75                  80

Met His Leu Ser Ser Leu Val Ser Glu Asp Ser Ala Val Tyr Tyr Cys
                85                  90                  95

Ala Arg Asp Ser Tyr Gly Ser Tyr Tyr Phe Asp Tyr Trp Gly Gln Gly
                100                 105                 110

Thr Thr Leu Thr Val Ser Ser
            115

<210> SEQ ID NO 369
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 369

```
Asp Ile Val Met Thr Gln Ser Pro Ser Ser Leu Ala Val Ser Ala Gly
1               5                   10                  15

Glu Lys Val Thr Met Thr Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Ile Leu Arg Thr Phe Gly Gly Gly Thr Lys Leu Glu Ile Lys
            100                 105                 110
```

<210> SEQ ID NO 370
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 370

```
Gln Val Gln Leu Gln Gln Ser Gly Pro Glu Leu Val Lys Pro Gly Ala
1               5                   10                  15

Ser Leu Lys Ile Ser Cys Lys Ala Ser Gly Tyr Ser Phe Ala Asn Tyr
            20                  25                  30

Tyr Thr His Trp Val Arg Gln Arg Pro Gly Gln Gly Leu Glu Trp Ile
        35                  40                  45

Gly Trp Leu Tyr Pro Gly Asn Gly Asp Thr Arg Tyr Asn Glu Lys Phe
    50                  55                  60

Lys Asp Lys Ala Thr Leu Thr Ala Asp Thr Ser Ser Asn Thr Ala Ser
65                  70                  75                  80

Met Gln Leu Asn Ser Leu Thr Ser Glu Asp Ser Ala Val Tyr Tyr Cys
                85                  90                  95

Thr Arg Asp Ser Tyr Gly Asn Tyr Phe Phe Asp Tyr Trp Gly Gln Gly
            100                 105                 110

Thr Thr Leu Ile Val Ser Ser
        115
```

<210> SEQ ID NO 371
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 371

```
Asp Ile Val Met Thr Gln Ser Pro Ser Ser Leu Ala Val Ser Ala Gly
1               5                   10                  15
```

```
Glu Lys Val Thr Met Ser Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Ser Pro Lys Leu Leu Ile Phe Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Phe Ile Leu Arg Thr Phe Gly Gly Gly Thr Lys Leu Glu Leu Lys
            100                 105                 110
```

<210> SEQ ID NO 372
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 372

```
Gln Val Gln Leu Gln Gln Ser Gly Ser Glu Leu Val Arg Pro Gly Ala
1               5                   10                  15

Ser Leu Lys Leu Ser Cys Lys Ala Ser Gly Tyr Thr Phe Thr Ser Tyr
             20                  25                  30

Trp Met His Trp Val Arg Gln Arg Pro Gly Gln Gly Leu Glu Trp Ile
         35                  40                  45

Gly Asn Ser Tyr Pro Gly Asp Leu Asn Val Asn Tyr Asp Glu Lys Phe
 50                  55                  60

Lys Asn Lys Val Thr Leu Ala Val Asp Thr Ser Ser Ser Thr Ala Phe
 65                  70                  75                  80

Leu Gln Leu Ser Ser Leu Thr Ser Glu Asp Ser Ala Val Tyr Tyr Cys
                 85                  90                  95

Thr Arg Asp Ala Tyr Ser Arg Tyr Phe Phe Asp Tyr Trp Gly Gln Gly
            100                 105                 110

Thr Thr Leu Thr Val Ser Ser
        115
```

<210> SEQ ID NO 373
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 373

```
Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Thr Glu Asp Leu Ala Val Tyr Tyr Cys Cys Gln
                 85                  90                  95
```

Ser Phe Ile Leu Arg Thr Phe Gly Gly Gly Thr Lys Leu Glu Ile Lys
                100                 105                 110

<210> SEQ ID NO 374
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 374

Gln Val Gln Leu Gln Gln Ser Gly Pro Glu Met Val Lys Pro Gly Ala
1               5                   10                  15

Ser Val Thr Ile Ser Cys Lys Thr Ser Gly Phe Thr Phe Thr Ser Tyr
            20                  25                  30

Tyr Ile His Trp Met Met Gln Arg Pro Gly Gln Gly Leu Glu Trp Ile
        35                  40                  45

Gly Trp Leu Tyr Pro Gly Asp Val Ser Thr Arg Tyr Asn Glu Lys Phe
    50                  55                  60

Arg Asp Lys Ala Thr Leu Thr Ala Asp Lys Ser Ser Thr Thr Ala Tyr
65                  70                  75                  80

Leu Tyr Leu Ser Ser Leu Thr Ser Glu Asp Ser Ala Val Tyr Phe Cys
                85                  90                  95

Ala Arg Asp Ser Ser Ala Ser Tyr Tyr Phe Asp Phe Trp Gly Gln Gly
                100                 105                 110

Thr Thr Leu Thr Val Ser Ser
        115

<210> SEQ ID NO 375
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 375

Asp Ile Val Met Thr Gln Ser Pro Ser Ser Leu Ala Val Ser Ala Gly
1               5                   10                  15

Glu Met Val Thr Leu His Cys Lys Ser Ser Gln Ser Leu Leu Asn Ile
            20                  25                  30

Arg Thr Arg Lys Asn Tyr Leu Ala Trp Tyr Leu Gln Lys Pro Gly Gln
        35                  40                  45

Ser Pro Arg Leu Leu Ile Tyr Trp Ala Ser Thr Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Val Tyr Tyr Cys Thr Gln
                85                  90                  95

Ser Phe Ile Leu Arg Thr Phe Gly Gly Gly Thr Lys Leu Glu Leu Lys
                100                 105                 110

<210> SEQ ID NO 376
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 376

Gln Val Gln Leu Gln Gln Pro Gly Ser Glu Leu Val Arg Pro Gly Ala
1               5                   10                  15

Ser Val Thr Leu Ser Cys Thr Ala Ser Gly Tyr Ser Phe Thr Ser Tyr
            20                  25                  30

Trp Met His Trp Val Lys Gln Arg Pro Gly Gln Gly Leu Glu Trp Val
        35                  40                  45

Gly Asn Ile Tyr Pro Gly Gly Glu Ile Ile Asn Tyr Ala Glu Lys Phe
    50                  55                  60

Lys Thr Lys Gly Thr Leu Thr Val Asp Ile Ser Ser Thr Ala Tyr
65                  70                  75                  80

Met His Leu Ser Ser Leu Thr Ser Asp Asp Ser Ala Val Tyr Tyr Cys
                85                  90                  95

Thr Arg Asp Thr Thr Gly Asn Tyr Phe Phe Asp Tyr Trp Gly Gln Gly
                100                 105                 110

Thr Thr Leu Thr Val Ser Ser
            115

<210> SEQ ID NO 377
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 377

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Leu
        35                  40                  45

Ser Pro Lys Leu Leu Ile Tyr Trp Ala Ser Arg Glu Ser Gly Val
    50                  55                  60

Pro Glu Arg Phe Thr Gly Ser Gly Ser Gly Thr Asp Phe Thr Leu Thr
65                  70                  75                  80

Ile Ser Ser Val Gln Thr Glu Asp Leu Ala Val Tyr Tyr Cys Thr Gln
                85                  90                  95

Ser Phe Ile Leu Arg Thr Phe Gly Gly Gly Thr Arg Leu Glu Ile Lys
                100                 105                 110

<210> SEQ ID NO 378
<211> LENGTH: 116
<212> TYPE: PRT
<213> ORGANISM: Artificial Sequence
<220> FEATURE:
<223> OTHER INFORMATION: an artificial synthesized sequence

<400> SEQUENCE: 378

Gln Ser Val Lys Glu Ser Glu Gly Gly Leu Phe Lys Pro Thr Asp Thr
1               5                   10                  15

Leu Thr Leu Thr Cys Thr Val Ser Gly Cys Ser Leu Ser Ser Cys Ala
            20                  25                  30

Ile Ser Trp Val Arg Gln Ala Pro Gly Lys Gly Leu Glu Trp Ile Gly
        35                  40                  45

Phe Met Ser Val Thr Gly Ser Ala Tyr Tyr Ala Asn Trp Ala Lys Ser
    50                  55                  60

Arg Ser Thr Ile Thr Arg Asn Thr Asn Glu Asn Thr Val Thr Leu Lys
65                  70                  75                  80

```
Met Thr Arg Leu Thr Ala Ala Asp Thr Ala Ile Tyr Phe Cys Ala Arg
            85                  90                  95

Val Gly Ile Gly Ser Gly Leu Asn Ile Trp Gly Gln Gly Thr Leu Val
            100                 105                 110

Thr Val Ser Ser
        115

<210> SEQ ID NO 379
<211> LENGTH: 110
<212> TYPE: PRT
<213> ORGANISM: Artificial Sequence
<220> FEATURE:
<223> OTHER INFORMATION: an artificial synthesized sequence

<400> SEQUENCE: 379

Asp Met Thr Gln Thr Pro Ser Ser Lys Ser Val Pro Val Gly Asp Thr
1               5                   10                  15

Val Thr Ile Asn Cys Gln Ala Ser Glu Thr Val Tyr Ser Asn Asn Tyr
            20                  25                  30

Leu Ala Trp Phe Gln Gln Lys Pro Gly Gln Pro Pro Lys Arg Leu Ile
        35                  40                  45

Tyr Gly Val Ser Thr Leu Asp Ser Gly Val Pro Pro Arg Phe Ser Gly
    50                  55                  60

Ser Gly Ser Gly Thr Gln Phe Thr Leu Thr Ile Ser Asp Val Val Cys
65                  70                  75                  80

Asp Asp Ala Ala Thr Tyr Tyr Cys Ala Gly Tyr Lys Thr Ser Ser Ser
                85                  90                  95

Tyr Ala Ile Ala Phe Gly Gly Gly Thr Glu Leu Glu Ile Leu
            100                 105                 110

<210> SEQ ID NO 380
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 380

Gln Val Gln Leu Gln Gln Ser Gly Pro Glu Leu Val Lys Pro Gly Ala
1               5                   10                  15

Ser Val Thr Ile Ser Cys Thr Ala Ser Gly Phe Thr Phe Thr Ser Tyr
            20                  25                  30

Tyr Ile His Trp Val Arg Gln Arg Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Thr Leu Thr Val Ser Ser
        115

<210> SEQ ID NO 381
<211> LENGTH: 112
<212> TYPE: PRT
```

```
<213> ORGANISM: Artificial Sequence
<220> FEATURE:
<223> OTHER INFORMATION: an artificial synthesized sequence

<400> SEQUENCE: 381

Asp Ile Val Met Thr Gln Ser Pro Ser Phe Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Arg Pro Gly Gln
        35                  40                  45

Ser Pro Lys Leu Leu Ile Tyr Trp Thr Ser Thr Arg Lys Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Lys Gln
                85                  90                  95

Ser Phe Ile Leu Arg Thr Phe Gly Gly Gly Thr Lys Leu Glu Ile Lys
            100                 105                 110

<210> SEQ ID NO 382
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 382

Glu Val Gln Leu Val Gln Ser Gly Ala Glu Val Lys Lys Pro Gly Ala
1               5                   10                  15

Ser Val Ile Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Arg Lys Tyr Asn Glu Lys Phe
50                  55                  60

Lys Asp Arg Val Thr Ile Ser Ala Asp Thr Ser Glu Ser Phe Ala Tyr
65                  70                  75                  80

Leu Gln Leu His Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 383
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 383

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45
```

Ser Pro Lys Leu Leu Ile Tyr Trp Thr Ser Thr Arg Lys Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
                100                 105                 110

<210> SEQ ID NO 384
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 384

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
                20                  25                  30

Tyr Ile His Trp Val Arg Gln Ala Pro Gly Gln Gly Leu Glu Trp Ile
            35                  40                  45

Gly Trp Ile Tyr Pro Glu Asn Asp Asn Arg Lys Tyr Asn Glu Lys Phe
        50                  55                  60

Lys Asp Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
                100                 105                 110

Thr Leu Val Thr Val Ser Ser
            115

<210> SEQ ID NO 385
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 385

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Thr Ser Thr Arg Lys Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
                100                 105                 110

```
<210> SEQ ID NO 386
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 386
```

Gln Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asn Tyr
            20                  25                  30

Tyr Ile His Trp Val Arg Gln Arg Pro Gly Gln Gly Leu Glu Trp Ile
        35                  40                  45

Gly Trp Ile Tyr Pro Gly Asp Val Ser Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Leu Leu Ser Gly Leu Thr Ser Glu Asp Ser Ala Ile Tyr Phe Cys
                85                  90                  95

Ala Arg Asp Gly Tyr Ser Phe Tyr Tyr Phe Asp Tyr Trp Gly Gln Gly
            100                 105                 110

Thr Thr Leu Thr Val Ser Ser
        115

```
<210> SEQ ID NO 387
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 387
```

Asp Ile Val Leu Thr Gln Ser Pro Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Thr Trp Tyr Gln Gln Lys Pro Gly Gln
        35                  40                  45

Ser Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Tyr Thr Leu Arg Thr Phe Gly Gly Gly Thr Lys Leu Glu Ile Lys
            100                 105                 110

```
<210> SEQ ID NO 388
<211> LENGTH: 119
<212> TYPE: PRT
<213> ORGANISM: Artificial Sequence
<220> FEATURE:
<223> OTHER INFORMATION: an artificial synthesized sequence

<400> SEQUENCE: 388
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
            35                  40                  45

Gly Trp Ile Tyr Pro Gly Asp Val Ser Thr Lys Tyr Asn Glu Lys Phe
 50                  55                  60

Lys Gly Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Gly Tyr Ser Phe Tyr Tyr Phe Asp Tyr Trp Gly Gln Gly
            100                 105                 110

Thr Leu Val Thr Val Ser Ser
            115

<210> SEQ ID NO 389
<211> LENGTH: 112
<212> TYPE: PRT
<213> ORGANISM: Artificial Sequence
<220> FEATURE:
<223> OTHER INFORMATION: an artificial synthesized sequence

<400> SEQUENCE: 389

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
             20                  25                  30

Arg Thr Arg Lys Asn Tyr Leu Thr Trp Tyr Gln Gln Lys Pro Gly Gln
         35                  40                  45

Pro Pro Lys Leu Leu Ile Tyr Trp Ala Ser Thr Arg Asp Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Thr Gln
                 85                  90                  95

Ser Tyr Thr Leu Arg Thr Phe Gly Gln Gly Thr Lys Val Glu Ile Lys
            100                 105                 110

<210> SEQ ID NO 390
<211> LENGTH: 125
<212> TYPE: PRT
<213> ORGANISM: Artificial Sequence
<220> FEATURE:
<223> OTHER INFORMATION: an artificial synthesized sequence

<400> SEQUENCE: 390

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
             20                  25                  30

Ala Met Asn Trp Val Arg Gln Ala Pro Gly Lys Gly Leu Glu Trp Val
             35                  40                  45

Gly Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

```
Ala Tyr Trp Gly Gln Gly Thr Leu Val Thr Val Ser Ser
        115                 120                 125

<210> SEQ ID NO 391
<211> LENGTH: 109
<212> TYPE: PRT
<213> ORGANISM: Artificial Sequence
<220> FEATURE:
<223> OTHER INFORMATION: an artificial synthesized sequence

<400> SEQUENCE: 391

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

CYTOTOXICITY-INDUCING THERAPEUTIC AGENT

CROSS-REFERENCE TO RELATED APPLICATIONS

This application is a U.S. National Phase of PCT Application No. PCT/JP2018/048409, filed Dec. 28, 2018, which claims the benefit of Japanese Patent Application No. 2017-254279, filed Dec. 28, 2017, each of which is incorporated herein by reference in its entirety.

REFERENCE TO SEQUENCE LISTING SUBMITTED ELECTRONICALLY

The content of the electronically submitted sequence listing (Name: 6663_0142 Sequence Listing.txt; Size: 288 kilobytes; and Date of Creation: Jun. 24, 2020) filed with the application is incorporated herein by reference in its entirety.

The present invention relates to multispecific antigen-binding molecules that comprise a first domain comprising a first antigen-binding domain binds to human DLL3 and a second domain comprising a second antigen-binding domain binds to T cell receptor complex, uses thereof, and such. The present invention also relates to novel monospecific antigen-binding molecules that comprise an antigen-binding domain binds to human DLL3, uses thereof, and such.

BACKGROUND ART

Cancer is one of the leading causes of death worldwide. With the exception of certain carcinomas, tumors are often inoperable when they are found. Conventional cancer treatments include radiation therapy, chemotherapy, and immunotherapy. These treatments are often not effective enough and eventually cancer recurrence or metastasis occurs after the treatment. Lack of tumor specificity is one of the factors that limit the maximum efficacy; therefore, more tumor-specific molecular targeted therapy has become an additional viable option in cancer treatment.

Antibodies are drawing attention as pharmaceuticals since they are highly stable in plasma and have few side effects. Among multiple therapeutic antibodies, some types of antibodies require effector cells to exert an anti-tumor response. Antibody dependent cell-mediated cytotoxicity (ADCC) is a cytotoxicity exhibited by effector cells against antibody-bound cells via binding of the Fc region of the antibody to Fc receptors present on NK cells and macrophages. To date, multiple therapeutic antibodies that can induce ADCC to exert anti-tumor efficacy have been developed as pharmaceuticals for treating cancer (NPL 1). Therapies targeting tumor-specific expressed antigens using conventional therapeutic antibodies show excellent anti-tumor activities, while administration of such antibodies could not always lead to satisfactory outcomes.

In addition to the antibodies that adopt ADCC by recruiting NK cells or macrophages as effector cells, T cell-recruiting antibodies (TR antibodies) that adopt cytotoxicity by recruiting T cells as effector cells have been known since the 1980s (NPL 2 to 4). A TR antibody is a bispecific antibody that recognizes and binds to any one of the subunits forming a T-cell receptor complex on T-cells, in particular the CD3 epsilon chain, and an antigen on cancer cells. Several TR antibodies are currently being developed. Catumaxomab, which is a TR antibody against EpCAM, has been approved in the EU for the treatment of malignant ascites. Furthermore, a type of TR antibody called "bispecific T-cell engager (BiTE)" has been recently found to exhibit a strong anti-tumor activity (NPL 5 and 6). Blinatumomab, which is a BiTE molecule against CD19, received FDA approval first in 2014. Blinatumomab has been proved to exhibit a much stronger cytotoxic activity against CD19/CD20-positive cancer cells in vitro compared with Rituximab, which induces antibody-dependent cell-mediated cytotoxicity (ADCC) and complement-dependent cytotoxicity (CDC) (NPL 7).

However, it is known that a trifunctional antibody binds to both a T-cell and a cell such as an NK cell or macrophage at the same time in a cancer antigen-independent manner, and as a result receptors expressed on the cells are cross-linked, and expression of various cytokines is induced in a cancer antigen-independent manner. Systemic administration of a trifunctional antibody is thought to cause cytokine storm-like side effects as a result of such induction of cytokine expression. In fact, it has been reported that, in the phase I clinical trial, a very low dose of 5 micrograms (micro g)/body was the maximum tolerance dose for systemic administration of catumaxomab to patients with non-small cell lung cancer, and that administration of a higher dose causes various severe side effects (NPL 8). When administered at such a low dose, catumaxomab can never reach the effective blood level. That is, the expected anti-tumor effect cannot be achieved by administrating catumaxomab at such a low dose.

Meanwhile, unlike catumaxomab, BiTE has no Fc gamma receptor-binding site, and therefore it does not cross-link the receptors expressed on T-cells and cells such as NK cells and macrophages in a cancer antigen-independent manner. Thus, it has been demonstrated that BiTE does not cause cancer antigen-independent cytokine induction which is observed when catumaxomab is administered. However, since BiTE is a modified low-molecular-weight antibody molecule without an Fc region, the problem is that its blood half-life after administration to a patient is significantly shorter than IgG-type antibodies conventionally used as therapeutic antibodies. In fact, the blood half-life of BiTE administered in vivo has been reported to be about several hours (NPL 9 and 10). In the clinical trials of blinatumomab, it is administered by continuous intravenous infusion using a minipump. This administration method is not only extremely inconvenient for patients but also has the potential risk of medical accidents due to device malfunction or the like. Thus, it cannot be said that such an administration method is desirable.

Delta-like 3 (DLL3) is a type I membrane protein belonging to Notch ligand family members. DLL3 is necessary for normal somite formation and patterning. Mutations in DLL3 cause rib defects or spondylolysis in autosomal recessive spondylocostal dysostosis patients (NPL 11 and 12). There exist previous studies reporting the amplification of the DLL3 gene on chromosome and increased expression of this gene in pancreatic cancer cell lines (NPL 13) and increased DLL3 expression in some glioma cases (NPL 14). In addition, DLL3 has been proposed previously in methods to diagnose and treat glioma, in addition to SCLC, using an ADCC enhanced antibody, antibody-drug conjugate (ADC), and T cell-engaging bispecific molecule using BiTE-Fc format (PTL 1, 2 and 3).

CITATION LIST

Patent Literature

[PTL 1] WO 2011/093097
[PTL 2] WO 2013/126746
[PTL 3] WO 2017/021349

Non-Patent Literature

[NPL 1] Clin Cancer Res. 2010 Jan. 1; 16(1):11-20.
[NPL 2] Nature. 1985 Apr. 18-24; 314(6012):628-31.
[NPL 3] Int J Cancer. 1988 Apr. 15; 41(4):609-15.
[NPL 4] Proc Natl Acad Sci USA. 1986 March; 83(5):1453-7.
[NPL 5] Proc Natl Acad Sci USA. 1995 Jul. 18; 92(15):7021-5.
[NPL 6] Drug Discov Today. 2005 Sep. 15; 10(18):1237-44.
[NPL 7] Int J Cancer. 2002 Aug. 20; 100(6):690-7.
[NPL 8] Cancer Immunol Immunother (2007) 56 (10), 1637-44.
[NPL 9] Cancer Immunol Immunother. (2006) 55 (5), 503-14.
[NPL 10] Cancer Immunol Immunother. (2009) 58 (1), 95-109.
[NPL 11] Bulman, M. P. et al. (2000) Nat Genet 24, 438-441.
[NPL 12] Tumpenny, P. D. et al. (2003) J Med Genet 40, 333-339.
[NPL 13] Phillips, H. S. (2006) Cancer Cell 9, 157-173.
[NPL 14] Mullendnore, M. E. (2009) Clin Cancer Res 15, 2291-2301.

SUMMARY OF INVENTION

Technical Problem

An objective of the present invention is to provide multispecific antigen-binding molecules that enable cancer treatment by having T cells close to DLL3-expressing cells and using the cytotoxicity of T cells against DLL3-expressing cancer cells, methods for producing the multispecific antigen-binding molecules, and therapeutic agents comprising such a multispecific antigen-binding molecule as an active ingredient for inducing cellular cytotoxicity. Another objective of the present invention is to provide pharmaceutical compositions for use in treating or preventing various cancers, which comprise one of the above-mentioned antigen-binding molecules as an active ingredient, and therapeutic methods using the pharmaceutical compositions. Another objective of the present invention is to provide novel monospecific antigen-binding molecules having human DLL3-binding activity, therapeutic agents comprising such a monospecific antigen-binding molecule as an active ingredient, and therapeutic methods using such a therapeutic agent.

Solution to Problem

The inventors found that multispecific antigen-binding molecules that comprise a first domain comprising a first antigen-binding domain binds to human DLL3, and a second domain comprising a second antigen-binding domain binds to T-cell receptor complex can damage cells expressing DLL3, and exert a superior cytotoxic/antitumor activity. The present invention provides the multispecific antigen-binding molecules and pharmaceutical compositions that can treat various cancers, especially those associated with DLL3 such as DLL3-positive tumors, by comprising the antigen-binding molecule as an active ingredient. The present invention also provides novel monospecific antigen-binding molecules that comprise an antigen-binding domain binds to human DLL3, and pharmaceutical compositions comprising such antigen-binding molecules.

More specifically, the present invention provides the following:

[1] A multispecific antigen-binding molecule that comprises:
    (1) a first domain comprising a first antigen-binding domain binds to human DLL3, and
    (2) a second domain comprising a second antigen-binding domain binds to T-cell receptor complex, wherein the first antigen-binding domain of (1) binds to an epitope within the region defined in SEQ ID NO: 7 in human DLL3.

[2] A multispecific antigen-binding molecule that comprises:
    (1) a first domain comprising a first antigen-binding domain binds to human DLL3, and
    (2) a second domain comprising a second antigen-binding domain binds to T-cell receptor complex, wherein the first antigen-binding domain of (1) comprises any one of (a1) to (a12) below:
    (a1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
    (a2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;
    (a3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;
    (a4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;
    (a5) an antibody variable fragment comprising the HVR-H1 sequence of SEQ ID NO: 51, the HVR-H2 sequence of SEQ ID NO: 52, the HVR-H3 sequence of SEQ ID NO: 53, the HVR-L1 sequence of SEQ ID NO: 54, the HVR-L2 sequence of SEQ ID NO: 55, and the HVR-L3 sequence of SEQ ID NO: 56;
    (a6) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
    (a7) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
    (a8) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;
    (a9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38;

(a10) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81;

(a11) an antibody variable fragment that binds to the same epitope of any of the antibody variable fragment selected from (a1) to (a10);

(a12) an antibody variable fragment that competes with the binding of any of the antibody variable fragment selected from (a1) to (a10).

[3] A multispecific antigen-binding molecule that comprises:
(1) a first domain comprising a first antigen-binding domain binds to human DLL3, and
(2) a second domain comprising a second antigen-binding domain binds to T-cell receptor complex,
wherein the first antigen-binding domain of (1) comprises any one of (b1) to (b21) below:

(b1) an antibody variable fragment comprising the HVR-H1 sequence identical to the amino acid sequences of the HVR-H1 region comprised in SEQ ID NO: 15, the HVR-H2 sequence identical to the amino acid sequences of the HVR-H2 region comprised in SEQ ID NO: 15, the HVR-H3 sequence identical to the amino acid sequences of the HVR-H3 region comprised in SEQ ID NO: 15, the HVR-L1 sequence identical to the amino acid sequences of the HVR-L1 region comprised in SEQ ID NO: 16, the HVR-L2 sequence identical to the amino acid sequences of the HVR-L2 region comprised in SEQ ID NO: 16, and the HVR-L3 sequence identical to the amino acid sequences of the HVR-L3 region comprised in SEQ ID NO: 16;

(b2) an antibody variable fragment comprising the HVR-H1 sequence identical to the amino acid sequences of the HVR-H1 region comprised in SEQ ID NO: 25, the HVR-H2 sequence identical to the amino acid sequences of the HVR-H2 region comprised in SEQ ID NO: 25, the HVR-H3 sequence identical to the amino acid sequences of the HVR-H3 region comprised in SEQ ID NO: 25, the HVR-L1 sequence identical to the amino acid sequences of the HVR-L1 region comprised in SEQ ID NO: 26, the HVR-L2 sequence identical to the amino acid sequences of the HVR-L2 region comprised in SEQ ID NO: 26, and the HVR-L3 sequence identical to the amino acid sequences of the HVR-L3 region comprised in SEQ ID NO: 26;

(b3) an antibody variable fragment comprising the HVR-H1 sequence identical to the amino acid sequences of the HVR-H1 region comprised in SEQ ID NO: 19, the HVR-H2 sequence identical to the amino acid sequences of the HVR-H2 region comprised in SEQ ID NO: 19, the HVR-H3 sequence identical to the amino acid sequences of the HVR-H3 region comprised in SEQ ID NO: 19, the HVR-L1 sequence identical to the amino acid sequences of the HVR-L1 region comprised in SEQ ID NO: 20, the HVR-L2 sequence identical to the amino acid sequences of the HVR-L2 region comprised in SEQ ID NO: 20, and the HVR-L3 sequence identical to the amino acid sequences of the HVR-L3 region comprised in SEQ ID NO: 20;

(b4) an antibody variable fragment comprising the HVR-H1 sequence identical to the amino acid sequences of the HVR-H1 region comprised in SEQ ID NO: 23, the HVR-H2 sequence identical to the amino acid sequences of the HVR-H2 region comprised in SEQ ID NO: 23, the HVR-H3 sequence identical to the amino acid sequences of the HVR-H3 region comprised in SEQ ID NO: 23, the HVR-L1 sequence identical to the amino acid sequences of the HVR-L1 region comprised in SEQ ID NO: 24, the HVR-L2 sequence identical to the amino acid sequences of the HVR-L2 region comprised in SEQ ID NO: 24, and the HVR-L3 sequence identical to the amino acid sequences of the HVR-L3 region comprised in SEQ ID NO: 24;

(b5) an antibody variable fragment comprising the HVR-H1 sequence identical to the amino acid sequences of the HVR-H1 region comprised in SEQ ID NO: 11, the HVR-H2 sequence identical to the amino acid sequences of the HVR-H2 region comprised in SEQ ID NO: 11, the HVR-H3 sequence identical to the amino acid sequences of the HVR-H3 region comprised in SEQ ID NO: 11, the HVR-L1 sequence identical to the amino acid sequences of the HVR-L1 region comprised in SEQ ID NO: 12, the HVR-L2 sequence identical to the amino acid sequences of the HVR-L2 region comprised in SEQ ID NO: 12, and the HVR-L3 sequence identical to the amino acid sequences of the HVR-L3 region comprised in SEQ ID NO: 12;

(b6) an antibody variable fragment comprising the HVR-H1 sequence identical to the amino acid sequences of the HVR-H1 region comprised in SEQ ID NO: 13, the HVR-H2 sequence identical to the amino acid sequences of the HVR-H2 region comprised in SEQ ID NO: 13, the HVR-H3 sequence identical to the amino acid sequences of the HVR-H3 region comprised in SEQ ID NO: 13, the HVR-L1 sequence identical to the amino acid sequences of the HVR-L1 region comprised in SEQ ID NO: 14, the HVR-L2 sequence identical to the amino acid sequences of the HVR-L2 region comprised in SEQ ID NO: 14, and the HVR-L3 sequence identical to the amino acid sequences of the HVR-L3 region comprised in SEQ ID NO: 14;

(b7) an antibody variable fragment comprising the HVR-H1 sequence identical to the amino acid sequences of the HVR-H1 region comprised in SEQ ID NO: 17, the HVR-H2 sequence identical to the amino acid sequences of the HVR-H2 region comprised in SEQ ID NO: 17, the HVR-H3 sequence identical to the amino acid sequences of the HVR-H3 region comprised in SEQ ID NO: 17, the HVR-L1 sequence identical to the amino acid sequences of the HVR-L1 region comprised in SEQ ID NO: 18, the HVR-L2 sequence identical to the amino acid sequences of the HVR-L2 region comprised in SEQ ID NO: 18, and the HVR-L3 sequence identical to the amino acid sequences of the HVR-L3 region comprised in SEQ ID NO: 18;

(b8) an antibody variable fragment comprising the HVR-H1 sequence identical to the amino acid sequences of the HVR-H1 region comprised in SEQ ID NO: 21, the HVR-H2 sequence identical to the amino acid sequences of the HVR-H2 region comprised in SEQ ID NO: 21, the HVR-H3 sequence identical to the amino acid sequences of the HVR-H3 region comprised in SEQ ID NO: 21, the HVR-L1 sequence identical to the amino acid sequences of the HVR-L1 region comprised in SEQ ID NO: 22, the HVR-L2 sequence identical to the amino acid sequences of the HVR-L2 region comprised in SEQ ID NO: 22, and the HVR-L3 sequence identical to the amino acid sequences of the HVR-L3 region comprised in SEQ ID NO: 22;

(b9) an antibody variable fragment comprising the HVR-H1 sequence identical to the amino acid sequences of the HVR-H1 region comprised in SEQ ID NO: 85, the HVR-H2 sequence identical to the amino acid sequences of the HVR-H2 region comprised in SEQ ID NO: 85, the HVR-H3 sequence identical to the amino acid sequences of the HVR-H3 region comprised in SEQ ID NO: 85, the HVR-L1 sequence identical to the amino acid sequences of the HVR-L1 region comprised in SEQ ID NO: 93, the HVR-L2 sequence identical to the amino acid sequences of the HVR-L2 region comprised in SEQ ID NO: 93, and the HVR-L3 sequence identical to the amino acid sequences of the HVR-L3 region comprised in SEQ ID NO: 93;

(b10) an antibody variable fragment comprising the HVR-H1 sequence identical to the amino acid sequences of the HVR-H1 region comprised in SEQ ID NO: 63, the HVR-H2 sequence identical to the amino acid sequences of the HVR-H2 region comprised in SEQ ID NO: 63, the HVR-H3 sequence identical to the amino acid sequences of the HVR-H3 region comprised in SEQ ID NO: 63, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b11) an antibody variable fragment comprising the HVR-H1 sequence identical to the amino acid sequences of the HVR-H1 region comprised in SEQ ID NO: 64, the HVR-H2 sequence identical to the amino acid sequences of the HVR-H2 region comprised in SEQ ID NO: 64, the HVR-H3 sequence identical to the amino acid sequences of the HVR-H3 region comprised in SEQ ID NO: 64, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b12) an antibody variable fragment comprising the HVR-H1 sequence identical to the amino acid sequences of the HVR-H1 region comprised in SEQ ID NO: 65, the HVR-H2 sequence identical to the amino acid sequences of the HVR-H2 region comprised in SEQ ID NO: 65, the HVR-H3 sequence identical to the amino acid sequences of the HVR-H3 region comprised in SEQ ID NO: 65, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b13) an antibody variable fragment comprising the HVR-H1 sequence identical to the amino acid sequences of the HVR-H1 region comprised in SEQ ID NO: 66, the HVR-H2 sequence identical to the amino acid sequences of the HVR-H2 region comprised in SEQ ID NO: 66, the HVR-H3 sequence identical to the amino acid sequences of the HVR-H3 region comprised in SEQ ID NO: 66, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b14) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b15) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 74, the HVR-L2 sequence identical to the amino acid sequences of the HVR-L2 region comprised in SEQ ID NO: 74, and the HVR-L3 sequence identical to the amino acid sequences of the HVR-L3 region comprised in SEQ ID NO: 74;

(b16) an antibody variable fragment comprising the HVR-H1 sequence identical to the amino acid sequences of the HVR-H1 region comprised in SEQ ID NO: 68, the HVR-H2 sequence identical to the amino acid sequences of the HVR-H2 region comprised in SEQ ID NO: 68, the HVR-H3 sequence identical to the amino acid sequences of the HVR-H3 region comprised in SEQ ID NO: 68, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b17) an antibody variable fragment comprising the HVR-H1 sequence identical to the amino acid sequences of the HVR-H1 region comprised in SEQ ID NO: 69, the HVR-H2 sequence identical to the amino acid sequences of the HVR-H2 region comprised in SEQ ID NO: 69, the HVR-H3 sequence identical to the amino acid sequences of the HVR-H3 region comprised in SEQ ID NO: 69, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b18) an antibody variable fragment comprising the HVR-H1 sequence identical to the amino acid sequences of the HVR-H1 region comprised in SEQ ID NO: 70, the HVR-H2 sequence identical to the amino acid sequences of the HVR-H2 region comprised in SEQ ID NO: 70, the HVR-H3 sequence identical to the amino acid sequences of the HVR-H3 region comprised in SEQ ID NO: 70, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b19) an antibody variable fragment comprising the HVR-H1 sequence identical to the amino acid sequences of the HVR-H1 region comprised in SEQ ID NO: 71, the HVR-H2 sequence identical to the amino acid sequences of the HVR-H2 region comprised in SEQ ID NO: 71, the HVR-H3 sequence identical to the amino acid sequences of the HVR-H3 region comprised in SEQ ID NO: 71, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b20) an antibody variable fragment that binds to the same epitope of any one of the antibody variable fragment selected from (b1) to (b19);

(b21) an antibody variable fragment that competes with the binding of any one of the antibody variable fragment selected from (b1) to (b19).

[4] A multispecific antigen-binding molecule that comprises:
(1) a first domain comprising a first antigen-binding domain binds to human DLL3, and
(2) a second domain comprising a second antigen-binding domain binds to T-cell receptor complex,
wherein the first antigen-binding domain of (1) comprises any one of the combinations of heavy chain variable region and light chain variable region selected from the following (c1) to (c22):

(c1) heavy chain variable region having the amino acid sequence of SEQ ID NO: 15 and light chain variable region having the amino acid sequence of SEQ ID NO: 16;

(c2) heavy chain variable region having the amino acid sequence of SEQ ID NO: 25 and light chain variable region having the amino acid sequence of SEQ ID NO: 26;

(c3) heavy chain variable region having the amino acid sequence of SEQ ID NO: 19 and light chain variable region having the amino acid sequence of SEQ ID NO: 20;

(c4) heavy chain variable region having the amino acid sequence of SEQ ID NO: 23 and light chain variable region having the amino acid sequence of SEQ ID NO: 24;

(c5) heavy chain variable region having the amino acid sequence of SEQ ID NO: 11 and light chain variable region having the amino acid sequence of SEQ ID NO: 12;

(c6) heavy chain variable region having the amino acid sequence of SEQ ID NO: 13 and light chain variable region having the amino acid sequence of SEQ ID NO: 14;

(c7) heavy chain variable region having the amino acid sequence of SEQ ID NO: 17 and light chain variable region having the amino acid sequence of SEQ ID NO: 18;

(c8) heavy chain variable region having the amino acid sequence of SEQ ID NO: 21 and light chain variable region having the amino acid sequence of SEQ ID NO: 22;

(c9) heavy chain variable region having the amino acid sequence of SEQ ID NO: 85 and light chain variable region having the amino acid sequence of SEQ ID NO: 93;

(c10) heavy chain variable region having the amino acid sequence of SEQ ID NO: 63 and light chain variable region having the amino acid sequence of SEQ ID NO: 72;

(c11) heavy chain variable region having the amino acid sequence of SEQ ID NO: 64 and light chain variable region having the amino acid sequence of SEQ ID NO: 72;

(c12) heavy chain variable region having the amino acid sequence of SEQ ID NO: 65 and light chain variable region having the amino acid sequence of SEQ ID NO: 72;

(c13) heavy chain variable region having the amino acid sequence of SEQ ID NO: 66 and light chain variable region having the amino acid sequence of SEQ ID NO: 73;

(c14) heavy chain variable region having the amino acid sequence of SEQ ID NO: 67 and light chain variable region having the amino acid sequence of SEQ ID NO: 73;

(c15) heavy chain variable region having the amino acid sequence of SEQ ID NO: 67 and light chain variable region having the amino acid sequence of SEQ ID NO: 74;

(c16) heavy chain variable region having the amino acid sequence of SEQ ID NO: 68 and light chain variable region having the amino acid sequence of SEQ ID NO: 72;

(c17) heavy chain variable region having the amino acid sequence of SEQ ID NO: 69 and light chain variable region having the amino acid sequence of SEQ ID NO: 73;

(c18) heavy chain variable region having the amino acid sequence of SEQ ID NO: 70 and light chain variable region having the amino acid sequence of SEQ ID NO: 73;

(c19) heavy chain variable region having the amino acid sequence of SEQ ID NO: 71 and light chain variable region having the amino acid sequence of SEQ ID NO: 73;

(c20) a heavy chain variable region that has an identity more than 80% of any one of the heavy chain variable region of (c1) to (c19), and a light chain variable region that has an identity more than 80% to any one of the light chain variable region of (c1) to (c19);

(c21) a heavy chain variable region that has an identity more than 90% of any one of the heavy chain variable region of (c1) to (c19), and a light chain variable region that has an identity more than 90% to any one of the light chain variable region of (c1) to (c19);

(c22) a heavy chain variable region that has an identity more than 95% of any one of the heavy chain variable region of (c1) to (c19), and a light chain variable region that has an identity more than 95% to any one of the light chain variable region of (c1) to (c19).

[5] The multispecific antigen-binding molecule of any one of [1] to [4], wherein the multispecific antigen-binding molecule has cytotoxic activity.

[6] The multispecific antigen-binding molecule of [5], wherein the cytotoxic activity is T-cell-dependent cytotoxic activity.

[7] The multispecific antigen-binding molecule of any one of [1] to [6], wherein the second antigen-binding domain in (2) binds to CD3 epsilon chain.

[8] The multispecific antigen-binding molecule of any one of [1] to [6], wherein the second antigen-binding domain in (2) binds to T-cell receptor.

[9] The multispecific antigen-binding molecule of any one of [1] to [8], wherein the second antigen-binding domain in (2) comprises any one of (d1) to (d12) below:

(d1) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 57 respectively, and the HVR-L1, HVR-L2 and HVR-L3 sequences identical to the amino acid sequences of the HVR-L1, HVR-L2 and HVR-L3 regions comprised in SEQ ID NO: 58 respectively;

(d2) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 98 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d3) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 99 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d4) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 100 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d5) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 101 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d6) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 102 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d7) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 298 respectively, and the HVR-L1, HVR-L2 and HVR-L3 sequences identical to the amino acid sequences of the HVR-L1, HVR-L2 and HVR-L3 regions comprised in SEQ ID NO: 299 respectively;

(d8) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 300 respectively, and the HVR-L1, HVR-L2 and HVR-L3 sequences identical to the amino acid sequences of the HVR-L1, HVR-L2 and HVR-L3 regions comprised in SEQ ID NO: 301 respectively;

(d9) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 302 respectively, and the HVR-L1, HVR-L2 and HVR-L3 sequences identical to the amino acid sequences of the HVR-L1, HVR-L2 and HVR-L3 regions comprised in SEQ ID NO: 303 respectively;

(d10) an antibody variable fragment comprising the HVR-H1, HVR-H2 and HVR-H3 sequences identical to the amino acid sequences of the HVR-H1, HVR-H2 and HVR-H3 regions comprised in any one selected from SEQ ID NO: 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388 and 390, and the HVR-L1, HVR-L2 and HVR-L3 sequences identical to the amino acid sequences of the HVR-L1, HVR-L2 and HVR-L3 regions comprised in any one selected from SEQ ID NO: 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389 and 391;

(d11) an antibody variable fragment that binds to the same epitope of any one of the antibody variable fragment selected from (d1) to (d10);

(d12) an antibody variable fragment that competes with the binding of any one of the antibody variable fragment selected from (d1) to (d10).

[10] The multispecific antigen-binding molecule of any one of [1] to [8], wherein the second antigen-binding domain in (2) comprises any one of (e1) to (e12) below:
(e1) heavy chain variable region having the amino acid sequence of SEQ ID NO: 57 and light chain variable region having the amino acid sequence of SEQ ID NO: 58;
(e2) heavy chain variable region having the amino acid sequence of SEQ ID NO: 98 and light chain variable region having the amino acid sequence of SEQ ID NO: 103;
(e3) heavy chain variable region having the amino acid sequence of SEQ ID NO: 99 and light chain variable region having the amino acid sequence of SEQ ID NO: 103;
(e4) heavy chain variable region having the amino acid sequence of SEQ ID NO: 100 and light chain variable region having the amino acid sequence of SEQ ID NO: 103;
(e5) heavy chain variable region having the amino acid sequence of SEQ ID NO: 101 and light chain variable region having the amino acid sequence of SEQ ID NO: 103;
(e6) heavy chain variable region having the amino acid sequence of SEQ ID NO: 102 and light chain variable region having the amino acid sequence of SEQ ID NO: 103;
(e7) heavy chain variable region having the amino acid sequence of SEQ ID NO: 300 and light chain variable region having the amino acid sequence of SEQ ID NO: 301;
(e8) heavy chain variable region having the amino acid sequence of SEQ ID NO: 302 and light chain variable region having the amino acid sequence of SEQ ID NO: 303;
(e9) heavy chain variable region and light chain variable region having any one of the amino acid sequence combination in Table 2A;
(e10) a heavy chain variable region that has an identity more than 80% of any one of the heavy chain variable region of (e1) to (e9), and a light chain variable region that has an identity more than 80% to any one of the light chain variable region of (e1) to (e9);
(e11) a heavy chain variable region that has an identity more than 90% of any one of the heavy chain variable region of (e1) to (e9), and a light chain variable region that has an identity more than 90% to any one of the light chain variable region of (e1) to (e9);
(e12) a heavy chain variable region that has an identity more than 95% of any one of the heavy chain variable region of (e1) to (e9), and a light chain variable region that has an identity more than 95% to any one of the light chain variable region of (e1) to (e9).

[11] The multispecific antigen-binding molecule of any one of [1] to [8], wherein the second antigen-binding domain in (2) comprises any one of (j1) to (j5) below:
(j1) an antibody variable fragment comprising the HVR-H1 sequence of SEQ ID NO: 136, the HVR-H2 sequence of SEQ ID NO: 137, the HVR-H3 sequence of SEQ ID NO: 138, the HVR-L1 sequence of SEQ ID NO: 139, the HVR-L2 sequence of SEQ ID NO: 140, and the HVR-L3 sequence of SEQ ID NO: 141;
(j2) an antibody variable fragment comprising the HVR-H1 sequence of SEQ ID NO: 142, the HVR-H2 sequence of SEQ ID NO: 143, the HVR-H3 sequence of SEQ ID NO: 144, the HVR-L1 sequence of SEQ ID NO: 145, the HVR-L2 sequence of SEQ ID NO: 146, and the HVR-L3 sequence of SEQ ID NO: 147;
(j3) an antibody variable fragment comprising the HVR sequences selected from any of the combinations in Table 2B;
(j4) an antibody variable fragment that binds to the same epitope of any of the antibody variable fragment selected from (j1) to (j3);
(j5) an antibody variable fragment that competes with the binding of any of the antibody variable fragment selected from (j1) to (j3).

[12] The multispecific antigen binding molecule of any one of [1] to [11], wherein the first antigen-binding domain or the second antigen-binding domain is an antibody variable fragment, or both of the first and second antigen-binding domains are antibody variable fragments.

[13] The multispecific antigen binding molecule of [12], wherein the antibody variable fragment is a Fab.

[14] The multispecific antigen binding molecule of any one of [1] to [13], wherein the multispecific antigen binding molecule further comprises:
(3) a third domain comprising an Fc region with reduced binding activity towards an Fc gamma receptor.

[15] A multispecific antigen-binding molecule that comprises:
(1) a first domain comprising a first antigen-binding domain binds to human DLL3,
(2) a second domain comprising a second antigen-binding domain binds to T-cell receptor complex, and
(3) a third domain comprising an Fc region with reduced binding activity towards an Fc gamma receptor.

[16] The multispecific antigen binding molecule of [15], wherein the first antigen-binding domain or the second antigen-binding domain is an antibody variable fragment, or both of the first and second antigen-binding domains are antibody variable fragments.

[17] The multispecific antigen binding molecule of [16], wherein the antibody variable fragment is a Fab.

[18] The multispecific antigen-binding molecule of any one of [14] to [17], wherein the Fc region of is an Fc region with an amino acid mutation at any of the Fc region-constituting amino acids of SEQ ID NOs: 112 to 115 (IgG1 to IgG4).

[19] The multispecific antigen-binding molecule of [18], wherein the Fc region is an Fc region with mutation of at least one amino acid selected from the following amino acid positions specified by EU numbering:
position 220, position 226, position 229, position 231, position 232, position 233, position 234, position 235, position 236, position 237, position 238, position 239, position 240, position 264, position 265, position 266, position 267, position 269, position 270, position 295, position 296, position 297, position 298, position 299, position 300, position 325, position 327, position 328, position 329, position 330, position 331, and position 332.

[20] The multispecific antigen-binding molecule of any one of [1] to [19], wherein the multispecific antigen-binding molecule is a bispecific antibody.

[21] The bispecific antibody of [20], wherein the antibody is a monoclonal antibody.

[22] A pharmaceutical composition comprising the multispecific antigen-binding molecule of any one of [1] to [19] or the bispecific antibody of [20] or [21], and a pharmaceutically acceptable carrier.

15

[23] The pharmaceutical composition of [22], which induces T-cell-dependent cytotoxicity.
[24] A pharmaceutical composition for use in treating or preventing cancer, which comprises the multispecific antigen-binding molecule of any one of [1] to [19] or the bispecific antibody of [20] or [21].
[25] A method for treating or preventing cancer, which comprises administering the antigen-binding molecule of any one of [1] to [19] or the bispecific antibody of [20] or [21] to a patient in need thereof.
[26] Use of the antigen-binding molecule of any one of [1] to [19] or the bispecific antibody of [20] or [21] in the manufacture of a pharmaceutical composition for treating or preventing cancer.
[27] Use of the antigen-binding molecule of any one of [1] to [19] or the bispecific antibody of [20] or [21] for treating or preventing cancer.
[28] The method of [25], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.
[29] The use of [26] or [27], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.
[30] The pharmaceutical composition of [24], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.
[31] An antigen-binding molecule that binds to an epitope within the region defined in SEQ ID NO: 7 in human DLL3.
[32] An antigen-binding molecule that comprises an antigen-binding domain comprising any one of (f1) to (f11) below:
  (f1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
  (f2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;
  (f3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;
  (f4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;
  (f5) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
  (f6) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
  (f7) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;
  (f8) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38;
  (f9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81;
  (f10) an antibody variable fragment that binds to the same epitope of any of the antibody variable fragment selected from (f1) to (f9);
  (f11) an antibody variable fragment that competes with the binding of any of the antibody variable fragment selected from (f1) to (f9).
[33] An antigen-binding molecule that comprises an antigen-binding domain comprising any one of (g1) to (g20) below:
  (g1) an antibody variable fragment comprising the HVR-H1 sequence identical to the amino acid sequences of the HVR-H1 region comprised in SEQ ID NO: 15, the HVR-H2 sequence identical to the amino acid sequences of the HVR-H2 region comprised in SEQ ID NO: 15, the HVR-H3 sequence identical to the amino acid sequences of the HVR-H3 region comprised in SEQ ID NO: 15, the HVR-L1 sequence identical to the amino acid sequences of the HVR-L1 region comprised in SEQ ID NO: 16, the HVR-L2 sequence identical to the amino acid sequences of the HVR-L2 region comprised in SEQ ID NO: 16, and the HVR-L3 sequence identical to the amino acid sequences of the HVR-L3 region comprised in SEQ ID NO: 16;
  (g2) an antibody variable fragment comprising the HVR-H1 sequence identical to the amino acid sequences of the HVR-H1 region comprised in SEQ ID NO: 25, the HVR-H2 sequence identical to the amino acid sequences of the HVR-H2 region comprised in SEQ ID NO: 25, the HVR-H3 sequence identical to the amino acid sequences of the HVR-H3 region comprised in SEQ ID NO: 25, the HVR-L1 sequence identical to the amino acid sequences of the HVR-L1 region comprised in SEQ ID NO: 26, the HVR-L2 sequence identical to the amino acid sequences of the HVR-L2 region comprised in SEQ ID NO: 26, and the HVR-L3 sequence identical to the amino acid sequences of the HVR-L3 region comprised in SEQ ID NO: 26;

(g3) an antibody variable fragment comprising the HVR-H1 sequence identical to the amino acid sequences of the HVR-H1 region comprised in SEQ ID NO: 19, the HVR-H2 sequence identical to the amino acid sequences of the HVR-H2 region comprised in SEQ ID NO: 19, the HVR-H3 sequence identical to the amino acid sequences of the HVR-H3 region comprised in SEQ ID NO: 19, the HVR-L1 sequence identical to the amino acid sequences of the HVR-L1 region comprised in SEQ ID NO: 20, the HVR-L2 sequence identical to the amino acid sequences of the HVR-L2 region comprised in SEQ ID NO: 20, and the HVR-L3 sequence identical to the amino acid sequences of the HVR-L3 region comprised in SEQ ID NO: 20;

(g4) an antibody variable fragment comprising the HVR-H1 sequence identical to the amino acid sequences of the HVR-H1 region comprised in SEQ ID NO: 23, the HVR-H2 sequence identical to the amino acid sequences of the HVR-H2 region comprised in SEQ ID NO: 23, the HVR-H3 sequence identical to the amino acid sequences of the HVR-H3 region comprised in SEQ ID NO: 23, the HVR-L1 sequence identical to the amino acid sequences of the HVR-L1 region comprised in SEQ ID NO: 24, the HVR-L2 sequence identical to the amino acid sequences of the HVR-L2 region comprised in SEQ ID NO: 24, and the HVR-L3 sequence identical to the amino acid sequences of the HVR-L3 region comprised in SEQ ID NO: 24;

(g5) an antibody variable fragment comprising the HVR-H1 sequence identical to the amino acid sequences of the HVR-H1 region comprised in SEQ ID NO: 11, the HVR-H2 sequence identical to the amino acid sequences of the HVR-H2 region comprised in SEQ ID NO: 11, the HVR-H3 sequence identical to the amino acid sequences of the HVR-H3 region comprised in SEQ ID NO: 11, the HVR-L1 sequence identical to the amino acid sequences of the HVR-L1 region comprised in SEQ ID NO: 12, the HVR-L2 sequence identical to the amino acid sequences of the HVR-L2 region comprised in SEQ ID NO: 12, and the HVR-L3 sequence identical to the amino acid sequences of the HVR-L3 region comprised in SEQ ID NO: 12;

(g6) an antibody variable fragment comprising the HVR-H1 sequence identical to the amino acid sequences of the HVR-H1 region comprised in SEQ ID NO: 13, the HVR-H2 sequence identical to the amino acid sequences of the HVR-H2 region comprised in SEQ ID NO: 13, the HVR-H3 sequence identical to the amino acid sequences of the HVR-H3 region comprised in SEQ ID NO: 13, the HVR-L1 sequence identical to the amino acid sequences of the HVR-L1 region comprised in SEQ ID NO: 14, the HVR-L2 sequence identical to the amino acid sequences of the HVR-L2 region comprised in SEQ ID NO: 14, and the HVR-L3 sequence identical to the amino acid sequences of the HVR-L3 region comprised in SEQ ID NO: 14;

(g7) an antibody variable fragment comprising the HVR-H1 sequence identical to the amino acid sequences of the HVR-H1 region comprised in SEQ ID NO: 17, the HVR-H2 sequence identical to the amino acid sequences of the HVR-H2 region comprised in SEQ ID NO: 17, the HVR-H3 sequence identical to the amino acid sequences of the HVR-H3 region comprised in SEQ ID NO: 17, the HVR-L1 sequence identical to the amino acid sequences of the HVR-L1 region comprised in SEQ ID NO: 18, the HVR-L2 sequence identical to the amino acid sequences of the HVR-L2 region comprised in SEQ ID NO: 18, and the HVR-L3 sequence identical to the amino acid sequences of the HVR-L3 region comprised in SEQ ID NO: 18;

(g8) an antibody variable fragment comprising the HVR-H1 sequence identical to the amino acid sequences of the HVR-H1 region comprised in SEQ ID NO: 21, the HVR-H2 sequence identical to the amino acid sequences of the HVR-H2 region comprised in SEQ ID NO: 21, the HVR-H3 sequence identical to the amino acid sequences of the HVR-H3 region comprised in SEQ ID NO: 21, the HVR-L1 sequence identical to the amino acid sequences of the HVR-L1 region comprised in SEQ ID NO: 22, the HVR-L2 sequence identical to the amino acid sequences of the HVR-L2 region comprised in SEQ ID NO: 22, and the HVR-L3 sequence identical to the amino acid sequences of the HVR-L3 region comprised in SEQ ID NO: 22;

(g9) an antibody variable fragment comprising the HVR-H1 sequence identical to the amino acid sequences of the HVR-H1 region comprised in SEQ ID NO: 63, the HVR-H2 sequence identical to the amino acid sequences of the HVR-H2 region comprised in SEQ ID NO: 63, the HVR-H3 sequence identical to the amino acid sequences of the HVR-H3 region comprised in SEQ ID NO: 63, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g10) an antibody variable fragment comprising the HVR-H1 sequence identical to the amino acid sequences of the HVR-H1 region comprised in SEQ ID NO: 64, the HVR-H2 sequence identical to the amino acid sequences of the HVR-H2 region comprised in SEQ ID NO: 64, the HVR-H3 sequence identical to the amino acid sequences of the HVR-H3 region comprised in SEQ ID NO: 64, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g11) an antibody variable fragment comprising the HVR-H1 sequence identical to the amino acid sequences of the HVR-H1 region comprised in SEQ ID NO: 65, the HVR-H2 sequence identical to the amino acid sequences of the HVR-H2 region comprised in SEQ ID NO: 65, the HVR-H3 sequence identical to the amino acid sequences of the HVR-H3 region comprised in SEQ ID NO: 65, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g12) an antibody variable fragment comprising the HVR-H1 sequence identical to the amino acid sequences of the HVR-H1 region comprised in SEQ ID NO: 66, the HVR-H2 sequence identical to the amino acid sequences of the HVR-H2 region comprised in SEQ ID NO: 66, the HVR-H3 sequence identical to the amino acid sequences of the HVR-H3 region comprised in SEQ ID NO: 66, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g13) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g14) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 74, the HVR-L2 sequence identical to the amino acid sequences of the HVR-L2 region comprised in SEQ ID NO: 74, and the HVR-L3 sequence identical to the amino acid sequences of the HVR-L3 region comprised in SEQ ID NO: 74;

(g15) an antibody variable fragment comprising the HVR-H1 sequence identical to the amino acid sequences of the HVR-H1 region comprised in SEQ ID NO: 68, the HVR-H2 sequence identical to the amino acid sequences of the HVR-H2 region comprised in SEQ ID NO: 68, the HVR-H3 sequence identical to the amino acid sequences of the HVR-H3 region comprised in SEQ ID NO: 68, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g16) an antibody variable fragment comprising the HVR-H1 sequence identical to the amino acid sequences of the HVR-H1 region comprised in SEQ ID NO: 69, the HVR-H2 sequence identical to the amino acid sequences of the HVR-H2 region comprised in SEQ ID NO: 69, the HVR-H3 sequence identical to the amino acid sequences of the HVR-H3 region comprised in SEQ ID NO: 69, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g17) an antibody variable fragment comprising the HVR-H1 sequence identical to the amino acid sequences of the HVR-H1 region comprised in SEQ ID NO: 70, the HVR-H2 sequence identical to the amino acid sequences of the HVR-H2 region comprised in SEQ ID NO: 70, the HVR-H3 sequence identical to the amino acid sequences of the HVR-H3 region comprised in SEQ ID NO: 70, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g18) an antibody variable fragment comprising the HVR-H1 sequence identical to the amino acid sequences of the HVR-H1 region comprised in SEQ ID NO: 71, the HVR-H2 sequence identical to the amino acid sequences of the HVR-H2 region comprised in SEQ ID NO: 71, the HVR-H3 sequence identical to the amino acid sequences of the HVR-H3 region comprised in SEQ ID NO: 71, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g19) an antibody variable fragment that binds to the same epitope of any one of the antibody variable fragment selected from (g1) to (g18);

(g20) an antibody variable fragment that competes with the binding of any one of the antibody variable fragment selected from (g1) to (g18).

[34] An antigen-binding molecule that comprises an antigen-binding domain comprises any one of (h1) to (h21) below:

(h1) heavy chain variable region having the amino acid sequence of SEQ ID NO: 15 and light chain variable region having the amino acid sequence of SEQ ID NO: 16;

(h2) heavy chain variable region having the amino acid sequence of SEQ ID NO: 25 and light chain variable region having the amino acid sequence of SEQ ID NO: 26;

(h3) heavy chain variable region having the amino acid sequence of SEQ ID NO: 19 and light chain variable region having the amino acid sequence of SEQ ID NO: 20;

(h4) heavy chain variable region having the amino acid sequence of SEQ ID NO: 23 and light chain variable region having the amino acid sequence of SEQ ID NO: 24;

(h5) heavy chain variable region having the amino acid sequence of SEQ ID NO: 11 and light chain variable region having the amino acid sequence of SEQ ID NO: 12;

(h6) heavy chain variable region having the amino acid sequence of SEQ ID NO: 13 and light chain variable region having the amino acid sequence of SEQ ID NO: 14;

(h7) heavy chain variable region having the amino acid sequence of SEQ ID NO: 17 and light chain variable region having the amino acid sequence of SEQ ID NO: 18;

(h8) heavy chain variable region having the amino acid sequence of SEQ ID NO: 21 and light chain variable region having the amino acid sequence of SEQ ID NO: 22;
(h9) heavy chain variable region having the amino acid sequence of SEQ ID NO: 63 and light chain variable region having the amino acid sequence of SEQ ID NO: 72;
(h10) heavy chain variable region having the amino acid sequence of SEQ ID NO: 64 and light chain variable region having the amino acid sequence of SEQ ID NO: 72;
(h11) heavy chain variable region having the amino acid sequence of SEQ ID NO: 65 and light chain variable region having the amino acid sequence of SEQ ID NO: 72;
(h12) heavy chain variable region having the amino acid sequence of SEQ ID NO: 66 and light chain variable region having the amino acid sequence of SEQ ID NO: 73;
(h13) heavy chain variable region having the amino acid sequence of SEQ ID NO: 67 and light chain variable region having the amino acid sequence of SEQ ID NO: 73;
(h14) heavy chain variable region having the amino acid sequence of SEQ ID NO: 67 and light chain variable region having the amino acid sequence of SEQ ID NO: 74;
(h15) heavy chain variable region having the amino acid sequence of SEQ ID NO: 68 and light chain variable region having the amino acid sequence of SEQ ID NO: 72;
(h16) heavy chain variable region having the amino acid sequence of SEQ ID NO: 69 and light chain variable region having the amino acid sequence of SEQ ID NO: 73;
(h17) heavy chain variable region having the amino acid sequence of SEQ ID NO: 70 and light chain variable region having the amino acid sequence of SEQ ID NO: 73;
(h18) heavy chain variable region having the amino acid sequence of SEQ ID NO: 71 and light chain variable region having the amino acid sequence of SEQ ID NO: 73;
(h19) a heavy chain variable region that has an identity more than 80% of any one of the heavy chain variable region of (h1) to (h18); and a light chain variable region that has an identity more than 80% to any one of the light chain variable region of (h1) to (h18);
(h20) a heavy chain variable region that has an identity more than 90% of any one of the heavy chain variable region of (h1) to (h18); and a light chain variable region that has an identity more than 90% to any one of the light chain variable region of (h1) to (h18);
(h21) a heavy chain variable region that has an identity more than 95% of any one of the heavy chain variable region of (h1) to (h18); and a light chain variable region that has an identity more than 95% to any one of the light chain variable region of (h1) to (h18).
[35] The antigen-binding molecule of any one of [31] to [34], wherein the antigen-binding molecule has cellular cytotoxic activity.
[36] The antigen-binding molecule of [35], wherein the cytotoxic activity is antibody dependent cellular cytotoxicity or complement dependent cytotoxicity.
[37] The antigen-binding molecule of any one of [31] to [36], wherein the antigen-binding molecule has internalization activity.
[38] The antigen-binding molecule of any one of [31] to [37], wherein the antigen-binding molecule is conjugated to a toxic compound.
[39] The antigen binding molecule of any one of [31] to [38], wherein the antigen-binding domain is an antibody variable fragment.
[40] The antigen binding molecule of [39], wherein the antibody variable fragment is a Fab.
[41] The antigen-binding molecule of any one of [31] to [40], wherein the antigen-binding molecule is an antibody.
[42] The antigen-binding molecule of [41], wherein the antigen-binding molecule is a monoclonal antibody.
[43] An antibody-drug-conjugate compound that comprises the antibody of [42].
[44] A pharmaceutical composition comprising the antigen-binding molecule of any one of [31] to [40] or the antibody of [41] or [42], and a pharmaceutically acceptable carrier.
[45] A pharmaceutical composition for use in treating or preventing cancer, which comprises the antigen-binding molecule of any one of [31] to [40] or the antibody of [41] or [42].
[46] A method for treating or preventing cancer, which comprises administering the antigen-binding molecule of any one of [31] to [40] or the antibody of [41] or [42] to a patient in need thereof.
[47] Use of the antigen-binding molecule of any one of [31] to [40] or the antibody of [41] or [42] in the manufacture of a pharmaceutical composition for treating or preventing cancer.
[48] Use of the antigen-binding molecule of any one of [31] to [40] or the antibody of [41] or [42] for treating or preventing cancer.
[49] The method of [46], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.
[50] The use of [47] or [48], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.
[51] The pharmaceutical composition of [45], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.
[52] A kit comprising the antigen-binding molecule of any one of [1] to [19] or the bispecific antibody of [20] or [21], and instructions for use.

[53] A kit comprising the antigen-binding molecule of any one of [31] to [40] or the antibody of [41] or [42], and instructions for use.

Advantageous Effects of Invention

The present invention provides multispecific antigen-binding molecules that enable cancer treatment by having T-cells close to DLL3-expressing cells and and using the cytotoxicity of T-cells against the DLL3-expressing cancer cells, methods for producing the multispecific antigen-binding molecules, and therapeutic agents containing such a multispecific antigen-binding molecule as an active ingredient for inducing cellular cytotoxicity, as a new approach of cancer treatment. Multispecific antigen-binding molecules of the present invention have strong anti-tumor activity, inducing cellular cytotoxicity, and can target and damage DLL3-expressing cells, thus enable treatment and prevention of various cancers. The present invention also provides novel monospecific antigen-binding molecules having human DLL3-binding activity, therapeutic agents comprising such a monospecific antigen-binding molecule as an active ingredient, and therapeutic methods using such a therapeutic agent.

BRIEF DESCRIPTION OF DRAWINGS

FIG. 9 shows TDCC of humanized anti-DLL3/CD3 bispecific antibodies against SK-MEL-30 cell lines. The anti-DLL3 arms of the tested bispecific antibodies were derived from DLA0136 or its humanized variant D30316AE03 (A), and DLA0841 or its humanized variants D30841AE08 and D30841AE11 (B), respectively.

DESCRIPTION OF EMBODIMENTS

Figure 1:
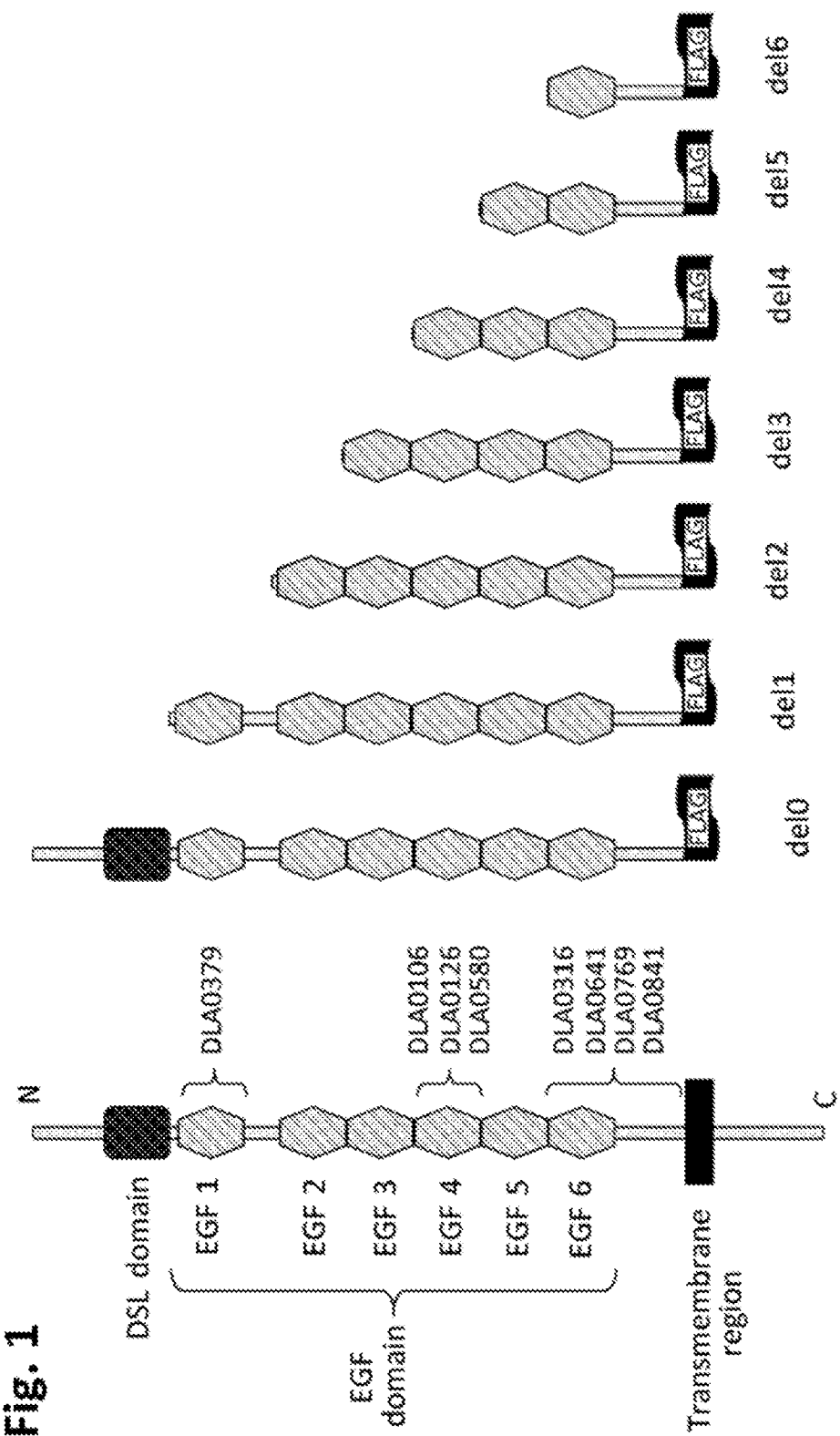
FIG. 1 is a schematic drawing showing the structures of the full-length human DLL3 and human DLL3 ECD fragment proteins prepared in Example 1. The epitope recognized by each of the anti-DLL3 antibodies selected in Example 3 is also shown. The EGF domain has six regions, EGF1 to EGF6 from the N-terminal side to the C-terminal side.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

The definitions and detailed description below are provided to facilitate understanding of the present invention illustrated herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Amino Acids

Herein, amino acids are described by one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Alteration of Amino Acids

For amino acid alteration in the amino acid sequence of an antigen-binding molecule, known methods such as site-directed mutagenesis methods (Kunkel et al. (Proc. Natl. Acad. Sci. USA (1985) 82, 488-492)) and overlap extension PCR may be appropriately employed. Furthermore, several known methods may also be employed as amino acid alteration methods for substitution to non-natural amino acids (Annu Rev. Biophys. Biomol. Struct. (2006) 35, 225-249; and Proc. Natl. Acad. Sci. U.S.A. (2003) 100 (11), 6353-6357). For example, it is suitable to use a cell-free translation system (Clover Direct (Protein Express)) containing a tRNA which has a non-natural amino acid bound to a complementary amber suppressor tRNA of one of the stop codons, the UAG codon (amber codon).

In the present specification, the meaning of the term "and/or" when describing the site of amino acid alteration includes every combination where "and" and "or" are suitably combined. Specifically, for example, "the amino acids at positions 33, 55, and/or 96 are substituted" includes the following variation of amino acid alterations: amino acid(s) at (a) position 33, (b) position 55, (c) position 96, (d) positions 33 and 55, (e) positions 33 and 96, (f) positions 55 and 96, and (g) positions 33, 55, and 96.

Furthermore, herein, as an expression showing alteration of amino acids, an expression that shows before and after a number indicating a specific position, one-letter or three-letter codes for amino acids before and after alteration, respectively, may be used appropriately. For example, the alteration N100bL or Asn100bLeu used when substituting an amino acid contained in an antibody variable region indicates substitution of Asn at position 100b (according to Kabat numbering) with Leu. That is, the number shows the amino acid position according to Kabat numbering, the one-letter or three-letter amino-acid code written before the number shows the amino acid before substitution, and the one-letter or three-letter amino-acid code written after the number shows the amino acid after substitution. Similarly the alteration P238D or Pro238Asp used when substituting an amino acid of the Fc region contained in an antibody constant region indicates substitution of Pro at position 238 (according to EU numbering) with Asp. That is, the number shows the amino acid position according to EU numbering, the one-letter or three-letter amino-acid code written before the number shows the amino acid before substitution, and the one-letter or three-letter amino-acid code written after the number shows the amino acid after substitution.

Antigen-Binding Molecule

The term "antigen-binding molecules", as used herein, refers to any molecule that comprises an antigen-binding domain, and may further refers to molecules such as a peptide or protein having a length of about five amino acids or more. The peptide and protein are not limited to those derived from a living organism, and for example, they may be a polypeptide produced from an artificially designed sequence. They may also be any of a naturally-occurring polypeptide, synthetic polypeptide, recombinant polypeptide, and such.

A favorable example of an antigen-binding molecule of the present invention is an antigen-binding molecule that comprises a plurality of antigen-binding domains. In certain embodiments, the antigen-binding molecule of the present invention is an antigen-binding molecule that comprises two antigen-binding domains with different antigen-binding specificities. In certain embodiments, the antigen-binding molecule of the present invention is an antigen-binding molecule that comprises two antigen-binding domains with different antigen-binding specificities, and an FcRn-binding domain contained in an antibody Fc region. As a method for extending the blood half-life of a protein administered to a living body, the method of adding an FcRn-binding domain of an antibody to the protein of interest and utilizing the function of FcRn-mediated recycling is well known.

Another favorable example of an antigen-binding molecule of the present invention is an antigen-binding molecule that comprises only one type of antigen-binding domains. In certain embodiments, the antigen-binding molecule of the present invention is an antigen-binding molecule that comprises two antigen-binding domains with the same antigen-binding specificity. In certain embodiments, the antigen-binding molecule of the present invention is an antigen-binding molecule that comprises two antigen-binding domains with the same antigen-binding specificity, and an Fc region.

Antigen-Binding Domain

The term "antigen-binding domain", as used herein, refers to an antibody portion which comprises a region that specifically binds and is complementary to the whole or a portion of an antigen. When the molecular weight of an antigen is large, an antibody can only bind to a particular portion of the antigen. The particular portion is called "epitope". An antigen-binding domain can be provided from one or more antibody variable domains. Preferably, the antigen-binding domains contain both the antibody light chain variable region (VL) and antibody heavy chain variable region (VH). Such preferable antigen-binding domains include, for example, "single-chain Fv (scFv)", "single-chain antibody", "Fv", "single-chain Fv2 (scFv2)", "Fab", and "F (ab')2".

The antigen-binding domains of antigen-binding molecules of the present invention may bind to the same epitope. The epitope can be present in a protein comprising the amino acid sequence of SEQ ID NO: 9 or 111. Alternatively, the antigen-binding domains of multispecific antigen-binding molecules of the present invention may individually bind to different epitopes. The epitope can be present in a protein comprising the amino acid sequence of SEQ ID NO: 9 or 111.

The antigen-binding domain of an antigen-binding molecule of the present invention "binds to DLL3 or T cell receptor complex". That is, DLL3 and a T cell receptor complex are preferable antigens of interest. As used herein, the phrase "binds to an antigen" refers to the binding activity of an antigen-binding domain, antibody, antigen-binding molecule, antibody variable fragment, or such (hereinafter, "antigen-binding domain or such") to bind to an antigen of interest at a level of specific binding higher than the level of non-specific or background binding. In other words, such an antigen-binding domain or such "binds to the antigen specifically/significantly" towards the antigen of interest. The specificity can be measured by any methods for detecting affinity or binding activity as mentioned herein or known in the art. The above-mentioned level of specific binding may be high enough to be recognized by a skilled person as being significant. For example, when a skilled person can detect or observe any significant or relatively strong signals or values of binding between the antigen-binding domain or such and the antigen of interest in a suitable binding assay, it can be said that the antigen-binding domain or such "binds to the antigen specifically/significantly" towards the antigen of interest. Sometimes, the phrase "binds to an antigen" has substantially the same meaning as the phrase "binds to an antigen specifically/significantly" in the art.

DLL3

The term "DLL3", as used herein, refers to any native DLL3 (Delta-like 3) from any vertebrate source, including mammals such as primates (e.g. humans) and rodents (e.g., mice and rats), unless otherwise indicated. The term encompasses "full-length" unprocessed DLL3 as well as any form of DLL3 that results from processing in the cell. The term also encompasses naturally occurring variants of DLL3, e.g., splice variants or allelic variants. The amino acid sequence of an exemplary human DLL3 is known as NCBI Reference Sequence (RefSeq) NM_016941.3, and the amino acid sequence of an exemplary cynomolgus DLL3 is known as NCBI Reference Sequence XP_005589253.1, and the amino acid sequence of an exemplary mouse DLL3 is known as NCBI Reference Sequence NM_007866.2. The amino acid sequence of cynomolgus DLL3 used in the working examples is shown in SEQ ID NO: 8.

The human DLL3 protein comprises a transmembrane (TM) region and an intracellular domain on the C-terminal side, and a DSL (Notch) domain on the N-terminal side (see, e.g., FIG. 1). In addition, DLL3 has an EGF domain comprising six regions, EGF1 to EGF6 from the N-terminal side to the C-terminal side. In some embodiments, the antigen-binding molecules or antibodies of the present invention bind to an epitope within the extracellular domain (ECD), i.e., the domain from the N-terminus to immediately before the TM region, but not to the TM region or the C-terminal intracellular domain. The molecules/antibodies of the present invention may bind to an epitope within any of the above-mentioned domains/regions within the ECD. In preferred embodiments, the molecules/antibodies of the present invention bind to an epitope within the region from EGF6 to immediately before the TM region. More specifically, the molecules/antibodies of the present invention may bind to an epitope within the regions defined in SEQ ID NO: 7 in human DLL3. In some embodiments, the molecules/antibodies of the present invention bind to the EGF1, EGF2, EGF3, EGF4, EGF5, or EGF6 region or a region from EGF6 to immediately before the TM region of human DLL3, or an epitope within the EGF1, EGF2, EGF3, EGF4, EGF5, or EGF6 region or a region from EGF6 to immediately before the TM region of human DLL3.

In human DLL3, the above-mentioned domains/regions have the following amino acid residues (see, e.g., www uniprot_org_uniprot/Q9NYJ7 or WO2013/126746):

Extracellular domain (ECD): amino acid residues at positions 1 to 492;
DSL domain: amino acid residues at positions 176 to 215;
EGF domain: amino acid residues at positions 216 to 465;
EGF1 region: amino acid residues at positions 216 to 249;
EGF2 region: amino acid residues at positions 274 to 310;
EGF3 region: amino acid residues at positions 312 to 351;
EGF4 region: amino acid residues at positions 353 to 389;
EGF5 region: amino acid residues at positions 391 to 427;
EGF6 region: amino acid residues at positions 429 to 465;
The region from EGF6 to immediately before the TM region: amino acid residues at positions 429 to 492;
TM region: amino acid residues at positions 493 to 513; and
C-terminal intracellular domain: amino acid residues at positions 516 to 618 (or 516 to 587 in some isoforms). The amino acid positions mentioned above also refers to the amino acid positions in the amino acid sequence shown in SEQ ID NO: 9.

Thus, the antigen-binding molecules or antibodies of the present invention may bind to an above-mentioned region/domain having the amino acid residues at the above-mentioned positions in human DLL3. That is, the antigen-binding molecules or antibodies of the present invention may bind to an epitope within the above-mentioned region/domain having the amino acid residues at the above-mentioned positions in human DLL3.

In some embodiments, due to their specificity, the antigen-binding molecules/antibodies of the present invention do not specifically bind to an above-mentioned region/domain of human DLL3, or an epitope within an above-mentioned region/domain of human DLL3. In some embodiments, the molecules/antibodies of the present invention do not specifically bind to an above-mentioned region/domain having the amino acid residues at the above-mentioned positions in human DLL3. In some embodiments, the molecules/antibodies of the present invention do not specifically bind to an epitope within the above-mentioned region/domain having the amino acid residues at the above-mentioned positions in human DLL3. In this context, the "specifically" may be reworded as "substantially".

The phrase "specifically bind to", as used herein, refers to activity of an antigen-binding molecule/antibody to bind to an antigen/region/domain/epitope of interest at a level of binding that includes specific binding. The phrase "not specifically bind to", as used herein, refers to activity of an antigen-binding molecule/antibody to bind to an antigen/region/domain/epitope of no interest at a level of binding that includes non-specific or background binding but does not include specific binding. The specificity can be measured by any methods mentioned in this specification or known in the art, e.g., epitope mapping or competition assay described herein. The above-mentioned level of non-specific or background binding may be zero, or may not be zero but near zero, or may be very low enough to be technically neglected by those skilled in the art. For example, when a skilled person cannot detect or observe any significant or relatively strong signal for binding between the molecule/antibody and the antigen/region/domain/epitope of no interest in a suitable binding assay, it can be said that the molecule/antibody does "not specifically bind to" the antigen/region/domain/epitope of no interest. Sometimes, the phrase "not specifically bind to" has substantially the same meaning as the phrase "not bind to" in the art.

The DLL3 protein used in the present invention may be a DLL3 protein having the sequence described above or may be a modified protein having a sequence derived from the sequence described above by the modification of one or more amino acids. Examples of the modified protein having a sequence derived from the sequence described above by the modification of one or more amino acids can include polypeptides having 70% or more, preferably 80% or more, more preferably 90% or more, even more preferably 95% or more identity with to the amino acid sequence described above. Alternatively, partial peptides of these DLL3 proteins may be used.

The DLL3 protein used in the present invention is not limited by its origin and is preferably a human or cynomolgus DLL3 protein.

In some embodiments, for the DLL3 protein, DLL3 ECD fragment proteins (or ECD variants) may be used. Depending on the site of truncation, the fragments/variants may comprise, from the N-terminal side to the C-terminal side, the DSL domain to EGF6, EGF1 to EGF6, EGF2 to EGF6, EGF3 to EGF6, EGF4 to EGF6, EGF5 and EGF6, or EGF6. The fragments/variants may further comprise a region spanning from immediately after the EGF6 region to immediately before the TM region. A Flag tag may be attached to the C terminus of the fragments/variants using a technique well-known in the art.

Affinity

"Affinity" refers to the strength of the sum total of noncovalent interactions between a single binding site of a molecule (e.g., an antigen-binding molecule or antibody) and its binding partner (e.g., an antigen). Unless indicated otherwise, as used herein, "binding affinity" refers to intrinsic binding affinity which reflects a 1:1 interaction between members of a binding pair (e.g., antigen-binding molecule and antigen, or antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

Methods to Determine Affinity

In certain embodiments, the antigen-binding domain of an antigen-binding molecule or antibody provided herein has a dissociation constant (Kd) of 1 micro M or less, 120 nM or less, 100 nM or less, 80 nM or less, 70 nM or less, 50 nM or less, 40 nM or less, 30 nM or less, 20 nM or less, 10 nM or less, 2 nM or less, 1 nM or less, 0.1 nM or less, 0.01 nM or less, or 0.001 nM or less (e.g., $10^{-8}$ M or less, $10^{-8}$ M to $10^{-13}$ M, $10^{-9}$ M to $10^{-13}$ M) for its antigen. In certain embodiments, the Kd value of the first antigen-binding domain of the antibody/antigen-binding molecule for DLL3 falls within the range of 1-40, 1-50, 1-70, 1-80, 30-50, 30-70, 30-80, 40-70, 40-80, or 60-80 nM.

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER (registered trademark) multi-well plates (Thermo Scientific) are coated overnight with 5 micro g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 micro L/well of scintillant (MICROSCINT-20™. Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE (registered trademark) surface plasmon resonance assay. For example, an assay using a BIACORE (registered trademark)-2000 or a BIACORE(registered trademark)-3000 (BIAcore, Inc., Piscataway, N.J.) is performed at 25 degrees C. with immobilized antigen CM5 chips at approximately 10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micro g/ml (approximately 0.2 micro M) before injection at a flow rate of 5 micro L/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25 degrees C. at a flow rate of approximately 25 micro L/min. Association rates ($k_{on}$) and dissociation rates ($k_{off}$) are calculated using a simple one-to-one Langmuir binding model (BIACORE (registered trademark) Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25 degrees C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

Methods for measuring the affinity of the antigen-binding domain of an antibody are described above, and one skilled in art can carry out affinity measurement for other antigen-binding domains.

Antibody

The term "antibody" herein is used in the broadest sense and encompasses various antibody structures, including but not limited to monoclonal antibodies, polyclonal antibodies, monospecific antibodies, multispecific antibodies (e.g., bispecific antibodies), and antibody fragments so long as they exhibit the desired antigen-binding activity.

In an aspect, the present invention provides a multispecific antigen-binding molecule or antibody.

In some embodiments, the multispecific antigen-binding molecule comprises:
(1) a first domain comprising a first antigen-binding domain binds to human DLL3, and
(2) a second domain comprising a second antigen-binding domain binds to T-cell receptor complex,
wherein the first antigen-binding domain of (1) binds to an epitope within the region defined in SEQ ID NO: 7 in human DLL3.

In some embodiments, in the multispecific antigen-binding molecule, the first antigen-binding domain of (1) is any one of (a1) to (a12) below:
(a1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
(a2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;
(a3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;
(a4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;
(a5) an antibody variable fragment comprising the HVR-H1 sequence of SEQ ID NO: 51, the HVR-H2 sequence of SEQ ID NO: 52, the HVR-H3 sequence of SEQ ID NO: 53, the HVR-L1 sequence of SEQ ID NO: 54, the HVR-L2 sequence of SEQ ID NO: 55, and the HVR-L3 sequence of SEQ ID NO: 56;
(a6) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
(a7) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
(a8) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;
(a9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38;
(a10) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81;
(a11) an antibody variable fragment that binds to the same epitope of any of the antibody variable fragment selected from (a1) to (a10);
(a12) an antibody variable fragment that competes with the binding of any of the antibody variable fragment selected from (a1) to (a10).

In some embodiments, in the multispecific antigen-binding molecule, the first antigen-binding domain of (1) is any one of (b1) to (b21) below:
(b1) an antibody variable fragment comprising the HVR-H1 sequence identical to the amino acid sequences of the HVR-H1 region comprised in SEQ ID NO: 15, the HVR-H2 sequence identical to the amino acid sequences of the HVR-H2 region comprised in SEQ ID NO: 15, the HVR-H3 sequence identical to the amino acid sequences of the HVR-H3 region comprised in SEQ ID NO: 15, the HVR-L1 sequence identical to the amino acid sequences of the HVR-L1 region comprised in SEQ ID NO: 16, the HVR-L2 sequence identical to the amino acid sequences of the HVR-L2 region comprised in SEQ ID NO: 16, and the HVR-L3 sequence identical to the amino acid sequences of the HVR-L3 region comprised in SEQ ID NO: 16;
(b2) an antibody variable fragment comprising the HVR-H1 sequence identical to the amino acid sequences of the HVR-H1 region comprised in SEQ ID NO: 25, the HVR-H2 sequence identical to the amino acid sequences of the HVR-H2 region comprised in SEQ ID NO: 25, the HVR-H3 sequence identical to the amino acid sequences of the HVR-H3 region comprised in SEQ ID NO: 25, the HVR-L1 sequence identical to the amino acid sequences of the HVR-L1 region comprised in SEQ ID NO: 26, the HVR-L2 sequence identical to the amino acid sequences of the HVR-L2 region comprised in SEQ ID NO: 26, and the HVR-L3 sequence identical to the amino acid sequences of the HVR-L3 region comprised in SEQ ID NO: 26;
(b3) an antibody variable fragment comprising the HVR-H1 sequence identical to the amino acid sequences of the HVR-H1 region comprised in SEQ ID NO: 19, the HVR-H2 sequence identical to the amino acid sequences of the HVR-H2 region comprised in SEQ ID NO: 19, the HVR-H3 sequence identical to the amino acid sequences of the HVR-H3 region comprised in SEQ ID NO: 19, the HVR-L1 sequence identical to the amino acid sequences of the HVR-L1 region comprised in SEQ ID NO: 20, the HVR-L2 sequence identical to the amino acid sequences of the HVR-L2 region comprised in SEQ ID NO: 20, and the HVR-L3 sequence identical to the amino acid sequences of the HVR-L3 region comprised in SEQ ID NO: 20;

(b4) an antibody variable fragment comprising the HVR-H1 sequence identical to the amino acid sequences of the HVR-H1 region comprised in SEQ ID NO: 23, the HVR-H2 sequence identical to the amino acid sequences of the HVR-H2 region comprised in SEQ ID NO: 23, the HVR-H3 sequence identical to the amino acid sequences of the HVR-H3 region comprised in SEQ ID NO: 23, the HVR-L1 sequence identical to the amino acid sequences of the HVR-L1 region comprised in SEQ ID NO: 24, the HVR-L2 sequence identical to the amino acid sequences of the HVR-L2 region comprised in SEQ ID NO: 24, and the HVR-L3 sequence identical to the amino acid sequences of the HVR-L3 region comprised in SEQ ID NO: 24;

(b5) an antibody variable fragment comprising the HVR-H1 sequence identical to the amino acid sequences of the HVR-H1 region comprised in SEQ ID NO: 11, the HVR-H2 sequence identical to the amino acid sequences of the HVR-H2 region comprised in SEQ ID NO: 11, the HVR-H3 sequence identical to the amino acid sequences of the HVR-H3 region comprised in SEQ ID NO: 11, the HVR-L1 sequence identical to the amino acid sequences of the HVR-L1 region comprised in SEQ ID NO: 12, the HVR-L2 sequence identical to the amino acid sequences of the HVR-L2 region comprised in SEQ ID NO: 12, and the HVR-L3 sequence identical to the amino acid sequences of the HVR-L3 region comprised in SEQ ID NO: 12;

(b6) an antibody variable fragment comprising the HVR-H1 sequence identical to the amino acid sequences of the HVR-H1 region comprised in SEQ ID NO: 13, the HVR-H2 sequence identical to the amino acid sequences of the HVR-H2 region comprised in SEQ ID NO: 13, the HVR-H3 sequence identical to the amino acid sequences of the HVR-H3 region comprised in SEQ ID NO: 13, the HVR-L1 sequence identical to the amino acid sequences of the HVR-L1 region comprised in SEQ ID NO: 14, the HVR-L2 sequence identical to the amino acid sequences of the HVR-L2 region comprised in SEQ ID NO: 14, and the HVR-L3 sequence identical to the amino acid sequences of the HVR-L3 region comprised in SEQ ID NO: 14;

(b7) an antibody variable fragment comprising the HVR-H1 sequence identical to the amino acid sequences of the HVR-H1 region comprised in SEQ ID NO: 17, the HVR-H2 sequence identical to the amino acid sequences of the HVR-H2 region comprised in SEQ ID NO: 17, the HVR-H3 sequence identical to the amino acid sequences of the HVR-H3 region comprised in SEQ ID NO: 17, the HVR-L1 sequence identical to the amino acid sequences of the HVR-L1 region comprised in SEQ ID NO: 18, the HVR-L2 sequence identical to the amino acid sequences of the HVR-L2 region comprised in SEQ ID NO: 18, and the HVR-L3 sequence identical to the amino acid sequences of the HVR-L3 region comprised in SEQ ID NO: 18;

(b8) an antibody variable fragment comprising the HVR-H1 sequence identical to the amino acid sequences of the HVR-H1 region comprised in SEQ ID NO: 21, the HVR-H2 sequence identical to the amino acid sequences of the HVR-H2 region comprised in SEQ ID NO: 21, the HVR-H3 sequence identical to the amino acid sequences of the HVR-H3 region comprised in SEQ ID NO: 21, the HVR-L1 sequence identical to the amino acid sequences of the HVR-L1 region comprised in SEQ ID NO: 22, the HVR-L2 sequence identical to the amino acid sequences of the HVR-L2 region comprised in SEQ ID NO: 22, and the HVR-L3 sequence identical to the amino acid sequences of the HVR-L3 region comprised in SEQ ID NO: 22;

(b9) an antibody variable fragment comprising the HVR-H1 sequence identical to the amino acid sequences of the HVR-H1 region comprised in SEQ ID NO: 85, the HVR-H2 sequence identical to the amino acid sequences of the HVR-H2 region comprised in SEQ ID NO: 85, the HVR-H3 sequence identical to the amino acid sequences of the HVR-H3 region comprised in SEQ ID NO: 85, the HVR-L1 sequence identical to the amino acid sequences of the HVR-L1 region comprised in SEQ ID NO: 93, the HVR-L2 sequence identical to the amino acid sequences of the HVR-L2 region comprised in SEQ ID NO: 93, and the HVR-L3 sequence identical to the amino acid sequences of the HVR-L3 region comprised in SEQ ID NO: 93;

(b10) an antibody variable fragment comprising the HVR-H1 sequence identical to the amino acid sequences of the HVR-H1 region comprised in SEQ ID NO: 63, the HVR-H2 sequence identical to the amino acid sequences of the HVR-H2 region comprised in SEQ ID NO: 63, the HVR-H3 sequence identical to the amino acid sequences of the HVR-H3 region comprised in SEQ ID NO: 63, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b11) an antibody variable fragment comprising the HVR-H1 sequence identical to the amino acid sequences of the HVR-H1 region comprised in SEQ ID NO: 64, the HVR-H2 sequence identical to the amino acid sequences of the HVR-H2 region comprised in SEQ ID NO: 64, the HVR-H3 sequence identical to the amino acid sequences of the HVR-H3 region comprised in SEQ ID NO: 64, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b12) an antibody variable fragment comprising the HVR-H1 sequence identical to the amino acid sequences of the HVR-H1 region comprised in SEQ ID NO: 65, the HVR-H2 sequence identical to the amino acid sequences of the HVR-H2 region comprised in SEQ ID NO: 65, the HVR-H3 sequence identical to the amino acid sequences of the HVR-H3 region comprised in SEQ ID NO: 65, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b13) an antibody variable fragment comprising the HVR-H1 sequence identical to the amino acid sequences of the HVR-H1 region comprised in SEQ ID NO: 66, the HVR-H2 sequence identical to the amino acid sequences of the HVR-H2 region comprised in SEQ ID NO: 66, the HVR-H3 sequence identical to the amino acid sequences of the HVR-H3 region comprised in SEQ ID NO: 66, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b14) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b15) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 74, the HVR-L2 sequence identical to the amino acid sequences of the HVR-L2 region comprised in SEQ ID NO: 74, and the HVR-L3 sequence identical to the amino acid sequences of the HVR-L3 region comprised in SEQ ID NO: 74;

(b16) an antibody variable fragment comprising the HVR-H1 sequence identical to the amino acid sequences of the HVR-H1 region comprised in SEQ ID NO: 68, the HVR-H2 sequence identical to the amino acid sequences of the HVR-H2 region comprised in SEQ ID NO: 68, the HVR-H3 sequence identical to the amino acid sequences of the HVR-H3 region comprised in SEQ ID NO: 68, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b17) an antibody variable fragment comprising the HVR-H1 sequence identical to the amino acid sequences of the HVR-H1 region comprised in SEQ ID NO: 69, the HVR-H2 sequence identical to the amino acid sequences of the HVR-H2 region comprised in SEQ ID NO: 69, the HVR-H3 sequence identical to the amino acid sequences of the HVR-H3 region comprised in SEQ ID NO: 69, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b18) an antibody variable fragment comprising the HVR-H1 sequence identical to the amino acid sequences of the HVR-H1 region comprised in SEQ ID NO: 70, the HVR-H2 sequence identical to the amino acid sequences of the HVR-H2 region comprised in SEQ ID NO: 70, the HVR-H3 sequence identical to the amino acid sequences of the HVR-H3 region comprised in SEQ ID NO: 70, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b19) an antibody variable fragment comprising the HVR-H1 sequence identical to the amino acid sequences of the HVR-H1 region comprised in SEQ ID NO: 71, the HVR-H2 sequence identical to the amino acid sequences of the HVR-H2 region comprised in SEQ ID NO: 71, the HVR-H3 sequence identical to the amino acid sequences of the HVR-H3 region comprised in SEQ ID NO: 71, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b20) an antibody variable fragment that binds to the same epitope of any one of the antibody variable fragment selected from (b1) to (b19);

(b21) an antibody variable fragment that competes with the binding of any one of the antibody variable fragment selected from (b1) to (b19).

In some embodiments, in the multispecific antigen-binding molecule, the first antigen-binding domain of (1) comprises any one of the combinations of heavy chain variable region and light chain variable region selected from the following (c1) to (c22):

(c1) heavy chain variable region having the amino acid sequence of SEQ ID NO: 15 and light chain variable region having the amino acid sequence of SEQ ID NO: 16;

(c2) heavy chain variable region having the amino acid sequence of SEQ ID NO: 25 and light chain variable region having the amino acid sequence of SEQ ID NO: 26;

(c3) heavy chain variable region having the amino acid sequence of SEQ ID NO: 19 and light chain variable region having the amino acid sequence of SEQ ID NO: 20;

(c4) heavy chain variable region having the amino acid sequence of SEQ ID NO: 23 and light chain variable region having the amino acid sequence of SEQ ID NO: 24;

(c5) heavy chain variable region having the amino acid sequence of SEQ ID NO: 11 and light chain variable region having the amino acid sequence of SEQ ID NO: 12;

(c6) heavy chain variable region having the amino acid sequence of SEQ ID NO: 13 and light chain variable region having the amino acid sequence of SEQ ID NO: 14;

(c7) heavy chain variable region having the amino acid sequence of SEQ ID NO: 17 and light chain variable region having the amino acid sequence of SEQ ID NO: 18;
(c8) heavy chain variable region having the amino acid sequence of SEQ ID NO: 21 and light chain variable region having the amino acid sequence of SEQ ID NO: 22;
(c9) heavy chain variable region having the amino acid sequence of SEQ ID NO: 85 and light chain variable region having the amino acid sequence of SEQ ID NO: 93;
(c10) heavy chain variable region having the amino acid sequence of SEQ ID NO: 63 and light chain variable region having the amino acid sequence of SEQ ID NO: 72;
(c11) heavy chain variable region having the amino acid sequence of SEQ ID NO: 64 and light chain variable region having the amino acid sequence of SEQ ID NO: 72;
(c12) heavy chain variable region having the amino acid sequence of SEQ ID NO: 65 and light chain variable region having the amino acid sequence of SEQ ID NO: 72;
(c13) heavy chain variable region having the amino acid sequence of SEQ ID NO: 66 and light chain variable region having the amino acid sequence of SEQ ID NO: 73;
(c14) heavy chain variable region having the amino acid sequence of SEQ ID NO: 67 and light chain variable region having the amino acid sequence of SEQ ID NO: 73;
(c15) heavy chain variable region having the amino acid sequence of SEQ ID NO: 67 and light chain variable region having the amino acid sequence of SEQ ID NO: 74;
(c16) heavy chain variable region having the amino acid sequence of SEQ ID NO: 68 and light chain variable region having the amino acid sequence of SEQ ID NO: 72;
(c17) heavy chain variable region having the amino acid sequence of SEQ ID NO: 69 and light chain variable region having the amino acid sequence of SEQ ID NO: 73;
(c18) heavy chain variable region having the amino acid sequence of SEQ ID NO: 70 and light chain variable region having the amino acid sequence of SEQ ID NO: 73;
(c19) heavy chain variable region having the amino acid sequence of SEQ ID NO: 71 and light chain variable region having the amino acid sequence of SEQ ID NO: 73;
(c20) a heavy chain variable region that has an identity more than 80% of any one of the heavy chain variable region of (c1) to (c19), and a light chain variable region that has an identity more than 80% to any one of the light chain variable region of (c1) to (c19);
(c21) a heavy chain variable region that has an identity more than 90% of any one of the heavy chain variable region of (c1) to (c19), and a light chain variable region that has an identity more than 90% to any one of the light chain variable region of (c1) to (c19);
(c22) a heavy chain variable region that has an identity more than 95% of any one of the heavy chain variable region of (c1) to (c19), and a light chain variable region that has an identity more than 95% to any one of the light chain variable region of (c1) to (c19).

In some embodiments, the multispecific antigen-binding molecule has cytotoxic activity. More specifically, the cytotoxic activity is T-cell-dependent cytotoxic activity (T-cell-dependent cellular cytotoxicity (TDCC)).

In some embodiments, in the multispecific antigen-binding molecule, the second antigen-binding domain in (2) binds to CD3. More specifically, in some embodiments, in the multispecific antigen-binding molecule, the second antigen-binding domain in (2) binds to CD3 epsilon chain.

In some embodiments, in the multispecific antigen-binding molecule, the second antigen-binding domain in (2) binds to T-cell receptor.

In some embodiments, in the multispecific antigen-binding molecule, the second antigen-binding domain in (2) is any one of (d1) to (d12) below:
(d1) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 57 respectively, and the HVR-L1, HVR-L2 and HVR-L3 sequences identical to the amino acid sequences of the HVR-L1, HVR-L2 and HVR-L3 regions comprised in SEQ ID NO: 58 respectively;
(d2) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 98 respectively, and the HVR-L1, HVR-L2 and HVR-L3 sequences identical to the amino acid sequences of the HVR-L1, HVR-L2 and HVR-L3 regions comprised in SEQ ID NO: 103 respectively;
(d3) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 99 respectively, and the HVR-L1, HVR-L2 and HVR-L3 sequences identical to the amino acid sequences of the HVR-L1, HVR-L2 and HVR-L3 regions comprised in SEQ ID NO: 103 respectively;
(d4) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 100 respectively, and the HVR-L1, HVR-L2 and HVR-L3 sequences identical to the amino acid sequences of the HVR-L1, HVR-L2 and HVR-L3 regions comprised in SEQ ID NO: 103 respectively;
(d5) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 101 respectively, and the HVR-L1, HVR-L2 and HVR-L3 sequences identical to the amino acid sequences of the HVR-L1, HVR-L2 and HVR-L3 regions comprised in SEQ ID NO: 103 respectively;
(d6) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 102 respectively, and the HVR-L1, HVR-L2 and HVR-L3 sequences identical to the amino acid sequences of the HVR-L1, HVR-L2 and HVR-L3 regions comprised in SEQ ID NO: 103 respectively;
(d7) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 298 respectively, and the HVR-L1, HVR-L2 and HVR-L3 sequences identical to the amino acid sequences of the HVR-L1, HVR-L2 and HVR-L3 regions comprised in SEQ ID NO: 299 respectively;

(d8) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 300 respectively, and the HVR-L1, HVR-L2 and HVR-L3 sequences identical to the amino acid sequences of the HVR-L1, HVR-L2 and HVR-L3 regions comprised in SEQ ID NO: 301 respectively;

(d9) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 302 respectively, and the HVR-L1, HVR-L2 and HVR-L3 sequences identical to the amino acid sequences of the HVR-L1, HVR-L2 and HVR-L3 regions comprised in SEQ ID NO: 303 respectively;

(d10) an antibody variable fragment comprising the HVR-H1, HVR-H2 and HVR-H3 sequences identical to the amino acid sequences of the HVR-H1, HVR-H2 and HVR-H3 regions comprised in any one selected from SEQ ID NO: 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388 and 390, and the HVR-L1, HVR-L2 and HVR-L3 sequences identical to the amino acid sequences of the HVR-L1, HVR-L2 and HVR-L3 regions comprised in any one selected from SEQ ID NO: 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389 and 391;

(d11) an antibody variable fragment that binds to the same epitope of any one of the antibody variable fragment selected from (d1) to (d10);

(d12) an antibody variable fragment that competes with the binding of any one of the antibody variable fragment selected from (d1) to (d10).

In some embodiments, in the multispecific antigen-binding molecule, the second antigen-binding domain in (2) is any one of (e1) to (e12) below:

(e1) heavy chain variable region having the amino acid sequence of SEQ ID NO: 57 and light chain variable region having the amino acid sequence of SEQ ID NO: 58;

(e2) heavy chain variable region having the amino acid sequence of SEQ ID NO: 98 and light chain variable region having the amino acid sequence of SEQ ID NO: 103;

(e3) heavy chain variable region having the amino acid sequence of SEQ ID NO: 99 and light chain variable region having the amino acid sequence of SEQ ID NO: 103;

(e4) heavy chain variable region having the amino acid sequence of SEQ ID NO: 100 and light chain variable region having the amino acid sequence of SEQ ID NO: 103;

(e5) heavy chain variable region having the amino acid sequence of SEQ ID NO: 101 and light chain variable region having the amino acid sequence of SEQ ID NO: 103;

(e6) heavy chain variable region having the amino acid sequence of SEQ ID NO: 102 and light chain variable region having the amino acid sequence of SEQ ID NO: 103;

(e7) heavy chain variable region having the amino acid sequence of SEQ ID NO: 300 and light chain variable region having the amino acid sequence of SEQ ID NO: 301;

(e8) heavy chain variable region having the amino acid sequence of SEQ ID NO: 302 and light chain variable region having the amino acid sequence of SEQ ID NO: 303;

(e9) heavy chain variable region and light chain variable region having any one of the amino acid sequence combination in Table 2A;

(e10) a heavy chain variable region that has an identity more than 80% of any one of the heavy chain variable region of (e1) to (e9), and a light chain variable region that has an identity more than 80% to any one of the light chain variable region of (e1) to (e9);

(e11) a heavy chain variable region that has an identity more than 90% of any one of the heavy chain variable region of (e1) to (e9), and a light chain variable region that has an identity more than 90% to any one of the light chain variable region of (e1) to (e9);

(e12) a heavy chain variable region that has an identity more than 95% of any one of the heavy chain variable region of (e1) to (e9), and a light chain variable region that has an identity more than 95% to any one of the light chain variable region of (e1) to (e9).

In some embodiments, in the multispecific antigen-binding molecule, the second antigen-binding domain in (2) is any one of (j1) to (j5) below:

(j1) an antibody variable fragment comprising the HVR-H1 sequence of SEQ ID NO: 136, the HVR-H2 sequence of SEQ ID NO: 137, the HVR-H3 sequence of SEQ ID NO: 138, the HVR-L1 sequence of SEQ ID NO: 139, the HVR-L2 sequence of SEQ ID NO: 140, and the HVR-L3 sequence of SEQ ID NO: 141;

(j2) an antibody variable fragment comprising the HVR-H1 sequence of SEQ ID NO: 142, the HVR-H2 sequence of SEQ ID NO: 143, the HVR-H3 sequence of SEQ ID NO: 144, the HVR-L1 sequence of SEQ ID NO: 145, the HVR-L2 sequence of SEQ ID NO: 146, and the HVR-L3 sequence of SEQ ID NO: 147;

(j3) an antibody variable fragment comprising the HVR sequences selected from any of the combinations in Table 2B;

(j4) an antibody variable fragment that binds to the same epitope of any of the antibody variable fragment selected from (j1) to (j3);

(j5) an antibody variable fragment that competes with the binding of any of the antibody variable fragment selected from (j1) to (j3).

In some embodiments, the multispecific antigen binding molecule further comprises:

(3) a third domain comprising an Fc region with reduced binding activity towards an Fc gamma receptor.

In some embodiments, the present invention provides a multispecific antigen-binding molecule that comprises:

(1) a first domain comprising a first antigen-binding domain binds to human DLL3

(2) a second domain comprising a second antigen-binding domain binds to T-cell receptor complex, and (3) a third domain comprising an Fc region with reduced binding activity towards an Fc gamma receptor.

In some embodiments, in the multispecific antigen-binding molecule, the Fc region of is an Fc region with an amino acid mutation at any of the Fc region-constituting amino acids of SEQ ID NOs: 112 to 115 (IgG1 to IgG4).

In some embodiments, in the multispecific antigen-binding molecule, the Fc region is an Fc region with mutation of at least one amino acid selected from the following amino acid positions specified by EU numbering:
position 220, position 226, position 229, position 231, position 232, position 233, position 234, position 235, position 236, position 237, position 238, position 239, position 240, position 264, position 265, position 266, position 267, position 269, position 270, position 295, position 296, position 297, position 298, position 299, position 300, position 325, position 327, position 328, position 329, position 330, position 331, and position 332.

In some embodiments, the multispecific antigen-binding molecule is a bispecific antibody.

In some embodiments, the bispecific antibody is a monoclonal antibody.

In preferred embodiments, the above-mentioned multispecific antigen-binding molecule/bispecific antibody/monoclonal antibody has T cell-dependent cellular cytotoxicity (TDCC) activity against cells expressing DLL3.

In another aspect, the present invention provides an antigen-binding molecule that binds to an epitope within the region defined in SEQ ID NO: 7 in human DLL3.

In some embodiments, the antigen-binding molecule comprises an antigen-binding domain comprising any one of (f1) to (f11) below:
(f1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
(f2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;
(f3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;
(f4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;
(f5) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
(f6) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
(f7) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;
(f8) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38;
(f9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81;
(f10) an antibody variable fragment that binds to the same epitope of any of the antibody variable fragment selected from (f1) to (f9);
(f11) an antibody variable fragment that competes with the binding of any of the antibody variable fragment selected from (f1) to (f9).

In some embodiments, the antigen-binding molecule comprises an antigen-binding domain comprising any one of (g1) to (g20) below:
(g1) an antibody variable fragment comprising the HVR-H1 sequence identical to the amino acid sequences of the HVR-H1 region comprised in SEQ ID NO: 15, the HVR-H2 sequence identical to the amino acid sequences of the HVR-H2 region comprised in SEQ ID NO: 15, the HVR-H3 sequence identical to the amino acid sequences of the HVR-H3 region comprised in SEQ ID NO: 15, the HVR-L1 sequence identical to the amino acid sequences of the HVR-L1 region comprised in SEQ ID NO: 16, the HVR-L2 sequence identical to the amino acid sequences of the HVR-L2 region comprised in SEQ ID NO: 16, and the HVR-L3 sequence identical to the amino acid sequences of the HVR-L3 region comprised in SEQ ID NO: 16;
(g2) an antibody variable fragment comprising the HVR-H1 sequence identical to the amino acid sequences of the HVR-H1 region comprised in SEQ ID NO: 25, the HVR-H2 sequence identical to the amino acid sequences of the HVR-H2 region comprised in SEQ ID NO: 25, the HVR-H3 sequence identical to the amino acid sequences of the HVR-H3 region comprised in SEQ ID NO: 25, the HVR-L1 sequence identical to the amino acid sequences of the HVR-L1 region comprised in SEQ ID NO: 26, the HVR-L2 sequence identical to the amino acid sequences of the HVR-L2 region comprised in SEQ ID NO: 26, and the HVR-L3 sequence identical to the amino acid sequences of the HVR-L3 region comprised in SEQ ID NO: 26;
(g3) an antibody variable fragment comprising the HVR-H1 sequence identical to the amino acid sequences of the HVR-H1 region comprised in SEQ ID NO: 19, the HVR-H2 sequence identical to the amino acid sequences of the HVR-H2 region comprised in SEQ ID NO: 19, the HVR-H3 sequence identical to the amino acid sequences of the HVR-H3 region comprised in SEQ ID NO: 19, the HVR-L1 sequence identical to the amino acid sequences of the HVR-L1 region comprised in SEQ ID NO: 20, the HVR-L2 sequence identical to the amino acid sequences of the HVR-L2 region comprised in SEQ ID NO: 20, and the HVR-L3 sequence identical to the amino acid sequences of the HVR-L3 region comprised in SEQ ID NO: 20;

(g4) an antibody variable fragment comprising the HVR-H1 sequence identical to the amino acid sequences of the HVR-H1 region comprised in SEQ ID NO: 23, the HVR-H2 sequence identical to the amino acid sequences of the HVR-H2 region comprised in SEQ ID NO: 23, the HVR-H3 sequence identical to the amino acid sequences of the HVR-H3 region comprised in SEQ ID NO: 23, the HVR-L1 sequence identical to the amino acid sequences of the HVR-L1 region comprised in SEQ ID NO: 24, the HVR-L2 sequence identical to the amino acid sequences of the HVR-L2 region comprised in SEQ ID NO: 24, and the HVR-L3 sequence identical to the amino acid sequences of the HVR-L3 region comprised in SEQ ID NO: 24;

(g5) an antibody variable fragment comprising the HVR-H1 sequence identical to the amino acid sequences of the HVR-H1 region comprised in SEQ ID NO: 11, the HVR-H2 sequence identical to the amino acid sequences of the HVR-H2 region comprised in SEQ ID NO: 11, the HVR-H3 sequence identical to the amino acid sequences of the HVR-H3 region comprised in SEQ ID NO: 11, the HVR-L1 sequence identical to the amino acid sequences of the HVR-L1 region comprised in SEQ ID NO: 12, the HVR-L2 sequence identical to the amino acid sequences of the HVR-L2 region comprised in SEQ ID NO: 12, and the HVR-L3 sequence identical to the amino acid sequences of the HVR-L3 region comprised in SEQ ID NO: 12;

(g6) an antibody variable fragment comprising the HVR-H1 sequence identical to the amino acid sequences of the HVR-H1 region comprised in SEQ ID NO: 13, the HVR-H2 sequence identical to the amino acid sequences of the HVR-H2 region comprised in SEQ ID NO: 13, the HVR-H3 sequence identical to the amino acid sequences of the HVR-H3 region comprised in SEQ ID NO: 13, the HVR-L1 sequence identical to the amino acid sequences of the HVR-L1 region comprised in SEQ ID NO: 14, the HVR-L2 sequence identical to the amino acid sequences of the HVR-L2 region comprised in SEQ ID NO: 14, and the HVR-L3 sequence identical to the amino acid sequences of the HVR-L3 region comprised in SEQ ID NO: 14;

(g7) an antibody variable fragment comprising the HVR-H1 sequence identical to the amino acid sequences of the HVR-H1 region comprised in SEQ ID NO: 17, the HVR-H2 sequence identical to the amino acid sequences of the HVR-H2 region comprised in SEQ ID NO: 17, the HVR-H3 sequence identical to the amino acid sequences of the HVR-H3 region comprised in SEQ ID NO: 17, the HVR-L1 sequence identical to the amino acid sequences of the HVR-L1 region comprised in SEQ ID NO: 18, the HVR-L2 sequence identical to the amino acid sequences of the HVR-L2 region comprised in SEQ ID NO: 18, and the HVR-L3 sequence identical to the amino acid sequences of the HVR-L3 region comprised in SEQ ID NO: 18;

(g8) an antibody variable fragment comprising the HVR-H1 sequence identical to the amino acid sequences of the HVR-H1 region comprised in SEQ ID NO: 21, the HVR-H2 sequence identical to the amino acid sequences of the HVR-H2 region comprised in SEQ ID NO: 21, the HVR-H3 sequence identical to the amino acid sequences of the HVR-H3 region comprised in SEQ ID NO: 21, the HVR-L1 sequence identical to the amino acid sequences of the HVR-L1 region comprised in SEQ ID NO: 22, the HVR-L2 sequence identical to the amino acid sequences of the HVR-L2 region comprised in SEQ ID NO: 22, and the HVR-L3 sequence identical to the amino acid sequences of the HVR-L3 region comprised in SEQ ID NO: 22;

(g9) an antibody variable fragment comprising the HVR-H1 sequence identical to the amino acid sequences of the HVR-H1 region comprised in SEQ ID NO: 63, the HVR-H2 sequence identical to the amino acid sequences of the HVR-H2 region comprised in SEQ ID NO: 63, the HVR-H3 sequence identical to the amino acid sequences of the HVR-H3 region comprised in SEQ ID NO: 63, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g10) an antibody variable fragment comprising the HVR-H1 sequence identical to the amino acid sequences of the HVR-H1 region comprised in SEQ ID NO: 64, the HVR-H2 sequence identical to the amino acid sequences of the HVR-H2 region comprised in SEQ ID NO: 64, the HVR-H3 sequence identical to the amino acid sequences of the HVR-H3 region comprised in SEQ ID NO: 64, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g11) an antibody variable fragment comprising the HVR-H1 sequence identical to the amino acid sequences of the HVR-H1 region comprised in SEQ ID NO: 65, the HVR-H2 sequence identical to the amino acid sequences of the HVR-H2 region comprised in SEQ ID NO: 65, the HVR-H3 sequence identical to the amino acid sequences of the HVR-H3 region comprised in SEQ ID NO: 65, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g12) an antibody variable fragment comprising the HVR-H1 sequence identical to the amino acid sequences of the HVR-H1 region comprised in SEQ ID NO: 66, the HVR-H2 sequence identical to the amino acid sequences of the HVR-H2 region comprised in SEQ ID NO: 66, the HVR-H3 sequence identical to the amino acid sequences of the HVR-H3 region comprised in SEQ ID NO: 66, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g13) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g14) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 74, the HVR-L2 sequence identical to the amino acid sequences of the HVR-L2 region comprised in SEQ ID NO: 74, and the HVR-L3 sequence identical to the amino acid sequences of the HVR-L3 region comprised in SEQ ID NO: 74;

(g15) an antibody variable fragment comprising the HVR-H1 sequence identical to the amino acid sequences of the HVR-H1 region comprised in SEQ ID NO: 68, the HVR-H2 sequence identical to the amino acid sequences of the HVR-H2 region comprised in SEQ ID NO: 68, the HVR-H3 sequence identical to the amino acid sequences of the HVR-H3 region comprised in SEQ ID NO: 68, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g16) an antibody variable fragment comprising the HVR-H1 sequence identical to the amino acid sequences of the HVR-H1 region comprised in SEQ ID NO: 69, the HVR-H2 sequence identical to the amino acid sequences of the HVR-H2 region comprised in SEQ ID NO: 69, the HVR-H3 sequence identical to the amino acid sequences of the HVR-H3 region comprised in SEQ ID NO: 69, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g17) an antibody variable fragment comprising the HVR-H1 sequence identical to the amino acid sequences of the HVR-H1 region comprised in SEQ ID NO: 70, the HVR-H2 sequence identical to the amino acid sequences of the HVR-H2 region comprised in SEQ ID NO: 70, the HVR-H3 sequence identical to the amino acid sequences of the HVR-H3 region comprised in SEQ ID NO: 70, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g18) an antibody variable fragment comprising the HVR-H1 sequence identical to the amino acid sequences of the HVR-H1 region comprised in SEQ ID NO: 71, the HVR-H2 sequence identical to the amino acid sequences of the HVR-H2 region comprised in SEQ ID NO: 71, the HVR-H3 sequence identical to the amino acid sequences of the HVR-H3 region comprised in SEQ ID NO: 71, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g19) an antibody variable fragment that binds to the same epitope of any one of the antibody variable fragment selected from (g1) to (g18);

(g20) an antibody variable fragment that competes with the binding of any one of the antibody variable fragment selected from (g1) to (g18).

In some embodiments, the antigen-binding molecule comprises an antigen-binding domain comprising any one of (h1) to (h21) below:

(h1) heavy chain variable region having the amino acid sequence of SEQ ID NO: 15 and light chain variable region having the amino acid sequence of SEQ ID NO: 16;

(h2) heavy chain variable region having the amino acid sequence of SEQ ID NO: 25 and light chain variable region having the amino acid sequence of SEQ ID NO: 26;

(h3) heavy chain variable region having the amino acid sequence of SEQ ID NO: 19 and light chain variable region having the amino acid sequence of SEQ ID NO: 20;

(h4) heavy chain variable region having the amino acid sequence of SEQ ID NO: 23 and light chain variable region having the amino acid sequence of SEQ ID NO: 24;

(h5) heavy chain variable region having the amino acid sequence of SEQ ID NO: 11 and light chain variable region having the amino acid sequence of SEQ ID NO: 12;

(h6) heavy chain variable region having the amino acid sequence of SEQ ID NO: 13 and light chain variable region having the amino acid sequence of SEQ ID NO: 14;

(h7) heavy chain variable region having the amino acid sequence of SEQ ID NO: 17 and light chain variable region having the amino acid sequence of SEQ ID NO: 18;

(h8) heavy chain variable region having the amino acid sequence of SEQ ID NO: 21 and light chain variable region having the amino acid sequence of SEQ ID NO: 22;

(h9) heavy chain variable region having the amino acid sequence of SEQ ID NO: 63 and light chain variable region having the amino acid sequence of SEQ ID NO: 72;

(h10) heavy chain variable region having the amino acid sequence of SEQ ID NO: 64 and light chain variable region having the amino acid sequence of SEQ ID NO: 72;

(h11) heavy chain variable region having the amino acid sequence of SEQ ID NO: 65 and light chain variable region having the amino acid sequence of SEQ ID NO: 72;

(h12) heavy chain variable region having the amino acid sequence of SEQ ID NO: 66 and light chain variable region having the amino acid sequence of SEQ ID NO: 73;
(h13) heavy chain variable region having the amino acid sequence of SEQ ID NO: 67 and light chain variable region having the amino acid sequence of SEQ ID NO: 73;
(h14) heavy chain variable region having the amino acid sequence of SEQ ID NO: 67 and light chain variable region having the amino acid sequence of SEQ ID NO: 74;
(h15) heavy chain variable region having the amino acid sequence of SEQ ID NO: 68 and light chain variable region having the amino acid sequence of SEQ ID NO: 72;
(h16) heavy chain variable region having the amino acid sequence of SEQ ID NO: 69 and light chain variable region having the amino acid sequence of SEQ ID NO: 73;
(h17) heavy chain variable region having the amino acid sequence of SEQ ID NO: 70 and light chain variable region having the amino acid sequence of SEQ ID NO: 73;
(h18) heavy chain variable region having the amino acid sequence of SEQ ID NO: 71 and light chain variable region having the amino acid sequence of SEQ ID NO: 73;
(h19) a heavy chain variable region that has an identity more than 80% of any one of the heavy chain variable region of (h1) to (h18); and a light chain variable region that has an identity more than 80% to any one of the light chain variable region of (h1) to (h18);
(h20) a heavy chain variable region that has an identity more than 90% of any one of the heavy chain variable region of (h1) to (h18); and a light chain variable region that has an identity more than 90% to any one of the light chain variable region of (h1) to (h18);
(h21) a heavy chain variable region that has an identity more than 95% of any one of the heavy chain variable region of (h1) to (h18); and a light chain variable region that has an identity more than 95% to any one of the light chain variable region of (h1) to (h18).

In some embodiments, the antigen-binding molecule has cellular cytotoxic activity.

In some embodiments, in the antigen-binding molecule, the cytotoxic activity is antibody dependent cellular cytotoxicity or complement dependent cytotoxicity.

In some embodiments, the antigen-binding molecule has internalization activity.

In some embodiments, the antigen-binding molecule is conjugated to a toxic compound.

In some embodiments, the antigen-binding molecule is an antibody.

In some embodiments, the antigen-binding molecule is a monoclonal antibody.

In some embodiments, the present invention provides an antibody-drug-conjugate compound that comprises the antibody.

Class of Antibody

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively. In preferred embodiments, the antibody of the present invention is an IgG-type antibody.

Framework

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

Human Consensus Framework

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

HVR

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
 (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
 (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));
 (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
 (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

Variable Region

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

Chimeric Antibody

The term "chimeric" antibody refers to an antibody in which a portion of the heavy and/or light chain is derived from a particular source or species, while the remainder of the heavy and/or light chain is derived from a different source or species. Similarly, the term "chimeric antibody variable domain" refers to an antibody variable region in which a portion of the heavy and/or light chain variable region is derived from a particular source or species, while the remainder of the heavy and/or light chain variable region is derived from a different source or species.

Humanized Antibody

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. A "humanized antibody variable region" refers to the variable region of a humanized antibody.

Human Antibody

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. A "human antibody variable region" refers to the variable region of a human antibody.

Methods for Producing an Antibody with Desired Binding Activity

Methods for producing an antibody with desired binding activity are known to those skilled in the art. Below is an example that describes a method for producing an antibody (anti-DLL3 antibody) that binds to DLL3 mentioned above. Antibodies that bind to a T-cell receptor complex and so on can also be produced as described below.

Anti-DLL3 antibodies can be obtained as polyclonal or monoclonal antibodies using known methods. The anti-DLL3 antibodies preferably produced are monoclonal antibodies derived from mammals. Such mammal-derived monoclonal antibodies include antibodies produced by hybridomas or host cells transformed with an expression vector carrying an antibody gene by genetic engineering techniques.

Monoclonal antibody-producing hybridomas can be produced using known techniques, for example, as described below. Specifically, mammals are immunized by conventional immunization methods using a DLL3 protein as a sensitizing antigen. Resulting immune cells are fused with known parental cells by conventional cell fusion methods. Then, hybridomas producing an anti-DLL3 antibody can be selected by screening for monoclonal antibody-producing cells using conventional screening methods.

Specifically, monoclonal antibodies are prepared as mentioned below. First, the DLL3 gene whose nucleotide sequence is disclosed in NCBI Reference Sequence NM_016941.3 or XP_005589253.1 can be expressed to produce the DLL3 protein which will be used as a sensitizing antigen for antibody preparation. Alternatively, a polynucleotide encoding the extracellular domain (ECD) of DLL3 can be expressed to produce an DLL3 ECD-containing protein. That is, a gene sequence encoding full-length DLL3 or DLL3 ECD is inserted into a known expression vector, and appropriate host cells are transformed with this vector. The desired full-length DLL3 or DLL3 ECD protein is purified from the host cells or their culture supernatants by known methods. Alternatively, it is possible to use a purified natural DLL3 protein as a sensitizing antigen.

The purified full-length DLL3 or DLL3 ECD protein can be used as a sensitizing antigen for use in immunization of mammals. Partial peptides of full-length DLL3 or DLL3 ECD can also be used as sensitizing antigens. In this case, the partial peptides may also be obtained by chemical synthesis from the DLL3 amino acid sequence. Furthermore, they may also be obtained by incorporating a portion of the DLL3 gene into an expression vector and expressing it. Moreover, they may also be obtained by degrading the DLL3 protein using proteases, but the region and size of the DLL3 peptide used as the partial peptide are not particularly limited to a special embodiment. As the preferred region, any sequence from the amino acid sequence may be selected. The number of amino acids constituting a peptide to be used as the sensitizing antigen is at least five or more, or preferably for example, six or more, or seven or more. More specifically, peptides consisting of 8 to 50 residues or preferably 10 to 30 residues may be used as the sensitizing antigen.

For sensitizing antigen, alternatively it is possible to use a fusion protein prepared by fusing a desired partial polypeptide or peptide of the full-length DLL3 or DLL3 ECD protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing DLL3 to be used as a sensitizing antigen, and immunization methods using DLL3 are also described in the Examples of this specification later.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as DLL3; and
there is no need to purify the antigen for immunization.

In order to prepare a monoclonal antibody of the present invention using DNA immunization, first, a DNA expressing a DLL3 protein is administered to an animal to be immunized. The DLL3-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized DLL3 can also be produced by the methods described in WO 2011/093097.

After immunizing a mammal as described above, an increase in the titer of a DLL3-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immunocyte. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:

P3(P3×63Ag8.653) (J. Immunol. (1979) 123 (4), 1548-1550);
P3×63Ag8U.1 (Current Topics in Microbiology and Immunology (1978)81, 1-7);
NS-1 (C. Eur. J. Immunol. (1976)6 (7), 511-519);
MPC-11 (Cell (1976) 8 (3), 405-415);
SP2/0 (Nature (1978) 276 (5685), 269-270);
FO (J. Immunol. Methods (1980) 35 (1-2), 1-21);
S194/5.XX0.BU.1 (J. Exp. Med. (1978) 148 (1), 313-323);
R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immunocytes to myeloma cells may be determined at one's own discretion, preferably, for example, one myeloma cell for every one to ten immunocytes. Culture media to be used for cell fusions include, for example, media that are suitable for the growth of myeloma cell lines, such as RPM11640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37 degrees C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, a DLL3-binding monoclonal antibody can bind to DLL3 expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, DLL3-expressing cells are first prepared. Cells preferably used for screening are mammalian cells in which DLL3 is forcedly expressed. As control, the activity of an antibody to bind to cell-surface DLL3 can be selectively detected using non-transformed mammalian cells as host cells. Specifically, hybridomas producing an anti-DLL3 monoclonal antibody can be isolated by selecting hybridomas that produce an antibody which binds to cells forced to express DLL3, but not to host cells.

Alternatively, the activity of an antibody to bind to immobilized DLL3-expressing cells can be assessed based on the principle of ELISA. For example, DLL3-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

Preferably, the present invention provides nucleic acids that encode a multispecific antigen-binding molecule or a monospecific antigen-binding molecule of the present invention. The present invention also provides a vector into which the nucleic acid encoding the multispecific antigen-binding molecule or the monospecific antigen-binding molecule is introduced, i.e., a vector comprising the nucleic acid. Furthermore, the present invention provides a cell comprising the nucleic acid or the vector. The present invention also provides a method for producing the multispecific antigen-binding molecule or the monospecific antigen-binding molecule by culturing the cell. The present invention further provides multispecific antigen-binding molecules or monospecific antigen-binding molecules produced by the method.

For example, a cDNA encoding the variable region (V region) of an anti-DLL3 antibody is prepared from hybridoma cells expressing the anti-DLL3 antibody. For this purpose, total RNA is first extracted from hybridomas. Methods used for extracting mRNAs from cells include, for example:
the guanidine ultracentrifugation method (Biochemistry (1979) 18(24), 5294-5299), and
the AGPC method (Anal. Biochem. (1987) 162(1), 156-159).

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into E. coli or such. After colony selection, the desired recombinant vector can be prepared from the colony-forming E. coli. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding gamma1, gamma2a, gamma2b, and gamma3 heavy chains and kappa and lambda light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the DLL3-binding activity of a reshaped immunoglobulin as an indicator. For example, when the objective is to isolate an antibody against DLL3, it is more preferred that the binding of the antibody to DLL3 is specific. A DLL3-binding antibody can be screened, for example, by the following steps:
(1) contacting a DLL3-expressing cell with an antibody comprising the V region encoded by a cDNA isolated from a hybridoma;
(2) detecting the binding of the antibody to the DLL3-expressing cell; and
(3) selecting an antibody that binds to the DLL3-expressing cell.

Methods for detecting the binding of an antibody to DLL3-expressing cells are known. Specifically, the binding of an antibody to DLL3-expressing cells can be detected by the above-described techniques such as FACS. Immobilized samples of DLL3-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having a desired binding activity.

After isolation of the cDNA encoding the V region of the anti-DLL3 antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-DLL3 antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region (C region). A chimeric antibody expression vector is constructed by fusing in frame the two genes digested with the same combination of restriction enzymes.

To produce an anti-DLL3 monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-DLL3 antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 94/11523).

There are various known host cell/expression vector combinations for antibody preparation by introducing isolated antibody genes into appropriate hosts. All of these expression systems are applicable to isolation of domains including antibody variable regions of the present invention. Appropriate eukaryotic cells used as host cells include animal cells, plant cells, and fungal cells. Specifically, the animal cells include, for example, the following cells.
(1) mammalian cells: CHO, COS, myeloma, baby hamster kidney (BHK), HeLa, Vero, or such;
(2) amphibian cells: *Xenopus* oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells: yeasts: the *Saccharomyces* genus such as *Saccharomyces cerevisiae*, and the *Pichia* genus such as *Pichia pastoris*; and filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat beta casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

Methods for Producing a Humanized Antibody

When an antigen-binding molecule described herein is administered to human, a domain derived from a genetically recombinant antibody that has been artificially modified to reduce the heterologous antigenicity against human and such, can be appropriately used as the domain of the antigen-binding molecule including an antibody variable region. Such genetically recombinant antibodies include, for example, humanized antibodies. These modified antibodies are appropriately produced by known methods. Furthermore, generally, the binding specificity of a certain antibody can be introduced into another antibody by CDR grafting.

Specifically, humanized antibodies prepared by grafting the CDR (or "HVR" as defined herein) of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Sato, K. et al., Cancer Res. (1993) 53: 851-856)

Methods for Producing a Human Antibody

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing a scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

Vector

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Host Cell

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Epitope

"Epitope" means an antigenic determinant in an antigen, and refers to an antigen site to which the antigen-binding domain of an antigen-binding molecule or antibody disclosed herein binds. Thus, for example, the epitope can be defined according to its structure. Alternatively, the epitope may be defined according to the antigen-binding activity of an antigen-binding molecule or antibody that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antigen-binding domain recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antigen-binding domain. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

Examples of a method for assessing the epitope binding by a test antigen-binding molecule or antibody containing an anti-DLL3 antigen-binding domain are described below. According to the examples below, methods for assessing the epitope binding by a test antigen-binding molecule or antibody containing an antigen-binding domain for an antigen other than DLL3, can also be appropriately conducted.

For example, whether a test antigen-binding molecule or antibody containing an anti-DLL3 antigen-binding domain recognizes a linear epitope in the DLL3 molecule can be confirmed for example as mentioned below. A linear peptide comprising an amino acid sequence forming the extracellular domain of DLL3 is synthesized for the above purpose. The peptide can be synthesized chemically, or obtained by genetic engineering techniques using a region encoding the amino acid sequence corresponding to the extracellular domain in a DLL3 cDNA. Then, a test antigen-binding molecule or antibody containing an anti-DLL3 antigen-binding domain is assessed for its binding activity towards a linear peptide comprising the amino acid sequence forming the extracellular domain. For example, an immobilized linear peptide can be used as an antigen by ELISA to evaluate the binding activity of the polypeptide complex towards the peptide. Alternatively, the binding activity towards a linear peptide can be assessed based on the level that the linear peptide inhibits the binding of the antigen-binding molecule or antibody to DLL3-expressing cells. These tests can demonstrate the binding activity of the antigen-binding molecule or antibody towards the linear peptide.

Whether a test antigen-binding molecule or antibody containing an anti-DLL3 antigen-binding domain recognizes a conformational epitope can be assessed as follows. DLL3-expressing cells are prepared for the above purpose. A test antigen-binding molecule or antibody containing an anti-DLL3 antigen-binding domain can be determined to recognize a conformational epitope when it strongly binds to DLL3-expressing cells upon contact, but does not substantially bind to an immobilized linear peptide comprising an amino acid sequence forming the extracellular domain of DLL3. Herein, "not substantially bind" means that the binding activity is 80% or less, generally 50% or less, preferably 30% or less, and particularly preferably 15% or less compared to the binding activity towards cells expressing DLL3.

Methods for assaying the binding activity of a test antigen-binding molecule or antibody containing an anti-DLL3 antigen-binding domain towards DLL3-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using DLL3-expressing cells as antigen.

In the ELISA format, the binding activity of a test antigen-binding molecule or antibody containing an anti-DLL3 antigen-binding domain towards DLL3-expressing cells can be assessed quantitatively by comparing the levels of signal generated by enzymatic reaction. Specifically, a test polypeptide complex is added to an ELISA plate onto which DLL3-expressing cells are immobilized. Then, the test antigen-binding molecule or antibody bound to the cells is detected using an enzyme-labeled antibody that recognizes the test antigen-binding molecule or antibody. Alternatively, when FACS is used, a dilution series of a test antigen-binding molecule or antibody is prepared, and the antibody binding titer for DLL3-expressing cells can be determined to compare the binding activity of the test antigen-binding molecule or antibody towards DLL3-expressing cells.

The binding of a test antigen-binding molecule or antibody towards an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter)

Preferable methods for assaying the binding activity of a test antigen-binding molecule or antibody containing an anti-DLL3 antigen-binding domain towards an antigen include, for example, the following method. First, DLL3-expressing cells are reacted with a test antigen-binding molecule or antibody, and then this is stained with an FITC-labeled secondary antibody that recognizes the antigen-binding molecule or antibody. The test antigen-binding molecule or antibody is appropriately diluted with a suitable buffer to prepare the antigen-binding molecule or antibody at a desired concentration. For example, the antigen-binding molecule or antibody can be used at a concentration within the range of 10 micro g/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antigen-binding molecule or antibody, which is represented by the quantity of the test antigen-binding molecule or antibody bound, can be determined by measuring the Geometric Mean value.

Whether a test antigen-binding molecule or antibody containing an anti-DLL3 antigen-binding domain shares a common epitope with another antigen-binding molecule or antibody can be assessed based on the competition between the two antigen-binding molecules or antibodies for the same epitope. The competition between the antigen-binding molecules or antibodies can be detected by cross-blocking assay or the like. For example, the competitive ELISA assay is a preferred cross-blocking assay.

Specifically, in cross-blocking assay, the DLL3 protein immobilized to the wells of a microtiter plate is pre-incubated in the presence or absence of a candidate competitor antigen-binding molecule or antibody, and then a test antigen-binding molecule or antibody is added thereto. The quantity of test antigen-binding molecule or antibody bound to the DLL3 protein in the wells is indirectly correlated with the binding ability of a candidate competitor antigen-binding molecule or antibody that competes for the binding to the same epitope. That is, the greater the affinity of the competitor antigen-binding molecule or antibody for the same epitope, the lower the binding activity of the test antigen-binding molecule or antibody towards the DLL3 protein-coated wells.

The quantity of the test antigen-binding molecule or antibody bound to the wells via the DLL3 protein can be readily determined by labeling the antigen-binding molecule or antibody in advance. For example, a biotin-labeled antigen-binding molecule or antibody is measured using an avidin/peroxidase conjugate and appropriate substrate. In particular, cross-blocking assay that uses enzyme labels such as peroxidase is called "competitive ELISA assay". The antigen-binding molecule or antibody can also be labeled with other labeling substances that enable detection or measurement. Specifically, radiolabels, fluorescent labels, and such are known.

When the candidate competitor antigen-binding molecule or antibody can block the binding by a test antigen-binding molecule or antibody containing an anti-DLL3 antigen-binding domain by at least 20%, preferably at least 20 to 50%, and more preferably at least 50% compared to the binding activity in a control experiment conducted in the absence of the competitor antigen-binding molecule or antibody, the test antigen-binding molecule or antibody is determined to substantially bind to the same epitope bound by the competitor antigen-binding molecule or antibody, or compete for the binding to the same epitope.

When the structure of an epitope bound by a test antigen-binding molecule or antibody containing an anti-DLL3 antigen-binding domain has already been identified, whether the test and control antigen-binding molecules or antibodies share a common epitope can be assessed by comparing the binding activities of the two antigen-binding molecules or antibodies towards a peptide prepared by introducing amino acid mutations into the peptide forming the epitope.

To measure the above binding activities, for example, the binding activities of test and control antigen-binding molecules or antibodies towards a linear peptide into which a mutation is introduced are compared in the above ELISA format. Besides the ELISA methods, the binding activity towards the mutant peptide bound to a column can be determined by flowing test and control antigen-binding molecules or antibodies in the column, and then quantifying the antigen-binding molecule or antibody eluted in the elution solution. Methods for adsorbing a mutant peptide to a column, for example, in the form of a GST fusion peptide, are known.

Alternatively, when the identified epitope is a conformational epitope, whether test and control antigen-binding molecules or antibodies share a common epitope can be assessed by the following method. First, DLL3-expressing cells and cells expressing DLL3 with a mutation introduced into the epitope are prepared. The test and control antigen-binding molecules or antibodies are added to a cell suspension prepared by suspending these cells in an appropriate buffer such as PBS. Then, the cell suspensions are appropriately washed with a buffer, and an FITC-labeled antibody that recognizes the test and control antigen-binding molecules or antibodies is added thereto. The fluorescence intensity and number of cells stained with the labeled antibody are determined using FACSCalibur (BD). The test and control antigen-binding molecules or antibodies are appropriately diluted using a suitable buffer, and used at desired concentrations. For example, they may be used at a concentration within the range of 10 micro g/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antigen-binding molecules or antibodies, which are represented by the quantity of labeled antibody bound, can be determined by measuring the Geometric Mean value.

In the above method, whether an antigen-binding molecule or antibody does "not substantially bind to cells expressing mutant DLL3 (or a DLL3 variant)" can be assessed, for example, by the following method. First, the test and control antigen-binding molecules or antibodies bound to cells expressing mutant DLL3 are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the antigen-binding molecule or antibody, the comparison value (delta Geo-Mean) can be calculated according to the following formula to determine the ratio of increase in fluorescence intensity as a result of the binding by the antigen-binding molecule or antibody.

delta Geo-Mean=Geo-Mean (in the presence of the antigen-binding molecule or antibody)/Geo-Mean (in the absence of the antigen-binding molecule or antibody)

The Geometric Mean comparison value (delta Geo-Mean value for the mutant DLL3 molecule) determined by the above analysis, which reflects the quantity of a test antigen-binding molecule or antibody bound to cells expressing mutant DLL3, is compared to the delta Geo-Mean comparison value that reflects the quantity of the test antigen-binding molecule or antibody bound to DLL3-expressing cells. In this case, the concentrations of the test antigen-binding molecule or antibody used to determine the delta Geo-Mean comparison values for DLL3-expressing cells and cells expressing mutant DLL3 are particularly preferably adjusted to be equal or substantially equal. An antigen-binding molecule or antibody that has been confirmed to recognize an epitope in DLL3 is used as a control antigen-binding molecule or antibody.

If the delta Geo-Mean comparison value of a test antigen-binding molecule or antibody for cells expressing mutant DLL3 is smaller than the delta Geo-Mean comparison value of the test antigen-binding molecule or antibody for DLL3-expressing cells by at least 80%, preferably 50%, more preferably 30%, and particularly preferably 15%, then the test antigen-binding molecule or antibody "does not substantially bind to cells expressing mutant DLL3 (or a DLL3 variant)". The formula for determining the Geo-Mean (Geometric Mean) value is described in the CELL QUEST Software User's Guide (BD biosciences). When the comparison shows that the comparison values are substantially equivalent, the epitope for the test and control antigen-binding molecules or antibodies can be determined to be the same.

Antibody that Binds to the Same Epitope

An antigen-binding molecule or an antibody comprising an antigen-binding domain that "binds to the same epitope" as a reference antibody refers to an antigen-binding molecule or an antibody that blocks binding of the reference antibody to its antigen in a competition assay by 50% or more, and conversely, the reference antibody blocks binding of the antigen-binding molecule or the antibody to its antigen in a competition assay by 50% or more. An exemplary competition assay such as cross-blocking assay is provided above.

Specificity

"Specific" means that a molecule that binds specifically to one or more binding partners does not show any significant binding to molecules other than the partners. Furthermore, "specific" is also used when an antigen-binding domain is specific to a particular epitope of multiple epitopes contained in an antigen. When an epitope bound by an antigen-binding domain is contained in multiple different antigens, an antigen-binding molecule containing the antigen-binding domain can bind to various antigens that have the epitope.

Antibody Fragment

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')₂; diabodies; linear antibodies; single-chain antibody molecules (e.g. scFv); and monospecific or multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region as defined herein.

Variable Fragment (Fv)

Herein, the term "variable fragment (Fv)" refers to the minimum unit of an antibody-derived antigen-binding domain that is composed of a pair of the antibody light chain variable region (VL) and antibody heavy chain variable region (VH). In 1988, Skerra and Pluckthun found that homogeneous and active antibodies can be prepared from the *E. coli* periplasm fraction by inserting an antibody gene downstream of a bacterial signal sequence and inducing expression of the gene in *E. coli* (Science (1988) 240(4855), 1038-1041). In the Fv prepared from the periplasm fraction, VH associates with VL in a manner so as to bind to an antigen. Herein, the term "antibody variable fragment" refers to any fragment that comprises at least one antibody light chain variable region (VL) and at least one antibody heavy chain variable region (VH).

scFv, Single-Chain Antibody, and Sc(Fv)2

Herein, the terms "scFv", "single-chain antibody", and "sc(Fv)2" all refer to an antibody fragment of a single polypeptide chain that contains variable regions derived from the heavy and light chains, but not the constant region. In general, a single-chain antibody also contains a polypeptide linker between the VH and VL domains, which enables formation of a desired structure that is thought to allow antigen binding. The single-chain antibody is discussed in detail by Pluckthun in "The Pharmacology of Monoclonal Antibodies, Vol. 113, Rosenburg and Moore, eds., Springer-Verlag, New York, 269-315 (1994)". See also International Patent Publication WO 1988/001649; U.S. Pat. Nos. 4,946,778 and 5,260,203. In a particular embodiment, the single-chain antibody can be bispecific and/or humanized.

scFv is an antigen-binding domain in which VH and VL forming Fv are linked together by a peptide linker (Proc. Natl. Acad. Sci. U.S.A. (1988) 85(16), 5879-5883). VH and VL can be retained in close proximity by the peptide linker.

sc(Fv)2 is a single-chain antibody in which four variable regions of two VL and two VH are linked by linkers such as peptide linkers to form a single chain (J Immunol. Methods (1999) 231(1-2), 177-189). The two VH and two VL may be derived from different monoclonal antibodies. Such sc(Fv)2 preferably includes, for example, a bispecific sc(Fv)2 that recognizes two epitopes present in a single antigen as disclosed in the Journal of Immunology (1994) 152(11), 5368-5374. sc(Fv)2 can be produced by methods known to those skilled in the art. For example, sc(Fv)2 can be produced by linking scFv by a linker such as a peptide linker.

Herein, the form of an antigen-binding domain forming an sc(Fv)2 include an antibody in which the two VH units and two VL units are arranged in the order of VH, VL, VH, and VL ([VH]-linker-[VL]-linker-[VH]-linker-[VL]) beginning from the N terminus of a single-chain polypeptide. The order of the two VH units and two VL units is not limited to the above form, and they may be arranged in any order. Examples of the form are listed below.

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The molecular form of sc(Fv)2 is also described in detail in WO 2006/132352. According to these descriptions, those skilled in the art can appropriately prepare desired sc(Fv)2 to produce the polypeptide complexes disclosed herein.

Furthermore, the antigen-binding molecules or antibodies of the present invention may be conjugated with a carrier polymer such as PEG or an organic compound such as an anticancer agent. Alternatively, a sugar chain addition sequence is preferably inserted into the antigen-binding molecules or antibodies such that the sugar chain produces a desired effect.

The linkers to be used for linking the variable regions of an antibody comprise arbitrary peptide linkers that can be introduced by genetic engineering, synthetic linkers, and linkers disclosed in, for example, Protein Engineering, 9(3), 299-305, 1996. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids. When sc(Fv)2 contains three peptide linkers, their length may be all the same or different.

For example, such peptide linkers include:

Ser

Gly Ser

Gly Gly Ser

Ser Gly Gly

Gly Gly Gly Ser (SEQ ID NO: 116)

(SEQ ID NO: 117)

```
               -continued
Ser Gly Gly Gly (SEQ ID NO: 118)
Gly Gly Gly Gly Ser (SEQ ID NO: 119)
Ser Gly Gly Gly Gly (SEQ ID NO: 120)
Gly Gly Gly Gly Gly Ser (SEQ ID NO: 121)
Ser Gly Gly Gly Gly Gly (SEQ ID NO: 122)
Gly Gly Gly Gly Gly Gly Ser (SEQ ID NO: 123)
Ser Gly Gly Gly Gly Gly Gly (Gly Gly Gly Gly Ser (SEQ ID NO: 118))n (Ser Gly Gly Gly Gly (SEQ ID NO: 119))n
``` where n is an integer of 1 or larger. The length or sequences of peptide linkers can be selected accordingly by those skilled in the art depending on the purpose.

Synthetic linkers (chemical crosslinking agents) are routinely used to crosslink peptides, and examples include:
N-hydroxy succinimide (NHS),
disuccinimidyl suberate (DSS),
bis(sulfosuccinimidyl) suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES), and
bis[2-(sulfosuccinimidoxycarbonyloxy)ethyl] sulfone (sulfo-BSOCOES). These crosslinking agents are commercially available.

In general, three linkers are required to link four antibody variable regions together. The linkers to be used may be of the same type or different types.

Fab, F(ab')2, and Fab'

"Fab" consists of a single light chain, and a CH1 domain and variable region from a single heavy chain. The heavy chain of Fab molecule cannot form disulfide bonds with another heavy chain molecule.

"F(ab')2" or "Fab" is produced by treating an immunoglobulin (monoclonal antibody) with a protease such as pepsin and papain, and refers to an antibody fragment generated by digesting an immunoglobulin (monoclonal antibody) near the disulfide bonds present between the hinge regions in each of the two H chains. For example, papain cleaves IgG upstream of the disulfide bonds present between the hinge regions in each of the two H chains to generate two homologous antibody fragments, in which an L chain comprising VL (L-chain variable region) and CL (L-chain constant region) is linked to an H-chain fragment comprising VH (H-chain variable region) and CH gamma 1 (gamma 1 region in an H-chain constant region) via a disulfide bond at their C-terminal regions. Each of these two homologous antibody fragments is called Fab'.

"F(ab')2" consists of two light chains and two heavy chains comprising the constant region of a CH1 domain and a portion of CH2 domains so that disulfide bonds are formed between the two heavy chains. The F(ab')2 disclosed herein can be preferably produced as follows. A whole monoclonal antibody or such comprising a desired antigen-binding domain is partially digested with a protease such as pepsin; and Fc fragments are removed by adsorption onto a Protein A column. The protease is not particularly limited, as long as it can cleave the whole antibody in a selective manner to produce F(ab')2 under an appropriate setup enzyme reaction condition such as pH. Such proteases include, for example, pepsin and ficin.

Fc Region

The term "Fc region" or "Fc domain" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

Native Sequence Fc Region

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

Variant Fc Region

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

Fc Receptor

The term "Fc receptor" or "FcR" refers to a receptor that binds to the Fc region of an antibody. In some embodiments, an FcR is a native human FcR. In some embodiments, an FcR is one which binds an IgG antibody (a gamma receptor) and includes receptors of the Fc gamma RI, Fc gamma RII, and Fc gamma RIII subclasses, including allelic variants and alternatively spliced forms of those receptors. Fc gamma RII receptors include Fc gamma RIIA (an "activating receptor") and Fc gamma RIIB (an "inhibiting receptor"), which have similar amino acid sequences that differ primarily in the cytoplasmic domains thereof. Activating receptor Fc gamma RIIA contains an immunoreceptor tyrosine-based activation motif (ITAM) in its cytoplasmic domain. Inhibiting receptor Fc gamma RIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

Binding to human FcRn in vivo and plasma half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with increased or decreased binding to FcRs. See also, e.g., Shields et al. J. Biol. Chem. 9(2):6591-6604 (2001).

Fc Gamma Receptor

Fc gamma receptor refers to a receptor capable of binding to the Fc domain of monoclonal IgG1, IgG2, IgG3, or IgG4 antibodies, and includes all members belonging to the family of proteins substantially encoded by an Fc gamma receptor gene. In human, the family includes Fc gamma RI (CD64) including isoforms Fc gamma RIa, Fc gamma RIb and Fc gamma RIc; Fc gamma RII (CD32) including isoforms Fc gamma RIIa (including allotype H131 and R131), Fc gamma RIIb (including Fc gamma RIIb-1 and Fc gamma RIIb-2), and Fc gamma RIIc; and Fc gamma RIII (CD16) including isoform Fc gamma RIIIa (including allotype V158 and F158) and Fc gamma RIIb (including allotype Fc gamma RIIIb-NA1 and Fc gamma RIIIb-NA2); as well as all unidentified human Fc gamma receptors, Fc gamma receptor isoforms, and allotypes thereof. However, Fc gamma receptor is not limited to these examples. Without being limited thereto, Fc gamma receptor includes those derived from humans, mice, rats, rabbits, and monkeys. Fc gamma receptor may be derived from any organisms. Mouse Fc gamma receptor includes, without being limited to, Fc gamma RI (CD64), Fc gamma RII (CD32), Fc gamma RIII (CD16), and Fc gamma RIII-2 (CD16-2), as well as all unidentified mouse Fc gamma receptors, Fc gamma receptor isoforms, and allotypes thereof. Such preferred Fc gamma receptors include, for example, human Fc gamma RI (CD64), Fc gamma RIIA (CD32), Fc gamma RIIB (CD32), Fc gamma RIIIA (CD16), and/or Fc gamma RIIIB (CD16). The polynucleotide sequence and amino acid sequence of Fc gamma RI are shown in NCBI Reference Sequence NM_000566.3 (SEQ ID NO: 124) and NP_000557.1 (SEQ ID NO: 125), respectively; the polynucleotide sequence and amino acid sequence of Fc gamma RIIA are shown in BC020823.1 (SEQ ID NO: 126) and AAH20823.1 (SEQ ID NO: 127), respectively; the polynucleotide sequence and amino acid sequence of Fc gamma RIIB are shown in BC146678.1 (SEQ ID NO: 128) and AAI46679.1 (SEQ ID NO: 129), respectively; the polynucleotide sequence and amino acid sequence of Fc gamma RIIIA are shown in BC033678.1 (SEQ ID NO: 130) and AAH33678.1 (SEQ ID NO: 131), respectively; and the polynucleotide sequence and amino acid sequence of Fc gamma RIIIB are shown in BC128562.1 (SEQ ID NO: 132) and AAI28563.1 (SEQ ID NO: 133), respectively (RefSeq accession numbers). Whether an Fc gamma receptor has binding activity to the Fe domain of a monoclonal IgG1, IgG2, IgG3, or IgG4 antibody can be assessed by ALPHA screen (Amplified Luminescent Proximity Homogeneous Assay), surface plasmon resonance (SPR)-based BIACORE method, and others (Proc. Natl. Acad. Sci. USA (2006) 103(11), 4005-4010), in addition to the above-described FACS and ELISA formats.

Meanwhile, "Fc ligand" or "effector ligand" refers to a molecule and preferably a polypeptide that binds to an antibody Fc domain, forming an Fc/Fc ligand complex. The molecule may be derived from any organisms. The binding of an Fc ligand to Fc preferably induces one or more effector functions. Such Fc ligands include, but are not limited to, Fc receptors, Fc gamma receptor, Fc alpha receptor, Fc beta receptor, FcRn, C1q, and C3, mannan-binding lectin, mannose receptor, *Staphylococcus* Protein A, *Staphylococcus* Protein G, and viral Fc gamma receptors. The Fc ligands also include Fc receptor homologs (FcRH) (Davis et al., (2002) Immunological Reviews 190, 123-136), which are a family of Fc receptors homologous to Fc gamma receptor. The Fc ligands also include unidentified molecules that bind to Fc.

Fc Gamma Receptor-Binding Activity

The impaired binding activity of Fc domain to any of the Fc gamma receptors Fc gamma RI, Fc gamma RIIA, Fc gamma RIIB, Fc gamma RIIIA, and/or Fc gamma RIIIB can be assessed by using the above-described FACS and ELISA formats as well as ALPHA screen (Amplified Luminescent Proximity Homogeneous Assay) and surface plasmon resonance (SPR)-based BIACORE method (Proc. Natl. Acad. Sci. USA (2006) 103(11), 4005-4010). In some embodiments, an antigen-binding molecule or antibody of the present invention comprises a domain comprising an Fc region with reduced binding activity towards an Fc gamma receptor.

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule or antibody is immobilized to the donor beads and glutathione S-transferase (GST)-tagged Fc gamma receptor is immobilized to the acceptor beads. In the absence of an antigen-binding molecule or antibody comprising a competitive mutant Fc domain, Fc gamma receptor interacts with an antigen-binding molecule or antibody comprising a wild-type Fc domain, inducing a signal of 520 to 620 nm as a result. The antigen-binding molecule or antibody having a non-tagged mutant Fc domain competes with the antigen-binding molecule or antibody comprising a wild-type Fc domain for the interaction with Fc gamma receptor. The relative binding affinity can be determined by quantifying the reduction of fluorescence as a result of competition. Methods for biotinylating the antigen-binding molecules or antibodies such as antibodies using Sulfo-NHS-biotin or the like are known. Appropriate methods for adding the GST tag to an Fc gamma receptor include methods that involve fusing polypeptides encoding Fc gamma receptor and GST in-frame, expressing the fused gene using cells introduced with a vector carrying the gene, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is preferably used in the BIACORE methods. Examples of such inhibition assay are described in Proc. Natl. Acad. Sci. USA (2006) 103(11), 4005-4010.

Functional Fc Region

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein. In some embodiments, an antigen-binding molecule or antibody of the present invention comprises a domain comprising a functional Fc region with effector functions.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Human Effector Cells

"Human effector cells" refer to leukocytes that express one or more FcRs and perform effector functions. In certain embodiments, the cells express at least Fc gamma RIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

Fc Region with a Reduced Fc Gamma Receptor-Binding Activity

Herein, "a reduced Fc gamma receptor-binding activity" means, for example, that based on the above-described analysis method the competitive activity of a test antigen-binding molecule or antibody is 50% or less, preferably 45% or less, 40% or less, 35% or less, 30% or less, 20% or less, or 15% or less, and particularly preferably 10% or less, 9% or less, 8% or less, 7% or less, 6% or less, 5% or less, 4% or less, 3% or less, 2% or less, or 1% or less than the competitive activity of a control antigen-binding molecule or antibody.

Antigen-binding molecules or antibodies comprising the Fc domain of a monoclonal IgG1, IgG2, IgG3, or IgG4 antibody can be appropriately used as control antigen-binding molecules or antibodies. The Fc domain structures are shown in SEQ ID NOs: 112 (A is added to the N terminus of RefSeq accession number AAC82527.1), 113 (A is added to the N terminus of RefSeq accession number AAB59393.1), 114 (A is added to the N terminus of RefSeq accession number CAA27268.1), and 115 (A is added to the N terminus of RefSeq accession number AAB59394.1). Furthermore, when an antigen-binding molecule or antibody comprising an Fc domain mutant of an antibody of a particular isotype is used as a test substance, the effect of the mutation of the mutant on the Fc gamma receptor-binding activity is assessed using as a control an antigen-binding molecule or antibody comprising an Fc domain of the same isotype. As described above, antigen-binding molecules or antibodies comprising an Fc domain mutant whose Fc gamma receptor-binding activity has been judged to be reduced are appropriately prepared.

Such known mutants include, for example, mutants having a deletion of amino acids 231A-238S (EU numbering) (WO 2009/011941), as well as mutants C226S, C229S, P238S, (C220S) (J. Rheumatol (2007) 34, 11); C226S and C229S (Hum. Antibod. Hybridomas (1990) 1(1), 47-54); C226S, C229S, E233P, L234V, and L235A (Blood (2007) 109, 1185-1192).

Specifically, the preferred antigen-binding molecules or antibodies include those comprising an Fc domain with a mutation (such as substitution) of at least one amino acid selected from the following amino acid positions: 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, or 332 (EU numbering), in the amino acids forming the Fc domain of an antibody of a particular isotype. The isotype of antibody from which the Fc domain originates is not particularly limited, and it is possible to use an appropriate Fc domain derived from a monoclonal IgG1, IgG2, IgG3, or IgG4 antibody. It is preferable to use Fc domains derived from IgG1 antibodies.

The preferred antigen-binding molecules or antibodies include, for example, those comprising an Fc domain which has any one of the substitutions shown below, whose positions are specified according to EU numbering (each number represents the position of an amino acid residue in the EU numbering; and the one-letter amino acid symbol before the number represents the amino acid residue before substitution, while the one-letter amino acid symbol after the number represents the amino acid residue after the substitution) in the amino acids forming the Fc domain of IgG1 antibody:

(a) L234F, L235E, P331S;
(b) C226S, C229S, P238S;
(c) C226S, C229S; or
(d) C226S, C229S, E233P, L234V, L235A;

as well as those having an Fc domain which has a deletion of the amino acid sequence at positions 231 to 238.

Furthermore, the preferred antigen-binding molecules or antibodies also include those comprising an Fc domain that has any one of the substitutions shown below, whose positions are specified according to EU numbering in the amino acids forming the Fc domain of an IgG2 antibody:
(e) H268Q, V309L, A330S, and P331S;
(f) V234A;
(g) G237A;
(h) V234A and G237A;
(i) A235E and G237A; or
(j) V234A, A235E, and G237A.

Each number represents the position of an amino acid residue in EU numbering; and the one-letter amino acid symbol before the number represents the amino acid residue before substitution, while the one-letter amino acid symbol after the number represents the amino acid residue after the substitution.

Furthermore, the preferred antigen-binding molecules or antibodies also include those comprising an Fc domain that has any one of the substitutions shown below, whose positions are specified according to EU numbering in the amino acids forming the Fc domain of an IgG3 antibody:
(k) F241A;
(l) D265A; or
(m) V264A.

Each number represents the position of an amino acid residue in EU numbering; and the one-letter amino acid symbol before the number represents the amino acid residue before substitution, while the one-letter amino acid symbol after the number represents the amino acid residue after the substitution.

Furthermore, the preferred antigen-binding molecules or antibodies also include those comprising an Fc domain that has any one of the substitutions shown below, whose positions are specified according to EU numbering in the amino acids forming the Fc domain of an IgG4 antibody:
(n) L235A, G237A, and E318A;
(o) L235E; or
(p) F234A and L235A.

Each number represents the position of an amino acid residue in EU numbering; and the one-letter amino acid symbol before the number represents the amino acid residue before substitution, while the one-letter amino acid symbol after the number represents the amino acid residue after the substitution.

The other preferred antigen-binding molecules or antibodies include, for example, those comprising an Fc domain in which any amino acid at position 233, 234, 235, 236, 237, 327, 330, or 331 (EU numbering) in the amino acids forming the Fc domain of an IgG1 antibody is substituted with an amino acid of the corresponding position in EU numbering in the corresponding IgG2 or IgG4.

The preferred antigen-binding molecules or antibodies also include, for example, those comprising an Fc domain in which any one or more of the amino acids at positions 234, 235, and 297 (EU numbering) in the amino acids forming the Fc domain of an IgG1 antibody is substituted with other amino acids. The type of amino acid after substitution is not particularly limited; however, the antigen-binding molecules or antibodies comprising an Fc domain in which any one or more of the amino acids at positions 234, 235, and 297 are substituted with alanine are particularly preferred.

The preferred antigen-binding molecules or antibodies also include, for example, those comprising an Fc domain in which an amino acid at position 265 (EU numbering) in the amino acids forming the Fc domain of an IgG1 antibody is substituted with another amino acid. The type of amino acid after substitution is not particularly limited; however, antigen-binding molecules or antibodies comprising an Fc domain in which an amino acid at position 265 is substituted with alanine are particularly preferred.

Antigen-Binding Domains Binds to DLL3

The phrase "an antigen-binding domain binds to DLL3" or "an anti-DLL3 antigen-binding domain" as used herein refers to an antigen-binding domain that specifically binds to the above-mentioned DLL3 protein, or the whole or a portion of a partial peptide of the DLL3 protein.

In certain embodiments, the antigen-binding domain binds to DLL3 is a domain comprising antibody light-chain and heavy-chain variable regions (VL and VH). Suitable examples of such domains comprising antibody light-chain and heavy-chain variable regions include "single chain Fv (scFv)", "single chain antibody", "Fv", "single chain Fv 2 (scFv2)", "Fab", "F(ab')2", etc. In specific embodiments, the antigen-binding domain binds to DLL3 is a domain comprising an antibody variable fragment. Domains comprising an antibody variable fragment may be provided from variable domains of one or a plurality of antibodies.

In certain embodiments, the antigen-binding domain binds to DLL3 comprises the heavy-chain variable region and light-chain variable region of an anti-DLL3 antibody. In certain embodiments, the antigen-binding domain binds to DLL3 is a domain comprising a Fab structure.

Preferably, the anti-DLL3 antigen-binding domain comprises a Heavy chain variable region of any one of SEQ ID NOs: 15, 25, and 63 to 71, and a Light chain variable region of any one of SEQ ID NOs: 16, 26, and 72 to 74.

In some embodiments, the anti-DLL3 antigen-binding domain binds specifically to the extracellular domain of DLL3. In some embodiments, the anti-DLL3 antigen-binding domain binds specifically to an epitope within the extracellular domain of DLL3. In some embodiments, the anti-DLL3 antigen-binding domain binds to the DLL3 protein expressed on the surface of eukaryotic cells. In some embodiments, the anti-DLL3 antigen-binding domain binds to the DLL3 protein expressed on the surface of cancer cells.

In specific embodiments, the antigen-binding domain binds to DLL3 comprises any one of the antibody variable/constant region sequences shown in Tables TA and 1B below.

Table 1A shows SEQ ID NOs of the generated anti-DLL3 antibodies.

TABLE 1A

| Antibody name | Variable region | | Constant region | |
| --- | --- | --- | --- | --- |
| | Heavy chain | Light chain | Heavy chain | Light chain |
| DLA0316-SG1 | 15 | 16 | 60 | 10 |
| D30316AE01-SG1 | 63 | 72 | 60 | 62 |
| D30316AE02-SG1 | 64 | 72 | 60 | 62 |
| D30316AE03-SG1 | 65 | 72 | 60 | 62 |
| DLA0841-SG1 | 25 | 26 | 60 | 10 |
| D30841AE05-SG1 | 66 | 73 | 60 | 62 |
| D30841AE08-SG1 | 67 | 73 | 60 | 62 |
| D30841AE11-SG1 | 67 | 74 | 60 | 62 |
| D30841AE12-SG1 | 68 | 73 | 60 | 62 |
| D30841AE13-SG1 | 69 | 73 | 60 | 62 |
| D30841AE14-SG1 | 70 | 73 | 60 | 62 |
| D30841AE15-SG1 | 71 | 73 | 60 | 62 |

Table 1B shows SEQ ID NOs of the HVR (CDR) sequences of the generated anti-DLL3 antibodies.

TABLE 1B

| Antibody name | Hyper variable region (HVR) | | | | | |
|---|---|---|---|---|---|---|
| | HCDR1 | HCDR2 | HCDR3 | LCDR1 | LCDR2 | LCDR3 |
| DLA0316-SG1 | 27 | 28 | 29 | 30 | 31 | 32 |
| D30316AE01-SG1 | 27 | 28 | 29 | 30 | 31 | 32 |
| D30316AE02-SG1 | 27 | 75 | 29 | 30 | 31 | 32 |
| D30316AE03-SG1 | 27 | 76 | 29 | 30 | 31 | 32 |
| DLA0841-SG1 | 33 | 34 | 35 | 36 | 37 | 38 |
| D30841AE05-SG1 | 77 | 78 | 79 | 36 | 37 | 38 |
| D30841AE08-SG1 | 77 | 78 | 80 | 36 | 37 | 38 |
| D30841AE11-SG1 | 77 | 78 | 80 | 36 | 37 | 81 |
| D30841AE12-SG1 | 77 | 78 | 80 | 36 | 37 | 38 |
| D30841AE13-SG1 | 77 | 78 | 80 | 36 | 37 | 38 |
| D30841AE14-SG1 | 77 | 78 | 80 | 36 | 37 | 38 |
| D30841AE15-SG1 | 77 | 78 | 80 | 36 | 37 | 38 |

In specific embodiments, the antigen-binding domain binds to DLL3 is a domain that comprises an antibody variable fragment that competes for binding to DLL3 with any one of the antibody variable regions shown in Table TA, or competes for binding to DLL3 with any antibody variable fragment that comprises the HVR sequence identical with the HVR regions of the antibody variable regions shown in Table TA, or competes for binding to DLL3 with any antibody variable fragment that comprises the HVR sequence identical with the ones shown in Table 1B. In specific embodiments, the antigen-binding domain binds to DLL3 is a domain that comprises an antibody variable fragment that binds to the same epitope within DLL3 as any one of the antibody variable regions shown in Table TA, or binds to the same epitope within DLL3 as any antibody variable fragment that comprises the HVR sequence identical with the HVR regions of the antibody variable regions shown in Table TA, or binds to the same epitope within DLL3 as any antibody variable fragment that comprises the HVR sequence identical with the ones shown in Table 1B.

Alternatively, the antigen-binding domain binds to DLL3 comprises an antibody variable fragment that competes for binding to DLL3 with any one of the above-mentioned antibody variable fragments. Alternatively, the antigen-binding domain binds to DLL3 comprises an antibody variable fragment that binds to the same epitope to which any one of the above-mentioned antibody variable fragments binds on DLL3.

Antigen-Binding Domains Bind to T Cell Receptor Complex

The phrase "an antigen-binding domain binds to T cell receptor complex" or "an anti-T cell receptor complex antigen-binding domain" as used herein refers to an antigen-binding domain that specifically binds to the whole or a portion of a partial peptide of a T cell receptor complex. The T cell receptor complex may be a T cell receptor itself, or an adaptor molecule constituting a T cell receptor complex along with a T cell receptor. CD3 is suitable as an adaptor molecule.

In certain embodiments, the antigen-binding domain binds to T cell receptor complex is a domain comprising antibody light-chain and heavy-chain variable regions (VL and VH). Suitable examples of such domains comprising antibody light-chain and heavy-chain variable regions include "single chain Fv (scFv)", "single chain antibody", "Fv", "single chain Fv 2 (scFv2)", "Fab", "F(ab')2", etc. In specific embodiments, the antigen-binding domain binds to T cell receptor complex is a domain comprising an antibody variable fragment. Domains comprising an antibody variable fragment may be provided from variable domains of one or a plurality of antibodies.

In certain embodiments, the antigen-binding domain binds to T cell receptor complex comprises the heavy-chain variable region and light-chain variable region of an anti-Tcell receptor complex antibody. In certain embodiments, the antigen-binding domain binds to T cell receptor complex-binding activity is a domain comprising a Fab structure.

Antigen-Binding Domains Bind to T Cell Receptor

The phrase "an antigen-binding domain binds to T cell receptor" or "an anti-T cell receptor antigen-binding domain" as used herein refers to an antigen-binding domain that specifically binds to the whole or a portion of a partial peptide of a T cell receptor. The portion of a T cell receptor to which the antigen-binding domain binds may be a variable region of the T cell receptor or a constant region of the T cell receptor; however, an epitope present in the constant region is preferred. Examples of the constant region sequence include the T cell receptor alpha chain of RefSeq Accession No. CAA26636.1 (SEQ ID NO: 104), the T cell receptor beta chain of RefSeq Accession No. C25777 (SEQ ID NO: 105), the T cell receptor gamma 1 chain of RefSeq Accession No. A26659 (SEQ ID NO: 106), the T cell receptor gamma 2 chain of RefSeq Accession No. AAB63312.1 (SEQ ID NO: 107), and the T cell receptor delta chain of RefSeq Accession No. AAA61033.1 (SEQ ID NO: 108).

In certain embodiments, the antigen-binding domain binds to T cell receptor is a domain comprising antibody light-chain and heavy-chain variable regions (VL and VH). Suitable examples of such domains comprising antibody light-chain and heavy-chain variable regions include "single chain Fv (scFv)", "single chain antibody", "Fv", "single chain Fv 2 (scFv2)", "Fab", "F(ab')2", etc. In specific embodiments, the antigen-binding domain binds to T cell receptor is a domain comprising an antibody variable fragment. Domains comprising an antibody variable fragment may be provided from variable domains of one or a plurality of antibodies.

In certain embodiments, the antigen-binding domain binds to T cell receptor comprises the heavy-chain variable region and light-chain variable region of an anti-T cell receptor antibody. In certain embodiments, the antigen-binding domain binds to T cell receptor is a domain comprising a Fab structure.

Antigen-Binding Domains Bind to CD3

The phrase "an antigen-binding domain binds to CD3" or "an anti-CD3 antigen-binding domain" as used herein refers to an antigen-binding domain that specifically binds to the whole or a portion of a partial peptide of CD3. The antigen-binding domain binds to CD3 may be any epitope-binding domain as long as the epitope exists in the gamma-chain, delta-chain, or epsilon-chain sequence that constitutes human CD3. Regarding the structure of the gamma chain, delta chain, or epsilon chain constituting CD3, their polynucleotide sequences are disclosed in RefSeq Accession NOs. NM_000073.2, NM_000732.4 and NM_000733.3, and their polypeptide sequences are shown in NP_000064.1 (SEQ ID NO: 109), NP_000723.1 (SEQ ID NO: 110), and NP_000724.1 (SEQ ID NO: 111) (RefSeq accession numbers). In some embodiments, an antigen-binding molecule or antibody of the present invention comprises a domain comprising an antigen variable region that binds to CD3 epsilon chain.

In certain embodiments, the antigen-binding domain binds to CD3 is a domain comprising antibody light-chain and heavy-chain variable regions (VL and VH). Suitable examples of such domains comprising antibody light-chain and heavy-chain variable regions include "single chain Fv (scFv)", "single chain antibody", "Fv", "single chain Fv 2 (scFv2)", "Fab", "F(ab')2", etc. In specific embodiments, the antigen-binding domain binds to CD3 is a domain comprising an antibody variable fragment. Domains comprising an antibody variable fragment may be provided from variable domains of one or a plurality of antibodies.

In certain embodiments, the antigen-binding domain binds to CD3 comprises the heavy-chain variable region and light-chain variable region of an anti-CD3 antibody. In certain embodiments, the antigen-binding domain binds to CD3 is a domain comprising a Fab structure.

The anti-CD3 antigen-binding domains of the present invention may bind to any epitope, as long as the epitope is located within the gamma chain, delta chain, or epsilon chain sequence forming human CD3. In the present invention, preferred anti-CD3 antigen-binding domains include those comprising a CD3 antibody light-chain variable region (VL) and a CD3 antibody heavy-chain variable region (VH), which bind to an epitope in the extracellular domain of the epsilon chain of a human CD3 complex. Such preferred anti-CD3 antigen-binding domains include those comprising a CD3 antibody light-chain variable region (VL) and a CD3 antibody heavy-chain variable region (VH) of the OKT3 antibody (Proc. Natl. Acad. Sci. USA (1980) 77, 4914-4917) or various known CD3 antibodies such as an antibody with the light-chain variable region (VL) of NCBI Accession No. AAB24132 and the heavy-chain variable region (VH) of NCBI Accession No. AAB24133 (Int. J. Cancer Suppl. 7, 45-50 (1992)). Furthermore, such appropriate anti-CD3 antigen-binding domains include those derived from a CD3 antibody with desired characteristics, which are obtained by immunizing a desired animal with the gamma chain, delta chain, or epsilon chain forming human CD3 by the above-described methods. Appropriate anti-CD3 antibodies from which an anti-CD3 antigen-binding domain is derived include human antibodies and antibodies appropriately humanized as described above.

Preferably, the anti-CD3 antigen-binding domain comprises a Heavy chain variable region of any one of the heavy chain variable region shown in Table 2B, and a Light chain variable region of any one of the light chain variable region shown in Table 2B.

In some embodiments, the anti-CD3 antigen-binding domain havi binds specifically to CD3 epsilon chain. In some embodiments, the anti-CD3 antigen-binding domain binds specifically to an epitope within CD3 epsilon chain. In some embodiments, the anti-CD3 antigen-binding domain binds to the CD3 epsilon chain expressed on the surface of eukaryotic cells. In some embodiments, the anti-CD3 antigen-binding domain binds to the CD3 epsilon chain expressed on the surface of T cells.

In specific embodiments, the antigen-binding domain binds to CD3 comprises any one of the antibody variable region sequences shown in Tables 2A below. In specific embodiments, the antigen-binding domain binds to CD3 comprises any one of the combinations of the heavy chain variable region and light chain variable region shown in Table 2A. In specific embodiments, the antigen-binding domain binds CD3 comprises the HVR sequences comprised in the antibody variable regions shown in Table 2A.

Table 2A shows SEQ ID NOs of the variable regions of the anti-CD3 antigen-binding domain.

TABLE 2A

| Name | SEQ ID NOs | |
|---|---|---|
| | Heavy chain variable region | Light chain variable region |
| No. 12 | 57 | 58 |
| TR01 | 98 | 103 |
| AN104 | 99 | 103 |
| AN119 | 100 | 103 |
| AN121 | 101 | 103 |
| AN395 | 102 | 103 |
| hu40G5c | 298 | 299 |
| 40G5c | 300 | 301 |
| 38E4v1 | 302 | 303 |
| 38E4v2 | 304 | 305 |
| 38E4v3 | 306 | 307 |
| 38E4v4 | 308 | 309 |
| 38E4v5 | 310 | 311 |
| 38E4v6 | 312 | 313 |
| 38E4v7 | 314 | 315 |
| 38E4v8 | 316 | 317 |
| 38E4v9 | 318 | 319 |
| 38E4c | 320 | 321 |
| UCHT1v9 | 322 | 323 |
| UCHT1 v1 | 324 | 325 |
| UCHT1 vM1 | 326 | 327 |
| SP34 | 328 | 329 |
| SP34v52 | 330 | 331 |
| hu41D9a | 332 | 333 |
| 41 D9a | 334 | 335 |
| hu13A3 | 336 | 337 |
| 13A3.v2 | 338 | 339 |
| 13A3 | 340 | 341 |
| hu30A1 | 342 | 343 |
| 30A1 | 344 | 345 |
| 30A1 .v2 | 346 | 347 |
| 21A9 | 348 | 349 |
| 21B2 | 350 | 351 |
| 125A1 | 552 | 353 |
| 72H6 | 354 | 355 |
| 19B1 | 356 | 357 |
| 71 H7 | 358 | 359 |
| 14C7 | 360 | 361 |
| 127B3 | 362 | 363 |
| 18F12 | 364 | 365 |
| 27H5-1 | 366 | 367 |
| 39B7 | 368 | 369 |
| 40D2 | 370 | 371 |
| 79B7 | 372 | 373 |
| 95A2 | 374 | 375 |
| 118G9 | 376 | 377 |
| Rab17 | 378 | 379 |
| 38E4 | 380 | 381 |
| 1217 | 382 | 383 |
| hu38E4 | 384 | 385 |
| 40G5 | 386 | 387 |
| hu40G5 | 388 | 389 |
| humuSP34 | 390 | 391 |

In specific embodiments, the antigen-binding domain binds to CD3 comprises any one of the combinations of HVR sequences shown in Table 2B below.

Table 2B shows SEQ ID NOs of the HVR (CDR) sequences of the anti-CD3 antigen-binding domain.

TABLE 2B

| Name | SEQ ID NOs | | | | | |
|---|---|---|---|---|---|---|
| | HVR-H1 | HVR-H2 | HVR-H3 | HVR-L1 | HVR-L2 | HVR-L3 |
| 40G5c | 136 | 137 | 138 | 139 | 140 | 141 |
| 38E4v1 | 142 | 143 | 144 | 145 | 146 | 147 |

TABLE 2B-continued

| Name | HVR-H1 | HVR-H2 | HVR-H3 | HVR-L1 | HVR-L2 | HVR-L3 |
|---|---|---|---|---|---|---|
| 38E4v2 | 142 | 143 | 148 | 145 | 146 | 147 |
| 38E4v3 | 142 | 143 | 144 | 145 | 146 | 149 |
| 38E4v4 | 142 | 143 | 144 | 145 | 146 | 150 |
| 38E4v5 | 142 | 143 | 144 | 145 | 146 | 151 |
| 38E4v6 | 142 | 143 | 152 | 145 | 146 | 147 |
| 38E4v7 | 142 | 143 | 153 | 145 | 146 | 147 |
| 38E4v8 | 142 | 143 | 154 | 145 | 146 | 147 |
| 38E4v9 | 142 | 143 | 155 | 145 | 146 | 147 |
| 38E4c | 142 | 143 | 156 | 145 | 146 | 157 |
| UCHT1v9 | 158 | 159 | 160 | 161 | 162 | 163 |
| UCHT1 v1 | 158 | 164 | 160 | 161 | 162 | 163 |
| UCHT1 vM1 | 158 | 165 | 160 | 161 | 162 | 163 |
| SP34v52 | 166 | 167 | 168 | 169 | 170 | 171 |
| 41 D9a | 172 | 173 | 174 | 175 | 176 | 177 |
| 13A3 | 178 | 179 | 180 | 181 | 182 | 183 |
| 30A1 | 194 | 185 | 186 | 187 | 188 | 189 |
| 30A1 .v2 | 190 | 191 | 192 | 193 | 194 | 195 |
| h21A9 | 196 | 197 | 198 | 199 | 200 | 201 |
| 21B2 | 202 | 203 | 204 | 205 | 206 | 207 |
| 125A1 | 208 | 209 | 210 | 211 | 212 | 213 |
| 72H6 | 214 | 215 | 216 | 217 | 218 | 219 |
| 19B1 | 220 | 221 | 222 | 223 | 224 | 225 |
| 71 H7 | 226 | 227 | 228 | 229 | 230 | 231 |
| 14C7 | 232 | 233 | 234 | 235 | 236 | 237 |
| 127B3 | 238 | 239 | 240 | 241 | 242 | 243 |
| 18F12 | 244 | 245 | 246 | 247 | 248 | 249 |
| 27H5-1 | 250 | 251 | 252 | 253 | 354 | 255 |
| 39B7 | 256 | 257 | 258 | 359 | 260 | 261 |
| 40D2 | 262 | 263 | 264 | 265 | 266 | 267 |
| 79B7 | 268 | 269 | 270 | 271 | 272 | 273 |
| 95A2 | 274 | 275 | 276 | 277 | 278 | 279 |
| 118G9 | 280 | 281 | 282 | 283 | 284 | 285 |
| Rab17 | 286 | 287 | 288 | 389 | 290 | 291 |
| 43H8 | 292 | 293 | 294 | 295 | 296 | 297 |

In specific embodiments, the antigen-binding domain binds to CD3 is a domain that comprises an antibody variable fragment that competes for binding to CD3 with any one of the antibody variable regions shown in Table 2A, or competes for binding to CD3 with any antibody variable fragment that comprises the HVR sequence identical with the HVR regions of the antibody variable regions shown in Table 2A, or competes for binding to CD3 with any antibody variable fragment that comprises the HVR sequence identical with the ones shown in Table 2B. In specific embodiments, the antigen-binding domain binds to CD3 is a domain that comprises an antibody variable fragment that binds to the same epitope within CD3 as any one of the antibody variable regions shown in Table 2A, or binds to the same epitope within CD3 as any antibody variable fragment that comprises the HVR sequence identical with the HVR regions of the antibody variable regions shown in Table 2A, or binds to the same epitope within CD3 as any antibody variable fragment that comprises the HVR sequence identical with the ones shown in Table 2B.

Alternatively, the antigen-binding domain binds to CD3 comprises an antibody variable fragment that competes for binding to CD3 with any one of the above-mentioned antibody variable fragments/antibody variable regions. Alternatively, the antigen-binding domain binds to CD3 comprises an antibody variable fragment that binds to the same epitope to which any one of the above-mentioned antibody variable fragments/antibody variable regions bind on CD3.

Multispecific Antigen-Binding Molecules

"Multispecific antigen-binding molecules" refers to antigen-binding molecules that bind specifically to more than one antigen. In a favorable embodiment, multispecific antigen-binding molecules of the present invention comprise two or more antigen-binding domains, and different antigen-binding domains bind specifically to different antigens.

The multispecific antigen-binding molecule of the present invention comprises a first antigen-binding domain binds to DLL3, and a second antigen-binding domain binds to T cell receptor complex. The combinations of an antigen-binding domain binds to DLL3 selected from those described in "Antigen-binding domains bind to DLL3" above and an antigen-binding domain binds to T cell receptor complex selected from those described in "Antigen-binding domains bind to T-cell receptor complex" to "Antigen-binding domains bind to CD3" above can be used.

For example, the first antigen-binding domain is a domain comprising antibody heavy-chain and light-chain variable regions, and/or the second antigen-binding domain is a domain comprising antibody heavy-chain and light-chain variable regions. Alternatively, the first antigen-binding domain is a domain comprising an antibody variable fragment, and/or the second antigen-binding domain is a domain comprising an antibody variable fragment. Alternatively, the first antigen-binding domain is a domain comprising a Fab structure, and/or the second antigen-binding domain is a domain comprising a Fab structure.

In certain embodiments, the present invention provides a multispecific antigen-binding molecule comprising a first antigen-binding domain binds to DLL3, and a second antigen-binding domain binds to T cell receptor complex. In certain embodiments, the present invention provides bispecific antigen-binding molecules that comprise a first antigen-binding domain binds to DLL3, a second antigen-binding domain binds to T cell receptor complex, and a domain comprising an Fc region that has a reduced Fc gamma receptor-binding activity. The Fc region may have a reduced Fc gamma receptor-binding activity compared with the Fc domain of an IgG1, IgG2, IgG3, or IgG4 antibody. In an embodiment, the Fc region is an Fc region with an amino acid mutation at any of the Fc region-constituting amino acids of SEQ ID NOs: 112 to 115 (IgG1 to IgG4).

In certain embodiments, the present invention provides bispecific antibodies that comprise a first antibody variable fragment binds to DLL3, and a second antibody variable fragment binds to CD3. In certain embodiments, the present invention provides bispecific antibodies that comprise a first antibody variable fragment binds to DLL3, a second antibody variable fragment binds to CD3, and an Fc region that has a reduced Fc gamma receptor-binding activity. In certain embodiments, the present invention provides bispecific antibodies that comprise a first antibody variable fragment binds to DLL3, a second antibody variable fragment binds to CD3 epsilon chain, and an Fc region that has a reduced Fc gamman receptor-binding activity compared with naturally occurring IgG Fc regions.

Examples of a preferred embodiment of the "multispecific antigen-binding molecule" of the present invention include multispecific antibodies. When an Fc region with reduced Fc gamma receptor-binding activity is used as the multispecific antibody Fc region, an Fc region derived from the multispecific antibody may be used appropriately. Bispecific antibodies are particularly preferred as the multispecific antibodies of the present invention. In this case, a bispecific antibody is an antibody having two different specificities. IgG-type bispecific antibodies can be secreted from a hybrid hybridoma (quadroma) produced by fusing two types of hybridomas that produce IgG antibodies (Milstein et al., Nature (1983) 305, 537-540).

Furthermore, IgG-type bispecific antibodies are secreted by introducing the genes of L chains and H chains constituting the two types of IgGs of interest, i.e., a total of four genes, into cells, and co-expressing them. However, the number of combinations of H and L chains of IgG that can be produced by these methods is theoretically ten combinations. Accordingly, it is difficult to purify an IgG comprising the desired combination of H and L chains from ten types of IgGs. Furthermore, theoretically, the amount of secretion of the IgG having the desired combination will decrease remarkably, and therefore large-scale culturing will be necessary, and production costs will increase further.

Therefore, techniques for promoting the association among H chains and between L and H chains having the desired combinations can be applied to the multispecific antigen-binding molecules of the present invention.

For example, techniques for suppressing undesired H-chain association by introducing electrostatic repulsion at the interface of the second constant region or the third constant region of the antibody H chain (CH2 or CH3) can be applied to multispecific antibody association (WO2006/106905).

In the technique of suppressing unintended H-chain association by introducing electrostatic repulsion at the interface of CH2 or CH3, examples of amino acid residues in contact at the interface of the other constant region of the H chain include regions corresponding to the residues at EU numbering positions 356, 439, 357, 370, 399, and 409 in the CH3 region.

More specifically, examples include an antibody comprising two types of H-chain CH3 regions, in which one to three pairs of amino acid residues in the first H-chain CH3 region, selected from the pairs of amino acid residues indicated in (1) to (3) below, carry the same type of charge: (1) amino acid residues comprised in the H chain CH3 region at EU numbering positions 356 and 439; (2) amino acid residues comprised in the H-chain CH3 region at EU numbering positions 357 and 370; and (3) amino acid residues comprised in the H-chain CH3 region at EU numbering positions 399 and 409.

Furthermore, the antibody may be an antibody in which pairs of the amino acid residues in the second H-chain CH3 region which is different from the first H-chain CH3 region mentioned above, are selected from the aforementioned pairs of amino acid residues of (1) to (3), wherein the one to three pairs of amino acid residues that correspond to the aforementioned pairs of amino acid residues of (1) to (3) carrying the same type of charges in the first H-chain CH3 region mentioned above carry opposite charges from the corresponding amino acid residues in the first H-chain CH3 region mentioned above.

Each of the amino acid residues indicated in (1) to (3) above come close to each other during association. Those skilled in the art can find out positions that correspond to the above-mentioned amino acid residues of (1) to (3) in a desired H-chain CH3 region or H-chain constant region by homology modeling and such using commercially available software, and amino acid residues of these positions can be appropriately subjected to modification.

In the antibodies mentioned above, "charged amino acid residues" are preferably selected, for example, from amino acid residues included in either one of the following groups:
(a) glutamic acid (E) and aspartic acid (D); and
(b) lysine (K), arginine (R), and histidine (H).

In the above-mentioned antibodies, the phrase "carrying the same charge" means, for example, that all of the two or more amino acid residues are selected from the amino acid residues included in either one of groups (a) and (b) mentioned above. The phrase "carrying opposite charges" means, for example, that when at least one of the amino acid residues among two or more amino acid residues is selected from the amino acid residues included in either one of groups (a) and (b) mentioned above, the remaining amino acid residues are selected from the amino acid residues included in the other group.

In a preferred embodiment, the antibodies mentioned above may have their first H-chain CH3 region and second H-chain CH3 region crosslinked by disulfide bonds.

In the present invention, amino acid residues subjected to modification are not limited to the above-mentioned amino acid residues of the antibody variable regions or the antibody constant regions. Those skilled in the art can identify the amino acid residues that form an interface in mutant polypeptides or heteromultimers by homology modeling and such using commercially available software; and amino acid residues of these positions can then be subjected to modification so as to regulate the association.

Other known techniques can also be used for the association of multispecific antibodies of the present invention. Fc region-containing polypeptides comprising different amino acids can be efficiently associated with each other by substituting an amino acid side chain present in one of the H-chain Fc regions of the antibody with a larger side chain (knob), and substituting an amino acid side chain present in the corresponding Fc region of the other H chain with a smaller side chain (hole) to allow placement of the knob within the hole (WO1996/027011; Ridgway J B et al., Protein Engineering (1996) 9, 617-621; Merchant A. M. et al. Nature Biotechnology (1998) 16, 677-681; and US20130336973).

In addition, other known techniques can also be used for formation of multispecific antibodies of the present invention. Association of polypeptides having different sequences can be induced efficiently by complementary association of CH3 using a strand-exchange engineered domain CH3 produced by changing part of one of the H-chain CH3s of an antibody to a corresponding IgA-derived sequence and introducing a corresponding IgA-derived sequence into the complementary portion of the other H-chain CH3 (Protein Engineering Design & Selection, 23; 195-202, 2010). This known technique can also be used to efficiently form multispecific antibodies of interest.

In addition, technologies for antibody production using association of antibody CH1 and CL and association of VH and VL as described in WO 2011/028952, WO2014/018572, and Nat Biotechnol. 2014 February; 32(2):191-8; technologies for producing bispecific antibodies using separately prepared monoclonal antibodies in combination (Fab Arm Exchange) as described in WO2008/119353 and WO2011/131746; technologies for regulating association between antibody heavy-chain CH3s as described in WO2012/058768 and WO2013/063702; technologies for producing bispecific antibodies composed of two types of light chains and one type of heavy chain as described in WO2012/023053; technologies for producing bispecific antibodies using two bacterial cell strains that individually express one of the chains of an antibody comprising a single H chain and a single L chain as described by Christoph et al. (Nature Biotechnology Vol. 31, p 753-758 (2013)); and such may be used for the formation of multispecific antibodies.

Alternatively, even when a multispecific antibody of interest cannot be formed efficiently, a multispecific antibody of the present invention can be obtained by separating and purifying the multispecific antibody of interest from the produced antibodies. For example, a method for enabling purification of two types of homomeric forms and the heteromeric antibody of interest by ion-exchange chromatography by imparting a difference in isoelectric points by introducing amino acid substitutions into the variable regions of the two types of H chains has been reported (WO2007114325). To date, as a method for purifying heteromeric antibodies, methods using Protein A to purify a heterodimeric antibody comprising a mouse IgG2a H chain that binds to Protein A and a rat IgG2b H chain that does not bind to Protein A have been reported (WO98050431 and WO95033844). Furthermore, a heterodimeric antibody can be purified efficiently on its own by using H chains comprising substitution of amino acid residues at EU numbering positions 435 and 436, which is the IgG-Protein A binding site, with Tyr, His, or such which are amino acids that yield a different Protein A affinity, or using H chains with a different protein A affinity, to change the interaction of each of the H chains with Protein A, and then using a Protein A column.

Alternatively, a common L chain that can provide binding ability to a plurality of different H chains can be obtained and used as the common L chain of a multispecific antibody. Efficient expression of a multispecific IgG can be achieved by introducing the genes of such a common L chain and a plurality of different H chains into cells to express the IgG (Nature Biotechnology (1998) 16, 677-681). A method for selecting a common L chain that shows a strong binding ability to any of the different H chains can also be used when selecting the common H chain (WO 2004/065611).

Furthermore, an Fc region whose Fc region C-terminal heterogeneity has been improved can be appropriately used as an Fc region of the present invention. More specifically, the present invention provides Fc regions produced by deleting glycine at position 446 and lysine at position 447 as specified by EU numbering from the amino acid sequences of two polypeptides constituting an Fc region derived from IgG1, IgG2, IgG3, or IgG4.

A plurality, such as two or more, of these technologies can be used in combination. Furthermore, these technologies can be appropriately and separately applied to the two H chains to be associated. Furthermore, these techniques can be used in combination with the above-mentioned Fc region which has reduced binding activity to an Fc gamma receptor. Furthermore, an antigen-binding molecule of the present invention may be a molecule produced separately so that it has the same amino acid sequence, based on the antigen-binding molecule subjected to the above-described modifications.

Preferably, the antigen-binding molecule of the present invention may comprise a first antigen-binding domain binds to DLL3, and a second antigen-binding domain binds to T cell receptor complex. In an embodiment, the second antigen-binding domain binds to T cell receptor. In another embodiment, the second antigen-binding domain binds to CD3 epsilon chain. In an embodiment, the first antigen-binding domain binds to human DLL3. In a further embodiment, the first antigen-binding domain binds to DLL3 on the surface of a eukaryotic cell. In an embodiment, the first antigen-binding domain binds to human DLL3 on the surface of a eukaryotic cell, preferably a cancer cell.

The phrase "anti-DLL3 arm" in this specification refers to the antibody heavy chain and antibody light chain which binds to DLL3 in a bispecific antibody. The phrase "anti-CD3 arm" in this specification refers to the antibody heavy chain and antibody light chain which binds to CD3 in a bispecific antibody.

Preferably, the antigen-binding molecule of the present invention may have cellular cytotoxicity (also referred to as "cytotoxicity). In an embodiment, the cellular cytotoxicity is T cell-dependent cellular cytotoxicity (TDCC). In another embodiment, the cytotoxicity is a cellular cytotoxicity towards cells expressing DLL3 on their surfaces. The DLL3-expressing cells may be cancer cells.

In a preferred aspect, an antibody (or antigen-binding molecule) of the present invention has cytotoxicity (or cellular cytotoxicity), or preferably T cell-dependent cellular cytotoxicity (TDCC) against DLL3-expressing cells such as cancer cells. DLL3 may be expressed on the surface of such cells. The (cellular) cytotoxicity or TDCC of an antibody (or antigen-binding molecule) of the present invention can be evaluated by any suitable method known in the art. For example, the method described in some Examples can be used for measuring TDCC. In this case, the cytotoxic activity is assessed by the rate of cell growth inhibition by an antibody (or antigen-binding molecule) of the present invention. Cell growth is measured using a suitable analyzer such as xCELLigence Real-Time Cell Analyzer. Cancer cells are used as target cells, and they are seeded on a multi-well plate at a suitable cell concentration (for example, about $10^4$ cells/well). On the following day, a test antibody prepared at an appropriate concentration (for example, 0.001-10 nM) is added to the plate. After 15 minutes of reaction, a solution containing T cells (such as PBMC) is added thereto at a suitable effector (PBMC)/target (cancer cell) ratio such as the ratio of 10. The reaction is carried out with carbon dioxide gas. After the addition of T cells, the Cell Growth Inhibition (CGI) rate (%) is determined using the equation: CGI rate (%)=(A−B)×100/(A−1), where A represents the mean Cell Index value of wells without the antibody (or antigen-binding molecule), i.e., containing only target cells and T cells; and B represents the mean Cell Index value of wells with the antibody (or antigen-binding molecule). The Cell Index values used in the calculation are normalized values, i.e., the Cell Index value at the time point immediately before antibody addition is defined as 1. If the CGI rate of an antibody (or antigen-binding molecule) is high, i.e., has a significantly positive value, it can be said that the antibody (or antigen-binding molecule) has TDCC activity and is more preferable in the present invention.

Alternatively, cytotoxic activity can be assessed by the calcein-acetoxymethyl release assay. Cancer cells are used as target cells. The target cells are labeled with calcein-acetoxymethyl and then washed. A test antibody (for example, 0.001-10 nM) is pipetted into a plate and a calcein-labeled target cell suspension is added thereto. After leaving the plates at room temperature, an effector cell (such as PBMC) suspension is added thereto. After stirring the plate, it is centrifuged, and incubated in a $CO_2$ incubator. After the plate is stirred well and centrifuged, culture medium from each well is transferred to another plate. Absorbance (495 nm, reference 515 nm) is measured. For maximal release, the cells may be lysed with 0.5% NP-40. The fluorescence value of the culture medium background is subtracted from the value of the experimental release (A), the target cell spontaneous release (B), and the target cell maximal release (C). The cytotoxicity was calculated using the following formula: Cytotoxicity (%)=(A−B)/(C−B)× 100. If this value of an antibody (or antigen-binding molecule) is high, i.e., has a significantly positive value, it can be said that the antibody (or antigen-binding molecule) has TDCC activity and is more preferable in the present invention.

Monospecific Antigen-Binding Molecules

The term "monospecific antigen-binding molecule" is used to refer to antigen-binding molecules that specifically bind to only one type of antigen. A favorable example of a monospecific antigen-binding molecule is an antigen-binding molecule that comprises a single type of antigen-binding domain. Monospecific antigen-binding molecules can comprise a single antigen-binding domain or a plurality of antigen-binding domains of the same type. A favorable example of monospecific antigen-binding molecules is a monospecific antibody. When the monospecific antigen-binding molecule is a monospecific antibody of the IgG form, the monospecific antibody comprises two antibody variable fragments that have the same antigen-binding specificity.

The monospecific antigen-binding molecule of the present invention comprises an antigen-binding domain binds to DLL3. The antigen-binding domain binds to DLL3 may be any one of those described in "Antigen-binding domains bind to DLL3" above.

The term "monospecific antigen-binding molecule binds to DLL3" refer to a monospecific antigen-binding molecule that is capable of binding DLL3 with sufficient affinity such that the antibody is useful as a diagnostic and/or therapeutic agent in targeting DLL3. In one embodiment, the extent of binding of a monospecific antigen-binding molecule binds to DLL3 to an unrelated, non-DLL3 protein is less than about 10% of the binding to DLL3 as measured, e.g., by a radioimmunoassay (RIA). In certain embodiments, a monospecific antigen-binding molecule binds to DLL3 has a dissociation constant (Kd) of 1 micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$ M to $10^{-13}$ M, e.g., from $10^{-9}$ M to $10^{-13}$ M).

In some embodiments, the monospecific antigen-binding molecule binds to DLL3 in the present invention comprises a functional Fc region possessing an effector function, such as C1q binding; CDC; Fc receptor binding; ADCC; phagocytosis; down regulation of cell surface receptors (e.g. B cell receptor; BCR).

Antibody-Dependent Cell-Mediated Cytotoxicity

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express Fc gamma RIII only, whereas monocytes express Fc gamma RI, Fc gamma RII, and Fc gamma RIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998).

Immunoconjugates

The invention also provides immunoconjugates comprising an antigen-binding molecule herein, for example a monospecific antigen-binding molecule binds to DLL3, conjugated to one or more cytotoxic agents, such as chemotherapeutic agents or drugs, growth inhibitory agents, toxic compounds, toxins (e.g., protein toxins, enzymatically active toxins of bacterial, fungal, plant, or animal origin, or fragments thereof), or radioactive isotopes. In some embodiments, the present invention provides an antigen-binding molecule or antibody that is conjugated to a toxic compound. In other words, the present invention provides an antibody-drug-conjugate compound that comprises an antigen-binding molecule or antibody.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antigen-binding molecule (such as a monospecific antigen-binding molecule binds to DLL3) as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antigen-binding molecule (such as a monospecific antigen-binding molecule binds to DLL3) as described herein conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example Tc-99m or $^{123}$I or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antigen-binding molecule (such as a monospecific antigen-binding molecule binds to DLL3) and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Cancer

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

Tumor

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein.

In preferred embodiments, the cancer is a cancer (including cancer tissues or cells) expressing DLL3. In some embodiments, the cancer is pancreatic cancer, glioma, small cell lung cancer (SCLC), or melanoma.

Pharmaceutical Formulation

The term "pharmaceutical formulation" refers to a preparation which is in such form as to permit the biological activity of an active ingredient contained therein to be effective, and which contains no additional components which are unacceptably toxic to a subject to which the formulation would be administered.

Pharmaceutically Acceptable Carrier

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

Treatment

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

In one aspect, the invention is based, in part, on multispecific antigen-binding molecules that comprises a first antigen-binding domain binds to DLL3, and a second antigen-binding domain binds to T-cell receptor complex, and use thereof. Antigen-binding molecules and antibodies of the invention are useful, e.g., for the diagnosis or treatment of tumor, especially colorectal tumor and gastric tumor.

Pharmaceutical Composition

A pharmaceutical composition of the present invention, a therapeutic agent for inducing cellular cytotoxicity, a cell growth-suppressing agent, or an anticancer agent of the present invention may be formulated with different types of antigen-binding molecules, if needed. For example, the cytotoxic action against cells expressing an antigen can be enhanced by a cocktail of multiple antigen-binding molecules of the present invention.

If necessary, the antigen-binding molecules of the present invention may be encapsulated in microcapsules (microcapsules made from hydroxymethylcellulose, gelatin, poly[methylmethacrylate], and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for preparing agents as sustained-release agents are known, and these can be applied to the antigen-binding molecules of the present invention (J. Biomed. Mater. Res. (1981) 15, 267-277; Chemtech. (1982) 12, 98-105; U.S. Pat. No. 3,773,719; European Patent Application (EP) Nos. EP58481 and EP133988; Biopolymers (1983) 22, 547-556).

The pharmaceutical compositions, cell growth-suppressing agents, or anticancer agents of the present invention may be administered either orally or parenterally to patients. Parental administration is preferred. Specifically, such administration methods include injection, nasal administration, transpulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present invention can be administered locally or systemically by injection. Furthermore, appropriate administration methods can be selected according to the patient's age and symptoms. The administered dose can be selected, for example, from the range of 0.0001 mg to 1,000 mg per kg of body weight for each administration. Alternatively, the dose can be selected, for example, from the range of 0.001 mg/body to 100,000 mg/body per patient. However, the dose of a pharmaceutical composition of the present invention is not limited to these doses.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

Preferably, a pharmaceutical composition of the present invention comprises a antigen-binding molecule of the invention. In an embodiment, the composition is a pharmaceutical composition for use in inducing cellular cytotoxicity. In another embodiment, the composition is a pharmaceutical composition for use in treating or preventing cancer. Preferably, the cancer is an above-mentioned cancer. The pharmaceutical composition of the present invention can be used for treating or preventing cancer. Thus, the present invention provides a method for treating or preventing cancer, in which the antigen-binding molecule of the present invention is administered to a patient in need thereof.

Furthermore, the present invention provides use of an above-mentioned antigen-binding molecule or antibody in the manufacture of a pharmaceutical composition for treating or preventing cancer. The present invention also provides use of the antigen-binding molecule/antibody/pharmaceutical composition for treating or preventing cancer.

The present invention also provides methods for damaging cells expressing DLL3 or for suppressing the cell growth by contacting the cells expressing DLL3 with an antigen-binding molecule of the present invention that binds to DLL3. Monoclonal antibodies that bind to DLL3 are described above as an antigen-binding molecule of the present invention, which is included in the therapeutic agents for inducing cellular cytotoxicity, cell growth-suppressing agents, and anticancer agents of the present invention. Cells to which an antigen-binding molecule of the present invention binds are not particularly limited, as long as they express DLL3. Specifically, in the present invention, the preferred cancer antigen-expressing cells include pancreatic cancer cells, glioma cells, melanoma cells, or small cell lung cancer (SCLC) cells.

In the present invention, "contact" can be carried out, for example, by adding an antigen-binding molecule of the present invention to culture media of cells expressing DLL3 cultured in vitro. In this case, an antigen-binding molecule to be added can be used in an appropriate form, such as a solution or solid prepared by lyophilization or the like. When the antigen-binding molecule of the present invention is added as an aqueous solution, the solution may be a pure aqueous solution containing the antigen-binding molecule alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The added concentration is not particularly limited; however, the final concentration in a culture medium is preferably in a range of 1 pg/ml to 1 g/ml, more preferably 1 ng/ml to 1 mg/ml, and still more preferably 1 micro g/ml to 1 mg/ml.

In another embodiment of the present invention, "contact" can also be carried out by administration to nonhuman animals transplanted with DLL3-expressing cells in vivo or to animals having cancer cells expressing DLL3 endogenously. The administration method may be oral or parenteral. Parenteral administration is particularly preferred. Specifically, the parenteral administration method includes injection, nasal administration, pulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present invention can be administered locally or systemically by injection. Furthermore, an appropriate administration method can be selected according to the age and symptoms of an animal subject. When the antigen-binding molecule is administered as an aqueous solution, the solution may be a pure aqueous solution containing the antigen-binding molecule alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The administered dose can be selected, for example, from the range of 0.0001 to 1,000 mg per kg of body weight for each administration. Alternatively, the dose can be selected, for example, from the range of 0.001 to 100,000 mg/body for each patient. However, the dose of an antigen-binding molecule of the present invention is not limited to these examples.

The methods described below are preferably used as a method for assessing or determining cellular cytotoxicity caused by contacting an antigen-binding molecule of the present invention with DLL3-expressing cells to which the antigen-binding domain forming the antigen-binding molecules of the present invention binds. The methods for assessing or determining the cytotoxic activity in vitro include methods for determining the activity of cytotoxic T-cells or the like. Whether an antigen-binding molecule of the present invention has the activity of inducing T-cell mediated cellular cytotoxicity can be determined by known methods (see, for example, Current protocols in Immunology, Chapter 7. Immunologic studies in humans, Editor, John E, Coligan et al., John Wiley & Sons, Inc., (1993)). In the cytotoxicity assay, an antigen-binding molecule whose antigen-binding domain binds to an antigen different from DLL3 and which is not expressed in the cells is used as a control antigen-binding molecule. The control antigen-binding molecule is assayed in the same manner. Then, the activity is assessed by testing whether an antigen-binding molecule of the present invention exhibits a stronger cytotoxic activity than that of a control antigen-binding molecule.

Meanwhile, the in vivo cytotoxic activity is assessed or determined, for example, by the following procedure. Cells expressing the antigen to which the antigen-binding domain forming an antigen-binding molecule of the present invention binds are transplanted intracutaneously or subcutaneously to a nonhuman animal subject. Then, from the day of transplantation or thereafter, a test antigen-binding molecule is administered into vein or peritoneal cavity every day or at intervals of several days. The tumor size is measured over time. Difference in the change of tumor size can be defined as the cytotoxic activity. As in an in vitro assay, a control antigen-binding molecule is administered. The antigen-binding molecule of the present invention can be judged to have cytotoxic activity when the tumor size is smaller in the group administered with the antigen-binding molecule of the present invention than in the group administered with the control antigen-binding molecule.

An MTT method and measurement of isotope-labeled thymidine uptake into cells are preferably used to assess or determine the effect of contact with an antigen-binding molecule of the present invention to suppress the growth of cells expressing an antigen to which the antigen-binding domain forming the antigen-binding molecule binds. Meanwhile, the same methods described above for assessing or determining the in vivo cytotoxic activity can be used preferably to assess or determine the activity of suppressing cell growth in vivo.

The present invention also provides kits for use in a method of the present invention, which contain an antigen-binding molecule of the present invention or an antigen-binding molecule produced by a method of the present invention. The kits may be packaged with an additional pharmaceutically acceptable carrier or medium, or instruction manual describing how to use the kits, etc.

In addition, the present invention relates to antigen-binding molecules of the present invention or antigen-binding molecules produced by a method of the present invention for use in a method of the present invention.

In another embodiment, internalizing antibodies are provided. In other words, the present invention provides an antibody or an antigen-binding molecule that has internalization activity. Such Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the target protein may be used. For example, based upon the variable region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA 90: 7889-7893 (1993). The internalization activity of an antibody (or an antigen-binding molecule) can be determined, for example, by the method described in Reference Example 18 of European Patent Publication No. 3015115 (WO2014/208482).

Expression and Purification of DLL3 Extracellular Domain (ECD) Fragment Proteins A DLL3 extracellular domain (ECD) fragment protein (or truncated variants thereof), optionally with Flag-tag on C-terminus, can be expressed transiently using appropriate vectors and cells. Cultivation supernatants containing the proteins are applied to a column packed with affinity resin and eluted. Fractions containing the proteins are collected and subsequently applied to a filtration column equilibrated with buffer. Fractions containing the proteins are then pooled and stored at −80 degrees Celsius (C) until use. ECD fragment proteins may be used for epitope mapping or competition assay by known methods or the methods described herein.

Establishment of Cell Lines Expressing DLL3

To establish a cell line expressing DLL3, a DLL3 cDNA is inserted into an expression vector, and this is introduced into cells by, for example, electroporation. After introduction, an agent for selection (such as Geneticin) is added, and the cells are cultured to obtain a cell line that is resistant to it. Transfected cell lines may be plated in a plate by limiting dilution, and expanded. The established cell line may be used for assessing TDCC activity of an antigen-binding molecule or antibody of the present invention against cells expressing DLL3.

Generation and Screening of Anti-DLL3 Antibodies (Monospecific)

Anti-DLL3 antibodies may be prepared, selected and assayed as described below. An animal such as rabbit is immunized with DLL3 or a fragment thereof. After the final immunization, the spleen and blood are collected from the immunized animal. Antigen-specific B-cells are stained and sorted with a cell sorter, and plated in plates at a density of one cell per well together with, e.g., EL4 cells (European Collection of Cell Cultures), and cultured. After cultivation, B-cell culture supernatants are collected for further analysis and pellets may be cryopreserved. ELISA screening may be conducted to test specificity of antibodies in B-cell culture supernatants. DLL3-expressing cells are immobilized onto a plate pre-coated with BSA and a biocomaptible anchor for cell membrane. Immobilized cells are incubated with B-cell culture supernatants. The cells are washed, and, e.g., a goat anti-rabbit IgG polyclonal antibody HRP conjugate is added. The cells are further incubated on ice, and a substrate is added and optimal density is suitably analyzed. B-cell clones are screened for binding to DLL3-expressing cells, and clones are selected as DLL3-specific binders. The selected clones are purified from cryopreserved cell pellets.

The DNAs of the antibody heavy chain variable regions are amplified by reverse transcription PCR and ligated with DNA encoding a human IgG1 heavy chain constant region, to form corresponding heavy chains. The DNAs of the antibody light chain variable regions are amplified by reverse transcription PCR and ligated with DNA encoding a light chain constant region, to form corresponding light chains. Cloned antibodies are expressed in cells, and purified from culture supernatants for functional evaluation. The monospecific antibodies may be used for producing anti-DLL3/anti-CD3 bispecific antibodies by known methods.

Epitope Mapping of Selected Anti-DLL3 Antibodies (Monospecific)

The structures of DLL3 and DLL3 ECD fragment proteins are schematically shown in FIG. 1. These DLL3 ECD fragment proteins may be used for epitope mapping of anti-DLL3 antibodies, for example, as described below. Plates are coated with a fragment protein, and blocked with a buffer. Blocking buffer is removed and an anti-DLL3 antibody is incubated with the immobilized protein, and washed with a buffer. Any suitable detection system including an anti-flag antibody can be used to assess antibody binding. For example, Monoclonal ANTI-FLAG M2-Peroxidase, Clone M2 (Sigma-Aldrich) is added and incubated and washed. Then, a substrate is added and optical density (e.g., OD405) is determined. The OD405 value represents the reactivity of the tested antibody against the fragment protein. Antibody epitopes can be inferred by testing which domain deletion (see FIG. 1) abrogates antibody binding. That is, if an antibody fails to bind to a certain deletion construct among a panel of sequential deletion constructs shortened, for example, from the N-terminus (FIG. 1), then it can be said that this construct does not contain the epitope of the antibody and longer deletion constructs to which the antibody can bind, or more specifically the N terminal region of the shortest one among such longer deletion constructs, contain the epitope of the antibody.

Functional Evaluation of Anti-DLL3/CD3 Bispecific Antibodies

Anti-DLL3/CD3 bispecific antibodies may be evaluated for their in vivo anti-tumor efficacy in a xenograft model, as described below. Cancer cell lines are transplanted into NOD scid mice, and the NOD scid mice with confirmed tumor formation are subjected to transplantation of T cells grown by in vitro culturing of human PBMCs. The mice (referred to as T cell-injected model) are treated by administration of the bispecific antibodies. For example, in anti-tumor efficacy tests of the bispecific antibodies using the T cell-injected model, the following may be performed. T cells are expansively cultured using PBMCs and a suitable media such as a T cell activation/expansion kit/human (MACS Miltenyi biotec). A human cancer cell line is mixed with a suitable support material such as Matrigel™ Basement Membrane Matrix (BD), and transplanted to a region of NOD scid mice. On the day before transplantation (day −1, when defining day 0 as the day of transplantation), an anti-asialo-GM1 antibody is administered intraperitoneally to the mice. On day 10 after the transplantation, the mice are separated into groups according to their body weight and tumor size, and the anti-asialo-GM1 antibody is administered again intraperitoneally to the mice. On the following day, T cells obtained by the aforementioned expansive culturing are transplanted intraperitoneally to the mice. Four hours after T cell transplantation, the anti-DLL3/CD3 bispecific antibodies are administered intravenously through the caudate vein. Anti-tumor activities (inhibition of tumor volume increase) can be assessed in the bispecific antibody-administered group compared to the solvent-administered control group.

Humanization and Optimization of Anti-DLL3 Monospecific Antibodies

Variable regions of the heavy and light chains of humanized DLL3 antibodies can be designed using human germline frameworks. The polynucleotides of the designed heavy and light chain variable regions are cloned into expression vectors containing the heavy chain constant region sequence and the light chain constant region sequence, respectively. Humanized antibodies are transiently expressed in cells, and BIAcore analysis is carried out as described above. Selected humanized antibodies are further optimized. To avoid chemical degradations such as deamidation, isomerization, succinimide formation, methionine and tryptophan oxidation and cysteinylation of unpaired cysteine in CDR regions, the sequences of the selected humanized antibodies may be mutated to 18 other amino acids, excluding the original amino acid and Cysteine. The variants are transiently expressed and purified by the method described above. Purified variant monoclonal antibodies are assessed by BIAcore using the method described above, and variants of interest which can bind to DLL3 as the parent antibody are selected. Antibodies with a combination of these mutations in the CDRs are then generated.

Competition Analysis of Anti-DLL3 Antibodies

Preparation of Biotin-Labelled Anti-DLL3 Antibodies

Variable heavy and light chain sequences (VH and VL) of anti-DLL3 antibodies are cloned into expression vectors. Anti-DLL3 antibodies may be labelled with NHS-PEG4-Biotin, thereby preparing biotin-labelled anti-DLL3 antibodies.

Octet Assay

Octet (registered trademark) RED384 (Fortebio) can be used to perform competitive binding assays by epitope binning for a panel of antibodies. A biotinylated antibody is loaded to a streptavidin (SA) biosensor. Next, the sensor is exposed to DLL3, followed by exposure to a second antibody. Raw data is processed using ForteBio's Data Analysis Software 7.0 and the antibody pairs are assessed for competitive binding. Additional binding by the second antibody indicates an unoccupied epitope (non-competitor), while no binding indicates epitope blocking (competitor). To determine if there is a competitive antibody binding, Antibody A is first immobilized to streptavidin biosensor and the sequential binding of the complex of antigen with Antibody B is measured. The competition ratio of Antibody B to Antibody A is calculated using the following equation:

Competition Ratio (Antibody $B$ to Antibody $A$)=
[Binding Response (Antibody $B$-Antigen)]/
[Binding Response (Antigen-Antibody $A$)]

If the competition ratio is low, i.e., close to 0, then it can be said that Antibody A and Antibody B do not compete with each other for the same epitope.

Preparation of an Anti-DLL3/Anti-CD3 Bispecific Antibody

An anti-DLL3 monospecific antibody and an anti-CD3 antibody can be used to generate an anti-DLL3/CD3 bispecific antibody using a conventional method published elsewhere. The anti-CD3 antibody used may bind to an epitope within a region in CD3 epsilon chain. The bispecific antibody generated may contain a silent Fc with attenuated affinity for the Fc gamma receptor. In addition, the Fab arm exchange technique reported in, e.g., WO 2016159213 may be used to make the bispecific antibody.

BIAcore Analysis for Binding Affinity Evaluation of Anti-DLL3 Arm (or Anti-CD3 Arm) in the Anti-DLL3/CD3 Bispecific Antibodies Binding affinity of anti-DLL3 arm (or anti-CD3 arm) in the anti-DLL3/CD3 antibodies to DLL3 can be assessed, e.g., at pH 7.4 and 37 degrees C. using BIAcore. For example, anti-human Fc (GE Healthcare) is immobilized onto all flow cells of a CM4 sensor chip using amine coupling kit (GE Healthcare). The bispecific antibodies are captured onto the anti-Fc sensor surface, and then DLL3 (or CD3) is injected over the flow cell. Antibodies and analytes may be prepared in ACES pH 7.4 containing 20 mM ACES, 150 mM NaCl, 0.05% Tween 20, 0.005% $NaN_3$. Sensor surface is regenerated each cycle with 3M $MgCl_2$. Binding affinity is determined by processing and fitting the data to 1:1 binding model.

All documents cited herein are incorporated herein by reference.

EXAMPLES

The following are examples of methods and compositions of the invention. It is understood that various other embodiments may be practiced, given the general description provided above.

Example 1. Expression and Purification of Human DLL3 Extracellular Domain (ECD) Fragment Proteins and Cynomolgus DLL3 ECD Protein As human DLL3 extracellular domain (ECD) fragment proteins, human DLL3 ECD with Flag-tag (SEQ ID NO: 135) on C-terminus (SEQ ID NO: 1, hereinafter referred to as del0) and truncated human DLL3 ECD variants with Flag-tag on C-terminus (SEQ ID NOs: 2 to 7, hereinafter referred to as del1 to del6, respectively) were expressed transiently using FreeStyle 293-F Cells (Thermo Fisher Scientific). Cultivation supernatants containing human DLL3 ECD fragment proteins were applied to a column packed with anti-Flag M2 affinity resin (Sigma) and eluted with Flag peptide (Sigma). Fractions containing human DLL3 ECD fragment proteins were collected and subsequently applied to a Superdex 200 gel filtration column (GE healthcare) equilibrated with 1× D-PBS. Fractions containing human DLL3 ECD fragment proteins were then pooled and stored at −80 degrees Celsius (C).

Cynomolgus DLL3 ECD with Myc-tag on N-terminus and His-tag on C-terminus (SEQ ID NO: 8, hereinafter referred to as Myc-cynoDLL3-His) was expressed transiently using FreeStyle 293-F Cells (Thermo Fisher Scientific). Cultivation supernatant containing cynomolgus DLL3 ECD protein was applied to a HisTrap HP column (GE Healthcare) and eluted with imidazole. Fractions containing cynomolgus DLL3 ECD protein were collected and subsequently applied to a Superdex 200 gel filtration column (GE healthcare) equilibrated with 1× D-PBS. Fractions containing cynomolgus DLL3 ECD protein were then pooled and stored at −80 degrees C.

Example 2. Establishment of Ba/F3 Cell Line Expressing Human DLL3

Human DLL3 cDNA encoding delta-like protein 3 isoform 1 precursor (NCBI accession No. NP_058637.1 SEQ ID NO: 9) was inserted into the expression vector pCXND3 (described in WO2008/156083).

Linearized human DLL3-pCXND3 was introduced into mouse IL-3-dependent pro-B cell-derived cell line Ba/F3 by electroporation (LONZA, 4D-Nucleofector X).

After introduction, Geneticin was added, and the cells were cultured to obtain a cell line that was resistant to Geneticin. Transfected cells were plated in a 96-well plate by limiting dilution and were expanded. Established cell line was named hDLL3/BaF_H3.

Example 3: Generation and Screening of Anti-DLL3 Antibodies (Monospecific)

Anti-DLL3 antibodies were prepared, selected and assayed as described below.

Twelve week old NZW rabbits were immunized intradermally with human DLL3 ECD and cynomolgus DLL3 ECD proteins prepared as described in Example 1 alternately (50-100 micrograms (micro g)/dose/rabbit). Six days after the final immunization, the spleen and blood were collected from the immunized rabbits. Antigen-specific B-cells were stained with Myc-cynoDLL3-His and Anti-c-myc-FITC (Miltenyi Biotech), sorted with FCM cell sorter (FACS aria III, BD), and plated in 96-well plates at a density of one cell per well together with 25,000 cells/well of EL4 cells (European Collection of Cell Cultures) and activated rabbit T-cell conditioned medium diluted 20 times, and were cultured for 7-12 days. EL4 cells were treated with mitomycin C (Sigma, Cat No. M4287) for 2 hours and washed 3 times in advance. The activated rabbit T-cell conditioned medium was prepared by culturing rabbit thymocytes in RPMI-1640 containing Phytohemagglutinin-M (Roche, Cat No. 1 1082132-001), phorbol 12-myristate 13-acetate (Sigma, Cat No. P1585) and 2% FBS. After cultivation, B-cell culture supernatants were collected for further analysis and pellets were cryopreserved.

ELISA screening was conducted to test specificity of antibodies in B-cell culture supernatants. Human DLL3 expressing Ba/F3 (hDLL3/BaF_H3 established in Example 2, $2.5 \times 10^4$ cells) were immobilized onto a Nunc MaxiSorp 384-well plate (Sigma-Aldrich) which was pre-coated with BSA (Sigma-Aldrich) and SUNBRIGHT (registered trademark) OE-080CS as Biocomaptible Anchor for cell Membrane (YUKA SANGYO). Immobilized cells were incubated with 20 microliters (micro L) of B-cell culture supernatants for 1 hour. The supernatants were aspirated and the cells were washed with HEPES buffer (0.02 M HEPES, 5 mM KCl, 4 mM $NaHCO_3$, 138 mM NaCl, 2 mM $CaCl_2$), 5 mM Glucose, 0.4 mM $KH_2PO_4$, 0.34 mM $Na_2HPO_4$, and 0.1% BSA). After washing, goat anti-rabbit IgG polyclonal antibody HRP conjugate (BETHYL, A120-111P) was added. The cells were further incubated on ice for 1 hour and washed. Then, ABTS Microwell Peroxidase Substrate (Kirkegaard & Perry Laboratories) was added and OD405 was analyzed with SPECTRAMax 384 (Molecular Devices).

A total of 28,864 B-cell clones were screened for binding to human DLL3 expressing Ba/F3, and 846 clones were selected as DLL3-specific binders which bind to hDLL3/BaF_H3. The selected clones were designated as DLA0001 to DLA0846. RNAs of DLA0001 to DLA0846 were purified from cryopreserved cell pellets by using ZR-96 Quick-RNA kits (ZYMO RESEARCH, Cat No. R1053). The DNAs of the antibody heavy chain variable regions were amplified by reverse transcription PCR and ligated with DNA encoding a human IgG1 heavy chain constant region, to form corresponding heavy chains. The DNAs of the antibody light chain variable regions were amplified by reverse transcription PCR and ligated with DNA encoding hk0MC light chain constant region (the amino acid sequence is shown in SEQ ID NO: 10), to form corresponding light chains. Cloned antibodies were expressed in FreeStyle 293-F Cells (Thermo Fisher Scientific) and purified from culture supernatants for functional evaluation. Several anti-DLL3 antibodies listed in Table 3 were selected for further analysis.

The DNA of anti-DLL3 antibody (DLA0316) heavy chain variable regions was also ligated with DNA encoding rabbit IgG heavy chain constant region, and the DNA of anti-DLL3 antibody (DLA0316) light chain variable regions was ligated with DNA encoding rabbit kappa chain constant region. This antibody was transiently expressed in FreeStyle 293-F Cells (Thermo Fisher Scientific), and named DLA0316-rbIgG.

Table 3 shows SEQ ID NOs of the variable regions of selected anti-DLL3 antibodies.

TABLE 3

| Antibody name | Variable region | |
|---|---|---|
| | Heavy chain | Light chain |
| DLA0106 | 11 | 12 |
| DLA0126 | 13 | 14 |
| DLA0316 | 15 | 16 |
| DLA0379 | 17 | 18 |
| DLA0580 | 19 | 20 |
| DLA0641 | 21 | 22 |
| DLA0769 | 23 | 24 |
| DLA0841 | 25 | 26 |

Example 4. Epitope Mapping of Selected Anti-DLL3 Antibodies (Monospecific)

The schematic structures of the full-length DLL3 protein and human DLL3 ECD fragment proteins prepared in Example 1 are shown in FIG. 1. The human DLL3 ECD fragment proteins prepared in Example 1 were used for epitope mapping of anti-DLL3 antibodies.

Nunc MaxiSorp 384-well plates (Sigma-Aldrich) were coated with each of the human DLL3 ECD fragment proteins del0 to del6, and blocked with 20% Blocking One (NACALAI TESQUE). Blocking buffer was removed and recombinant anti-DLL3 antibodies were incubated with the immobilized proteins for 1 hour at room temperature and washed with HEPES buffer (0.05% Tween20, HEPES). Monoclonal ANTI-FLAG M2-Peroxidase, Clone M2 (Sigma-Aldrich) was then added and incubated for 1 hour at room temperature and washed. Then, ABTS Microwell Peroxidase Substrate (Kirkegaard & Perry Laboratories) was added and OD405 was analyzed with SPECTRAMax 384 (Molecular Devices).

Figure 2:
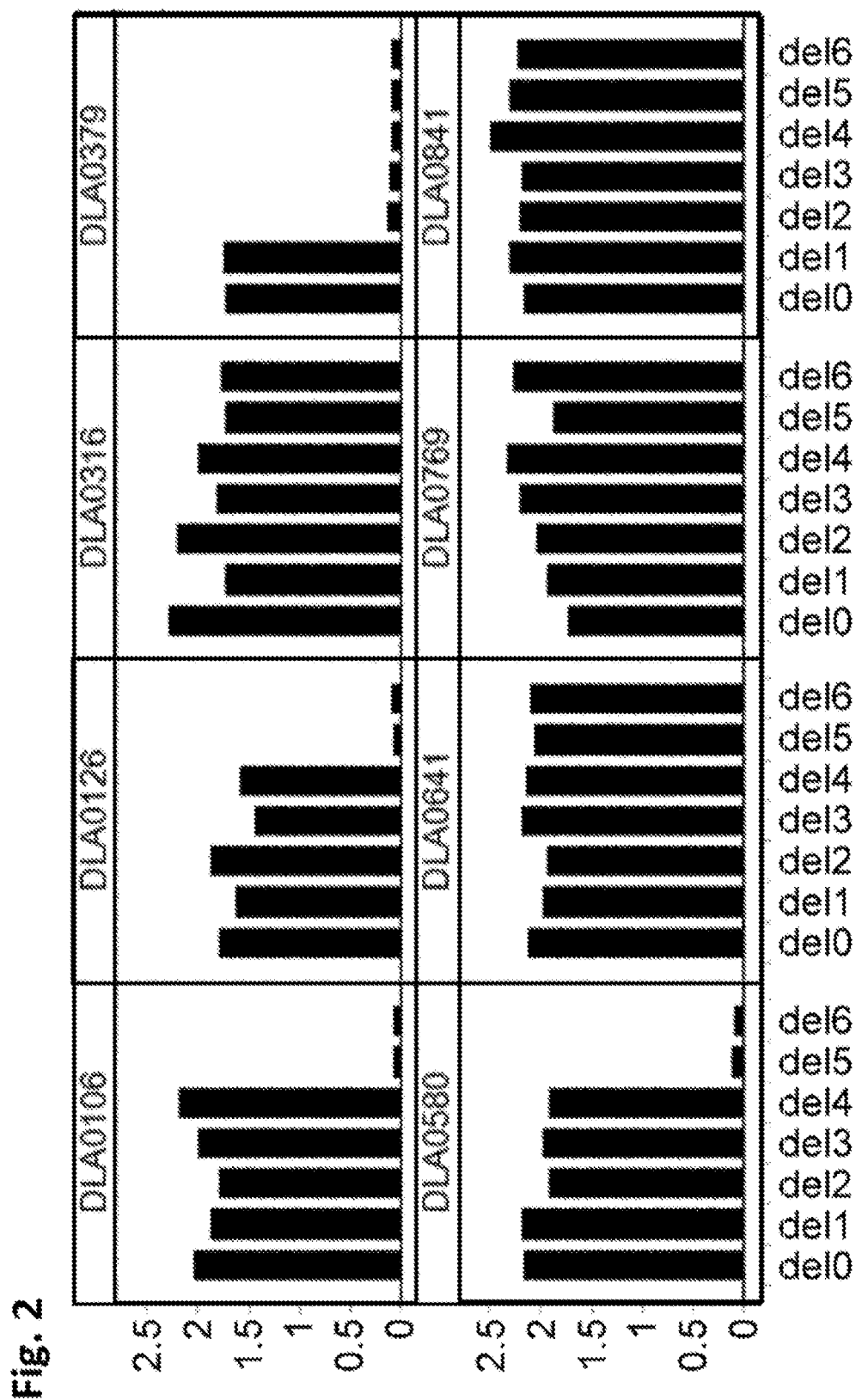
FIG. 2 shows the binding of the antibodies to the human DLL3 ECD fragment proteins. Names of the tested anti-DLL3 antibodies are shown on the top of each graph.

FIG. 2 shows the binding for the human DLL3 ECD fragment proteins. Each bar (OD405 value) represents the reactivity of the tested antibody against each of the human DLL3 ECD fragment proteins. Antibody epitopes can be inferred by testing which domain deletion abrogates antibody binding, and the epitope of each antibody is shown in FIG. 1.

Example 5: Generation and Functional Evaluation of Anti-DLL3/CD3 Bispecific Antibodies Example 5.1. Evaluation of DLL3 Expression on Cancer Cell Surface Expression of DLL3 on the cell surface of cultured cancer cell lines SK-MEL 30 (DSMZ), NCI-H1436 (ATCC), and NCI-H2227 (ATCC) was evaluated by flow cytometry.

Figure 3:
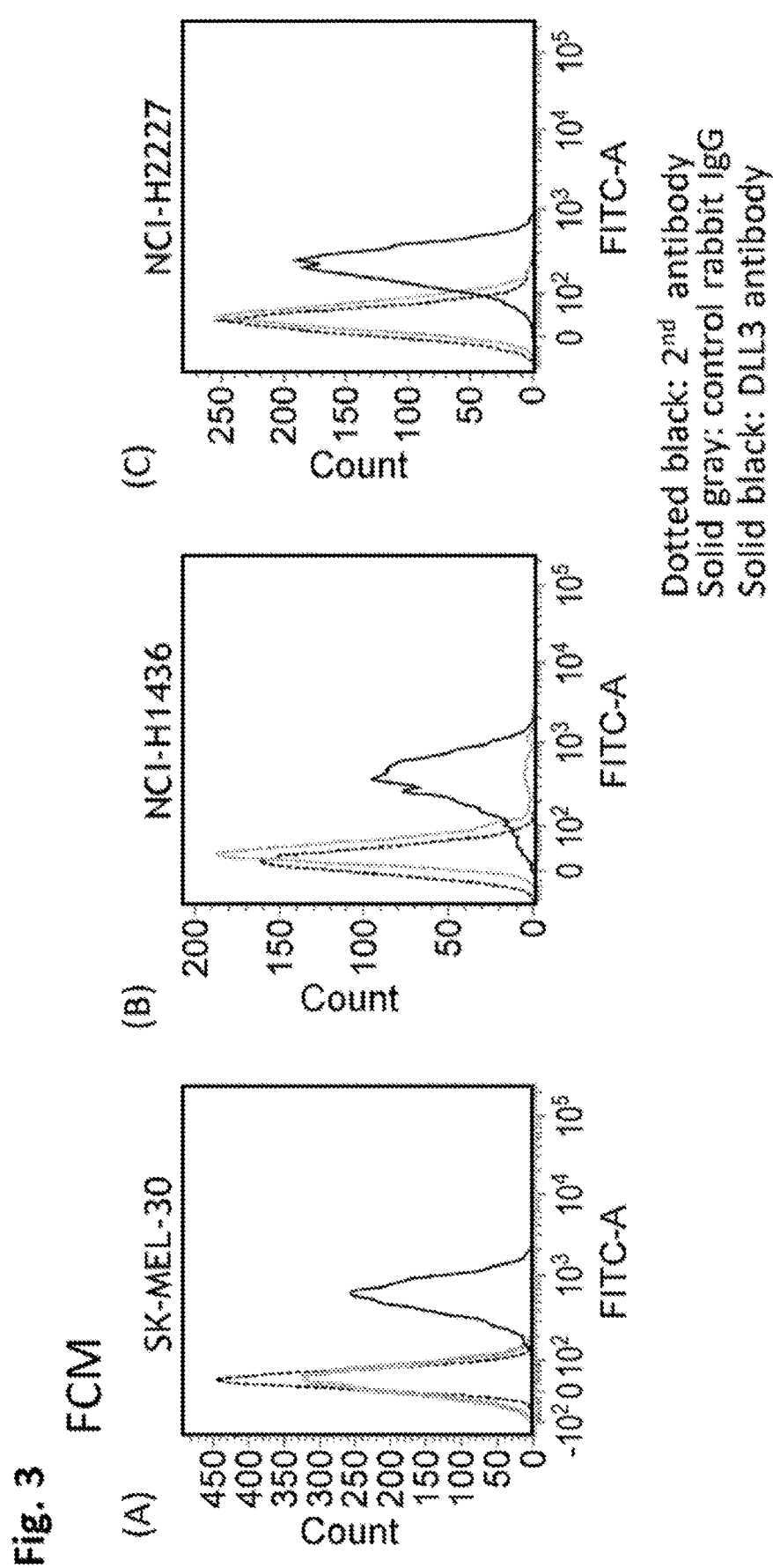
FIG. 3 shows DLL3 expression in SK-MEL-30 (A), NCI-H1436 (B) and NCI-H2227 (C) cancer cell lines. Dotted black line: 2nd antibody (BECKMAN COULTER) only, solid gray line: control rabbit IgG (CELL LAB), solid black line: DLL3 antibody (bivalent DLA0316).

The cancer cells ($5 \times 10^5$ cells) were washed with 0.5% BSA-supplemented CellWASH (BD Bioscience) (hereinafter referred to as FACS/PBS). Bivalent anti-DLL3 antibody (DLA0316-rbIgG) or the control antibody (rabbit IgG) was added at a final concentration of 20 micro g/mL in a 50 micro L solution. After being left to stand at 4 degrees C. for 30 to 60 minutes, the cells were washed with FACS/PBS, and an FITC-labeled goat anti-rabbit IgG antibody diluted 50-fold with FACS/PBS was added to the cells. After being left to stand at 4 degrees C. for further 30 minutes, the cells were washed with FACS/PBS, and analyzed by FACS Verse (Becton Dickinson). DLL3 was found to be expressed on each of the cancer cell lines (FIG. 3).

Example 5.2 Functional Characterization of Anti-DLL3/CD3 Bispecific Antibodies

Example 5.2.1 Preparation of Human Peripheral Blood Mononuclear Cells (PBMC) Solution Primary human PBMC solutions were freshly isolated from healthy volunteers.

For fresh PBMC solutions, 50 mL of peripheral blood was collected from each healthy volunteer (individual adult) using a syringe preloaded with 100 micro L of 1,000 units/mL heparin solution (Novo Heparin for injection, 5,000 units, Novo Nordisk). This peripheral blood was diluted two-fold in PBS (−), divided into four aliquots, and added to a Leucosep tube for lymphocyte separation (Cat. No. 227290, Greiner Bio-One) that had been loaded with 15 mL of Ficoll-Paque PLUS and subjected to centrifugation in advance. This separation tube was centrifuged (at 2,150 rpm for ten minutes at room temperature), and the mononuclear cell fraction was collected. The cells in the mononuclear cell fraction were washed once with Dulbecco's Modified Eagle's Medium containing 10% FBS (SIGMA) and adjusted to the cell density of $4 \times 10^6$ cells/mL using 10% FBS/RPMI1640. This cell suspension was used as the human PBMC solution in the experiments below.

Example 5.2.2 Measurement of T Cell-Dependent Cell Cytotoxicity (TDCC) of Anti-DLL3/CD3 Bispecific Antibodies by the Rate of Cell Growth Inhibition Some anti-DLL3 monospecific antibodies described in Table 3 and some anti-DLL3 antibodies described in WO2011/093097A1, together with an anti-CD3 antibody (variable region of heavy chain SEQ ID NO: 57, variable region of light chain SEQ ID NO: 58) were used to generate anti-DLL3/CD3 bispecific antibodies using conventional methods published elsewhere. The CDR sequences of the DLL3-binding arm in the anti-DLL3/CD3 bispecific antibodies are shown in Table 4.

Each of the generated bispecific antibodies contained an Fc region with attenuated affinity for the Fc gamma receptor.

Table 4 shows SEQ ID NOs of HVR (CDR) sequences of the DLL3-binding arm in anti-DLL3/CD3 bispecific antibodies.

TABLE 4

| | Hyper variable region (HVR) sequences of anti-DLL3 arm | | | | | |
|---|---|---|---|---|---|---|
| Antibody name | HCDR1 | HCDR2 | HCDR3 | LCDR1 | LCDR2 | LCDR3 |
| DLA0316/No. 12 | 27 | 28 | 29 | 30 | 31 | 32 |
| DLA0841/No. 12 | 33 | 34 | 35 | 36 | 37 | 38 |
| DLA0580/No. 12 | 39 | 40 | 41 | 42 | 43 | 44 |
| DLA0769/No. 12 | 45 | 46 | 47 | 48 | 49 | 50 |
| DL312/No. 12 | 51 | 52 | 53 | 54 | 55 | 56 |

"HCDR1", "HCDR2", "HCDR3", LCDR1", "LCDR2", and "LCDR3" in Table 4 correspond to HVR-H1, HVR-H2, HVR-H3, HVR-L1, HVR-L2, and HVR-L3, respectively.

Figure 4:
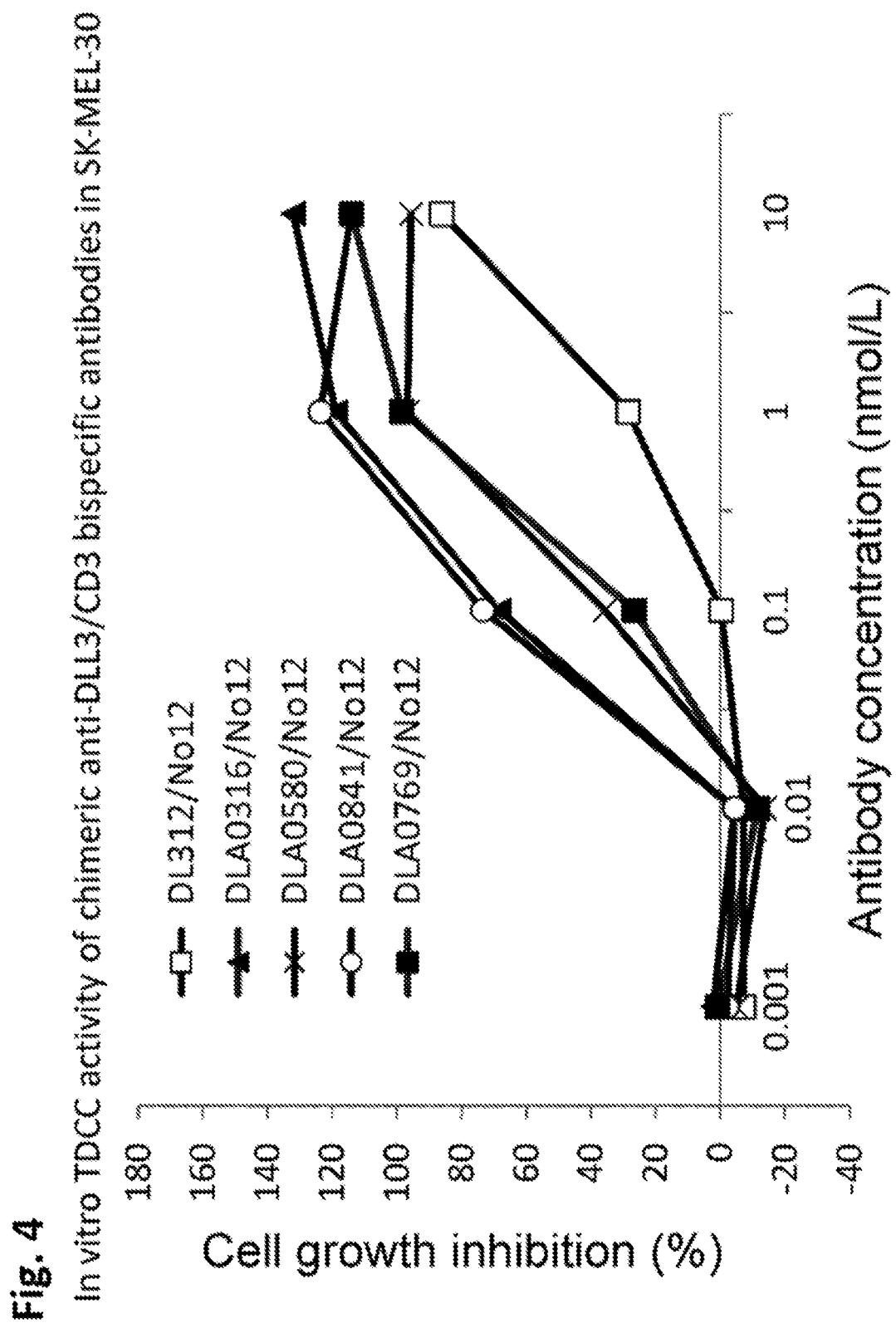
FIG. 4 shows T cell-dependent cellular cytotoxicity (TDCC) of anti-DLL3/CD3 bispecific antibodies (DL312/No. 12, DLA0316/No. 12, DLA0580/No. 12, DLA0814/No. 12, and DLA0769/No. 12) against SK-MEL-30 cell lines.

FIG. 4 shows the T cell-dependent cellular cytotoxicity (TDCC) of the generated anti-DLL3/CD3 bispecific antibodies. Cytotoxic activity was assessed by the rate of cell growth inhibition using xCELLigence Real-Time Cell Analyzer (Roche Diagnostics). The SK-MEL 30 human cancer cell line was used as target cells. Target cells were detached from the dish and plated onto E-plate 96 (Roche Diagnostics) in aliquots of 100 micro L/well by adjusting the cells to $1\times10^4$ cells/well, and the measurement of the cell growth was initiated using xCELLigence Real-Time Cell Analyzer. 24 hours later, the plate was removed and a 50 micro L aliquot of the respective antibodies prepared at each concentration (0.001, 0.01, 0.1, 1 or 10 nmol/L) was added to the plate. After 15 minutes of reaction at room temperature, 50 micro L of the fresh human PBMC solution prepared in Example 5.2.1 was added at an effector (PBMC)/target (SK-MEL 30) ratio of 2 (i.e., $2\times10^4$ cells/well), and the measurement of the cell growth was resumed using xCELLigence Real-Time Cell Analyzer. The reaction was carried out under the conditions of 5% carbon dioxide gas at 37 degrees C. 38 hours after the addition of PBMCs, the Cell Growth Inhibition (CGI) rate (%) was determined using the equation below. The Cell Index value obtained from xCELLigence Real-Time Cell Analyzer used in the calculation was a normalized value where the Cell Index value at the time point immediately before antibody addition was defined as 1.

Cell Growth Inhibition rate (%)=$(A-B)\times 100/(A-1)$

A represents the mean Cell Index value in wells without antibody addition (containing only target cells and human PBMCs), and B represents the mean Cell Index value of target wells containing one of the generated anti-DLL3/CD3 bispecific antibodies. The examinations were performed in triplicates.

All antibodies analyzed were subjected to TDCC assay using the SK-MEL-30 cell line. All the bispecific antibodies showed cell growth inhibition in a dose dependent manner, and the cell growth inhibition rates were over 80% at an antibody concentration of 10 nmol/L. The bispecific antibodies DLA0316/No. 12 and DLA0841/No. 12 showed the strongest TDCC activity (FIG. 4).

Example 5.2.3 Measurement of TDCC of Chimeric Anti-DLL3/CD3 Bispecific Antibodies by Calcein Release Assay in SCLCs TDCC of anti-DLL3/CD3 bispecific antibodies against small cell lung cancer cell lines was also analyzed. Cytotoxic activity was assessed by the calcein-acetoxymethyl release assay. The NCI-H1436 and NCI-H2227 human cancer cell lines were used as target cells. The assay was conducted in triplicate. The target cells were labeled with calcein-acetoxymethyl (Calcein-AM; Nacalai tesque) for 2 h at 37 degrees C. and then were washed. The anti-DLL3/CD3 bispecific antibodies prepared at each final concentration (0.001, 0.01, 0.1, 1 or 10 nM) were pipetted into a 96-well U-bottomed plate and, calcein-labeled target cell suspensions ($2\times10^5$ cells/mL) was added to each well. After leaving the plates for 15 minutes at room temperature, the effector cell (PBMC) suspension ($5\times10^6$ cells/mL) was added to the wells. After the 96-well plate was stirred, the plate was centrifuged at 1000 rpm for 2 minutes, and incubated in a 5% $CO_2$ incubator at 37 degrees C. for approximately 4 hours. After the 96-well plate was stirred well, and centrifuged at 1000 rpm for 5 minutes, a 100 micro L aliquot of culture medium from each well was transferred to a 96-well flat bottomed plate. Absorbance (495 nm, reference 515 nm) was measured with EnSpire (PerkinElmer). For maximal release, the cells were lysed with 0.5% NP-40. The fluorescence value of the culture medium background was subtracted from the value of the experimental release (A), the target cell spontaneous release (B), and the target cell maximal release (C). The cytotoxicity was calculated using the following formula:

Cytotoxicity (%)=$(A-B)/(C-B)\times 100$

Figure 5:
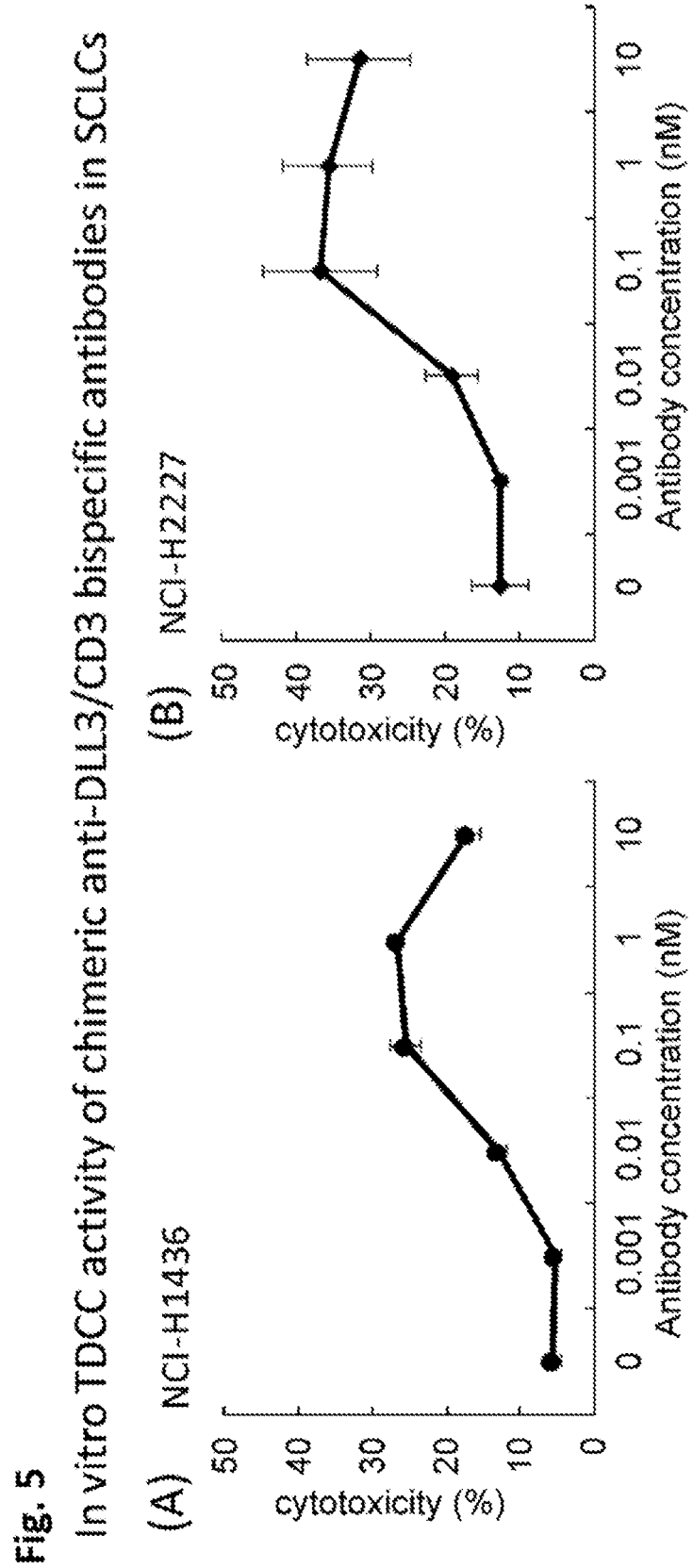
FIG. 5 shows TDCC of anti-DLL3/CD3 bispecific antibodies (DLA0316/No. 12) evaluated by calcein release assay against NCI-H1436 (A) and NCI-H2227 (B) SCLC cell lines.

FIG. 5 shows the TDCC of anti-DLL3/CD3 bispecific antibodies against small cell lung cancer cell lines. DLA0316/No. 12 showed cytotoxicity in a dose dependent manner against both of the two small cell lung cancer cell lines.

Example 6. Evaluation of the In Vivo Anti-Tumor Efficacy

Some of the above-described antibodies were evaluated for their in vivo efficacy using tumor-bearing models.

Evaluation of the in vivo anti-tumor efficacy was carried out using the anti-human DLL3/CD3 bispecific antibodies (DLA0316/No. 12, DLA0841/No. 12, and DLA0580/No. 12) which were confirmed to have cytotoxic activities in the in vitro assay described in Example 5. Cancer cell lines were transplanted into NOD scid mice, and the NOD scid mice with confirmed tumor formation were subjected to transplantation of T cells grown by in vitro culturing of human PBMCs. The mice (referred to as T cell-injected model) were treated by administration of the anti-human DLL3/CD3 bispecific antibodies.

More specifically, in anti-tumor efficacy tests of the anti-human DLL3/CD3 bispecific antibodies using the SK-MEL-30 (ATCC)-transplanted T cell-injected model, the tests below were performed. T cells were expansively cultured using purchased PBMCs and a T cell activation/expansion kit/human (MACS Miltenyi biotec). The human cancer cell line SK-MEL-30 ($1\times10^7$ cells) was mixed with Matrigell™ Basement Membrane Matrix (BD), and transplanted to the inguinal subcutaneous region of NOD scid mice (CLEA Japan, female, 6W to 8W). The day of transplantation was defined as day 0. On the day before transplantation (day 0), the anti-asialo-GM1 antibody (Wako Pure Chemicals) was administered intraperitoneally to the mice at 0.2 mg/mouse. On day 10 after the transplantation, the mice were separated into groups according to their body weight and tumor size, and the anti-asialo-GM1 antibody was administered again intraperitoneally to the mice at 0.2 mg/mouse. On the following day, T cells obtained by the aforementioned expansive culturing were transplanted intraperitoneally at $3 \times 10^7$ cells/mouse. Four hours after T cell transplantation, the anti-human DLL3/CD3 bispecific antibodies were administered intravenously through the caudate vein at 5 mg/kg and 1 mg/kg. The anti-human DLL3/CD3 bispecific antibodies were administered only once.

Figure 6:
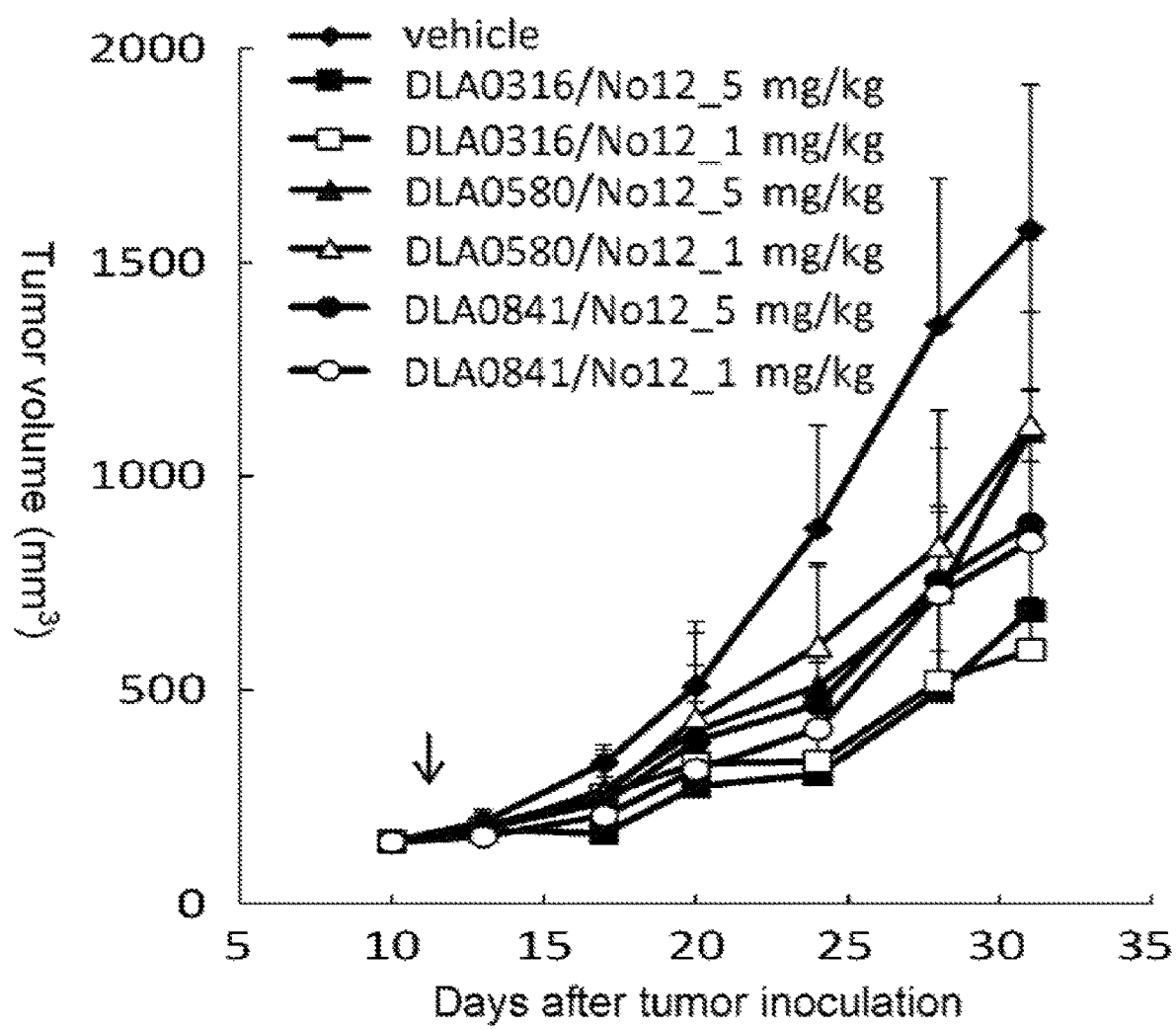
FIG. 6 shows in vivo anti-tumor efficacy of anti-DLL3/CD3 bispecific antibodies (DLA0316/No. 12, DLA0580/No. 12 and DLA0841/No. 12) in an SK-MEL-30 tumor-bearing T-cell injection model. The antibody used and its dose are also shown.

Anti-tumor activities (inhibition of tumor volume increase) were observed in the anti-human DLL3/CD3 bispecific antibody-administered group compared to the solvent-administered control group (FIG. 6).

The anti-tumor efficacy tests for DLA0316/No. 12 on the NCI-H1436-transplanted T cell-injected model were performed by similar methods. On day 16 after the tumor transplantation, the mice were separated into groups and T cells were transplanted on the following day. Three days after T cell transplantation, the anti-DLL3/CD3 bispecific antibodies were administered intravenously at 5 mg/kg, 1 mg/kg, and 0.2 mg/kg.

Figure 7:
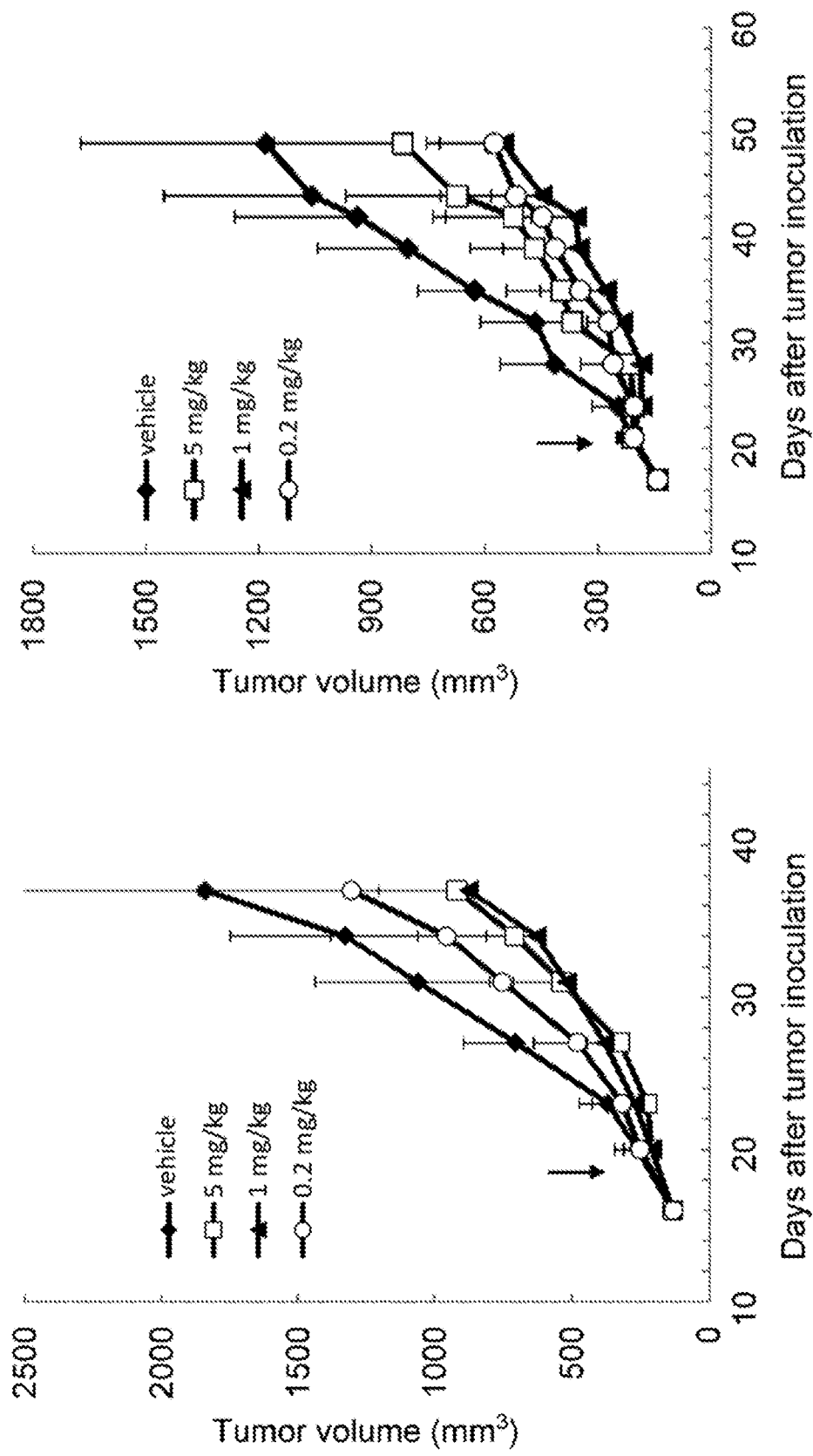
FIG. 7 shows in vivo anti-tumor efficacy of anti-DLL3/CD3 bispecific antibody (DLA0316/No. 12) in an SCLC tumor-bearing T-cell injection model. The cancer cell lines used were NCI-H1436 (A) and NCI-H2227 (B).

Anti-tumor activities (inhibition of tumor volume increase) were observed in the DLA0316/No. 12-administered group compared to the solvent-administered control group (FIG. 7A).

The anti-tumor efficacy tests for DLA0316/No. 12 on the NCI-H2227-transplanted T cell-injected model were performed by similar methods. On day 18 after the tumor transplantation, the mice were separated into groups and T cells were transplanted on day 17. Three days after T cell transplantation, the anti-DLL3/CD3 bispecific antibodies were administered intravenously at 5 mg/kg, 1 mg/kg, and 0.2 mg/kg.

Anti-tumor activities (inhibition of tumor volume increase) were observed in the DLA0316/No. 12-administered group compared to the solvent-administered control group (FIG. 7B).

Example 7. Humanization and Optimization of Anti-DLL3 Monospecific Antibodies

Variable regions of the heavy and light chains of humanized DLL3 antibodies were designed using human germline frameworks. The polynucleotides of the designed heavy and light chain variable regions were cloned into expression vectors containing the heavy chain constant region SG1 sequence (SEQ ID NO: 59 (the amino acid sequence is shown in SEQ ID NO: 60)) and the light chain constant region SK1 sequence (SEQ ID NO: 61 (the amino acid sequence is shown in SEQ ID NO: 62)), respectively. Humanized antibodies were transiently expressed in FreeStyle 293-F Cells (Thermo Fisher Scientific), and BIAcore analysis was carried out as described above. The sequences of humanized antibodies and their parental antibodies are shown in Table 5 below.

Selected humanized antibodies were further optimized. To avoid chemical degradations such as deamidation, isomerization, succinimide formation, methionine and tryptophan oxidation and cysteinylation of unpaired cysteine in CDR regions, amino acid residues within the sequences of the selected humanized antibodies were mutated to 18 other amino acids, excluding the original amino acid and Cysteine. The variants were transiently expressed and purified by the method described above. Purified variant monoclonal antibodies were assessed by BIAcore using the method described above, and variants of interest which could bind to human DLL3 and cynomolgus DLL3 as the parent antibody were selected. Antibodies with a combination of these mutations in the CDRs were then generated. The HVR (CDR) sequences of the antibodies containing these various mutations are shown in Table 6 below with the HVR (CDR) sequences of the parental antibodies.

Table 5 shows SEQ ID NOs of the generated anti-DLL3 antibodies.

TABLE 5

| Antibody name | Variable region | | Constant region | |
|---|---|---|---|---|
| | Heavy chain | Light chain | Heavy chain | Light chain |
| DLA0316-SG1 | 15 | 16 | 60 | 10 |
| D30316AE01-SG1 | 63 | 72 | 60 | 62 |
| D30316AE02-SG1 | 64 | 72 | 60 | 62 |
| D30316AE03-SG1 | 65 | 72 | 60 | 62 |
| DLA0841-SG1 | 25 | 26 | 60 | 10 |
| D30841AE05-SG1 | 66 | 73 | 60 | 62 |
| D30841AE08-SG1 | 67 | 73 | 60 | 62 |
| D30841AE11-SG1 | 67 | 74 | 60 | 62 |
| D30841AE12-SG1 | 68 | 73 | 60 | 62 |
| D30841AE13-SG1 | 69 | 73 | 60 | 62 |
| D30841AE14-SG1 | 70 | 73 | 60 | 62 |
| D30841AE15-SG1 | 71 | 73 | 60 | 62 |

Table 6 shows SEQ ID NOs of the HVR (CDR) sequences of the generated anti-DLL antibodies.

TABLE 6

| Antibody name | Hyper variable region (HVR) | | | | | |
|---|---|---|---|---|---|---|
| | HCDR1 | HCDR2 | HCDR3 | LCDR1 | LCDR2 | LCDR3 |
| DLA0316-SG1 | 27 | 28 | 29 | 30 | 31 | 32 |
| D30316AE01-SG1 | 27 | 28 | 29 | 30 | 31 | 32 |
| D30316AE02-SG1 | 27 | 75 | 29 | 30 | 31 | 32 |
| D30316AE03-SG1 | 27 | 76 | 29 | 30 | 31 | 32 |
| DLA0841-SG1 | 33 | 34 | 35 | 36 | 37 | 38 |
| D30841AE05-SG1 | 77 | 78 | 79 | 36 | 37 | 38 |
| D30841AE08-SG1 | 77 | 78 | 80 | 36 | 37 | 38 |
| D30841AE11-SG1 | 77 | 78 | 80 | 36 | 37 | 81 |
| D30841AE12-SG1 | 77 | 78 | 80 | 36 | 37 | 38 |
| D30841AE13-SG1 | 77 | 78 | 80 | 36 | 37 | 38 |
| D30841AE14-SG1 | 77 | 78 | 80 | 36 | 37 | 38 |
| D30841AE15-SG1 | 77 | 78 | 80 | 36 | 37 | 38 |

"HCDR1", "HCDR2", "HCDR3", LCDR1", "LCDR2", and "LCDR3" in Table 6 correspond to HVR-H1, HVR-H2, HVR-H3, HVR-L1, HVR-L2, and HVR-L3, respectively.

Example 8 Competition Analysis of Anti-DLL3 Antibodies

Preparation of Biotin-Labelled Anti-DLL3 Antibodies

Anti-DLL3 antibodies (DL301-SG1, DL306-SG1, DL309-SG1, DL312-SG1, DLL3-14-SG1, DLL3-22-SGT, DLL3-4-SGT and DLL3-6-SGT) which comprises variable regions of previously reported anti-DLL3 antibodies, were prepared in the same manner as described above. Variable heavy and light chain sequences (VH and VL) were cloned into expression vectors with SG1 (SEQ ID NO: 60) and with SK1 (SEQ ID NO: 62), respectively. The sequences of the anti-DLL3 antibodies are shown in Table 7 below.

Table 7 shows SEQ ID NOs of prepared anti-DLL3 antibodies.

TABLE 7

| Antibody name | Variable region | | Constant region | |
| --- | --- | --- | --- | --- |
| | Heavy chain | Light chain | Heavy chain | Light chain |
| DL301-SG1 | 82 | 90 | 60 | 62 |
| DL306-SG1 | 83 | 91 | 60 | 62 |
| DL309-SG1 | 84 | 92 | 60 | 62 |
| DL312-SG1 | 85 | 93 | 60 | 62 |
| DLL3-14-SG1 | 86 | 94 | 60 | 62 |
| DLL3-22-SG1 | 87 | 95 | 60 | 62 |
| DLL3-4-SG1 | 88 | 96 | 60 | 62 |
| DLL3-6-SG1 | 89 | 97 | 60 | 62 |

Anti-DLL3 antibodies (DL301-SG1, DL306-SGT, DL309-SGT, DL312-SGT, D30316AE02-SGT, and D30841AE05-SG1) were labelled with NHS-PEG4-Biotin (Thermo Fisher), thereby preparing biotin-labelled anti-DLL3 antibodies.

Octet Assay

Octet (registered trademark) RED384 (Fortebio) was used to perform competitive binding assays by epitope binning for a panel of antibodies. A biotinylated antibody (DL301-SG1, DL306-SG1, DL309-SG1, DL312-SG1, D30316AE02-SG1, and D30841AE05-SG1) at 40 nM was first loaded to a streptavidin (SA) biosensor. Next, the sensor is exposed to 20 nM of human DLL3, followed by exposure to 80 nM of second antibody. The second antibodies are DL301-SG1, DL306-SG1, DL309-SG1, DL312-SG1, D30316AE02-SG1, D30841AE05-SG1, DLL3-14-SG1, DLL3-22-SG1, DLL3-4-SG1 and DLL3-6-SG1. Raw data was processed using ForteBio's Data Analysis Software 7.0 and the antibody pairs were assessed for competitive binding. Additional binding by the second antibody indicates an unoccupied epitope (non-competitor), while no binding indicates epitope blocking (competitor).

To determine if there is a competitive antibody binding, antibody A was first immobilized to streptavidin biosensor and the sequential binding of the complex of antigen with antibody B was measured.

The competition ratio of antibody B to antibody A was calculated using the following equation: Competition Ratio (Antibody B to Antibody A)=[Binding Response (Antibody B-Antigen)]/[Binding Response (Antigen-Antibody A)]

Figure 8:
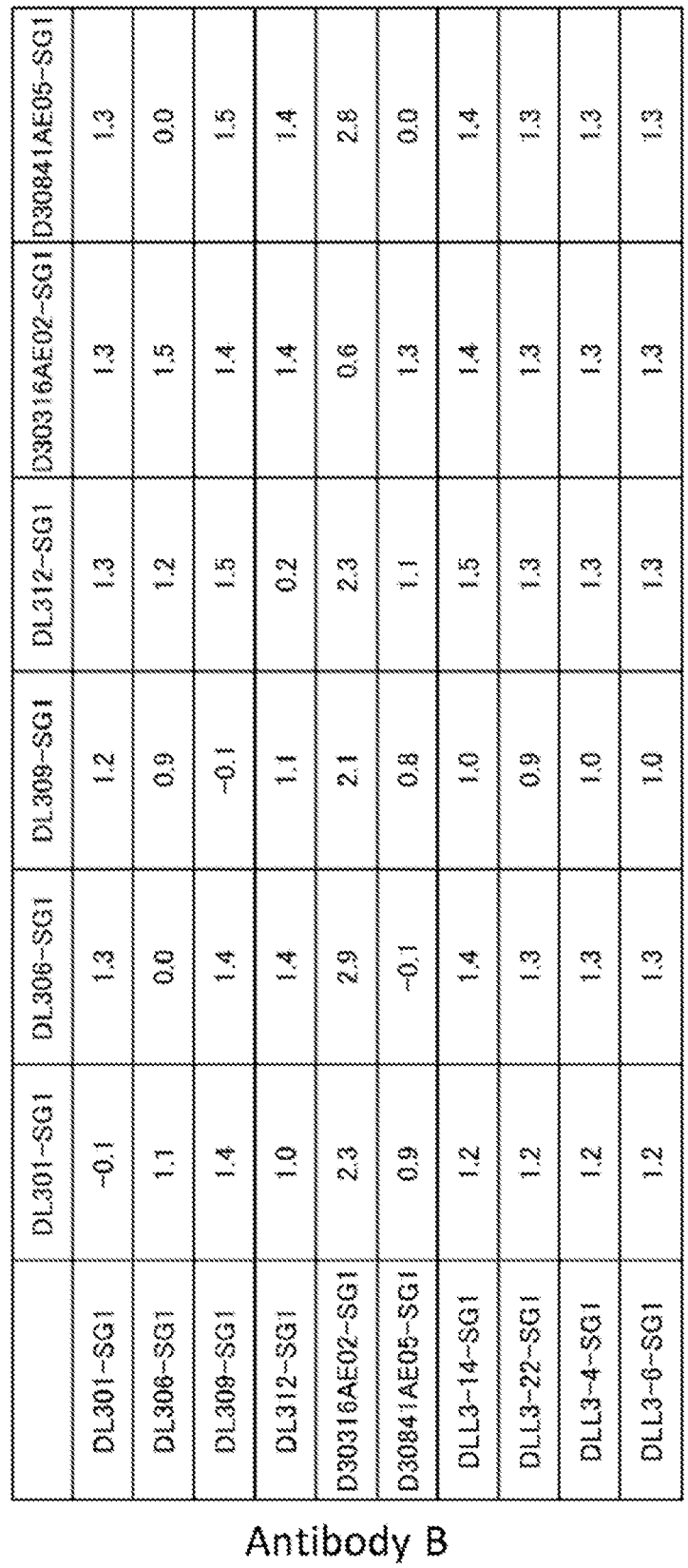
FIG. 8 shows competition ratio of Antibody B to Antibody A.

The results revealed that D30841AE05-SGT competes with DL306-SGT, and D30316AE02-SGT does not compete with other antibodies tested (FIG. 8).

Example 9 Preparation of an Anti-Human DLL3/Anti-Human CD3 Bispecific Antibody

The anti-DLL3 monospecific antibodies described in Table 5 and an anti-CD3 antibody were used to generate anti-DLL3/CD3 bispecific antibodies using conventional methods published elsewhere. The combination of anti-DLL3 arm and anti-CD3 arm are shown in Table 8.

The bispecific antibodies generated contain a silent Fc with attenuated affinity for the Fc gamma receptor. For these molecules, the Fab arm exchange technique reported by Igawa et al. (WO 2016159213) was used to make the bispecific antibodies.

Table 8 shows SEQ ID NOs of the variable regions of the prepared anti-DLL3/CD3 bispecific antibodies.

TABLE 8

| | anti-DLL3 arm | | anti-CD3 arm | |
| --- | --- | --- | --- | --- |
| Antibody name | Heavy chain variable region | Light chain variable region | Heavy chain variable region | Light chain variable region |
| DLA0316/TR01 | 15 | 16 | 98 | 103 |
| DLA0316/AN104 | 15 | 16 | 99 | 103 |
| DLA0316/AN119 | 15 | 16 | 100 | 103 |
| DLA0316/AN121 | 15 | 16 | 101 | 103 |
| DLA0316/AN395 | 15 | 16 | 102 | 103 |
| D30316AE03/TR01 | 65 | 72 | 98 | 103 |
| D30316AE03/AN104 | 65 | 72 | 99 | 103 |
| D30316AE03/AN119 | 65 | 72 | 100 | 103 |
| D30316AE03/AN121 | 65 | 72 | 101 | 103 |
| D30316AE03/AN395 | 65 | 72 | 102 | 103 |
| D30841AE08/TR01 | 67 | 73 | 98 | 103 |
| D30841AE11/TR01 | 67 | 74 | 98 | 103 |
| D30841AE08/AN121 | 67 | 73 | 101 | 103 |
| D30841AE11/AN121 | 67 | 74 | 101 | 103 |
| DLA0841/TR01 | 25 | 26 | 98 | 103 |
| DLA0841/AN121 | 25 | 26 | 101 | 103 |

Example 10 Biacore Analysis for Binding Affinity Evaluation of Anti-DLL3 Arm in the Anti-DLL3/CD3 Bispecific Antibodies Binding affinity of anti-DLL3 arm in the anti-DLL3/CD3 antibodies to human or cynomolgus DLL3 at pH 7.4 were assessed at 37 degrees C. using Biacore 8K instrument (GE Healthcare). Anti-human Fe (GE Healthcare) was immobilized onto all flow cells of a CM4 sensor chip using amine coupling kit (GE Healthcare). The bispecific antibodies were captured onto the anti-Fc sensor surfaces, and then recombinant human or cynomolgus DLL3 was injected over the flow cell. All antibodies and analytes were prepared in ACES pH 7.4 containing 20 mM ACES, 150 mM NaCl, 0.05% Tween 20, 0.005% $NaN_3$. Sensor surface was regenerated each cycle with 3M $MgCl_2$. Binding affinity were determined by processing and fitting the data to 1:1 binding model using Biacore 8K Evaluation software, version 2.0 (GE Healthcare).

The binding affinity of anti-DLL3 arm of the bispecific antibodies to recombinant DLL3 are shown in Table 9.

Table 9 shows binding affinity of anti-DLL3 arm of the bispecific antibodies.

TABLE 9

| | Human DLL3 | | | Cyno DLL3 | | |
|---|---|---|---|---|---|---|
| Ab name | ka (M$^{-1}$s$^{-1}$) | kd (s$^{-1}$) | KD (M) | ka (M$^{-1}$s$^{-1}$) | kd (s$^{-1}$) | KD (M) |
| DLA0316/TR01 | 2.47E+06 | 8.72E−05 | 3.53E−11 | 2.49E+06 | 4.96E−05 | 1.99E−11 |
| D30316AE03/TR01 | 2.34E+06 | 6.11E−05 | 2.61E−11 | 2.32E+06 | 2.72E−05 | 1.17E−11 |
| D30841AE08/TR01 | 2.47E+06 | 2.15E−04 | 8.72E−11 | 2.59E+06 | 1.91E−04 | 7.37E−11 |
| D30841AE11/TR01 | 1.88E+06 | 3.25E−04 | 1.72E−10 | 1.86E+06 | 2.65E−04 | 1.42E−10 |
| DLA0841/TR01 | 3.87E+06 | 2.47E−04 | 6.39E−11 | 3.83E+06 | 2.38E−04 | 6.21E−11 |

Example 11 Biacore Analysis for Binding Affinity Evaluation of Anti-CD3 Arm of the Anti-DLL3/CD3 Bispecific Antibodies Binding affinity of the anti-CD3 arm of the anti-DLL3/CD3 bispecific antibodies to CD3 at pH 7.4 was assessed at 37 degrees C. using Biacore 8K instrument (GE Healthcare). Anti-human Fc (GE Healthcare) was immobilized onto all flow cells of a CM4 sensor chip using amine coupling kit (GE Healthcare). The bispecific antibodies were captured onto the anti-Fc sensor surfaces, and then recombinant human CD3eg proteins (CD3 epsilon-gamma, heterodimer of CD3 epsilon and CD3 gamma) was injected over the flow cell. All antibodies and analytes were prepared in ACES pH 7.4 containing 20 mM ACES, 150 mM NaCl, 0.05% Tween 20, 0.005% NaN$_3$. Sensor surface was regenerated each cycle with 3M MgCl$_2$. Binding affinity were determined by processing and fitting the data to 1:1 binding model using Biacore 8K Evaluation software, version 2.0 (GE Healthcare).

The binding affinity of various anti-CD3 arms of bispecific antibodies to recombinant CD3eg proteins are shown in Table 10.

Table 10 shows binding affinity of the anti-CD3 arm of the bispecific antibodies.

TABLE 10

| Ab name | ka (M$^{-1}$s$^{-1}$) | kd (s$^{-1}$) | KD (M) |
|---|---|---|---|
| D30316AE03/TR01 | 1.34E+05 | 1.69E−02 | 1.27E−07 |
| D30316AE03/AN104 | 7.14E+04 | 2.66E−03 | 3.73E−08 |
| D30316AE03/AN119 | 1.45E+05 | 1.60E−03 | 1.10E−08 |
| D30316AE03/AN121 | 9.86E+04 | 7.44E−04 | 7.55E−09 |
| D30316AE03/AN395 | 2.42E+05 | 7.43E−03 | 3.07E−08 |

Example 12. Measurement of T Cell-Dependent Cell Cytotoxicity (TDCC) of Humanized Anti-DLL3/CD3 Bispecific Antibodies by the Rate of Cell Growth Inhibition The TDCC assay for the humanized anti-DLL3/CD3 bispecific antibodies was performed by methods similar to those described in Example 5.2.2. The SK-MEL 30 human cancer cell line was used as target cells and the assay time was for 48 or 72 hours. FIG. 9 shows the TDCC of humanized anti-DLL3/CD3 bispecific antibodies. Humanized antibodies showed the same level of TDCC activity compared with its parent clone, concluded as sufficient efficacy.

Example 13. Preparation of an Anti-Human DLL3/Anti-Human CD3 Bispecific Antibody The anti-DLL3 monospecific antibody D30841AE13-SG1 described in Table 5 and anti-CD3 antibodies were used to generate anti-DLL3/CD3 bispecific antibodies using conventional methods published elsewhere. The SEQ ID NOs are shown in Table 11.

Table 11 shows SEQ ID NOs of the variable regions of the prepared anti-DLL3/CD3 bispecific antibodies.

TABLE 11

| | anti-DLL3 arm | | anti-CD3 arm | |
|---|---|---|---|---|
| Antibody name | Heavy chain variable region | Light chain variable region | Heavy chain variable region | Light chain variable region |
| D30841AE13/TR01 | 69 | 73 | 98 | 103 |
| D30841AE13/hu40G5c | 69 | 73 | 298 | 299 |

The bispecific antibodies generated contain a silent Fc with attenuated affinity for the Fc gamma receptor. For these molecules, the Fab arm exchange technique reported by Igawa et al. (WO 2016159213) was used to make the bispecific antibodies.

Example 14. Measurement of T Cell-Dependent Cell Cytotoxicity (TDCC) of Humanized Anti-DLL3/CD3 Bispecific Antibodies by the Rate of Cell Growth Inhibition The TDCC assay of anti-DLL3/CD3 bispecific antibodies made in Example 13 was performed by methods similar to those described in Example 5.2.2. The SK-MEL 30 human cancer cell line was used as target cells. As for effector cells, frozen PBMCs were used. To prepare frozen PBMCs, cryovials were placed in the water bath at 37 degrees C. to thaw frozen cells. Cells were then dispensed into a 15 mL falcon tube containing 9 mL of media (media used to culture target cells). Cell suspension was then subjected to centrifugation at 1,200 rpm for 5 minutes at room temperature. The supernatant was aspirated gently and fresh warmed medium was added for resuspension. PBMCs were co-cultured with SK-MEL-30 at effector: target ratio of 5. 72 hours after addition of PBMC, cell growth inhibition rate (%) was plotted and shown in FIG. 10.

Figure 10:
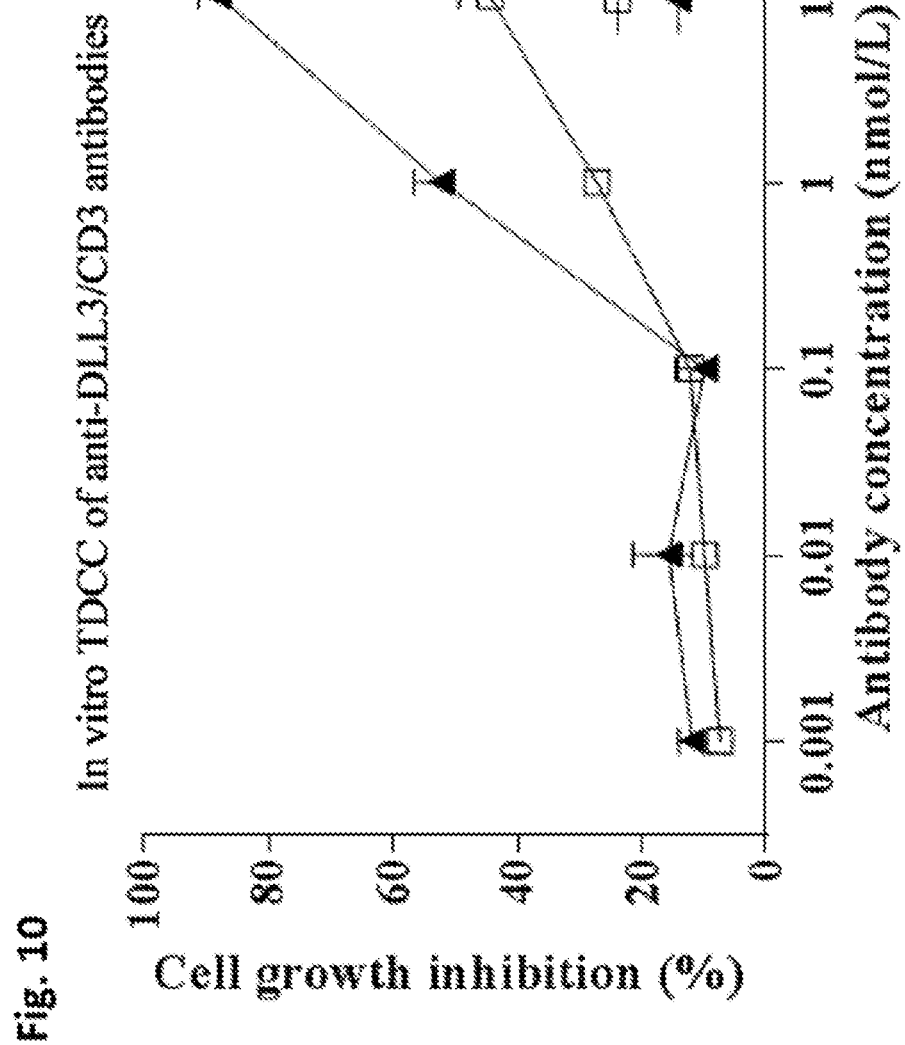
FIG. 10 shows TDCC of humanized anti-DLL3/CD3 bispecific antibodies against SK-MEL-30 cell line. The graph shows cytotoxicity of SK-MEL-30 when co-cultured with PBMC at E:T ratio of 5 in the presence of bi-specific humanized DLL3 antibodies with different anti-CD3 arms at 0.001 nM to 10 nM.

As shown in FIG. 10, both D30841AE13/TR01 and D30841AE13/hu40G5c showed TDCC activity at 1 and 10 nM concentration of bi-specific antibodies.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

INDUSTRIAL APPLICABILITY

The present invention provides novel antigen-binding molecules that have a strong anti-tumor activity and an excellent safety property of not inducing a cytokine storm or such independently from cancer antigens. Cytotoxicity-inducing agents that comprise an antigen-binding molecule of the present invention as an active ingredient can target DLL3-expressing cells and tumor tissues containing these cells and induce cell injury. Administration of an antigen-binding molecule or antibody of the present invention to patients makes it possible to have a desirable treatment that has not only a high level of safety but also a reduced physical burden, and is highly convenient.

Sequence Listing C1-A1723Psq.txt

The invention claimed is:

1. A multispecific antigen-binding molecule that comprises:
   (1) a first domain comprising a first antigen-binding domain binds to human DLL3, and
   (2) a second domain comprising a second antigen-binding domain binds to T-cell receptor complex,
   wherein the first antigen-binding domain of (1) comprises any one of (a1) to (a11) below:
   (a1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
   (a2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;
   (a3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;
   (a4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;
   (a5) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
   (a6) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
   (a7) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;
   (a8) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38;
   (a9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81;
   (a10) an antibody variable fragment that binds to the same epitope of any of the antibody variable fragment selected from (a1) to (a9);
   (a11) an antibody variable fragment that competes with the binding of any of the antibody variable fragment selected from (a1) to (a9).

2. The multispecific antigen-binding molecule of claim 1, wherein the multispecific antigen-binding molecule has cytotoxic activity.

3. The multispecific antigen-binding molecule of claim 2, wherein the cytotoxic activity is T-cell-dependent cytotoxic activity.

4. The multispecific antigen-binding molecule of claim 1, wherein the second antigen-binding domain in (2) binds to CD3 epsilon chain.

5. The multispecific antigen-binding molecule of claim 1, wherein the second antigen-binding domain in (2) binds to T-cell receptor.

6. The multispecific antigen binding molecule of claim 1, wherein the first antigen-binding domain or the second antigen-binding domain is an antibody variable fragment, or both of the first and second antigen-binding domains are antibody variable fragments.

7. The multispecific antigen binding molecule of claim 1, wherein the multispecific antigen binding molecule further comprises:
(3) a third domain comprising an Fc region with reduced binding activity towards an Fc gamma receptor.

8. The multispecific antigen-binding molecule of claim 7, wherein the Fc region of the third domain is an Fc region with an amino acid mutation at any of the Fc region-constituting amino acids of SEQ ID NOs: 112 to 115 (IgG1 to IgG4).

9. The multispecific antigen-binding molecule of claim 8, wherein the Fc region is an Fc region with mutation of at least one amino acid selected from the following amino acid positions specified by EU numbering: position 220, position 226, position 229, position 231, position 232, position 233, position 234, position 235, position 236, position 237, position 238, position 239, position 240, position 264, position 265, position 266, position 267, position 269, position 270, position 295, position 296, position 297, position 298, position 299, position 300, position 325, position 327, position 328, position 329, position 330, position 331, and position 332.

10. The multispecific antigen-binding molecule of claim 1, wherein the multispecific antigen-binding molecule is a bispecific antibody.

11. A pharmaceutical composition comprising the multispecific antigen-binding molecule of claim 1 and a pharmaceutically acceptable carrier.

12. The multispecific antigen-binding molecule of claim 1, wherein the first antigen-binding domain of (1) comprises:
(a9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38.

13. The multispecific antigen-binding molecule of claim 8, wherein the Fc region is an Fc region with mutation at position 235 by EU numbering.

14. The multispecific antigen-binding molecule of claim 12, wherein the Fc region is an Fc region with mutation at position 235 by EU numbering.

* * * * *